(12) United States Patent
Kumar et al.

(10) Patent No.: US 12,103,959 B2
(45) Date of Patent: Oct. 1, 2024

(54) MULTISPECIFIC BINDERS OF TGFBeta-SUPERFAMILY LIGANDS AND USES THEREOF

(71) Applicant: Acceleron Pharma Inc., Cambridge, MA (US)

(72) Inventors: Ravindra Kumar, Acton, MA (US); Dianne S. Sako, Medford, MA (US); Roselyne Castonguay, Watertown, MA (US); Tzu-Hsing Kuo, Chestnut Hill, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 184 days.

(21) Appl. No.: 17/052,785

(22) PCT Filed: May 2, 2019

(86) PCT No.: PCT/US2019/030469
§ 371 (c)(1),
(2) Date: Nov. 3, 2020

(87) PCT Pub. No.: WO2019/213442
PCT Pub. Date: Nov. 7, 2019

(65) Prior Publication Data
US 2022/0372107 A1   Nov. 24, 2022

Related U.S. Application Data

(60) Provisional application No. 62/666,547, filed on May 3, 2018, provisional application No. 62/779,998, filed on Dec. 14, 2018.

(51) Int. Cl.
| | | |
|---|---|---|
| C07K 14/705 | (2006.01) | |
| A61K 38/00 | (2006.01) | |
| C07K 14/71 | (2006.01) | |
| C07K 16/22 | (2006.01) | |

(52) U.S. Cl.
CPC ........ *C07K 14/70578* (2013.01); *C07K 14/71* (2013.01); *C07K 16/22* (2013.01); *A61K 38/00* (2013.01); *C07K 2319/02* (2013.01); *C07K 2319/30* (2013.01)

(58) Field of Classification Search
None
See application file for complete search history.

(56) References Cited

FOREIGN PATENT DOCUMENTS

| | | |
|---|---|---|
| JP | 2016-037488 A | 3/2016 |
| WO | WO-2011/109789 A2 | 9/2011 |
| WO | WO-2015/118175 A2 | 8/2015 |
| WO | WO-2016/164089 A2 | 10/2016 |
| WO | WO-2016/164501 A1 | 10/2016 |
| WO | WO-2018/009624 A1 | 1/2018 |
| WO | WO-2018/067873 A2 | 4/2018 |
| WO | WO-2018/067874 A1 | 4/2018 |
| WO | WO-2019/213446 A1 | 11/2019 |
| WO | WO-2019/241625 A1 | 12/2019 |

OTHER PUBLICATIONS

Aykul, et al., "Transforming Growth Factor-? Family Ligands Can Fuction as Antagonists by Competing for Type II Receptor Binding," The Journal of Biological Chemistry, vol. 291(20): 10792-10804 (2016).
ISR PCT/US2019/030469, dated Jul. 19, 2019 (7 pages).
Kumar et al., "Functionally diverse heteromeric traps for ligands of the transforming growth factor-[beta] superfamily," Scientific Reports, vol. 11(1): 16 pages (2021).
Staudacher, et al., "Activin and Transforming Growth Factor-Beta in Colorectal Cancer: The Force Awakens," Gastroenterology, vol. 150(4) Suppl. 1: S-366 (2016).
Supplementary European Search Report EP 19 79 6599, dated Jan. 4, 2022 (3 pages).
Hao et al., "Elevation of Expression of Smads 2, 3, and 4, Decorin and TGF-Beta in the Chronic Phase of Myocardial Infarct Scar Healing," Journal of Mol. Cell. Cardiol., vol. 31(3): 667-678 (1999).
Lei et al., Effect of Efonidipine on TGF-Berta1-Induced Cardiac Fiborsis Through Smad2-Dependent Pathway in Rat Cardiac Fibroblasts, Journal of Pharmacol. Sci., vol. 117(2): 98-105 (2011).

*Primary Examiner* — Ruixiang Li
(74) *Attorney, Agent, or Firm* — White & Case LLP

(57) ABSTRACT

In certain aspects, the disclosure provides multispecific binders (e.g., ActRIIA:TβRII heteromultimers comprising an ActRIIA polypeptide and a TβRII polypeptide). The disclosure further provides that such multispecific binders (e.g., ActRIIA:TβRII heteromultimer) may be used to treat various disorders or conditions.

8 Claims, 34 Drawing Sheets
Specification includes a Sequence Listing.

```
  1  mgrglrglw plhivlwtri astipphvqk svnndmivtd nngavkfpgi
 51  ckfcdvrfst cdnqkscmsn csitsicekp qevcvavwrk ndenitletv
101  chdpklpvhd filedaaspk cimkekkpg  etffmcscss decndniifs
151  eeyntsnpai llvifqvtgi slipplgvai sviiifycyr vnrqklsst
201  wetgktrklm efsehcaiil eddrsdisst canninhnte llpieldtiv
251  gkgrfaevyk aklkqntseg fetvavkifp yeeyaswkte kdifsdinlk
301  henilqfita eerktelgkq ywlitafhak gnlqeyltrh viswedirkl
351  gsslargiah lhsdhtpcgr plmpivhrdl kssnilvknd ltcclcdfgl
401  slrldptlsv ddlansgqvg tarymapevl esrmnienve sfkqtdvysm
451  alvlwemtsr cnavgevkdy eppfgskvre hpcvesmkdn vlrdgrpei
501  psfwlnhggi qmvceeltec wdhdpearlt aqcvaerfse leh

```
  1  mgrglirglw plhivlwtri astipphvqk sdvemeaqkd eiicpscnrt
 51  ahplrhinnd nivtdhngav kfpglcfcd vrfstcangk scmcncsits
101  icekpqevcv avwrkndeni tletvchdpk lpyhdfiled a

| | Fusion Protein | $k_a$ (1/Ms) | $k_d$ (1/s) | $K_D$ (pM) |
|---|---|---|---|---|
| TGFβ1 | hTβRII-hFc | $2.01 \times 10^6$ | $4.16 \times 10^{-4}$ | 207.0 |
| | hTβRII (G4S)2-hFc | $2.91 \times 10^6$ | $4.83 \times 10^{-4}$ | 165.8 |
| | hTβRII (G4S)3-hFc | $3.89 \times 10^6$ | $5.10 \times 10^{-4}$ | 92.4 |
| | hTβRII (G4S)4-hFc | $6.69 \times 10^6$ | $4.57 \times 10^{-4}$ | 68.4 |
| | hTβRII-extended hinge-hFc | $2.38 \times 10^6$ | $4.64 \times 10^{-4}$ | 195.5 |
| TGFβ3 | hTβRII-hFc | $1.99 \times 10^7$ | $1.57 \times 10^{-3}$ | 79.1 |
| | hTβRII (G4S)2-hFc | $1.74 \times 10^7$ | $1.81 \times 10^{-3}$ | 104.1 |
| | hTβRII (G4S)3-hFc | $2.09 \times 10^7$ | $8.32 \times 10^{-4}$ | 39.9 |
| | hTβRII (G4S)4-hFc | $8.80 \times 10^6$ | $2.76 \times 10^{-4}$ | 31.4 |
| | hTβRII-extended hinge-hFc | $1.51 \times 10^7$ | $1.39 \times 10^{-3}$ | 92.1 |

Figure 4A

TGFβ1

| Receptor | $k_a$ (1/Ms) | $k_d$ (1/s) | $K_D$ (pM) |
|---|---|---|---|
| hTβRII (G4S)5-hFc | $7.36 \times 10^7$ | $6.48 \times 10^{-4}$ | 8.8 |
| hTβRII (G4S)6-hFc | $1.66 \times 10^8$ | $6.32 \times 10^{-4}$ | 3.8 |

TGFβ3

| Receptor | $k_a$ (1/Ms) | $k_d$ (1/s) | $K_D$ (pM) |
|---|---|---|---|
| hTβRII (G4S)5-hFc | $1.47 \times 10^8$ | $4.35 \times 10^{-4}$ | 2.96 |
| hTβRII (G4S)6-hFc | $5.99 \times 10^7$ | $2.75 \times 10^{-4}$ | 4.60 |

Figure 4B

|  | IC$_{50}$ (nM) | | Ratio TGFβ1/TGFβ3 |
| --- | --- | --- | --- |
|  | TGFβ1 | TGFβ3 |  |
| hTβRII-hFc | 7.69 | 0.18 | 42 |
| hTβRII (G4S)2-hFc | 1.12 | 0.13 | 8.61 |
| hTβRII (G4S)3-hFc | 0.22 | 0.17 | 1.29 |
| hTβRII (G4S)4-hFc | 0.07 | 0.03 | 2.3 |
| hTβRII-extended hinge-hFc | 5.67 | 0.11 | 52 |

Figure 5E

| Construct | TGFβ1—IC50(nM) | TGFβ3—IC50(nM) | Ratio TGFβ1/TGFβ3 |
|---|---|---|---|
| hTβRII(G4S)5-hFc | 0.03 | 0.04 | 0.75 |
| hTβRII(G4S)6-hFc | 0.02 | 0.04 | 0.5 |

Figure 5F

```
IgG1  -------THTCPPCPAPELLGGPSVFLFPPKPKDTLMISRTPEVTCVVVDVSHEDPEVKF  53
IgG4  ---ESKYGPPCPSCPAPEFLGGPSVFLFPPKPKDTLMISRTPEVTCVVVDVSQEDPEVQF  57
IgG2  -------VECPPCPAPPVAG-PSVFLFPPKPKDTLMISRTPEVTCVVVDVSHEDPEVQF  51
IgG3  EPKSCDTPPPCPRCPAPELLGGPSVFLFPPKPKDTLMISRTPEVTCVVVDVSHEDPEVQF  60
         ** ****  *  *******************************,******.*

IgG1  NWYVDGVEVHNAKTKPREEQYNSTYRVVSVLTVLHQDWLNGKEYKCKVSNKALPAPIEKT  113
IgG4  NWYVDGVEVHNAKTKPREEQFNSTYRVVSVLTVLHQDWLNGKEYKCKVSNKGLPSSIEKT  117
IgG2  NWYVDGVEVHNAKTKPREEQFNSTFRVVSVLTVVHQDWLNGKEYKCKVSNKGLPAPIEKT  111
IgG3  KWYVDGVEVHNAKTKPREEQYNSTFRVVSVLTVLHQDWLNGKEYKCKVSNKALPAPIEKT  120
      :************.***.*******.*******************.**:.****

IgG1  ISKAKGQPREPQVYTLPPSREEMTKNQVSLTCLVKGFYPSDIAVEWESNGQPENNYKTTP  173
IgG4  ISKAKGQPREPQVYTLPPSQEEMTKNQVSLTCLVKGFYPSDIAVEWESNGQPENNYKTTP  177
IgG2  ISKTKGQPREPQVYTLPPSREEMTKNQVSLTCLVKGFYPSDIAVEWESNGQPENNYKTTP  171
IgG3  ISKTKGQPREPQVYTLPPSREEMTKNQVSLTCLVKGFYPSDIAVEWESSGQPENNYNTTP  180
      ***.***********:***********************.*******:***

IgG1  PVLDSDGSFFLYSKLTVDKSRWQQGNVFSCSVMHEALHNHYTQKSLSLSPGK  225
IgG4  PVLDSDGSFFLYSRLTVDKSRWQEGNVFSCSVMHEALHNHYTQKSLSLSLGK  229
IgG2  PMLDSDGSFFLYSKLTVDKSRWQQGNVFSCSVMHEALHNHYTQKSLSLSPGK  223
IgG3  PMLDSDGSFFLYSKLTVDKSRWQQGNIFSCSVMHEALHNRFTQKSLSLSPGK  232
      *.***********.*********.**:*************..******  **
```

Figure 6

```
ActRIIa   ILGRSETQEC  LFFNANWEKD  RTNQTGVEPC  YGDKDKRRHC  FATWKNISGS
ActRIIb   GRGEAETREC  IYYNANWELE  RTNQSGLERC  EGEQDKRLHC  YASWRNSSGT

IEIVKQGCWL  DDINCYDRTD  CVEKKDSPEV  YFCCCEGNMC  NEKFSYFPEM
          IELVKKGCWL  DDFNCYDRQE  CVATEENPQV  YFCCCEGNFC  NERFTHLPEA

EVTQPTSNPV  TPKPP
          GGPEVTYEPP  PTAPT
```

Figure 7

| | $IC_{50}$ (nM) | | | | | | |
|---|---|---|---|---|---|---|---|
| | GDF11 | Activin A | Activin B | BMP10 | TGFβ1 | TGFβ2 | TGFβ3 |
| ActRIIA-Fc:TβRII-Fc | 18.08 | 1.28 | 1.16 | UD* | 0.21 | UD* | 0.39 |
| ActRIIA-Fc:ActRIIA-Fc | 0.23 | 0.07 | 0.05 | 48.02 | UD* | UD* | UD* |
| TβRII-Fc:TβRII-Fc | UD* | UD* | UD* | UD* | 0.017 | UD* | 0.07 |

*UD = Unable to determine $IC_{50}$ at highest concentration tested (i.e., 20 μg/mL)

Figure 12

SEQUENCE LISTING

```
<160> NUMBER OF SEQ ID NOS: 214

<210> SEQ ID NO 1
<211> LENGTH: 567
<212> TYPE: PRT
<213> ORGANISM: Homo sapiens

<400> SEQUENCE: 1

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220
```

-continued

```
Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
                340                 345                 350

Ser Leu Ala Arg Gly Ile Ala His Leu His Ser Asp His Thr Pro Cys
                355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
                420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
        530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565
```

<210> SEQ ID NO 2
<211> LENGTH: 592
<212> TYPE: PRT
<213> ORGANISM: Homo sapiens

<400> SEQUENCE: 2

```
Met Gly Arg Gly Leu Leu Arg Gly Leu Trp Pro Leu His Ile Val Leu
1               5                   10                  15
```

-continued

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

```
Leu Ser Val Asp Asp Leu Ala Asn Ser Gly Gln Val Gly Thr Ala Arg
            435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
                500                 505                 510

Lys Asp Asn Val Leu Arg Asp Arg Gly Arg Pro Glu Ile Pro Ser Phe
            515                 520                 525

Trp Leu Asn His Gln Gly Ile Gln Met Val Cys Glu Thr Leu Thr Glu
            530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Gly Gly Gly
1

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Gly Gly Gly Gly Ser Gly Gly Gly Gly Ser
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Gly Gly Gly Gly Ser Gly Gly Gly Gly Ser Gly Gly Gly Gly Ser
1               5                   10                  15

<210> SEQ ID NO 6
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 6

Thr Gly Gly Gly Gly Ser Gly Gly Gly Ser Gly Gly Gly Gly Ser
1               5                   10                  15

Gly Gly Gly Gly Ser
            20

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Gly Gly Gly Pro Lys Ser Cys Asp Lys
1               5                   10

<210> SEQ ID NO 8
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggatgcaa tgaagagagg gctctgctgt gtgctgctgc tgtgtggagc agtcttcgtt        60
tcgcccggcg ccacgatccc accgcacgtt cagaagtcgg atgtggaaat ggaggcccag       120
aaagatgaaa tcatctgccc cagctgtaat aggactgccc atccactgag acatattaat       180
aacgacatga tagtcactga caacaacggt gcagtcaagt tccacaact  gtgtaaattt       240 tgtgatgtga gatttccac  ctgtgacaac cagaaatcct gcatgagcaa ctgcagcatc       300
acctccatct gtgagaagcc acaggaagtc tgtgtggctg tatggagaaa gaatgacgag       360
aacataacac tagagacagt ttgccatgac cccaagctcc cctaccatga ctttattctg       420
gaagatgctg cttctccaaa gtgcattatg aaggaaaaaa aaaagcctgg tgagactttc       480
ttcatgtgtt cctgtagctc tgatgagtgc aatgacaaca tcatcttctc agaagaatat       540
aacaccagca atcctgacac cggtggtgga actcacacat gcccaccgtg cccagcacct       600
gaactcctgg ggggaccgtc agtcttcctc ttccccccaa aacccaagga caccctcatg       660
atctcccgga cccctgaggt cacatgcgtg gtggtggacg tgagccacga agaccctgag       720
gtcaagttca actggtacgt ggacggcgtg gaggtgcata atgccaagac aaagccgcgg       780
gaggagcagt acaacagcac gtaccgtgtg gtcagcgtcc tcaccgtcct gcaccaggac       840
tggctgaatg gcaaggagta caagtgcaag gtctccaaca aagccctccc agcccccatc       900
gagaaaacca tctccaaagc caagggcag  ccccgagaac cacaggtgta caccctgccc       960
ccatcccggg aggagatgac caagaaccag gtcagcctga cctgcctggt caaaggcttc      1020
tatcccagcg acatcgccgt ggagtgggag agcaatgggc agccggagaa caactacaag      1080
accacgcctc ccgtgctgga ctccgacggc tccttcttcc tctatagcaa gctcaccgtg      1140
gacaagagca ggtggcagca ggggaacgtc ttctcatgct ccgtgatgca tgaggctctg      1200
cacaaccact acacgcagaa gagcctctcc ctgtctccgg gtaaatga                   1248
```

```
<210> SEQ ID NO 9
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Ala Met Lys Arg Gly Leu Cys Cys Val Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
                35                  40                  45

Cys Asn Arg Thr Ala His Pro Leu Arg His Ile Asn Asn Asp Met Ile
            50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
            115                 120                 125

His Asp Pro Lys Leu Pro Tyr His Asp Phe Ile Leu Glu Asp Ala Ala
            130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Thr His
                180                 185                 190

Thr Cys Pro Pro Cys Pro Ala Pro Glu Leu Leu Gly Gly Pro Ser Val
            195                 200                 205

Phe Leu Phe Pro Pro Lys Pro Lys Asp Thr Leu Met Ile Ser Arg Thr
210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
            275                 280                 285

Cys Lys Val Ser Asn Lys Ala Leu Pro Ala Pro Ile Glu Lys Thr Ile
290                 295                 300

Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
            355                 360                 365
```

Asp Gly Ser Phe Phe Leu Tyr Ser Lys Leu Thr Val Asp Lys Ser Arg
        370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 10
<211> LENGTH: 1284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggatgcaa tgaagagagg gctctgctgt gtgctgctgc tgtgtggagc agtcttcgtt      60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga caacaacggt gcagtcaagt ttccacaact gtgtaaattt    240
tgtgatgtga gattttccac ctgtgacaac cagaaatcct gcatgagcaa ctgcagcatc     300
acctccatct gtgagaagcc acaggaagtc tgtgtggctg tatggagaaa gaatgacgag     360
aacataacac tagagacagt ttgccatgac cccaagctcc cctaccatga ctttattctg     420
gaagatgctg cttctccaaa gtgcattatg aaggaaaaaa aaaagcctgg tgagactttc     480
ttcatgtgtt cctgtagctc tgatgagtgc aatgacaaca tcatcttctc agaagaatat     540
aacaccagca atcctgacac cggtggtgga ggaagtggtg gaggtggttc tggaggtggt     600
ggaagtactc acacatgccc accgtgccca gcacctgaac tcctgggggg accgtcagtc     660
ttcctcttcc ccccaaaacc caaggacacc ctcatgatct cccggacccc tgaggtcaca     720
tgcgtggtgg tggacgtgag ccacgaagac cctgaggtca agttcaactg gtacgtggac     780
ggcgtggagg tgcataatgc caagacaaag ccgcgggagg agcagtacaa cagcacgtac     840
cgtgtggtca gcgtcctcac cgtcctgcac caggactggc tgaatggcaa ggagtacaag     900
tgcaaggtct ccaacaaagc cctcccagcc cccatcgaga aaccatctc caaagccaaa      960 gggcagcccc gagaaccaca ggtgtacacc ctgcccccat cccgggagga gatgaccaag    1020
aaccaggtca gcctgacctg cctggtcaaa ggcttctatc ccagcgacat cgccgtggag    1080
tgggagagca atgggcagcc ggagaacaac tacaagacca cgcctcccgt gctggactcc    1140
gacggctcct tcttcctcta tagcaagctc accgtggaca agagcaggtg gcagcagggg    1200
aacgtcttct catgctccgt gatgcatgag gctctgcaca accactacac gcagaagagc    1260
ctctccctgt ctccgggtaa atga                                           1284

<210> SEQ ID NO 11
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Ala Met Lys Arg Gly Leu Cys Cys Val Leu Leu Leu Cys Gly
1               5                   10                  15

```
Ala Val Phe Val Ser Pro Gly Ala Thr Ile Pro Pro His Val Gln Lys
         20                  25                  30

Ser Asp Val Glu Met Glu Ala Gln Lys Asp Glu Ile Ile Cys Pro Ser
             35                  40                  45

Cys Asn Arg Thr Ala His Pro Leu Arg His Ile Asn Asn Asp Met Ile
 50                      55                  60

Val Thr Asp Asn Asn Gly Ala Val Lys Phe Pro Gln Leu Cys Lys Phe
 65                  70                  75                   80

Cys Asp Val Arg Phe Ser Thr Cys Asp Asn Gln Lys Ser Cys Met Ser
                 85                  90                  95

Asn Cys Ser Ile Thr Ser Ile Cys Glu Lys Pro Gln Glu Val Cys Val
             100                 105                 110

Ala Val Trp Arg Lys Asn Asp Glu Asn Ile Thr Leu Glu Thr Val Cys
             115                 120                 125

His Asp Pro Lys Leu Pro Tyr His Asp Phe Ile Leu Glu Asp Ala Ala
         130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                 165                 170                 175

Ser Glu Glu Tyr Asn Thr Ser Asn Pro Asp Thr Gly Gly Gly Ser
             180                 185                 190

Gly Gly Gly Gly Ser Gly Gly Gly Ser Thr His Thr Cys Pro Pro
         195                 200                 205

Cys Pro Ala Pro Glu Leu Leu Gly Gly Pro Ser Val Phe Leu Phe Pro
     210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                 245                 250                 255

Trp Tyr Val Asp Gly Val Glu Val His Asn Ala Lys Thr Lys Pro Arg
             260                 265                 270

Glu Glu Gln Tyr Asn Ser Thr Tyr Arg Val Val Ser Val Leu Thr Val
         275                 280                 285

Leu His Gln Asp Trp Leu Asn Gly Lys Glu Tyr Lys Cys Lys Val Ser
     290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Glu
                 325                 330                 335

Glu Met Thr Lys Asn Gln Val Ser Leu Thr Cys Leu Val Lys Gly Phe
             340                 345                 350

Tyr Pro Ser Asp Ile Ala Val Glu Trp Glu Ser Asn Gly Gln Pro Glu
         355                 360                 365

Asn Asn Tyr Lys Thr Thr Pro Pro Val Leu Asp Ser Asp Gly Ser Phe
     370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                 405                 410                 415

Thr Gln Lys Ser Leu Ser Leu Ser Pro Gly Lys
             420                 425
```

<210> SEQ ID NO 12
<211> LENGTH: 1299
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

| | | | | | |
|---|---|---|---|---|---|
| atggatgcaa | tgaagagagg | gctctgctgt | gtgctgctgc | tgtgtggagc | agtcttcgtt | 60 |
| tcgcccggcg | ccacgatccc | accgcacgtt | cagaagtcgg | atgtggaaat | ggaggcccag | 120 |
| aaagatgaaa | tcatctgccc | cagctgtaat | aggactgccc | atccactgag | acatattaat | 180 |
| aacgacatga | tagtcactga | caacaacggt | gcagtcaagt | ttccacaact | gtgtaaattt | 240 |
| tgtgatgtga | gattttccac | ctgtgacaac | cagaaatcct | gcatgagcaa | ctgcagcatc | 300 |
| acctccatct | gtgagaagcc | acaggaagtc | tgtgtggctg | tatggagaaa | gaatgacgag | 360 |
| aacataacac | tagagacagt | ttgccatgac | cccaagctcc | cctaccatga | ctttattctg | 420 |
| gaagatgctg | cttctccaaa | gtgcattatg | aaggaaaaaa | aaaagcctgg | tgagactttc | 480 |
| ttcatgtgtt | cctgtagctc | tgatgagtgc | aatgacaaca | tcatcttctc | agaagaatat | 540 |
| aacaccagca | atcctgacac | cggtggtgga | ggttctggag | gtggaggaag | tggtggaggt | 600 |
| ggttctggag | gtggtggaag | tactcacaca | tgcccaccgt | gcccagcacc | tgaactcctg | 660 |
| gggggaccgt | cagtcttcct | cttcccccca | aaacccaagg | acaccctcat | gatctcccgg | 720 |
| acccctgagg | tcacatgcgt | ggtggtggac | gtgagccacg | aagaccctga | ggtcaagttc | 780 |
| aactggtacg | tggacggcgt | ggaggtgcat | aatgccaaga | caaagccgcg | ggaggagcag | 840 |
| tacaacagca | cgtaccgtgt | ggtcagcgtc | ctcaccgtcc | tgcaccagga | ctggctgaat | 900 |
| ggcaaggagt | acaagtgcaa | ggtctccaac | aaagccctcc | cagcccccat | cgagaaaacc | 960 |
| atctccaaag | ccaaagggca | gccccgagaa | ccacaggtgt | acaccctgcc | cccatcccgg | 1020 |
| gaggagatga | ccaagaacca | ggtcagcctg | acctgcctgg | tcaaaggctt | ctatcccagc | 1080 |
| gacatcgccg | tggagtggga | gagcaatggg | cagccggaga | caactacaa | gaccacgcct | 1140 |
| cccgtgctgg | actccgacgg | ctccttcttc | ctctatagca | agctcaccgt | ggacaagagc | 1200 |
| aggtggcagc | aggggaacgt | cttctcatgc | tccgtgatgc | atgaggctct | gcacaaccac | 1260 |
| tacacgcaga | agagcctctc | cctgtctccg | ggtaaatga | | | 1299 |

<210> SEQ ID NO 13
<211> LENGTH: 432
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
 65                  70                  75                  80

Cys Asp Val Arg Phe Ser Thr Cys Asp Asn Gln Lys Ser Cys Met Ser
             85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Gly Gly Gly Gly Ser Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 14
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atggatgcaa tgaagagagg gctctgctgt gtgctgctgc tgtgtggagc agtcttcgtt    60
tcgcccggcg ccacgatccc accgcacgtt cagaagtcgg atgtggaaat ggaggcccag   120
aaagatgaaa tcatctgccc cagctgtaat aggactgccc atccactgag acatattaat   180
aacgacatga tagtcactga caacaacggt gcagtcaagt tccacaact gtgtaaattt    240
tgtgatgtga gattttccac ctgtgacaac cagaaatcct gcatgagcaa ctgcagcatc   300
acctccatct gtgagaagcc acaggaagtc tgtgtggctg tatggagaaa gaatgacgag   360
aacataacac tagagacagt ttgccatgac cccaagctcc cctaccatga ctttattctg   420
gaagatgctg cttctccaaa gtgcattatg aaggaaaaaa aaaagcctgg tgagactttc   480
ttcatgtgtt cctgtagctc tgatgagtgc aatgacaaca tcatcttctc agaagaatat   540
aacaccagca atcctgacac cggtggaggt ggttctggag gtggtggaag tactcacaca   600
tgcccaccgt gcccagcacc tgaactcctg ggggaccgt cagtcttcct cttccccca    660
aaacccaagg acaccctcat gatctcccgg acccctgagg tcacatgcgt ggtggtggac   720
gtgagccacg aagaccctga ggtcaagttc aactggtacg tggacggcgt ggaggtgcat   780
aatgccaaga caaagccgcg ggaggagcag tacaacagca cgtaccgtgt ggtcagcgtc   840
ctcaccgtcc tgcaccagga ctggctgaat ggcaaggagt acaagtgcaa ggtctccaac   900
aaagccctcc cagcccccat cgagaaaacc atctccaaag ccaagggca gccccgagaa    960
ccacaggtgt acaccctgcc cccatcccgg gaggagatga ccaagaacca ggtcagcctg   1020
acctgcctgg tcaaaggctt ctatcccagc gacatcgccg tggagtggga gagcaatggg   1080
cagccggaga acaactacaa gaccacgcct cccgtgctgg actccgacgg ctccttcttc   1140
ctctatagca agctcaccgt ggacaagagc aggtggcagc aggggaacgt cttctcatgc   1200
tccgtgatgc atgaggctct gcacaaccac tacacgcaga gagcctctc cctgtctccg    1260
ggtaaatga                                                           1269
```

<210> SEQ ID NO 15
<211> LENGTH: 422
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Asp Ala Met Lys Arg Gly Leu Cys Cys Val Leu Leu Cys Gly
1               5                   10                  15

Ala Val Phe Val Ser Pro Gly Ala Thr Ile Pro His Val Gln Lys
                20                  25                  30

Ser Asp Val Glu Met Glu Ala Gln Lys Asp Glu Ile Ile Cys Pro Ser
            35                  40                  45

Cys Asn Arg Thr Ala His Pro Leu Arg His Ile Asn Asn Asp Met Ile
        50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110
```

```
Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
                180                 185                 190

Gly Gly Gly Gly Ser Thr His Thr Cys Pro Pro Cys Pro Ala Pro Glu
            195                 200                 205

Leu Leu Gly Gly Pro Ser Val Phe Leu Phe Pro Pro Lys Pro Lys Asp
    210                 215                 220

Thr Leu Met Ile Ser Arg Thr Pro Glu Val Thr Cys Val Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Asn
            260                 265                 270

Ser Thr Tyr Arg Val Val Ser Val Leu Thr Val Leu His Gln Asp Trp
        275                 280                 285

Leu Asn Gly Lys Glu Tyr Lys Cys Lys Val Ser Asn Lys Ala Leu Pro
    290                 295                 300

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Glu Glu Met Thr Lys Asn
                325                 330                 335

Gln Val Ser Leu Thr Cys Leu Val Lys Gly Phe Tyr Pro Ser Asp Ile
            340                 345                 350

Ala Val Glu Trp Glu Ser Asn Gly Gln Pro Glu Asn Asn Tyr Lys Thr
        355                 360                 365

Thr Pro Pro Val Leu Asp Ser Asp Gly Ser Phe Phe Leu Tyr Ser Lys
    370                 375                 380

Leu Thr Val Asp Lys Ser Arg Trp Gln Gln Gly Asn Val Phe Ser Cys
385                 390                 395                 400

Ser Val Met His Glu Ala Leu His Asn His Tyr Thr Gln Lys Ser Leu
                405                 410                 415

Ser Leu Ser Pro Gly Lys
            420

<210> SEQ ID NO 16
<211> LENGTH: 1266
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atggatgcaa tgaagagagg gctctgctgt gtgctgctgc tgtgtggagc agtcttcgtt      60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga acaacggt gcagtcaagt ttccacaact gtgtaaattt       240
```

-continued

```
tgtgatgtga gattttccac ctgtgacaac cagaaatcct gcatgagcaa ctgcagcatc      300
acctccatct gtgagaagcc acaggaagtc tgtgtggctg tatggagaaa gaatgacgag      360
aacataacac tagagacagt ttgccatgac cccaagctcc cctaccatga ctttattctg      420
gaagatgctg cttctccaaa gtgcattatg aaggaaaaaa aaaagcctgg tgagactttc      480
ttcatgtgtt cctgtagctc tgatgagtgc aatgacaaca tcatcttctc agaagaatat      540
aacaccagca atcctgacac cggtggtgga cccaaatctt gtgacaaaac tcacacatgc      600
ccaccgtgcc cagcacctga actcctgggg ggaccgtcag tcttcctctt ccccccaaaa      660
cccaaggaca ccctcatgat ctcccggacc cctgaggtca catgcgtggt ggtggacgtg      720
agccacgaag accctgaggt caagttcaac tggtacgtgg acggcgtgga ggtgcataat      780
gccaagacaa agccgcggga ggagcagtac aacagcacgt accgtgtggt cagcgtcctc      840
accgtcctgc accaggactg gctgaatggc aaggagtaca agtgcaaggt ctccaacaaa      900 gcccteccag cccccatcga gaaaaccatc tccaaagcca agggcagccc cgagaaccac      960 aggtgtaca ccctgccccc atcccgggag gagatgacca agaaccaggt cagcctgacc     1020
tgcctggtca aaggcttcta tcccagcgac atcgccgtgg agtgggagag caatgggcag     1080
ccggagaaca actacaagac cacgcctccc gtgctggact ccgacggctc cttcttcctc     1140
tatagcaagc tcaccgtgga caagagcagg tggcagcagg ggaacgtctt ctcatgctcc     1200
gtgatgcatg aggctctgca caaccactac acgcagaaga gcctctccct gtccccgggt     1260
aaatga                                                                1266
```

<210> SEQ ID NO 17
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160
```

```
Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Pro Lys
            180                 185                 190

Ser Cys Asp Lys Thr His Thr Cys Pro Pro Cys Pro Ala Pro Glu Leu
            195                 200                 205

Leu Gly Gly Pro Ser Val Phe Leu Phe Pro Pro Lys Pro Lys Asp Thr
        210                 215                 220

Leu Met Ile Ser Arg Thr Pro Glu Val Thr Cys Val Val Val Asp Val
225                 230                 235                 240

Ser His Glu Asp Pro Glu Val Lys Phe Asn Trp Tyr Val Asp Gly Val
                245                 250                 255

Glu Val His Asn Ala Lys Thr Lys Pro Arg Glu Glu Gln Tyr Asn Ser
            260                 265                 270

Thr Tyr Arg Val Val Ser Val Leu Thr Val Leu His Gln Asp Trp Leu
        275                 280                 285

Asn Gly Lys Glu Tyr Lys Cys Lys Val Ser Asn Lys Ala Leu Pro Ala
        290                 295                 300

Pro Ile Glu Lys Thr Ile Ser Lys Ala Lys Gly Gln Pro Arg Glu Pro
305                 310                 315                 320

Gln Val Tyr Thr Leu Pro Pro Ser Arg Glu Glu Met Thr Lys Asn Gln
                325                 330                 335

Val Ser Leu Thr Cys Leu Val Lys Gly Phe Tyr Pro Ser Asp Ile Ala
            340                 345                 350

Val Glu Trp Glu Ser Asn Gly Gln Pro Glu Asn Asn Tyr Lys Thr Thr
        355                 360                 365

Pro Pro Val Leu Asp Ser Asp Gly Ser Phe Phe Leu Tyr Ser Lys Leu
        370                 375                 380

Thr Val Asp Lys Ser Arg Trp Gln Gln Gly Asn Val Phe Ser Cys Ser
385                 390                 395                 400

Val Met His Glu Ala Leu His Asn His Tyr Thr Gln Lys Ser Leu Ser
                405                 410                 415

Leu Ser Pro Gly Lys
            420

<210> SEQ ID NO 18
<211> LENGTH: 162
<212> TYPE: PRT
<213> ORGANISM: Homo sapiens

<400> SEQUENCE: 18

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95
```

-continued

```
Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
        130                 135                 140

Glu Cys Asn Asp Asn Ile Ile Phe Ser Glu Glu Tyr Asn Thr Ser Asn
145                 150                 155                 160

Pro Asp

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser
1               5

<210> SEQ ID NO 20
<211> LENGTH: 162
<212> TYPE: PRT
<213> ORGANISM: Homo sapiens

<400> SEQUENCE: 20

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
        130                 135                 140

Glu Cys Asn Asp Asn Ile Ile Phe Ser Glu Glu Tyr Asn Thr Ser Asn
145                 150                 155                 160

Pro Asp

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 21

Gly Gly Gly Gly Ser Gly Gly Gly Gly Ser
1               5                   10

<210> SEQ ID NO 22
<211> LENGTH: 22
<212> TYPE: PRT
<213> ORGANISM: Unknown
<220> FEATURE:
<223> OTHER INFORMATION: Description of Unknown:
      Leader sequence

<400> SEQUENCE: 22

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 23
<211> LENGTH: 22
<212> TYPE: PRT
<213> ORGANISM: Unknown
<220> FEATURE:
<223> OTHER INFORMATION: Description of Unknown:
      Tissue plasminogen activator peptide

<400> SEQUENCE: 23

Met Asp Ala Met Lys Arg Gly Leu Cys Cys Val Leu Leu Leu Cys Gly
1               5                   10                  15

Ala Val Phe Val Ser Pro
            20

<210> SEQ ID NO 24
<211> LENGTH: 21
<212> TYPE: PRT
<213> ORGANISM: Apis sp.

<400> SEQUENCE: 24

Met Lys Phe Leu Val Asn Val Ala Leu Val Phe Met Val Val Tyr Ile
1               5                   10                  15

Ser Tyr Ile Tyr Ala
            20

<210> SEQ ID NO 25
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr Gly Gly Gly Ser Gly Gly Gly Ser Gly Gly Gly Gly Ser
1               5                   10                  15

Gly Gly Gly Gly Ser Gly Gly Gly Ser Gly Gly Gly Gly Ser
            20                  25                  30

<210> SEQ ID NO 27
<211> LENGTH: 137
<212> TYPE: PRT
<213> ORGANISM: Homo sapiens

<400> SEQUENCE: 27

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 28
<211> LENGTH: 131
<212> TYPE: PRT
<213> ORGANISM: Homo sapiens

<400> SEQUENCE: 28

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr Asn Thr Ser
        115                 120                 125

Asn Pro Asp
    130

<210> SEQ ID NO 29
<211> LENGTH: 125
<212> TYPE: PRT
<213> ORGANISM: Homo sapiens

<400> SEQUENCE: 29

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
                20                  25                  30

Cys Met Ser Asn Cys Ser Ile Thr Ser Ile Cys Glu Lys Pro Gln Glu
            35                  40                  45

Val Cys Val Ala Val Trp Arg Lys Asn Asp Glu Asn Ile Thr Leu Glu
        50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Pro Gly
                85                  90                  95

Glu Thr Phe Phe Met Cys Ser Cys Ser Ser Asp Glu Cys Asn Asp Asn
                100                 105                 110

Ile Ile Phe Ser Glu Glu Tyr Asn Thr Ser Asn Pro Asp
            115                 120                 125

<210> SEQ ID NO 30
<211> LENGTH: 131
<212> TYPE: PRT
<213> ORGANISM: Homo sapiens

<400> SEQUENCE: 30

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Thr Phe Phe
                100                 105                 110

Met Cys Ser Cys Ser Ser Asp Glu Cys Asn Asp Asn Ile Ile Phe Ser
            115                 120                 125

Glu Glu Tyr
        130

<210> SEQ ID NO 31
<211> LENGTH: 125
<212> TYPE: PRT
<213> ORGANISM: Homo sapiens

<400> SEQUENCE: 31

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
        20                  25                  30

Cys Asp Asn Gln Lys Ser Cys Met Ser Asn Cys Ser Ile Thr Ser Ile
            35                  40                  45

Cys Glu Lys Pro Gln Glu Val Cys Val Ala Val Trp Arg Lys Asn Asp
50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr
        115                 120                 125

<210> SEQ ID NO 32
<211> LENGTH: 119
<212> TYPE: PRT
<213> ORGANISM: Homo sapiens

<400> SEQUENCE: 32

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
                20                  25                  30

Cys Met Ser Asn Cys Ser Ile Thr Ser Ile Cys Glu Lys Pro Gln Glu
            35                  40                  45

Val Cys Val Ala Val Trp Arg Lys Asn Asp Glu Asn Ile Thr Leu Glu
50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Lys Lys Lys Pro Gly
                85                  90                  95

Glu Thr Phe Phe Met Cys Ser Cys Ser Ser Asp Glu Cys Asn Asp Asn
            100                 105                 110

Ile Ile Phe Ser Glu Glu Tyr
        115

<210> SEQ ID NO 33
<211> LENGTH: 156
<212> TYPE: PRT
<213> ORGANISM: Homo sapiens

<400> SEQUENCE: 33

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
                20                  25                  30

Met Ile Val Thr Asp Asn Asn Gly Ala Val Lys Phe Pro Gln Leu Cys
            35                  40                  45

Lys Phe Cys Asp Val Arg Phe Ser Thr Cys Asp Asn Gln Lys Ser Cys
        50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

```
Val Cys His Asp Pro Lys Leu Pro Tyr His Asp Phe Ile Leu Glu Asp
            100                 105                 110

Ala Ala Ser Pro Lys Cys Ile Met Lys Glu Lys Lys Pro Gly Glu
        115                 120                 125

Thr Phe Phe Met Cys Ser Cys Ser Ser Asp Glu Cys Asn Asp Asn Ile
130                 135                 140

Ile Phe Ser Glu Glu Tyr Asn Thr Ser Asn Pro Asp
145                 150                 155

<210> SEQ ID NO 34
<211> LENGTH: 156
<212> TYPE: PRT
<213> ORGANISM: Homo sapiens

<400> SEQUENCE: 34

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr
145                 150                 155

<210> SEQ ID NO 35
<211> LENGTH: 150
<212> TYPE: PRT
<213> ORGANISM: Homo sapiens

<400> SEQUENCE: 35

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
            20                  25                  30

Met Ile Val Thr Asp Asn Asn Gly Ala Val Lys Phe Pro Gln Leu Cys
        35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
            100                 105                 110
```

```
Ala Ala Ser Pro Lys Cys Ile Met Lys Glu Lys Lys Pro Gly Glu
        115                 120                 125

Thr Phe Phe Met Cys Ser Cys Ser Ser Asp Glu Cys Asn Asp Asn Ile
    130                 135                 140

Ile Phe Ser Glu Glu Tyr
145             150

<210> SEQ ID NO 36
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
        130                 135

<210> SEQ ID NO 37
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110
```

```
Lys Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Gly Tyr Asn Thr Ser Asn
145                 150                 155                 160

Pro Asp

<210> SEQ ID NO 38
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asp
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr
    130

<210> SEQ ID NO 39
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asp Cys Ser Ile Thr Ser Ile Cys
65                  70                  75                  80

Glu Lys Pro Gln Glu Val Cys Val Ala Val Trp Arg Lys Asn Asp Glu
                85                  90                  95
```

```
Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr
145                 150                 155

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Thr Gly Gly Gly Gly Ser Gly Gly Gly Ser Gly Gly Gly Gly Ser
1               5                   10                  15

Gly Gly Gly Gly Ser Gly Gly Gly Gly Ser Gly Gly Gly Gly Ser Gly
                20                  25                  30

Gly Gly Gly Ser
        35

<210> SEQ ID NO 41
<211> LENGTH: 36
<212> TYPE: PRT
<213> ORGANISM: Homo sapiens

<400> SEQUENCE: 41

Gly Arg Cys Lys Ile Arg His Ile Gly Ser Asn Asn Arg Leu Gln Arg
1               5                   10                  15

Ser Thr Cys Gln Asn Thr Gly Trp Glu Ser Ala His Val Met Lys Thr
                20                  25                  30

Pro Gly Phe Arg
        35

<210> SEQ ID NO 42
<211> LENGTH: 223
<212> TYPE: PRT
<213> ORGANISM: Homo sapiens

<400> SEQUENCE: 42

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110
```

```
Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
                210                 215                 220

<210> SEQ ID NO 43
<211> LENGTH: 233
<212> TYPE: PRT
<213> ORGANISM: Homo sapiens

<400> SEQUENCE: 43

Gly Gly Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
                35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
                115                 120                 125

Pro Arg Glu Pro Gln Val Tyr Thr Leu Pro Pro Ser Arg Glu Glu Met
                130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
                180                 185                 190

Tyr Ser Lys Leu Thr Val Asp Lys Ser Arg Trp Gln Gln Gly Asn Val
                195                 200                 205

Phe Ser Cys Ser Val Met His Glu Ala Leu His Asn His Tyr Thr Gln
                210                 215                 220

Lys Ser Leu Ser Leu Ser Pro Gly Lys
225                 230

<210> SEQ ID NO 44
<211> LENGTH: 437
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 44

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Gly Gly Gly Gly Ser Gly
        195                 200                 205

Gly Gly Gly Ser Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380
```

```
Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys
        435

<210> SEQ ID NO 45
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
130                 135                 140

Ser Pro Lys Cys Ile Met Lys Glu Lys Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Gly Gly Gly Gly Ser Gly
        195                 200                 205

Gly Gly Gly Ser Gly Gly Gly Ser Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300
```

```
His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Glu Glu
        340                 345                 350

Met Thr Lys Asn Gln Val Ser Leu Thr Cys Leu Val Lys Gly Phe Tyr
    355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```

<210> SEQ ID NO 46
<211> LENGTH: 1314
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
atggatgcaa tgaagagagg gctctgctgt gtgctgctgc tgtgtggagc agtcttcgtt    60
tcgcccggcg ccacgatccc accgcacgtt cagaagtcgg atgtggaaat ggaggcccag   120
aaagatgaaa tcatctgccc cagctgtaat aggactgccc atccactgag acatattaat   180
aacgacatga tagtcactga caacaacggt gcagtcaagt tccacaact gtgtaaattt    240
tgtgatgtga gattttccac ctgtgacaac cagaaatcct gcatgagcaa ctgcagcatc   300
acctccatct gtgagaagcc acaggaagtc tgtgtggctg tatggagaaa gaatgacgag   360
aacataacac tagagacagt ttgccatgac cccaagctcc cctaccatga ctttattctg   420
gaagatgctg cttctccaaa gtgcattatg aaggaaaaaa aaaagcctgg tgagactttc   480
ttcatgtgtt cctgtagctc tgatgagtgc aatgacaaca tcatcttctc agaagaatat   540
aacaccagca atcctgacac cggtggagga ggttctggtg gtggaggttc tggaggtgga   600
ggaagtggtg gaggtggttc tggaggtggt ggaagtactc acacatgccc accgtgccca   660
gcacctgaac tcctgggggg accgtcagtc ttcctcttcc ccccaaaacc caaggacacc   720
ctcatgatct cccggacccc tgaggtcaca tgcgtggtgg tggacgtgag ccacgaagac   780
cctgaggtca agttcaactg gtacgtggac ggcgtggagg tgcataatgc caagacaaag   840
ccgcgggagg agcagtacaa cagcacgtac cgtgtggtca gcgtcctcac cgtcctgcac   900
caggactggc tgaatggcaa ggagtacaag tgcaaggtct ccaacaaagc cctcccagcc   960
cccatcgaga aaaccatctc caaagccaaa gggcagcccc gagaaccaca ggtgtacacc   1020
ctgcccccat cccgggagga tgaccaag aaccaggtca gcctgacctg cctggtcaaa  1080
ggcttctatc ccagcgacat cgccgtggag tgggagagca atgggcagcc ggagaacaac  1140
tacaagacca cgcctcccgt gctggactcc gacggctcct tcttcctcta tagcaagctc  1200
```

```
accgtggaca agagcaggtg gcagcagggg aacgtcttct catgctccgt gatgcatgag    1260
gctctgcaca accactacac gcagaagagc ctctccctgt ctccgggtaa atga          1314
```

<210> SEQ ID NO 47
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
atggatgcaa tgaagagagg gctctgctgt gtgctgctgc tgtgtggagc agtcttcgtt      60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga caacaacggt gcagtcaagt ttccacaact gtgtaaattt     240
tgtgatgtga gattttccac ctgtgacaac cagaaatcct gcatgagcaa ctgcagcatc     300
acctccatct gtgagaagcc acaggaagtc tgtgtggctg tatggagaaa gaatgacgag     360
aacataacac tagagacagt ttgccatgac cccaagctcc cctaccatga ctttattctg     420
gaagatgctg cttctccaaa gtgcattatg aaggaaaaaa aaagcctggt gagactttc     480 ttcatgtgtt cctgtagctc tgatgagtgc aatgacaaca tcatcttctc agaagaatat     540
aacaccagca atcctgacac cggtggaggt ggaagtggtg gaggaggttc tggtggtgga     600
ggttctggag gtgaggaag tggtggaggt ggttctggag gtggtggaag tactcacaca     660
tgcccaccgt gcccagcacc tgaactcctg ggggaccgt cagtcttcct cttccccca      720 aaacccaagg acaccctcat gatctcccgg acccctgagg tcacatgcgt ggtggtggac     780
gtgagccacg aagaccctga ggtcaagttc aactggtacg tggacggcgt ggaggtgcat     840
aatgccaaga caaagccgcg ggaggagcag tacaacagca cgtaccgtgt ggtcagcgtc     900
ctcaccgtcc tgcaccagga ctggctgaat ggcaaggagt acaagtgcaa ggtctccaac     960
aaagccctcc cagcccccat cgagaaaacc atctccaaag ccaaaggca gccccgagaa    1020 ccacaggtgt acaccctgcc cccatcccgg gaggagatga ccaagaacca ggtcagcctg    1080
acctgcctgg tcaaaggctt ctatcccagc gacatcgccg tggagtggga gagcaatggg    1140
cagccggaga acaactacaa gaccacgcct cccgtgctgg actccgacgg ctccttcttc    1200
ctctatagca agctcaccgt ggacaagagc aggtggcagc aggggaacgt cttctcatgc    1260
tccgtgatgc atgaggctct gcacaaccac tacacgcaga gagcctctc cctgtctccg    1320 ggtaaatga                                                           1329
```

<210> SEQ ID NO 48

<400> SEQUENCE: 48

000

<210> SEQ ID NO 49
<211> LENGTH: 225
<212> TYPE: PRT
<213> ORGANISM: Homo sapiens

<400> SEQUENCE: 49

```
Thr His Thr Cys Pro Pro Cys Pro Ala Pro Glu Leu Leu Gly Gly Pro
1               5                   10                  15
```

```
Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
210                 215                 220

Lys
225

<210> SEQ ID NO 50
<211> LENGTH: 513
<212> TYPE: PRT
<213> ORGANISM: Homo sapiens

<400> SEQUENCE: 50

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
130                 135                 140

Val Pro Leu Met Leu Ile Ala Gly Ile Val Ile Cys Ala Phe Trp Val
145                 150                 155                 160
```

```
Tyr Arg His His Lys Met Ala Tyr Pro Pro Val Leu Val Pro Thr Gln
            165                 170                 175
Asp Pro Gly Pro Pro Pro Ser Pro Leu Leu Gly Leu Lys Pro Leu
        180                 185                 190
Gln Leu Leu Glu Val Lys Ala Arg Gly Arg Phe Gly Cys Val Trp Lys
            195                 200                 205
Ala Gln Leu Leu Asn Glu Tyr Val Ala Val Lys Ile Phe Pro Ile Gln
            210                 215                 220
Asp Lys Gln Ser Trp Gln Asn Glu Tyr Glu Val Tyr Ser Leu Pro Gly
225                 230                 235                 240
Met Lys His Glu Asn Ile Leu Gln Phe Ile Gly Ala Glu Lys Arg Gly
            245                 250                 255
Thr Ser Val Asp Val Asp Leu Trp Leu Ile Thr Ala Phe His Glu Lys
            260                 265                 270
Gly Ser Leu Ser Asp Phe Leu Lys Ala Asn Val Val Ser Trp Asn Glu
            275                 280                 285
Leu Cys His Ile Ala Glu Thr Met Ala Arg Gly Leu Ala Tyr Leu His
            290                 295                 300
Glu Asp Ile Pro Gly Leu Lys Asp Gly His Lys Pro Ala Ile Ser His
305                 310                 315                 320
Arg Asp Ile Lys Ser Lys Asn Val Leu Leu Lys Asn Asn Leu Thr Ala
            325                 330                 335
Cys Ile Ala Asp Phe Gly Leu Ala Leu Lys Phe Glu Ala Gly Lys Ser
            340                 345                 350
Ala Gly Asp Thr His Gly Gln Val Gly Thr Arg Arg Tyr Met Ala Pro
            355                 360                 365
Glu Val Leu Glu Gly Ala Ile Asn Phe Gln Arg Asp Ala Phe Leu Arg
            370                 375                 380
Ile Asp Met Tyr Ala Met Gly Leu Val Leu Trp Glu Leu Ala Ser Arg
385                 390                 395                 400
Cys Thr Ala Ala Asp Gly Pro Val Asp Glu Tyr Met Leu Pro Phe Glu
            405                 410                 415
Glu Glu Ile Gly Gln His Pro Ser Leu Glu Asp Met Gln Glu Val Val
            420                 425                 430
Val His Lys Lys Lys Arg Pro Val Leu Arg Asp Tyr Trp Gln Lys His
            435                 440                 445
Ala Gly Met Ala Met Leu Cys Glu Thr Ile Glu Glu Cys Trp Asp His
            450                 455                 460
Asp Ala Glu Ala Arg Leu Ser Ala Gly Cys Val Gly Glu Arg Ile Thr
465                 470                 475                 480
Gln Met Gln Arg Leu Thr Asn Ile Ile Thr Thr Glu Asp Ile Val Thr
            485                 490                 495
Val Val Thr Met Val Thr Asn Val Asp Phe Pro Pro Lys Glu Ser Ser
            500                 505                 510
Leu

<210> SEQ ID NO 51
<211> LENGTH: 115
<212> TYPE: PRT
<213> ORGANISM: Homo sapiens

<400> SEQUENCE: 51

Ile Leu Gly Arg Ser Glu Thr Gln Glu Cys Leu Phe Phe Asn Ala Asn
1               5                   10                  15
```

```
Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 52
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
            100

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56
<211> LENGTH: 1539
<212> TYPE: DNA
```

<213> ORGANISM: Homo sapiens

<400> SEQUENCE: 56

```
atgggagctg ctgcaaagtt ggcgtttgcc gtctttctta tctcctgttc ttcaggtgct    60
atacttggta gatcagaaac tcaggagtgt cttttcttta atgctaattg ggaaaaagac   120
agaaccaatc aaactggtgt tgaaccgtgt tatggtgaca agataaacg gcggcattgt    180
tttgctacct ggaagaatat ttctggttcc attgaaatag tgaaacaagg ttgttggctg   240
gatgatatca actgctatga caggactgat tgtgtagaaa aaaagacag ccctgaagta    300
tattttttgtt gctgtgaggg caatatgtgt aatgaaaagt tttcttattt tccggagatg  360
gaagtcacac agcccacttc aaatccagtt acacctaagc cacccctatta caacatcctg  420
ctctattcct tggtgccact tatgttaatt gcggggattg tcatttgtgc attttgggtg   480
tacaggcatc acaagatggc ctaccctcct gtacttgttc caactcaaga cccaggacca   540
cccccacctt ctccattact aggttttgaaa ccactgcagt tattagaagt gaaagcaagg   600
ggaagatttg gttgtgtctg gaaagcccag ttgcttaacg aatatgtggc tgtcaaaata   660
tttccaatac aggacaaaca gtcatggcaa aatgaatacg aagtctacag tttgcctgga   720
atgaagcatg agaacatatt acagttcatt ggtgcagaaa acgaggcac cagtgttgat    780
gtggatcttt ggctgatcac agcatttcat gaaaagggtt cactatcaga ctttcttaag   840
gctaatgtgg tctcttggaa tgaactgtgt catattgcag aaaccatggc tagaggattg   900
gcatatttac atgaggatat acctggccta aaagatggcc acaaacctgc catatctcac   960
agggacatca aaagtaaaaa tgtgctgttg aaaaacaacc tgacagcttg cattgctgac  1020
tttgggttgg ccttaaaatt tgaggctggc aagtctgcag gcgataccca tggacaggtt  1080
ggtacccgga ggtacatggc tccagaggta ttagagggtg ctataaactt ccaaagggat  1140
gcatttttga ggatagatat gtatgccatg ggattagtcc tatgggaact ggcttctcgc  1200
tgtactgctg cagatggacc tgtagatgaa tacatgttgc catttgagga ggaaattggc  1260
cagcatccat ctcttgaaga catgcaggaa gttgttgtgc ataaaaaaaa gaggcctgtt  1320
ttaagagatt attggcagaa acatgctgga atggcaatgc tctgtgaaac cattgaagaa  1380
tgttgggatc acgacgcaga agccaggtta tcagctggat gtgtaggtga agaattacc   1440
cagatgcaga gactaacaaa tattattacc acagaggaca ttgtaacagt ggtcacaatg  1500
gtgacaaatg ttgactttcc tcccaaagaa tctagtcta                          1539
```

<210> SEQ ID NO 57
<211> LENGTH: 345
<212> TYPE: DNA
<213> ORGANISM: Homo sapiens

<400> SEQUENCE: 57

```
atacttggta gatcagaaac tcaggagtgt cttttcttta atgctaattg ggaaaaagac    60
agaaccaatc aaactggtgt tgaaccgtgt tatggtgaca agataaacg gcggcattgt    120
tttgctacct ggaagaatat ttctggttcc attgaaatag tgaaacaagg ttgttggctg   180
gatgatatca actgctatga caggactgat tgtgtagaaa aaaagacag ccctgaagta    240
tattttttgtt gctgtgaggg caatatgtgt aatgaaaagt tttcttattt tccggagatg  300
gaagtcacac agcccacttc aaatccagtt acacctaagc caccc                   345
```

<210> SEQ ID NO 58
<211> LENGTH: 225

<212> TYPE: PRT
<213> ORGANISM: Homo sapiens

<400> SEQUENCE: 58

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
    210                 215                 220

Lys
225

<210> SEQ ID NO 59
<211> LENGTH: 223
<212> TYPE: PRT
<213> ORGANISM: Homo sapiens

<400> SEQUENCE: 59

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
            85                  90                  95

Cys Lys Val Ser Asn Lys Gly Leu Pro Ala Pro Ile Glu Lys Thr Ile
            100                 105                 110

```
Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 60
<211> LENGTH: 232
<212> TYPE: PRT
<213> ORGANISM: Homo sapiens

<400> SEQUENCE: 60

Glu Pro Lys Ser Cys Asp Thr Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Gln Phe Lys Trp Tyr Val
50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
210                 215                 220

Ser Leu Ser Leu Ser Pro Gly Lys
225                 230

<210> SEQ ID NO 61
<211> LENGTH: 279
<212> TYPE: PRT
<213> ORGANISM: Homo sapiens
```

<400> SEQUENCE: 61

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Leu His Gln Asp
130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 62
<211> LENGTH: 229
<212> TYPE: PRT
<213> ORGANISM: Homo sapiens

<400> SEQUENCE: 62

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 63
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Gly
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly
1

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Gly Gly Gly Gly
1               5

<210> SEQ ID NO 66
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 66

Ser Gly Gly Gly Gly
1               5

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gly Gly Gly
1

<210> SEQ ID NO 68
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Lys Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Lys Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

```
<210> SEQ ID NO 69
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Asp Thr Thr Pro Pro Val Leu
                165                 170                 175

Asp Ser Asp Gly Ser Phe Phe Leu Tyr Ser Asp Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 70
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60
```

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Tyr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 71
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

```
Asp Ser Asp Gly Ser Phe Phe Leu Thr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 72
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Lys Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 73
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 73

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Cys Thr
            115                 120                 125

Leu Pro Pro Ser Arg Glu Glu Met Thr Lys Asn Gln Val Ser Leu Ser
130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 74
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Phe Arg Pro Glu Val His Leu
            115                 120                 125

Leu Pro Pro Ser Arg Glu Glu Met Thr Lys Asn Gln Val Ser Leu Thr
        130                 135                 140

Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
210                 215                 220

Ser Pro Gly Lys
225

<210> SEQ ID NO 75
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Pro Ser Glu Glu Leu Ala Leu Asn Glu Leu Val Thr Leu
    130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
            180                 185                 190

Val Ala Ala Glu Asp Trp Lys Lys Gly Asp Thr Phe Ser Cys Ser Val
        195                 200                 205

Met His Glu Ala Leu His Asn His Tyr Thr Gln Lys Ser Leu Asp Arg
210                 215                 220

Ser Pro Gly Lys
225

<210> SEQ ID NO 76
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
210                 215                 220

Lys Gly Gly Ser Ala Gln Leu Glu Lys Glu Leu Gln Ala Leu Glu Lys
225                 230                 235                 240

Glu Asn Ala Gln Leu Glu Trp Glu Leu Gln Ala Leu Glu Lys Glu Leu
                245                 250                 255

Ala Gln Gly Ala Thr
            260

<210> SEQ ID NO 77
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Ser Ala Gln Leu Lys Lys Lys Leu Gln Ala Leu Lys Lys
225                 230                 235                 240

Lys Asn Ala Gln Leu Lys Trp Lys Leu Gln Ala Leu Lys Lys Lys Leu
                245                 250                 255

Ala Gln Gly Ala Thr
            260

<210> SEQ ID NO 78
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Cys Arg Glu Glu Met Thr Glu Asn Gln Val Ser Leu Trp
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Asn His Tyr Thr Gln Asp Ser Leu Ser Leu Ser Pro Gly
        210                 215                 220

Lys
225

<210> SEQ ID NO 79
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Cys Thr
            115                 120                 125

Leu Pro Pro Ser Arg Glu Glu Met Thr Lys Asn Gln Val Ser Leu Ser
        130                 135                 140

Cys Ala Val Lys Gly Phe Tyr Pro Ser Asp Ile Ala Val Glu Trp Glu
145                 150                 155                 160

Ser Arg Gly Gln Pro Glu Asn Asn Tyr Lys Thr Thr Pro Pro Val Leu
                165                 170                 175

Asp Ser Arg Gly Ser Phe Phe Leu Val Ser Lys Leu Thr Val Asp Lys
            180                 185                 190

```
Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 80
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Lys Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn Arg Tyr Thr Gln Lys Ser Leu Ser Leu Ser Pro Gly
    210                 215                 220

Lys
225

<210> SEQ ID NO 81

<400> SEQUENCE: 81

000

<210> SEQ ID NO 82
<211> LENGTH: 386
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 82

```
Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
    130                 135                 140

Gly Ser Gly Gly Gly Gly Ser Gly Gly Gly Gly Ser Gly Gly Gly Gly
145                 150                 155                 160

Ser Thr His Thr Cys Pro Pro Cys Pro Ala Pro Glu Leu Leu Gly Gly
                165                 170                 175

Pro Ser Val Phe Leu Phe Pro Pro Lys Pro Lys Asp Thr Leu Met Ile
            180                 185                 190

Ser Arg Thr Pro Glu Val Thr Cys Val Val Val Asp Val Ser His Glu
        195                 200                 205

Asp Pro Glu Val Lys Phe Asn Trp Tyr Val Asp Gly Val Glu Val His
    210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Ala Leu Pro Ala Pro Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Arg Lys Glu Met Thr Lys Asn Gln Val Ser Leu
    290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Lys Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
        355                 360                 365

Glu Ala Leu His Asn His Tyr Thr Gln Lys Ser Leu Ser Leu Ser Pro
    370                 375                 380

Gly Lys
385
```

<210> SEQ ID NO 83
<211> LENGTH: 1161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atggatgcaa tgaagagagg gctctgctgt gtgctgctgc tgtgtggagc agtcttcgtt      60
tcgcccggcg ccgctatact tggtagatca gaaactcagg agtgtctttt ctttaatgct    120
aattgggaaa aagacagaac caatcaaact ggtgttgaac cgtgttatgg tgacaaagat    180
aaacggcggc attgttttgc tacctggaag aatatttctg gttccattga atagtgaaa     240
caaggttgtt ggctggatga tatcaactgc tatgacagga ctgattgtgt agaaaaaaaa    300
gacagccctg aagtatattt ctgttgctgt gagggcaata tgtgtaatga aaagtttttct   360
tatttttccgg agatggaagt cacacagccc acttcaaatc cagttacacc taagccaccc    420
accggtggtg gaggttctgg aggtggagga agtggtggag gtggttctgg aggtggtgga    480
agtactcaca catgcccacc gtgcccagca cctgaactcc tggggggacc gtcagtcttc    540
ctcttccccc caaaacccaa ggacaccctc atgatctccc ggacccctga ggtcacatgc    600
gtggtggtgg acgtgagcca cgaagaccct gaggtcaagt tcaactggta cgtggacggc    660
gtggaggtgc ataatgccaa gacaaagccg cgggaggagc agtacaacag cacgtaccgt    720
gtggtcagcg tcctcaccgt cctgcaccag gactggctga atggcaagga gtacaagtgc    780
aaggtctcca acaaagccct cccagccccc atcgagaaaa ccatctccaa agccaaaggg    840
cagccccgag aaccacaggt gtacaccctg cccccatccc ggaaggagat gaccaagaac    900
caggtcagcc tgacctgcct ggtcaaaggc ttctatccca gcgacatcgc cgtggagtgg    960
gagagcaatg ggcagccgga gaacaactac aagaccacgc ctcccgtgct ggagtccgac   1020
ggctccttct tcctctatag caagctcacc gtggacaaga gcaggtggca gcagggaac    1080
gtcttctcat gctccgtgat gcatgaggct ctgcacaacc actacacgca gaagagcctc   1140
tccctgtctc cgggtaaatg a                                              1161

<210> SEQ ID NO 84
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

```
Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Ser Gly Gly Gly Ser Gly Gly
            115                 120                 125

Gly Gly Ser Gly Gly Gly Ser Thr His Thr Cys Pro Pro Cys Pro
        130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Lys Glu Met
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Lys Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360

<210> SEQ ID NO 85
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60
```

```
Val Thr Asp Asn Asn Gly Ala Val Lys Phe Pro Gln Leu Cys Lys Phe
 65                  70                  75                  80

Cys Asp Val Arg Phe Ser Thr Cys Asp Asn Gln Lys Ser Cys Met Ser
             85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Gly Gly Gly Gly Ser Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
            325                 330                 335

Pro Pro Ser Arg Glu Glu Met Thr Lys Asn Gln Val Ser Leu Thr Cys
        340                 345                 350

Leu Val Lys Gly Phe Tyr Pro Ser Asp Ile Ala Val Glu Trp Glu Ser
    355                 360                 365

Asn Gly Gln Pro Glu Asn Asn Tyr Asp Thr Thr Pro Val Leu Asp
            370                 375                 380

Ser Asp Gly Ser Phe Phe Leu Tyr Ser Asp Leu Thr Val Asp Lys Ser
385                 390                 395                 400

Arg Trp Gln Gln Gly Asn Val Phe Ser Cys Ser Val Met His Glu Ala
            405                 410                 415

Leu His Asn His Tyr Thr Gln Lys Ser Leu Ser Leu Ser Pro Gly Lys
        420                 425                 430

<210> SEQ ID NO 86
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 86

```
atggatgcga tgaaacgcgg cctgtgctgc gtgctgctgc tgtgcggcgc ggtgtttgtg      60
agcccgggcg ccaccattcc gccgcatgtg cagaaaagcg atgtggaaat ggaagcgcag     120
aaagatgaaa ttatttgccc gagctgcaac cgcaccgcgc atccgctgcg ccatattaac     180
aacgatatga ttgtgaccga taacaacggc gcggtgaaat ttccgcagct gtgcaaattt     240
tgcgatgtgc gctttagcac ctgcgataac cagaaaagct gcatgagcaa ctgcagcatt     300
accagcattt gcgaaaaacc gcaggaagtg tgcgtggcgg tgtggcgcaa aaacgatgaa     360
aacattaccc tggaaaccgt gtgccatgat ccgaaactgc cgtatcatga ttttattctg     420
gaagatgcgg cgagcccgaa atgcattatg aaagaaaaaa aaaaaccggg cgaaaccttt     480
tttatgtgca gctgcagcag cgatgaatgc aacgataaca ttattttag cgaagaatat     540
aacaccagca acccggatac cggtggcggc ggcagcggcg gcggcggcag cggcggcggc     600
ggcagcggcg gcggcggcag cacccatacc tgcccgccgt gccggcgcc ggaactgctg     660
ggcggcccga gcgtgtttct gtttccgccg aaaccgaaag taccctgat gattagccgc     720
accccggaag tgacctgcgt ggtggtggat gtgagccatg aagatccgga agtgaaattt     780
aactggtatg tggatggcgt ggaagtgcat aacgcgaaaa ccaaaccgcg cgaagaacag     840
tataacagca cctatcgcgt ggtgagcgtg ctgaccgtgc tgcatcagga ttggctgaac     900
ggcaaagaat ataaatgcaa agtgagcaac aaagcgctgc cggcgccgat tgaaaaaacc     960
attagcaaag cgaaaggcca gccgcgcgaa ccgcaggtgt ataccctgcc gccgagccgc    1020
gaagaaatga ccaaaaacca ggtgagcctg acctgcctgg tgaaaggctt ttatccgagc    1080
gatattgcgg tggaatggga agcaacggc cagccggaaa acaactatga taccacccccg   1140
ccggtgctgg atagcgatgg cagctttttt ctgtatagcg atctgaccgt ggataaaagc    1200
cgctggcagc agggcaacgt gttagctgc agcgtgatgc atgaagcgct gcataaccat    1260
tatacccaga aagcctgag cctgagcccg ggcgatgatg atgataaagc gcatcatcat   1320
catcatcatt aa                                                       1332
```

<210> SEQ ID NO 87
<211> LENGTH: 408
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110
```

Asp Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
        130                 135                 140

Glu Cys Asn Asp Asn Ile Ile Phe Ser Glu Glu Tyr Asn Thr Ser Asn
145                 150                 155                 160

Pro Asp Thr Gly Gly Gly Gly Ser Gly Gly Gly Gly Ser Gly Gly Gly
                165                 170                 175

Gly Ser Gly Gly Gly Gly Ser Thr His Thr Cys Pro Pro Cys Pro Ala
            180                 185                 190

Pro Glu Leu Leu Gly Gly Pro Ser Val Phe Leu Phe Pro Pro Lys Pro
        195                 200                 205

Lys Asp Thr Leu Met Ile Ser Arg Thr Pro Glu Val Thr Cys Val Val
    210                 215                 220

Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
                245                 250                 255

Tyr Asn Ser Thr Tyr Arg Val Val Ser Val Leu Thr Val Leu His Gln
            260                 265                 270

Asp Trp Leu Asn Gly Lys Glu Tyr Lys Cys Lys Val Ser Asn Lys Ala
        275                 280                 285

Leu Pro Ala Pro Ile Glu Lys Thr Ile Ser Lys Ala Lys Gly Gln Pro
    290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
                325                 330                 335

Asp Ile Ala Val Glu Trp Glu Ser Asn Gly Gln Pro Glu Asn Asn Tyr
            340                 345                 350

Asp Thr Thr Pro Pro Val Leu Asp Ser Asp Gly Ser Phe Phe Leu Tyr
        355                 360                 365

Ser Asp Leu Thr Val Asp Lys Ser Arg Trp Gln Gln Gly Asn Val Phe
    370                 375                 380

Ser Cys Ser Val Met His Glu Ala Leu His Asn His Tyr Thr Gln Lys
385                 390                 395                 400

Ser Leu Ser Leu Ser Pro Gly Lys
                405

<210> SEQ ID NO 88
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
        50                  55                  60

Cys Phe Ala Thr Trp Lys Asn Ile Ser Gly Ser Ile Glu Ile Val Lys
 65                  70                  75                  80

Gln Gly Cys Trp Leu Asp Asp Ile Asn Cys Tyr Asp Arg Thr Asp Cys
                 85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
            115                 120                 125

Gln Pro Thr Ser Asn Pro Val Thr Pro Lys Pro Pro Thr Gly Gly Gly
            130                 135                 140

Gly Ser Gly Gly Gly Ser Gly Gly Gly Ser Gly Gly Gly Gly
145                 150                 155                 160

Ser Thr His Thr Cys Pro Pro Cys Pro Ala Pro Glu Leu Leu Gly Gly
                165                 170                 175

Pro Ser Val Phe Leu Phe Pro Pro Lys Pro Lys Asp Thr Leu Met Ile
                180                 185                 190

Ser Arg Thr Pro Glu Val Thr Cys Val Val Val Asp Val Ser His Glu
            195                 200                 205

Asp Pro Glu Val Lys Phe Asn Trp Tyr Val Asp Gly Val Glu Val His
            210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Ala Leu Pro Ala Pro Ile Glu
            260                 265                 270

Lys Thr Ile Ser Lys Ala Lys Gly Gln Pro Arg Glu Pro Gln Val Tyr
            275                 280                 285

Thr Leu Pro Pro Cys Arg Glu Glu Met Thr Lys Asn Gln Val Ser Leu
            290                 295                 300

Trp Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Lys Leu Thr Val Asp
                340                 345                 350

Lys Ser Arg Trp Gln Gln Gly Asn Val Phe Ser Cys Ser Val Met His
            355                 360                 365

Glu Ala Leu His Asn His Tyr Thr Gln Lys Ser Leu Ser Leu Ser Pro
            370                 375                 380

Gly Lys
385

<210> SEQ ID NO 89
<211> LENGTH: 1161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
atggatgcaa tgaagagagg gctctgctgt gtgctgctgc tgtgtggagc agtcttcgtt      60
tcgcccggcg ccgctatact tggtagatca gaaactcagg agtgtctttt ctttaatgct     120
aattgggaaa aagacagaac caatcaaact ggtgttgaac cgtgttatgg tgacaaagat     180
aaacggcggc attgttttgc tacctggaag aatatttctg gttccattga aatagtgaaa     240
caaggttgtt ggctggatga tatcaactgc tatgacagga ctgattgtgt agaaaaaaaa     300
gacagccctg aagtatattt ctgttgctgt gagggcaata tgtgtaatga aaagttttct     360
tattttccgg agatggaagt cacacagccc acttcaaatc cagttacacc taagccaccc     420
accggtggtg gaggttctgg aggtggagga agtggtggag gtggttctgg aggtggtgga     480
agtactcaca catgcccacc gtgcccagca cctgaactcc tggggggacc gtcagtcttc     540
ctcttccccc caaaacccaa ggacaccctc atgatctccc ggacccctga ggtcacatgc     600
gtggtggtgg acgtgagcca cgaagaccct gaggtcaagt tcaactggta cgtggacggc     660
gtggaggtgc ataatgccaa gacaaagccg cgggaggagc agtacaacag cacgtaccgt     720
gtggtcagcg tcctcaccgt cctgcaccag gactggctga atggcaagga gtacaagtgc     780
aaggtctcca acaaagccct cccagccccc atcgagaaaa ccatctccaa agccaaaggg     840
cagccccgag aaccacaggt gtacaccctg cccccatgcc gggaggagat gaccaagaac     900
caggtcagcc tgtggtgcct ggtcaaaggc ttctatccca gcgacatcgc cgtggagtgg     960
gagagcaatg ggcagccgga gaacaactac aagaccacgc ctcccgtgct ggactccgac    1020
ggctccttct tcctctatag caagctcacc gtggacaaga gcaggtggca gcagggaac     1080
gtcttctcat gctccgtgat gcatgaggct ctgcacaacc actacacgca gaagagcctc    1140
tccctgtctc cgggtaaatg a                                               1161
```

<210> SEQ ID NO 90
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Gly Ser Gly Gly Gly Gly Ser Gly Gly
        115                 120                 125
```

Gly Gly Ser Gly Gly Gly Ser Thr His Thr Cys Pro Cys Pro
            130             135             140

Ala Pro Glu Leu Leu Gly Pro Ser Val Phe Leu Phe Pro Pro Lys
145             150             155             160

Pro Lys Asp Thr Leu Met Ile Ser Arg Thr Pro Glu Val Thr Cys Val
                165             170             175

Val Val Asp Val Ser His Glu Asp Pro Glu Val Lys Phe Asn Trp Tyr
            180             185             190

Val Asp Gly Val Glu Val His Asn Ala Lys Thr Lys Pro Arg Glu Glu
        195             200             205

Gln Tyr Asn Ser Thr Tyr Arg Val Val Ser Val Leu Thr Val Leu His
    210             215             220

Gln Asp Trp Leu Asn Gly Lys Glu Tyr Lys Cys Lys Val Ser Asn Lys
225             230             235             240

Ala Leu Pro Ala Pro Ile Glu Lys Thr Ile Ser Lys Ala Lys Gly Gln
                245             250             255

Pro Arg Glu Pro Gln Val Tyr Thr Leu Pro Pro Cys Arg Glu Glu Met
            260             265             270

Thr Lys Asn Gln Val Ser Leu Trp Cys Leu Val Lys Gly Phe Tyr Pro
        275             280             285

Ser Asp Ile Ala Val Glu Trp Glu Ser Asn Gly Gln Pro Glu Asn Asn
    290             295             300

Tyr Lys Thr Thr Pro Pro Val Leu Asp Ser Asp Gly Ser Phe Phe Leu
305             310             315             320

Tyr Ser Lys Leu Thr Val Asp Lys Ser Arg Trp Gln Gln Gly Asn Val
                325             330             335

Phe Ser Cys Ser Val Met His Glu Ala Leu His Asn His Tyr Thr Gln
            340             345             350

Lys Ser Leu Ser Leu Ser Pro Gly Lys
        355             360

<210> SEQ ID NO 91
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

```
Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Ser
                180                 185                 190

Gly Gly Gly Gly Ser Gly Gly Gly Ser Gly Gly Gly Ser Thr
            195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
                260                 265                 270

Lys Thr Lys Pro Arg Glu Glu Gln Tyr Asn Ser Thr Tyr Arg Val Val
    275                 280                 285

Ser Val Leu Thr Val Leu His Gln Asp Trp Leu Asn Gly Lys Glu Tyr
        290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Cys Thr Leu
                325                 330                 335

Pro Pro Ser Arg Glu Glu Met Thr Lys Asn Gln Val Ser Leu Ser Cys
                340                 345                 350

Ala Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Val Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
                420                 425                 430
```

<210> SEQ ID NO 92
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
atggatgcaa tgaagagagg ctctgctgt gtgctgctgc tgtgtggagc agtcttcgtt      60
tcgcccggcg ccacgatccc accgcacgtt cagaagtcgg atgtggaaat ggaggcccag    120
aaagatgaaa tcatctgccc cagctgtaat aggactgccc atccactgag acatattaat    180
aacgacatga tagtcactga caacaacggt gcagtcaagt ttccacaact gtgtaaattt    240

```
tgtgatgtga gattttccac ctgtgacaac cagaaatcct gcatgagcaa ctgcagcatc    300
acctccatct gtgagaagcc acaggaagtc tgtgtggctg tatggagaaa gaatgacgag    360
aacataacac tagagacagt ttgccatgac cccaagctcc cctaccatga ctttattctg    420
gaagatgctg cttctccaaa gtgcattatg aaggaaaaaa aaaagcctgg tgagactttc    480
ttcatgtgtt cctgtagctc tgatgagtgc aatgacaaca tcatcttctc agaagaatat    540
aacaccagca atcctgacac cggtggtgga ggttctggag gtggaggaag tggtggaggt    600
ggttctggag gtggtggaag tactcacaca tgcccaccgt gcccagcacc tgaactcctg    660
gggggaccgt cagtcttcct cttccccca aaacccaagg acaccctcat gatctcccgg    720
acccctgagg tcacatgcgt ggtggtggac gtgagccacg aagaccctga ggtcaagttc    780
aactggtacg tggacggcgt ggaggtgcat aatgccaaga caaagccgcg ggaggagcag    840
tacaacagca cgtaccgtgt ggtcagcgtc ctcaccgtcc tgcaccagga ctggctgaat    900
ggcaaggagt acaagtgcaa ggtctccaac aaagccctcc cagcccccat cgagaaaacc    960
atctccaaag ccaaagggca gccccgagaa ccacaggtgt gcaccctgcc cccatcccgg   1020
gaggagatga ccaagaacca ggtcagcctg tcctgcgccg tcaaaggctt ctatcccagc   1080
gacatcgccg tggagtggga gagcaatggg cagccggaga caactacaa gaccacgcct   1140 cccgtgctgg actccgacgg ctccttcttc ctcgtgagca agctcaccgt ggacaagagc   1200
aggtggcagc aggggaacgt cttctcatgc tccgtgatgc atgaggctct gcacaaccac   1260
tacacgcaga agagcctctc cctgtctccg ggtaaatga                          1299
```

<210> SEQ ID NO 93
<211> LENGTH: 408
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160
```

```
Pro Asp Thr Gly Gly Gly Ser Gly Gly Gly Ser Gly Gly Gly
            165                 170                 175

Gly Ser Gly Gly Gly Gly Ser Thr His Thr Cys Pro Cys Pro Ala
            180                 185                 190

Pro Glu Leu Leu Gly Gly Pro Ser Val Phe Leu Phe Pro Pro Lys Pro
            195                 200                 205

Lys Asp Thr Leu Met Ile Ser Arg Thr Pro Glu Val Thr Cys Val Val
    210                 215                 220

Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
            245                 250                 255

Tyr Asn Ser Thr Tyr Arg Val Val Ser Val Leu Thr Val Leu His Gln
            260                 265                 270

Asp Trp Leu Asn Gly Lys Glu Tyr Lys Cys Lys Val Ser Asn Lys Ala
    275                 280                 285

Leu Pro Ala Pro Ile Glu Lys Thr Ile Ser Lys Ala Lys Gly Gln Pro
            290                 295                 300

Arg Glu Pro Gln Val Cys Thr Leu Pro Pro Ser Arg Glu Glu Met Thr
305                 310                 315                 320

Lys Asn Gln Val Ser Leu Ser Cys Ala Val Lys Gly Phe Tyr Pro Ser
            325                 330                 335

Asp Ile Ala Val Glu Trp Glu Ser Asn Gly Gln Pro Glu Asn Asn Tyr
            340                 345                 350

Lys Thr Thr Pro Pro Val Leu Asp Ser Asp Gly Ser Phe Phe Leu Val
    355                 360                 365

Ser Lys Leu Thr Val Asp Lys Ser Arg Trp Gln Gln Gly Asn Val Phe
370                 375                 380

Ser Cys Ser Val Met His Glu Ala Leu His Asn His Tyr Thr Gln Lys
385                 390                 395                 400

Ser Leu Ser Leu Ser Pro Gly Lys
            405

<210> SEQ ID NO 94
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gly Ala Thr Ile Pro Pro His Val Gln Lys Ser Asp Val Glu Met Glu
1               5                   10                  15

Ala Gln Lys Asp Glu Ile Ile Cys Pro Ser Cys Asn Arg Thr Ala His
            20                  25                  30

Pro Leu Arg His Ile Asn Asn Asp Met Ile Val Thr Asp Asn Asn Gly
            35                  40                  45

Ala Val Lys Phe Pro Gln Leu Cys Lys Phe Cys Asp Val Arg Phe Ser
    50                  55                  60

Thr Cys Asp Asn Gln Lys Ser Cys Met Ser Asn Cys Ser Ile Thr Ser
65                  70                  75                  80

Ile Cys Glu Lys Pro Gln Glu Val Cys Val Ala Val Trp Arg Lys Asn
            85                  90                  95
```

```
Asp Glu Asn Ile Thr Leu Glu Thr Val Cys His Asp Pro Lys Leu Pro
                100                 105                 110

Tyr His Asp Phe Ile Leu Glu Asp Ala Ala Ser Pro Lys Cys Ile Met
            115                 120                 125

Lys Glu Lys Lys Pro Gly Glu Thr Phe Phe Met Cys Ser Cys Ser
130                 135                 140

Ser Asp Glu Cys Asn Asp Asn Ile Ile Phe Ser Glu Glu Tyr Asn Thr
145                 150                 155                 160

Ser Asn Pro Asp Thr Gly Gly Gly Ser Gly Gly Gly Ser Gly
                165                 170                 175

Gly Gly Gly Ser Gly Gly Gly Gly Ser Thr His Thr Cys Pro Pro Cys
            180                 185                 190

Pro Ala Pro Glu Leu Leu Gly Gly Pro Ser Val Phe Leu Phe Pro Pro
            195                 200                 205

Lys Pro Lys Asp Thr Leu Met Ile Ser Arg Thr Pro Glu Val Thr Cys
210                 215                 220

Val Val Val Asp Val Ser His Glu Asp Pro Glu Val Lys Phe Asn Trp
225                 230                 235                 240

Tyr Val Asp Gly Val Glu Val His Asn Ala Lys Thr Lys Pro Arg Glu
            245                 250                 255

Glu Gln Tyr Asn Ser Thr Tyr Arg Val Val Ser Val Leu Thr Val Leu
            260                 265                 270

His Gln Asp Trp Leu Asn Gly Lys Glu Tyr Lys Cys Lys Val Ser Asn
            275                 280                 285

Lys Ala Leu Pro Ala Pro Ile Glu Lys Thr Ile Ser Lys Ala Lys Gly
            290                 295                 300

Gln Pro Arg Glu Pro Gln Val Tyr Thr Leu Pro Pro Ser Arg Glu Glu
305                 310                 315                 320

Met Thr Lys Asn Gln Val Ser Leu Thr Cys Leu Val Lys Gly Phe Tyr
            325                 330                 335

Pro Ser Asp Ile Ala Val Glu Trp Glu Ser Asn Gly Gln Pro Glu Asn
            340                 345                 350

Asn Tyr Lys Thr Thr Pro Pro Val Leu Asp Ser Asp Gly Ser Phe Phe
            355                 360                 365

Leu Tyr Ser Lys Leu Thr Val Asp Lys Ser Arg Trp Gln Gln Gly Asn
            370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
                405                 410

<210> SEQ ID NO 95
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Thr Ile Pro Pro His Val Gln Lys Ser Asp Val Glu Met Glu Ala
1               5                   10                  15

Gln Lys Asp Glu Ile Ile Cys Pro Ser Cys Asn Arg Thr Ala His Pro
            20                  25                  30
```

```
Leu Arg His Ile Asn Asn Asp Met Ile Val Thr Asp Asn Asn Gly Ala
        35                  40                  45

Val Lys Phe Pro Gln Leu Cys Lys Phe Cys Asp Val Arg Phe Ser Thr
 50                  55                  60

Cys Asp Asn Gln Lys Ser Cys Met Ser Asn Cys Ser Ile Thr Ser Ile
 65                  70                  75                  80

Cys Glu Lys Pro Gln Glu Val Cys Val Ala Val Trp Arg Lys Asn Asp
                 85                  90                  95

Glu Asn Ile Thr Leu Glu Thr Val Cys His Asp Pro Lys Leu Pro Tyr
            100                 105                 110

His Asp Phe Ile Leu Glu Asp Ala Ala Ser Pro Lys Cys Ile Met Lys
            115                 120                 125

Glu Lys Lys Lys Pro Gly Glu Thr Phe Phe Met Cys Ser Cys Ser Ser
130                 135                 140

Asp Glu Cys Asn Asp Asn Ile Ile Phe Ser Glu Glu Tyr Asn Thr Ser
145                 150                 155                 160

Asn Pro Asp Thr Gly Gly Gly Ser Gly Gly Gly Ser Gly Gly
                165                 170                 175

Gly Gly Ser Gly Gly Gly Ser Thr His Thr Cys Pro Pro Cys Pro
            180                 185                 190

Ala Pro Glu Leu Leu Gly Gly Pro Ser Val Phe Leu Phe Pro Pro Lys
            195                 200                 205

Pro Lys Asp Thr Leu Met Ile Ser Arg Thr Pro Glu Val Thr Cys Val
            210                 215                 220

Val Val Asp Val Ser His Glu Asp Pro Glu Val Lys Phe Asn Trp Tyr
225                 230                 235                 240

Val Asp Gly Val Glu Val His Asn Ala Lys Thr Lys Pro Arg Glu Glu
                245                 250                 255

Gln Tyr Asn Ser Thr Tyr Arg Val Val Ser Val Leu Thr Val Leu His
            260                 265                 270

Gln Asp Trp Leu Asn Gly Lys Glu Tyr Lys Cys Lys Val Ser Asn Lys
            275                 280                 285

Ala Leu Pro Ala Pro Ile Glu Lys Thr Ile Ser Lys Ala Lys Gly Gln
            290                 295                 300

Pro Arg Glu Pro Gln Val Tyr Thr Leu Pro Pro Ser Arg Glu Glu Met
305                 310                 315                 320

Thr Lys Asn Gln Val Ser Leu Thr Cys Leu Val Lys Gly Phe Tyr Pro
                325                 330                 335

Ser Asp Ile Ala Val Glu Trp Glu Ser Asn Gly Gln Pro Glu Asn Asn
            340                 345                 350

Tyr Lys Thr Thr Pro Pro Val Leu Asp Ser Asp Gly Ser Phe Phe Leu
            355                 360                 365

Tyr Ser Lys Leu Thr Val Asp Lys Ser Arg Trp Gln Gln Gly Asn Val
370                 375                 380

Phe Ser Cys Ser Val Met His Glu Ala Leu His Asn His Tyr Thr Gln
385                 390                 395                 400

Lys Ser Leu Ser Leu Ser Pro Gly Lys
                405

<210> SEQ ID NO 96
<211> LENGTH: 408
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 96

```
Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Thr Gly Gly Gly Gly Ser Gly Gly Gly Gly Ser Gly Gly Gly
                165                 170                 175

Gly Ser Gly Gly Gly Gly Ser Thr His Thr Cys Pro Pro Cys Pro Ala
            180                 185                 190

Pro Glu Leu Leu Gly Gly Pro Ser Val Phe Leu Phe Pro Pro Lys Pro
        195                 200                 205

Lys Asp Thr Leu Met Ile Ser Arg Thr Pro Glu Val Thr Cys Val Val
    210                 215                 220

Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
                245                 250                 255

Tyr Asn Ser Thr Tyr Arg Val Val Ser Val Leu Thr Val Leu His Gln
            260                 265                 270

Asp Trp Leu Asn Gly Lys Glu Tyr Lys Cys Lys Val Ser Asn Lys Ala
        275                 280                 285

Leu Pro Ala Pro Ile Glu Lys Thr Ile Ser Lys Ala Lys Gly Gln Pro
    290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
                325                 330                 335

Asp Ile Ala Val Glu Trp Glu Ser Asn Gly Gln Pro Glu Asn Asn Tyr
            340                 345                 350

Lys Thr Thr Pro Pro Val Leu Asp Ser Asp Gly Ser Phe Phe Leu Tyr
        355                 360                 365

Ser Lys Leu Thr Val Asp Lys Ser Arg Trp Gln Gln Gly Asn Val Phe
    370                 375                 380

Ser Cys Ser Val Met His Glu Ala Leu His Asn His Tyr Thr Gln Lys
385                 390                 395                 400
```

```
Ser Leu Ser Leu Ser Pro Gly Lys
                405

<210> SEQ ID NO 97
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp Thr Gly Gly Gly Ser Gly Gly Gly Ser Gly Gly Gly Gly
                165                 170                 175

Ser Gly Gly Gly Ser Thr His Thr Cys Pro Pro Cys Pro Ala Pro
            180                 185                 190

Glu Leu Leu Gly Gly Pro Ser Val Phe Leu Phe Pro Pro Lys Pro Lys
            195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
        275                 280                 285

Pro Ala Pro Ile Glu Lys Thr Ile Ser Lys Ala Lys Gly Gln Pro Arg
    290                 295                 300

Glu Pro Gln Val Tyr Thr Leu Pro Pro Ser Arg Glu Glu Met Thr Lys
305                 310                 315                 320

Asn Gln Val Ser Leu Thr Cys Leu Val Lys Gly Phe Tyr Pro Ser Asp
                325                 330                 335
```

-continued

```
Ile Ala Val Glu Trp Glu Ser Asn Gly Gln Pro Glu Asn Asn Tyr Lys
                340                 345                 350

Thr Thr Pro Pro Val Leu Asp Ser Asp Gly Ser Phe Phe Leu Tyr Ser
                355                 360                 365

Lys Leu Thr Val Asp Lys Ser Arg Trp Gln Gln Gly Asn Val Phe Ser
                370                 375                 380

Cys Ser Val Met His Glu Ala Leu His Asn His Tyr Thr Gln Lys Ser
385                 390                 395                 400

Leu Ser Leu Ser Pro Gly Lys
                405

<210> SEQ ID NO 98
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Pro Pro His Val Gln Lys Ser Asp Val Glu Met Glu Ala Gln Lys Asp
1               5                   10                  15

Glu Ile Ile Cys Pro Ser Cys Asn Arg Thr Ala His Pro Leu Arg His
                20                  25                  30

Ile Asn Asn Asp Met Ile Val Thr Asp Asn Asn Gly Ala Val Lys Phe
                35                  40                  45

Pro Gln Leu Cys Lys Phe Cys Asp Val Arg Phe Ser Thr Cys Asp Asn
                50                  55                  60

Gln Lys Ser Cys Met Ser Asn Cys Ser Ile Thr Ser Ile Cys Glu Lys
65                  70                  75                  80

Pro Gln Glu Val Cys Val Ala Val Trp Arg Lys Asn Asp Glu Asn Ile
                85                  90                  95

Thr Leu Glu Thr Val Cys His Asp Pro Lys Leu Pro Tyr His Asp Phe
                100                 105                 110

Ile Leu Glu Asp Ala Ala Ser Pro Lys Cys Ile Met Lys Glu Lys Lys
                115                 120                 125

Lys Pro Gly Glu Thr Phe Phe Met Cys Ser Cys Ser Ser Asp Glu Cys
                130                 135                 140

Asn Asp Asn Ile Ile Phe Ser Glu Glu Tyr Asn Thr Ser Asn Pro Asp
145                 150                 155                 160

Thr Gly Gly Gly Gly Ser Gly Gly Gly Ser Gly Gly Gly Gly Ser
                165                 170                 175

Gly Gly Gly Gly Ser Thr His Thr Cys Pro Pro Cys Pro Ala Pro Glu
                180                 185                 190

Leu Leu Gly Gly Pro Ser Val Phe Leu Phe Pro Pro Lys Pro Lys Asp
                195                 200                 205

Thr Leu Met Ile Ser Arg Thr Pro Glu Val Thr Cys Val Val Val Asp
                210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
                260                 265                 270
```

Leu Asn Gly Lys Glu Tyr Lys Cys Lys Val Ser Asn Lys Ala Leu Pro
            275                 280                 285

Ala Pro Ile Glu Lys Thr Ile Ser Lys Ala Lys Gly Gln Pro Arg Glu
290                 295                 300

Pro Gln Val Tyr Thr Leu Pro Pro Ser Arg Glu Glu Met Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
            340                 345                 350

Thr Pro Pro Val Leu Asp Ser Asp Gly Ser Phe Phe Leu Tyr Ser Lys
                355                 360                 365

Leu Thr Val Asp Lys Ser Arg Trp Gln Gln Gly Asn Val Phe Ser Cys
370                 375                 380

Ser Val Met His Glu Ala Leu His Asn His Tyr Thr Gln Lys Ser Leu
385                 390                 395                 400

Ser Leu Ser Pro Gly Lys
                405

<210> SEQ ID NO 99
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Pro His Val Gln Lys Ser Asp Val Glu Met Glu Ala Gln Lys Asp Glu
1               5                   10                  15

Ile Ile Cys Pro Ser Cys Asn Arg Thr Ala His Pro Leu Arg His Ile
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Thr
145                 150                 155                 160

Gly Gly Gly Gly Ser Gly Gly Gly Ser Gly Gly Gly Gly Ser Gly
                165                 170                 175

Gly Gly Gly Ser Thr His Thr Cys Pro Pro Cys Pro Ala Pro Glu Leu
            180                 185                 190

Leu Gly Gly Pro Ser Val Phe Leu Phe Pro Pro Lys Pro Lys Asp Thr
        195                 200                 205

```
Leu Met Ile Ser Arg Thr Pro Glu Val Thr Cys Val Val Asp Val
    210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
                260                 265                 270

Asn Gly Lys Glu Tyr Lys Cys Lys Val Ser Asn Lys Ala Leu Pro Ala
                275                 280                 285

Pro Ile Glu Lys Thr Ile Ser Lys Ala Lys Gly Gln Pro Arg Glu Pro
            290                 295                 300

Gln Val Tyr Thr Leu Pro Pro Ser Arg Glu Glu Met Thr Lys Asn Gln
305                 310                 315                 320

Val Ser Leu Thr Cys Leu Val Lys Gly Phe Tyr Pro Ser Asp Ile Ala
                325                 330                 335

Val Glu Trp Glu Ser Asn Gly Gln Pro Glu Asn Asn Tyr Lys Thr Thr
                340                 345                 350

Pro Pro Val Leu Asp Ser Asp Gly Ser Phe Phe Leu Tyr Ser Lys Leu
                355                 360                 365

Thr Val Asp Lys Ser Arg Trp Gln Gln Gly Asn Val Phe Ser Cys Ser
            370                 375                 380

Val Met His Glu Ala Leu His Asn His Tyr Thr Gln Lys Ser Leu Ser
385                 390                 395                 400

Leu Ser Pro Gly Lys
                405

<210> SEQ ID NO 100
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

His Val Gln Lys Ser Asp Val Glu Met Glu Ala Gln Lys Asp Glu Ile
1               5                   10                  15

Ile Cys Pro Ser Cys Asn Arg Thr Ala His Pro Leu Arg His Ile Asn
                20                  25                  30

Asn Asp Met Ile Val Thr Asp Asn Asn Gly Ala Val Lys Phe Pro Gln
            35                  40                  45

Leu Cys Lys Phe Cys Asp Val Arg Phe Ser Thr Cys Asp Asn Gln Lys
    50                  55                  60

Ser Cys Met Ser Asn Cys Ser Ile Thr Ser Ile Cys Glu Lys Pro Gln
65                  70                  75                  80

Glu Val Cys Val Ala Val Trp Arg Lys Asn Asp Glu Asn Ile Thr Leu
                85                  90                  95

Glu Thr Val Cys His Asp Pro Lys Leu Pro Tyr His Asp Phe Ile Leu
                100                 105                 110

Glu Asp Ala Ala Ser Pro Lys Cys Ile Met Lys Glu Lys Lys Lys Pro
            115                 120                 125

Gly Glu Thr Phe Phe Met Cys Ser Cys Ser Ser Asp Glu Cys Asn Asp
        130                 135                 140
```

```
Asn Ile Ile Phe Ser Glu Glu Tyr Asn Thr Ser Asn Pro Asp Thr Gly
145                 150                 155                 160

Gly Gly Gly Ser Gly Gly Gly Ser Gly Gly Gly Ser Gly Gly
                165                 170                 175

Gly Gly Ser Thr His Thr Cys Pro Pro Cys Pro Ala Pro Glu Leu Leu
            180                 185                 190

Gly Gly Pro Ser Val Phe Leu Phe Pro Pro Lys Pro Lys Asp Thr Leu
            195                 200                 205

Met Ile Ser Arg Thr Pro Glu Val Thr Cys Val Val Val Asp Val Ser
210                 215                 220

His Glu Asp Pro Glu Val Lys Phe Asn Trp Tyr Val Asp Gly Val Glu
225                 230                 235                 240

Val His Asn Ala Lys Thr Lys Pro Arg Glu Glu Gln Tyr Asn Ser Thr
                245                 250                 255

Tyr Arg Val Val Ser Val Leu Thr Val Leu His Gln Asp Trp Leu Asn
                260                 265                 270

Gly Lys Glu Tyr Lys Cys Lys Val Ser Asn Lys Ala Leu Pro Ala Pro
                275                 280                 285

Ile Glu Lys Thr Ile Ser Lys Ala Lys Gly Gln Pro Arg Glu Pro Gln
290                 295                 300

Val Tyr Thr Leu Pro Pro Ser Arg Glu Glu Met Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
                340                 345                 350

Pro Val Leu Asp Ser Asp Gly Ser Phe Phe Leu Tyr Ser Lys Leu Thr
                355                 360                 365

Val Asp Lys Ser Arg Trp Gln Gln Gly Asn Val Phe Ser Cys Ser Val
370                 375                 380

Met His Glu Ala Leu His Asn His Tyr Thr Gln Lys Ser Leu Ser Leu
385                 390                 395                 400

Ser Pro Gly Lys

<210> SEQ ID NO 101
<211> LENGTH: 115
<212> TYPE: PRT
<213> ORGANISM: Homo sapiens

<400> SEQUENCE: 101

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
                35                  40                  45

Gly Ser Ile Glu Ile Val Lys Gln Gly Cys Trp Leu Asp Asp Ile Asn
            50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110
```

Lys Pro Pro
        115

<210> SEQ ID NO 102
<211> LENGTH: 115
<212> TYPE: PRT
<213> ORGANISM: Ovis aries

<400> SEQUENCE: 102

Ile Leu Gly Arg Ser Glu Thr Gln Glu Cys Ile Phe Tyr Asn Ala Asn
1               5                   10                  15

Trp Glu Arg Asp Arg Thr Asn Arg Thr Gly Val Glu Ser Cys Tyr Gly
            20                  25                  30

Asp Lys Asp Lys Arg Arg His Cys Phe Ala Thr Trp Lys Asn Ile Ser
        35                  40                  45

Gly Ser Ile Asp Ile Val Lys Gln Gly Cys Trp Leu Asp Asp Ile Asn
    50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 103
<211> LENGTH: 115
<212> TYPE: PRT
<213> ORGANISM: Myotis davidii

<400> SEQUENCE: 103

Ile Leu Gly Arg Ser Glu Thr Gln Glu Cys Ile Phe Tyr Asn Ala Asn
1               5                   10                  15

Trp Glu Arg Asp Lys Thr Asn Arg Thr Gly Val Glu Leu Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 104
<211> LENGTH: 115
<212> TYPE: PRT
<213> ORGANISM: Gallus gallus

<400> SEQUENCE: 104

Ile Leu Gly Arg Ser Glu Thr Gln Glu Cys Ile Tyr Tyr Asn Ala Asn
1               5                   10                  15

```
Trp Glu Lys Asp Lys Thr Asn Arg Ser Gly Ile Glu Pro Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
            50                  55                  60

Cys Tyr Asp Arg Asn Asp Cys Ile Glu Lys Lys Asp Ser Pro Glu Val
 65              70                  75                  80

Phe Phe Cys Cys Cys Glu Gly Asn Met Cys Asn Glu Arg Phe Phe Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 105
<211> LENGTH: 115
<212> TYPE: PRT
<213> ORGANISM: Bos taurus

<400> SEQUENCE: 105

Ile Leu Gly Arg Ser Glu Thr Gln Glu Cys Ile Phe Tyr Asn Ala Asn
 1               5                  10                  15

Trp Glu Arg Asp Arg Thr Asn Arg Thr Gly Val Glu Ser Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
            50                  55                  60

Cys Tyr Asp Arg Thr Asp Cys Ile Glu Lys Lys Asp Ser Pro Glu Val
 65              70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 106
<211> LENGTH: 115
<212> TYPE: PRT
<213> ORGANISM: Condylura cristata

<400> SEQUENCE: 106

Ile Leu Gly Arg Ser Glu Thr Gln Glu Cys Leu Phe Phe Asn Ala Asn
 1               5                  10                  15

Trp Glu Arg Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
            50                  55                  60

Cys Tyr Asp Arg Thr Asp Cys Ile Glu Lys Lys Asp Ser Pro Glu Val
 65              70                  75                  80

Tyr Phe Cys Cys Cys Glu Gly Asn Met Cys Asn Glu Lys Phe Ser Tyr
                85                  90                  95
```

```
Phe Pro Glu Met Glu Val Thr Gln Pro Thr Ser Asn Pro Val Thr Pro
            100                 105                 110

Lys Ala Pro
        115

<210> SEQ ID NO 107
<211> LENGTH: 115
<212> TYPE: PRT
<213> ORGANISM: Tyto alba

<400> SEQUENCE: 107

Ile Leu Gly Arg Ser Glu Thr Gln Glu Cys Ile Tyr Tyr Asn Ala Asn
1               5                   10                  15

Trp Glu Lys Asp Lys Thr Asn Arg Ser Gly Ile Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
50                  55                  60

Cys Tyr Asp Arg Asn Asp Cys Ile Glu Lys Lys Asp Ser Pro Glu Val
65                  70                  75                  80

Phe Phe Cys Cys Cys Glu Gly Asn Met Cys Asn Glu Arg Phe Phe Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 108

<400> SEQUENCE: 108

000

<210> SEQ ID NO 109

<400> SEQUENCE: 109

000

<210> SEQ ID NO 110
<211> LENGTH: 317
<212> TYPE: PRT
<213> ORGANISM: Homo sapiens

<400> SEQUENCE: 110

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95
```

```
Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
            130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
            210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
            245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn
305                 310                 315

<210> SEQ ID NO 111
<211> LENGTH: 288
<212> TYPE: PRT
<213> ORGANISM: Homo sapiens

<400> SEQUENCE: 111

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
            50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
            130                 135                 140
```

```
Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285
```

<210> SEQ ID NO 112
<211> LENGTH: 344
<212> TYPE: PRT
<213> ORGANISM: Homo sapiens

<400> SEQUENCE: 112

```
Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
        130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220
```

```
Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Lys Lys Cys
            245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
            340

<210> SEQ ID NO 113
<211> LENGTH: 315
<212> TYPE: PRT
<213> ORGANISM: Homo sapiens

<400> SEQUENCE: 113

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
                100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
            195                 200                 205

Lys Cys Ile Lys Ala Lys Ser Cys Glu Asp Ile Gln Cys Thr Gly Gly
210                 215                 220

Lys Lys Cys Leu Trp Asp Phe Lys Val Gly Arg Gly Arg Cys Ser Leu
225                 230                 235                 240
```

```
Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Asp Glu Asp Gln Asp
    290                 295                 300

Tyr Ser Phe Pro Ile Ser Ser Ile Leu Glu Trp
305                 310                 315

<210> SEQ ID NO 114
<211> LENGTH: 12
<212> TYPE: PRT
<213> ORGANISM: Homo sapiens

<400> SEQUENCE: 114

Lys Lys Cys Arg Met Asn Lys Lys Asn Lys Pro Arg
1               5                   10

<210> SEQ ID NO 115
<211> LENGTH: 12
<212> TYPE: PRT
<213> ORGANISM: Unknown
<220> FEATURE:
<223> OTHER INFORMATION: Description of Unknown:
      Heparin binding domain
<220> FEATURE:
<221> NAME/KEY: MOD_RES
<222> LOCATION: (1)..(2)
<223> OTHER INFORMATION: Basic amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Basic amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (7)..(8)
<223> OTHER INFORMATION: Basic amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Basic amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Basic amino acid
<220> FEATURE:
<223> OTHER INFORMATION: See specification as filed for detailed
      description of substitutions and preferred embodiments

<400> SEQUENCE: 115

Xaa Xaa Xaa Xaa Xaa Xaa Xaa Xaa Xaa Xaa Xaa Xaa
1               5                   10
```

<210> SEQ ID NO 116
<211> LENGTH: 65
<212> TYPE: PRT
<213> ORGANISM: Homo sapiens

<400> SEQUENCE: 116

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr
65

<210> SEQ ID NO 117
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr
    50                  55                  60

<210> SEQ ID NO 118
<211> LENGTH: 70
<212> TYPE: PRT
<213> ORGANISM: Homo sapiens

<400> SEQUENCE: 118

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45

Cys Ala Leu Leu Lys Ala Arg Cys Lys Glu Gln Pro Glu Leu Glu Val
    50                  55                  60

Gln Tyr Gln Gly Arg Cys
65                  70

<210> SEQ ID NO 119
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 119

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
                35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
                100                 105                 110

Ala Leu Leu Lys Ala Arg Cys Lys Glu Gln Pro Glu Leu Glu Val Gln
            115                 120                 125

Tyr Gln Gly Arg Cys
        130

<210> SEQ ID NO 120
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
                35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
                100                 105                 110

Ala Leu Leu Lys Ala Arg Cys Lys Glu Gln Pro Glu Leu Glu Val Gln
            115                 120                 125

Tyr Gln Gly Arg Cys Lys Lys Thr Cys Glu Asn Val Asp Cys Gly Pro
        130                 135                 140

Gly Lys Lys Cys Arg Met Asn Lys Lys Asn Lys Pro Arg Cys Val Cys
145                 150                 155                 160

Ala Pro Asp Cys Ser Asn Ile Thr Trp Lys Gly Pro Val Cys Gly Leu
                165                 170                 175

Asp Gly Lys Thr Tyr Arg Asn Glu Cys Ala Leu Leu Lys Ala Arg Cys
            180                 185                 190

Lys Glu Gln Pro Glu Leu Glu Val Gln Tyr Gln Gly Arg Cys
                195                 200                 205
```

-continued

```
<210> SEQ ID NO 121
<211> LENGTH: 145
<212> TYPE: PRT
<213> ORGANISM: Homo sapiens

<400> SEQUENCE: 121

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45

Cys Ala Leu Leu Lys Ala Arg Cys Lys Glu Gln Pro Glu Leu Glu Val
    50                  55                  60

Gln Tyr Gln Gly Arg Cys Lys Lys Thr Cys Arg Asp Val Phe Cys Pro
65                  70                  75                  80

Gly Ser Ser Thr Cys Val Val Asp Gln Thr Asn Asn Ala Tyr Cys Val
                85                  90                  95

Thr Cys Asn Arg Ile Cys Pro Glu Pro Ala Ser Ser Glu Gln Tyr Leu
            100                 105                 110

Cys Gly Asn Asp Gly Val Thr Tyr Ser Ser Ala Cys His Leu Arg Lys
        115                 120                 125

Ala Thr Cys Leu Leu Gly Arg Ser Ile Gly Leu Ala Tyr Glu Gly Lys
    130                 135                 140

Cys
145

<210> SEQ ID NO 122
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Arg Asp Val Phe Cys Pro Gly
    130                 135                 140

Ser Ser Thr Cys Val Val Asp Gln Thr Asn Asn Ala Tyr Cys Val Thr
145                 150                 155                 160
```

```
Cys Asn Arg Ile Cys Pro Glu Pro Ala Ser Ser Glu Gln Tyr Leu Cys
            165                 170                 175

Gly Asn Asp Gly Val Thr Tyr Ser Ser Ala Cys His Leu Arg Lys Ala
        180                 185                 190

Thr Cys Leu Leu Gly Arg Ser Ile Gly Leu Ala Tyr Glu Gly Lys Cys
        195                 200                 205

<210> SEQ ID NO 123
<211> LENGTH: 320
<212> TYPE: PRT
<213> ORGANISM: Homo sapiens

<400> SEQUENCE: 123

Met Val Arg Ala Arg His Gln Pro Gly Gly Leu Cys Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

<210> SEQ ID NO 124
```

<211> LENGTH: 291
<212> TYPE: PRT
<213> ORGANISM: Homo sapiens

<400> SEQUENCE: 124

Gly Asn Cys Trp Leu Arg Gln Ala Lys Asn Gly Arg Cys Gln Val Leu
1               5                   10                  15
Tyr Lys Thr Glu Leu Ser Lys Glu Glu Cys Cys Ser Thr Gly Arg Leu
            20                  25                  30
Ser Thr Ser Trp Thr Glu Glu Asp Val Asn Asp Asn Thr Leu Phe Lys
        35                  40                  45
Trp Met Ile Phe Asn Gly Gly Ala Pro Asn Cys Ile Pro Cys Lys Glu
    50                  55                  60
Thr Cys Glu Asn Val Asp Cys Gly Pro Gly Lys Lys Cys Arg Met Asn
65                  70                  75                  80
Lys Lys Asn Lys Pro Arg Cys Val Cys Ala Pro Asp Cys Ser Asn Ile
                85                  90                  95
Thr Trp Lys Gly Pro Val Cys Gly Leu Asp Gly Lys Thr Tyr Arg Asn
            100                 105                 110
Glu Cys Ala Leu Leu Lys Ala Arg Cys Lys Glu Gln Pro Glu Leu Glu
        115                 120                 125
Val Gln Tyr Gln Gly Arg Cys Lys Lys Thr Cys Arg Asp Val Phe Cys
    130                 135                 140
Pro Gly Ser Ser Thr Cys Val Val Asp Gln Thr Asn Asn Ala Tyr Cys
145                 150                 155                 160
Val Thr Cys Asn Arg Ile Cys Pro Glu Pro Ala Ser Ser Glu Gln Tyr
                165                 170                 175
Leu Cys Gly Asn Asp Gly Val Thr Tyr Ser Ser Ala Cys His Leu Arg
            180                 185                 190
Lys Ala Thr Cys Leu Leu Gly Arg Ser Ile Gly Leu Ala Tyr Glu Gly
        195                 200                 205
Lys Cys Ile Lys Ala Lys Ser Cys Glu Asp Ile Gln Cys Thr Gly Gly
    210                 215                 220
Lys Lys Cys Leu Trp Asp Phe Lys Val Gly Arg Gly Arg Cys Ser Leu
225                 230                 235                 240
Cys Asp Glu Leu Cys Pro Asp Ser Lys Ser Asp Glu Pro Val Cys Ala
                245                 250                 255
Ser Asp Asn Ala Thr Tyr Ala Ser Glu Cys Ala Met Lys Glu Ala Ala
            260                 265                 270
Cys Ser Ser Gly Val Leu Leu Glu Val Lys His Ser Gly Ser Cys Asn
        275                 280                 285
Ser Ile Ser
    290

<210> SEQ ID NO 125
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Cys Trp Leu Arg Gln Ala Lys Asn Gly Arg Cys Gln Val Leu Tyr Lys
1               5                   10                  15
Thr Glu Leu Ser Lys Glu Glu Cys Cys Ser Thr Gly Arg Leu Ser Thr
            20                  25                  30

```
Ser Trp Thr Glu Glu Asp Val Asn Asp Asn Thr Leu Phe Lys Trp Met
         35                  40                  45

Ile Phe Asn Gly Gly Ala Pro Asn Cys Ile Pro Cys Lys Glu Thr Cys
 50                  55                  60

Glu Asn Val Asp Cys Gly Pro Gly Lys Lys Cys Arg Met Asn Lys Lys
 65                  70                  75                  80

Asn Lys Pro Arg Cys Val Cys Ala Pro Asp Cys Ser Asn Ile Thr Trp
                 85                  90                  95

Lys Gly Pro Val Cys Gly Leu Asp Gly Lys Thr Tyr Arg Asn Glu Cys
                100                 105                 110

Ala Leu Leu Lys Ala Arg Cys Lys Glu Gln Pro Glu Leu Glu Val Gln
             115                 120                 125

Tyr Gln Gly Arg Cys Lys Lys Thr Cys Arg Asp Val Phe Cys Pro Gly
         130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
                180                 185                 190

Thr Cys Leu Leu Gly Arg Ser Ile Gly Leu Ala Tyr Glu Gly Lys Cys
             195                 200                 205

Ile Lys Ala Lys Ser Cys Glu Asp Ile Gln Cys Thr Gly Gly Lys Lys
         210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
                260                 265                 270

Ser Gly Val Leu Leu Glu Val Lys His Ser Gly Ser Cys Asn Ser Ile
             275                 280                 285

Ser

<210> SEQ ID NO 126
<211> LENGTH: 225
<212> TYPE: PRT
<213> ORGANISM: Homo sapiens

<400> SEQUENCE: 126

Thr His Thr Cys Pro Cys Pro Ala Pro Glu Leu Leu Gly Gly Pro
 1               5                  10                  15

Ser Val Phe Leu Phe Pro Pro Lys Pro Lys Asp Thr Leu Met Ile Ser
             20                  25                  30

Arg Thr Pro Glu Val Thr Cys Val Val Asp Val Ser His Glu Asp
         35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
             85                  90                  95

Tyr Lys Cys Lys Val Ser Asn Lys Ala Leu Pro Ala Pro Ile Glu Lys
                100                 105                 110
```

```
Thr Ile Ser Lys Ala Lys Gly Gln Pro Arg Glu Pro Gln Val Tyr Thr
            115                 120                 125
Leu Pro Pro Ser Arg Glu Glu Met Thr Lys Asn Gln Val Ser Leu Thr
        130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
    210                 215                 220
Lys
225

<210> SEQ ID NO 127
<211> LENGTH: 223
<212> TYPE: PRT
<213> ORGANISM: Homo sapiens

<400> SEQUENCE: 127

Val Glu Cys Pro Pro Cys Pro Ala Pro Pro Val Ala Gly Pro Ser Val
1               5                   10                  15
Phe Leu Phe Pro Pro Lys Pro Lys Asp Thr Leu Met Ile Ser Arg Thr
            20                  25                  30
Pro Glu Val Thr Cys Val Val Val Asp Val Ser His Glu Asp Pro Glu
        35                  40                  45
Val Gln Phe Asn Trp Tyr Val Asp Gly Val Glu Val His Asn Ala Lys
    50                  55                  60
Thr Lys Pro Arg Glu Glu Gln Phe Asn Ser Thr Phe Arg Val Val Ser
65                  70                  75                  80
Val Leu Thr Val Val His Gln Asp Trp Leu Asn Gly Lys Glu Tyr Lys
                85                  90                  95
Cys Lys Val Ser Asn Lys Gly Leu Pro Ala Pro Ile Glu Lys Thr Ile
            100                 105                 110
Ser Lys Thr Lys Gly Gln Pro Arg Glu Pro Gln Val Tyr Thr Leu Pro
        115                 120                 125
Pro Ser Arg Glu Glu Met Thr Lys Asn Gln Val Ser Leu Thr Cys Leu
    130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Met Leu Asp Ser
                165                 170                 175
Asp Gly Ser Phe Phe Leu Tyr Ser Lys Leu Thr Val Asp Lys Ser Arg
            180                 185                 190
Trp Gln Gln Gly Asn Val Phe Ser Cys Ser Val Met His Glu Ala Leu
        195                 200                 205
His Asn His Tyr Thr Gln Lys Ser Leu Ser Leu Ser Pro Gly Lys
    210                 215                 220

<210> SEQ ID NO 128
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 128

Thr Gly Gly Gly
1

<210> SEQ ID NO 129
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Ala Pro Gly Gly Gly Gly Ala Ala Ala Ala Ala Gly Gly Gly
1               5                   10                  15

Gly Gly Gly Ala Pro
            20

<210> SEQ ID NO 130
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gly Ala Pro Gly Gly Gly Gly Ala Ala Ala Ala Ala Gly Gly Gly
1               5                   10                  15

Gly Gly Gly Ala Pro Gly Gly Gly Gly Ala Ala Ala Ala Ala Gly
            20                  25                  30

Gly Gly Gly Gly Gly Ala Pro
        35

<210> SEQ ID NO 131
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gly Ala Pro Gly Gly Gly Gly Ala Ala Ala Ala Ala Gly Gly Gly
1               5                   10                  15

Gly Gly Gly Ala Pro Gly Gly Gly Gly Ala Ala Ala Ala Ala Gly
            20                  25                  30

Gly Gly Gly Gly Gly Ala Pro Gly Gly Gly Gly Ala Ala Ala Ala
        35                  40                  45

Ala Gly Gly Gly Gly Gly Gly Ala Pro
    50                  55

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 132

Ala Leu Glu Val Leu Phe Gln Gly Pro
1               5

<210> SEQ ID NO 133

<400> SEQUENCE: 133

000

<210> SEQ ID NO 134

<400> SEQUENCE: 134

000

<210> SEQ ID NO 135
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Cys Ser Ser
    290                 295                 300

Gly Val Leu Leu Glu Val Lys His Ser Gly Ser Cys Asn Thr Gly Gly
305                 310                 315                 320

Gly Val Glu Cys Pro Pro Cys Pro Ala Pro Val Ala Gly Pro Ser
            325                 330                 335

Val Phe Leu Phe Pro Pro Lys Pro Lys Asp Thr Leu Met Ile Ser Arg
            340                 345                 350

Thr Pro Glu Val Thr Cys Val Val Val Asp Val Ser His Glu Asp Pro
            355                 360                 365

Glu Val Gln Phe Asn Trp Tyr Val Asp Gly Val Glu Val His Asn Ala
    370                 375                 380

Lys Thr Lys Pro Arg Glu Glu Gln Phe Asn Ser Thr Phe Arg Val Val
385                 390                 395                 400

Ser Val Leu Thr Val Val His Gln Asp Trp Leu Asn Gly Lys Glu Tyr
            405                 410                 415

Lys Cys Lys Val Ser Asn Lys Gly Leu Pro Ala Pro Ile Glu Lys Thr
            420                 425                 430

Ile Ser Lys Thr Lys Gly Gln Pro Arg Glu Pro Gln Val Tyr Thr Leu
            435                 440                 445

Pro Pro Ser Arg Glu Glu Met Thr Lys Asn Gln Val Ser Leu Thr Cys
450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Met Leu Asp
            485                 490                 495

Ser Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu Ala
            515                 520                 525

Leu His Asn His Tyr Thr Gln Lys Ser Leu Ser Leu Ser Pro Gly Lys
            530                 535                 540

<210> SEQ ID NO 136
<211> LENGTH: 1641
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
atggtccgcg cgaggcacca gccgggtggg ctttgcctcc tgctgctgct gctctgccag        60
ttcatggagg accgcagtgc ccaggctggg aactgctggc tccgtcaagc gaagaacggc       120
cgctgccagg tcctgtacaa gaccgaactg agcaaggagg agtgctgcag caccggccgg       180
ctgagcacct cgtggaccga ggaggacgtg aatgacaaca cactcttcaa gtggatgatt       240
ttcaacgggg cgcccccaa ctgcatcccc tgtaaagaaa cgtgtgagaa cgtggactgt       300
ggacctggga aaaatgccg aatgaacaag aagaacaaac cccgctgcgt ctgcgccccg       360
gattgttcca acatcacctg gaagggtcca gtctgcgggc tggatgggaa aacctaccgc       420

```
aatgaatgtg cactcctaaa ggcaagatgt aaagagcagc cagaactgga agtccagtac    480
caaggcagat gtaaaaagac ttgtcgggat gtttttctgtc caggcagctc cacatgtgtg   540
gtggaccaga ccaataatgc ctactgtgtg acctgtaatc ggatttgccc agagcctgct   600
tcctctgagc aatatctctg tgggaatgat ggagtcacct actccagtgc ctgccacctg   660
agaaaggcta cctgcctgct gggcagatct attggattag cctatgaggg aaagtgtatc   720
aaagcaaagt cctgtgaaga tatccagtgc actggtggga aaaaatgttt atgggatttc   780
aaggttggga gaggccggtg ttccctctgt gatgagctgt gccctgacag taagtcggat   840
gagcctgtct gtgccagtga caatgccact tatgccagcg agtgtgccat gaaggaagct   900
gcctgctcct caggtgtgct actggaagta aagcactccg gatcttgcaa caccggtggt   960
ggagtcgagt gccaccgtg cccagcacca cctgtggcag accgtcagt cttcctcttc     1020 ccccaaaac ccaaggacac cctcatgatc tcccggaccc ctgaggtcac gtgcgtggtg     1080
gtggacgtga gccacgaaga ccccgaggtc cagttcaact ggtacgtgga cggcgtggag    1140
gtgcataatg ccaagacaaa gccacgggag gagcagttca acagcacgtt ccgtgtggtc   1200
agcgtcctca ccgtcgtgca ccaggactgg ctgaacggca aggagtacaa gtgcaaggtc   1260
tccaacaaag gcctcccagc ccccatcgag aaaaccatct ccaaaaccaa agggcagccc   1320
cgagaaccac aggtgtacac cctgccccca tcccgggagg agatgaccaa gaaccaggtc   1380
agcctgacct gcctggtcaa aggcttctac cccagcgaca tcgccgtgga gtgggagagc   1440
aatgggcagc cggagaacaa ctacaagacc acacctccca tgctggactc cgacggctcc   1500
ttcttcctct acagcaagct caccgtggac aagagcaggt ggcagcaggg gaacgtcttc   1560
tcatgctccg tgatgcatga ggctctgcac aaccactaca cgcagaagag cctctccctg   1620
tctccgggta aatgagaatt c                                             1641
```

<210> SEQ ID NO 137
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
        50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

```
Val Gln Tyr Gln Gly Arg Cys Lys Lys Thr Cys Arg Asp Val Phe Cys
130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
                180                 185                 190

Lys Ala Thr Cys Leu Leu Gly Arg Ser Ile Gly Leu Ala Tyr Glu Gly
                195                 200                 205

Lys Cys Ile Lys Ala Lys Ser Cys Glu Asp Ile Gln Cys Thr Gly Gly
210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
                275                 280                 285

Thr Gly Gly Gly Val Glu Cys Pro Pro Cys Pro Ala Pro Pro Val Ala
290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Gln Phe Asn Trp Tyr Val Asp Gly Val Glu Val
                340                 345                 350

His Asn Ala Lys Thr Lys Pro Arg Glu Glu Gln Phe Asn Ser Thr Phe
                355                 360                 365

Arg Val Val Ser Val Leu Thr Val Val His Gln Asp Trp Leu Asn Gly
                370                 375                 380

Lys Glu Tyr Lys Cys Lys Val Ser Asn Lys Gly Leu Pro Ala Pro Ile
385                 390                 395                 400

Glu Lys Thr Ile Ser Lys Thr Lys Gly Gln Pro Arg Glu Pro Gln Val
                405                 410                 415

Tyr Thr Leu Pro Pro Ser Arg Glu Glu Met Thr Lys Asn Gln Val Ser
                420                 425                 430

Leu Thr Cys Leu Val Lys Gly Phe Tyr Pro Ser Asp Ile Ala Val Glu
                435                 440                 445

Trp Glu Ser Asn Gly Gln Pro Glu Asn Asn Tyr Lys Thr Thr Pro Pro
450                 455                 460

Met Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
                500                 505                 510

Pro Gly Lys
515

<210> SEQ ID NO 138
<211> LENGTH: 513
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Cys Trp Leu Arg Gln Ala Lys Asn Gly Arg Cys Gln Val Leu Tyr Lys
1               5                   10                  15
Thr Glu Leu Ser Lys Glu Glu Cys Cys Ser Thr Gly Arg Leu Ser Thr
            20                  25                  30
Ser Trp Thr Glu Glu Asp Val Asn Asp Asn Thr Leu Phe Lys Trp Met
        35                  40                  45
Ile Phe Asn Gly Gly Ala Pro Asn Cys Ile Pro Cys Lys Glu Thr Cys
50                  55                  60
Glu Asn Val Asp Cys Gly Pro Gly Lys Lys Cys Arg Met Asn Lys Lys
65                  70                  75                  80
Asn Lys Pro Arg Cys Val Cys Ala Pro Asp Cys Ser Asn Ile Thr Trp
                85                  90                  95
Lys Gly Pro Val Cys Gly Leu Asp Gly Lys Thr Tyr Arg Asn Glu Cys
            100                 105                 110
Ala Leu Leu Lys Ala Arg Cys Lys Glu Gln Pro Glu Leu Glu Val Gln
        115                 120                 125
Tyr Gln Gly Arg Cys Lys Lys Thr Cys Arg Asp Val Phe Cys Pro Gly
130                 135                 140
Ser Ser Thr Cys Val Val Asp Gln Thr Asn Asn Ala Tyr Cys Val Thr
145                 150                 155                 160
Cys Asn Arg Ile Cys Pro Glu Pro Ala Ser Ser Glu Gln Tyr Leu Cys
                165                 170                 175
Gly Asn Asp Gly Val Thr Tyr Ser Ser Ala Cys His Leu Arg Lys Ala
            180                 185                 190
Thr Cys Leu Leu Gly Arg Ser Ile Gly Leu Ala Tyr Glu Gly Lys Cys
        195                 200                 205
Ile Lys Ala Lys Ser Cys Glu Asp Ile Gln Cys Thr Gly Gly Lys Lys
210                 215                 220
Cys Leu Trp Asp Phe Lys Val Gly Arg Gly Arg Cys Ser Leu Cys Asp
225                 230                 235                 240
Glu Leu Cys Pro Asp Ser Lys Ser Asp Glu Pro Val Cys Ala Ser Asp
                245                 250                 255
Asn Ala Thr Tyr Ala Ser Glu Cys Ala Met Lys Glu Ala Ala Cys Ser
            260                 265                 270
Ser Gly Val Leu Leu Glu Val Lys His Ser Gly Ser Cys Asn Thr Gly
        275                 280                 285
Gly Gly Val Glu Cys Pro Pro Cys Pro Ala Pro Val Ala Gly Pro
290                 295                 300
Ser Val Phe Leu Phe Pro Pro Lys Pro Lys Asp Thr Leu Met Ile Ser
305                 310                 315                 320
Arg Thr Pro Glu Val Thr Cys Val Val Val Asp Val Ser His Glu Asp
                325                 330                 335
Pro Glu Val Gln Phe Asn Trp Tyr Val Asp Gly Val Glu Val His Asn
            340                 345                 350
Ala Lys Thr Lys Pro Arg Glu Glu Gln Phe Asn Ser Thr Phe Arg Val
        355                 360                 365
Val Ser Val Leu Thr Val Val His Gln Asp Trp Leu Asn Gly Lys Glu
370                 375                 380
```

```
Tyr Lys Cys Lys Val Ser Asn Lys Gly Leu Pro Ala Pro Ile Glu Lys
385                 390                 395                 400

Thr Ile Ser Lys Thr Lys Gly Gln Pro Arg Glu Pro Gln Val Tyr Thr
            405                 410                 415

Leu Pro Pro Ser Arg Glu Glu Met Thr Lys Asn Gln Val Ser Leu Thr
        420                 425                 430

Cys Leu Val Lys Gly Phe Tyr Pro Ser Asp Ile Ala Val Glu Trp Glu
            435                 440                 445

Ser Asn Gly Gln Pro Glu Asn Asn Tyr Lys Thr Thr Pro Pro Met Leu
        450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys

<210> SEQ ID NO 139
<211> LENGTH: 571
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
        130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220
```

```
Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Lys Lys Cys
            245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
            325                 330                 335

Pro Ile Ser Ser Ile Leu Glu Trp Thr Gly Gly Val Glu Cys Pro
            340                 345                 350

Pro Cys Pro Ala Pro Pro Val Ala Gly Pro Ser Val Phe Leu Phe Pro
            355                 360                 365

Pro Lys Pro Lys Asp Thr Leu Met Ile Ser Arg Thr Pro Glu Val Thr
            370                 375                 380

Cys Val Val Val Asp Val Ser His Glu Asp Pro Glu Val Gln Phe Asn
385                 390                 395                 400

Trp Tyr Val Asp Gly Val Glu Val His Asn Ala Lys Thr Lys Pro Arg
            405                 410                 415

Glu Glu Gln Phe Asn Ser Thr Phe Arg Val Val Ser Val Leu Thr Val
            420                 425                 430

Val His Gln Asp Trp Leu Asn Gly Lys Glu Tyr Lys Cys Lys Val Ser
            435                 440                 445

Asn Lys Gly Leu Pro Ala Pro Ile Glu Lys Thr Ile Ser Lys Thr Lys
            450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Met Leu Asp Ser Asp Gly Ser Phe
            515                 520                 525

Phe Leu Tyr Ser Lys Leu Thr Val Asp Lys Ser Arg Trp Gln Gln Gly
            530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
            565                 570

<210> SEQ ID NO 140
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 140

```
atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gtgcccccaa ctgcatcccc tgtaaagaaa cgtgtgagaa cgtggactgt     300
ggacctggga aaaatgccg aatgaacaag aagaacaaac ccgctgcgt ctgcgccccg       360
gattgttcca acatcacctg gaagggtcca gtctgcgggc tggatgggaa aacctaccgc     420
aatgaatgtg cactcctaaa ggcaagatgt aaagagcagc agaactggaa gtccagtac     480
caaggcagat gtaaaaagac ttgtcgggat gttttctgtc caggcagctc acatgtgtg     540
gtggaccaga ccaataatgc ctactgtgtg acctgtaatc ggatttgccc agagcctgct     600
tcctctgagc aatatctctg tgggaatgat ggagtcacct actccagtgc ctgccacctg     660
agaaaggcta cctgcctgct gggcagatct attggattag cctatgaggg aaagtgtatc     720
aaagcaaagt cctgtgaaga tatccagtgc actggtggga aaaatgtttt atgggatttc     780
aaggttggga gaggccggtg ttccctctgt gatgagctgt gccctgacag taagtcggat     840
gagcctgtct gtgccagtga caatgccact tatgccagcg agtgtgccat gaaggaagct     900
gcctgctcct caggtgtgct actggaagta agcactccg gatcttgcaa ctccatttcg     960
gaagacaccg aggaagagga ggaagatgaa gaccaggact acagctttcc tatatcttct    1020
attctagagt ggaccggtgg tggagtcgag tgcccaccgt gcccagcacc acctgtggca    1080
ggaccgtcag tcttcctctt cccccaaaa cccaaggaca ccctcatgat ctcccggacc     1140
cctgaggtca cgtgcgtggt ggtggacgtg agccacgaag accccgaggt ccagttcaac    1200
tggtacgtgg acggcgtgga ggtgcataat gccaagacaa agccacggga ggagcagttc    1260
aacagcacgt tccgtgtggt cagcgtcctc accgtcgtgc accaggactg gctgaacggc    1320
aaggagtaca agtgcaaggt ctccaacaaa ggcctcccag cccccatcga gaaaaccatc    1380
tccaaaacca agggcagcc ccgagaacca caggtgtaca ccctgccccc atcccgggag     1440
gagatgacca gaaccaggt cagcctgacc tgcctggtca aaggcttcta ccccagcgac    1500
atcgccgtgg agtgggagag caatgggcag ccggagaaca actacaagac cacacctccc    1560
atgctggact ccgacggctc cttcttcctc tacagcaagc tcaccgtgga caagagcagg    1620
tggcagcagg ggaacgtctt ctcatgctcc gtgatgcatg aggctctgca caaccactac    1680
acgcagaaga gcctctccct gtctccgggt aaatgagaat tc                        1722
```

<210> SEQ ID NO 141
<211> LENGTH: 542
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Gly Asn Cys Trp Leu Arg Gln Ala Lys Asn Gly Arg Cys Gln Val Leu
1               5                   10                  15
Tyr Lys Thr Glu Leu Ser Lys Glu Glu Cys Cys Ser Thr Gly Arg Leu
            20                  25                  30
```

```
Ser Thr Ser Trp Thr Glu Glu Asp Val Asn Asp Asn Thr Leu Phe Lys
         35                  40                  45

Trp Met Ile Phe Asn Gly Gly Ala Pro Asn Cys Ile Pro Cys Lys Glu
     50                  55                  60

Thr Cys Glu Asn Val Asp Cys Gly Pro Gly Lys Lys Cys Arg Met Asn
 65                  70                  75                  80

Lys Lys Asn Lys Pro Arg Cys Val Cys Ala Pro Asp Cys Ser Asn Ile
                 85                  90                  95

Thr Trp Lys Gly Pro Val Cys Gly Leu Asp Gly Lys Thr Tyr Arg Asn
                100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
        130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Asp Glu Asp Gln Asp
    290                 295                 300

Tyr Ser Phe Pro Ile Ser Ser Ile Leu Glu Trp Thr Gly Gly Gly Val
305                 310                 315                 320

Glu Cys Pro Pro Cys Pro Ala Pro Val Ala Gly Pro Ser Val Phe
                325                 330                 335

Leu Phe Pro Pro Lys Pro Lys Asp Thr Leu Met Ile Ser Arg Thr Pro
                340                 345                 350

Glu Val Thr Cys Val Val Val Asp Val Ser His Glu Asp Pro Glu Val
            355                 360                 365

Gln Phe Asn Trp Tyr Val Asp Gly Val Glu Val His Asn Ala Lys Thr
        370                 375                 380

Lys Pro Arg Glu Glu Gln Phe Asn Ser Thr Phe Arg Val Val Ser Val
385                 390                 395                 400

Leu Thr Val Val His Gln Asp Trp Leu Asn Gly Lys Glu Tyr Lys Cys
                405                 410                 415

Lys Val Ser Asn Lys Gly Leu Pro Ala Pro Ile Glu Lys Thr Ile Ser
            420                 425                 430

Lys Thr Lys Gly Gln Pro Arg Glu Pro Gln Val Tyr Thr Leu Pro Pro
        435                 440                 445
```

```
Ser Arg Glu Glu Met Thr Lys Asn Gln Val Ser Leu Thr Cys Leu Val
    450                 455                 460

Lys Gly Phe Tyr Pro Ser Asp Ile Ala Val Glu Trp Glu Ser Asn Gly
465                 470                 475                 480

Gln Pro Glu Asn Asn Tyr Lys Thr Thr Pro Pro Met Leu Asp Ser Asp
                485                 490                 495

Gly Ser Phe Phe Leu Tyr Ser Lys Leu Thr Val Asp Lys Ser Arg Trp
            500                 505                 510

Gln Gln Gly Asn Val Phe Ser Cys Ser Val Met His Glu Ala Leu His
            515                 520                 525

Asn His Tyr Thr Gln Lys Ser Leu Ser Leu Ser Pro Gly Lys
    530                 535                 540

<210> SEQ ID NO 142
<211> LENGTH: 540
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Arg Asp Val Phe Cys Pro Gly
    130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
            180                 185                 190

Thr Cys Leu Leu Gly Arg Ser Ile Gly Leu Ala Tyr Glu Gly Lys Cys
        195                 200                 205

Ile Lys Ala Lys Ser Cys Glu Asp Ile Gln Cys Thr Gly Gly Lys Lys
    210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
            260                 265                 270
```

Ser Gly Val Leu Leu Glu Val Lys His Ser Gly Ser Cys Asn Ser Ile
        275                 280                 285

Ser Glu Asp Thr Glu Glu Glu Glu Asp Glu Asp Gln Asp Tyr Ser
    290                 295                 300

Phe Pro Ile Ser Ser Ile Leu Glu Trp Thr Gly Gly Val Glu Cys
305                 310                 315                 320

Pro Pro Cys Pro Ala Pro Val Ala Gly Pro Ser Val Phe Leu Phe
                325                 330                 335

Pro Pro Lys Pro Lys Asp Thr Leu Met Ile Ser Arg Thr Pro Glu Val
                340                 345                 350

Thr Cys Val Val Val Asp Val Ser His Glu Asp Pro Glu Val Gln Phe
                355                 360                 365

Asn Trp Tyr Val Asp Gly Val Glu Val His Asn Ala Lys Thr Lys Pro
        370                 375                 380

Arg Glu Glu Gln Phe Asn Ser Thr Phe Arg Val Val Ser Val Leu Thr
385                 390                 395                 400

Val Val His Gln Asp Trp Leu Asn Gly Lys Glu Tyr Lys Cys Lys Val
                405                 410                 415

Ser Asn Lys Gly Leu Pro Ala Pro Ile Glu Lys Thr Ile Ser Lys Thr
        420                 425                 430

Lys Gly Gln Pro Arg Glu Pro Gln Val Tyr Thr Leu Pro Pro Ser Arg
        435                 440                 445

Glu Glu Met Thr Lys Asn Gln Val Ser Leu Thr Cys Leu Val Lys Gly
        450                 455                 460

Phe Tyr Pro Ser Asp Ile Ala Val Glu Trp Glu Ser Asn Gly Gln Pro
465                 470                 475                 480

Glu Asn Asn Tyr Lys Thr Thr Pro Pro Met Leu Asp Ser Asp Gly Ser
                485                 490                 495

Phe Phe Leu Tyr Ser Lys Leu Thr Val Asp Lys Ser Arg Trp Gln Gln
                500                 505                 510

Gly Asn Val Phe Ser Cys Ser Val Met His Glu Ala Leu His Asn His
        515                 520                 525

Tyr Thr Gln Lys Ser Leu Ser Leu Ser Pro Gly Lys
        530                 535                 540

<210> SEQ ID NO 143
<211> LENGTH: 549
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Val Arg Ala Arg His Gln Pro Gly Gly Leu Cys Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

```
Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
            130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
            210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
        290                 295                 300

Gly Val Leu Leu Glu Val Lys His Ser Gly Ser Cys Asn Ser Ile Ser
305                 310                 315                 320

Thr Gly Gly Gly Thr His Thr Cys Pro Pro Cys Pro Ala Pro Glu Leu
                325                 330                 335

Leu Gly Gly Pro Ser Val Phe Leu Phe Pro Pro Lys Pro Lys Asp Thr
            340                 345                 350

Leu Met Ile Ser Arg Thr Pro Glu Val Thr Cys Val Val Val Asp Val
            355                 360                 365

Ser His Glu Asp Pro Glu Val Lys Phe Asn Trp Tyr Val Asp Gly Val
        370                 375                 380

Glu Val His Asn Ala Lys Thr Lys Pro Arg Glu Glu Gln Tyr Asn Ser
385                 390                 395                 400

Thr Tyr Arg Val Val Ser Val Leu Thr Val Leu His Gln Asp Trp Leu
            405                 410                 415

Asn Gly Lys Glu Tyr Lys Cys Lys Val Ser Asn Lys Ala Leu Pro Ala
            420                 425                 430

Pro Ile Glu Lys Thr Ile Ser Lys Ala Lys Gly Gln Pro Arg Glu Pro
            435                 440                 445

Gln Val Tyr Thr Leu Pro Pro Ser Arg Glu Glu Met Thr Lys Asn Gln
        450                 455                 460

Val Ser Leu Thr Cys Leu Val Lys Gly Phe Tyr Pro Ser Asp Ile Ala
465                 470                 475                 480

Val Glu Trp Glu Ser Asn Gly Gln Pro Glu Asn Asn Tyr Lys Thr Thr
                485                 490                 495
```

```
Pro Pro Val Leu Asp Ser Asp Gly Ser Phe Phe Leu Tyr Ser Lys Leu
            500                 505                 510

Thr Val Asp Lys Ser Arg Trp Gln Gln Gly Asn Val Phe Ser Cys Ser
            515                 520                 525

Val Met His Glu Ala Leu His Asn His Tyr Thr Gln Lys Ser Leu Ser
        530                 535                 540

Leu Ser Pro Gly Lys
545

<210> SEQ ID NO 144
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Thr Gly Gly His Thr Cys Pro Pro Cys Pro Ala
    290                 295                 300
```

-continued

```
Pro Glu Leu Leu Gly Gly Pro Ser Val Phe Leu Phe Pro Pro Lys Pro
305                 310                 315                 320

Lys Asp Thr Leu Met Ile Ser Arg Thr Pro Glu Val Thr Cys Val Val
                325                 330                 335

Val Asp Val Ser His Glu Asp Pro Glu Val Lys Phe Asn Trp Tyr Val
            340                 345                 350

Asp Gly Val Glu Val His Asn Ala Lys Thr Lys Pro Arg Glu Glu Gln
        355                 360                 365

Tyr Asn Ser Thr Tyr Arg Val Val Ser Val Leu Thr Val Leu His Gln
    370                 375                 380

Asp Trp Leu Asn Gly Lys Glu Tyr Lys Cys Lys Val Ser Asn Lys Ala
385                 390                 395                 400

Leu Pro Ala Pro Ile Glu Lys Thr Ile Ser Lys Ala Lys Gly Gln Pro
                405                 410                 415

Arg Glu Pro Gln Val Tyr Thr Leu Pro Pro Ser Arg Glu Glu Met Thr
            420                 425                 430

Lys Asn Gln Val Ser Leu Thr Cys Leu Val Lys Gly Phe Tyr Pro Ser
        435                 440                 445

Asp Ile Ala Val Glu Trp Glu Ser Asn Gly Gln Pro Glu Asn Asn Tyr
    450                 455                 460

Lys Thr Thr Pro Pro Val Leu Asp Ser Asp Gly Ser Phe Phe Leu Tyr
465                 470                 475                 480

Ser Lys Leu Thr Val Asp Lys Ser Arg Trp Gln Gln Gly Asn Val Phe
                485                 490                 495

Ser Cys Ser Val Met His Glu Ala Leu His Asn His Tyr Thr Gln Lys
            500                 505                 510

Ser Leu Ser Leu Ser Pro Gly Lys
        515                 520

<210> SEQ ID NO 145
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125
```

Tyr Gln Gly Arg Cys Lys Lys Thr Cys Arg Asp Val Phe Cys Pro Gly
            130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
            180                 185                 190

Thr Cys Leu Leu Gly Arg Ser Ile Gly Leu Ala Tyr Glu Gly Lys Cys
        195                 200                 205

Ile Lys Ala Lys Ser Cys Glu Asp Ile Gln Cys Thr Gly Gly Lys Lys
210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
            260                 265                 270

Ser Gly Val Leu Leu Glu Val Lys His Ser Gly Ser Cys Asn Ser Ile
        275                 280                 285

Ser Thr Gly Gly Gly Thr His Thr Cys Pro Pro Cys Pro Ala Pro Glu
290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
            340                 345                 350

Val Glu Val His Asn Ala Lys Thr Lys Pro Arg Glu Glu Gln Tyr Asn
        355                 360                 365

Ser Thr Tyr Arg Val Val Ser Val Leu Thr Val Leu His Gln Asp Trp
370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Ala Lys Gly Gln Pro Arg Glu
                405                 410                 415

Pro Gln Val Tyr Thr Leu Pro Pro Ser Arg Glu Glu Met Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Asn Gly Gln Pro Glu Asn Asn Tyr Lys Thr
450                 455                 460

Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510

Ser Leu Ser Pro Gly Lys
        515

<210> SEQ ID NO 146
<211> LENGTH: 547

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
290                 295                 300

Gly Val Leu Leu Glu Val Lys His Ser Gly Ser Cys Asn Ser Ile Ser
305                 310                 315                 320

Thr Gly Gly Gly Val Glu Cys Pro Cys Pro Ala Pro Pro Val Ala
                325                 330                 335

Gly Pro Ser Val Phe Leu Phe Pro Pro Lys Pro Lys Asp Thr Leu Met
            340                 345                 350

Ile Ser Arg Thr Pro Glu Val Thr Cys Val Val Val Asp Val Ser His
        355                 360                 365

Glu Asp Pro Glu Val Gln Phe Asn Trp Tyr Val Asp Gly Val Glu Val
370                 375                 380
```

```
His Asn Ala Lys Thr Lys Pro Arg Glu Glu Gln Phe Asn Ser Thr Phe
385                 390                 395                 400

Arg Val Val Ser Val Leu Thr Val Val His Gln Asp Trp Leu Asn Gly
                405                 410                 415

Lys Glu Tyr Lys Cys Lys Val Ser Asn Lys Gly Leu Pro Ala Pro Ile
            420                 425                 430

Glu Lys Thr Ile Ser Lys Thr Lys Gly Gln Pro Arg Glu Pro Gln Val
        435                 440                 445

Tyr Thr Leu Pro Pro Ser Arg Glu Glu Met Thr Lys Asn Gln Val Ser
    450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Met Leu Asp Ser Asp Gly Ser Phe Phe Leu Tyr Ser Lys Leu Thr Val
            500                 505                 510

Asp Lys Ser Arg Trp Gln Gln Gly Asn Val Phe Ser Cys Ser Val Met
        515                 520                 525

His Glu Ala Leu His Asn His Tyr Thr Gln Lys Ser Leu Ser Leu Ser
    530                 535                 540

Pro Gly Lys
545

<210> SEQ ID NO 147
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175
```

```
Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Thr Gly Gly Val Glu Cys Pro Pro Cys Pro Ala Pro
    290                 295                 300

Pro Val Ala Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Gln Phe Asn Trp Tyr Val Asp Gly
            340                 345                 350

Val Glu Val His Asn Ala Lys Thr Lys Pro Arg Glu Glu Gln Phe Asn
        355                 360                 365

Ser Thr Phe Arg Val Val Ser Val Leu Thr Val Val His Gln Asp Trp
    370                 375                 380

Leu Asn Gly Lys Glu Tyr Lys Cys Lys Val Ser Asn Lys Gly Leu Pro
385                 390                 395                 400

Ala Pro Ile Glu Lys Thr Ile Ser Lys Thr Lys Gly Gln Pro Arg Glu
                405                 410                 415

Pro Gln Val Tyr Thr Leu Pro Pro Ser Arg Glu Glu Met Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Asn Gly Gln Pro Glu Asn Asn Tyr Lys Thr
    450                 455                 460

Thr Pro Pro Met Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510

Ser Leu Ser Pro Gly Lys
        515

<210> SEQ ID NO 148
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 148

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Arg Asp Val Phe Cys Pro Gly
130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
            180                 185                 190

Thr Cys Leu Leu Gly Arg Ser Ile Gly Leu Ala Tyr Glu Gly Lys Cys
        195                 200                 205

Ile Lys Ala Lys Ser Cys Glu Asp Ile Gln Cys Thr Gly Gly Lys Lys
210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
            260                 265                 270

Ser Gly Val Leu Leu Glu Val Lys His Ser Gly Ser Cys Asn Ser Ile
        275                 280                 285

Ser Thr Gly Gly Gly Val Glu Cys Pro Pro Cys Pro Ala Pro Pro Val
290                 295                 300

Ala Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Gln Phe Asn Trp Tyr Val Asp Gly Val Glu
            340                 345                 350

Val His Asn Ala Lys Thr Lys Pro Arg Glu Glu Gln Phe Asn Ser Thr
        355                 360                 365

Phe Arg Val Val Ser Val Leu Thr Val Val His Gln Asp Trp Leu Asn
370                 375                 380

Gly Lys Glu Tyr Lys Cys Lys Val Ser Asn Lys Gly Leu Pro Ala Pro
385                 390                 395                 400

```
Ile Glu Lys Thr Ile Ser Lys Thr Lys Gly Gln Pro Arg Glu Pro Gln
                405                 410                 415

Val Tyr Thr Leu Pro Pro Ser Arg Glu Glu Met Thr Lys Asn Gln Val
            420                 425                 430

Ser Leu Thr Cys Leu Val Lys Gly Phe Tyr Pro Ser Asp Ile Ala Val
        435                 440                 445

Glu Trp Glu Ser Asn Gly Gln Pro Glu Asn Asn Tyr Lys Thr Thr Pro
    450                 455                 460

Pro Met Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
            500                 505                 510

Ser Pro Gly Lys
        515

<210> SEQ ID NO 149
<211> LENGTH: 375
<212> TYPE: PRT
<213> ORGANISM: Homo sapiens

<400> SEQUENCE: 149

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240
```

```
Phe Pro Gly Pro Gly Glu Asp Gly Leu Asn Pro Phe Leu Glu Val Lys
            245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
        290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
                355                 360                 365

Val Asp Arg Cys Gly Cys Ser
        370                 375

<210> SEQ ID NO 150
<211> LENGTH: 407
<212> TYPE: PRT
<213> ORGANISM: Homo sapiens

<400> SEQUENCE: 150

Met Val Leu Ala Ala Pro Leu Leu Gly Phe Leu Leu Leu Ala Leu
1               5                   10                  15

Glu Leu Arg Pro Arg Gly Glu Ala Glu Gly Pro Ala Ala Ala Ala
            20                  25                  30

Ala Ala Ala Ala Ala Ala Ala Ala Ala Gly Val Gly Gly Glu Arg Ser
            35                  40                  45

Ser Arg Pro Ala Pro Ser Val Ala Pro Glu Pro Asp Gly Cys Pro Val
        50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Gly Arg Arg His Ile Arg Ile Arg Ser Leu
    210                 215                 220
```

```
Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
            245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
            275                 280                 285

Val Leu Glu Asn Thr Lys Arg Ser Arg Arg Asn Leu Gly Leu Asp Cys
        290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
            325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
            355                 360                 365

Gly Pro Cys Cys Thr Pro Thr Lys Met Ser Pro Ile Asn Met Leu Tyr
370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Tyr Trp Met Gln
1               5

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Ile Tyr Pro Gly Asp Gly Asp Thr Arg Tyr Thr Gln Lys Phe Lys
1               5                   10                  15

Gly

<210> SEQ ID NO 153
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 153

Ala Arg Met Gly Gly Tyr Asp Arg Tyr Tyr Phe Asp Tyr
1               5                   10

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Lys Ser Ser Gln Ser Leu Leu Asn Ser Ala Asn Gln Lys Asn Tyr Leu
1               5                   10                  15

Ala

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Phe Ala Ser Thr Arg Glu Ser
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Gln His Tyr Asn Thr Pro Leu Thr
1               5

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Tyr Thr Phe Thr Ser Tyr Trp Met Gln
1               5                   10

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Ile Tyr Pro Gly Asp Gly Asp Thr
1               5
```

```
<210> SEQ ID NO 159
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Arg Met Gly Gly Tyr Asp Arg Tyr Tyr Phe Asp Tyr
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Lys Ser Ser Gln Ser Leu Leu Asn Ser Ala Asn Gln Lys Asn Tyr Leu
1               5                   10                  15

Ala

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Phe Ala Ser Thr Arg Glu Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Gln His Tyr Asn Thr Pro Leu Thr
1               5

<210> SEQ ID NO 163
<211> LENGTH: 224
<212> TYPE: PRT
<213> ORGANISM: Homo sapiens

<400> SEQUENCE: 163

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80
```

```
Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
            210                 215                 220

<210> SEQ ID NO 164
<211> LENGTH: 546
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
            85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
            130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
            165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205
```

```
Asn Asp Gly Val Thr Tyr Ser Ser Ala Cys His Leu Arg Lys Ala Thr
210                 215                 220
Cys Leu Leu Gly Arg Ser Ile Gly Leu Ala Tyr Glu Gly Lys Cys Ile
225                 230                 235                 240
Lys Ala Lys Ser Cys Glu Asp Ile Gln Cys Thr Gly Lys Lys Cys
                245                 250                 255
Leu Trp Asp Phe Lys Val Gly Arg Gly Arg Cys Ser Leu Cys Asp Glu
                260                 265                 270
Leu Cys Pro Asp Ser Lys Ser Asp Glu Pro Val Cys Ala Ser Asp Asn
                275                 280                 285
Ala Thr Tyr Ala Ser Glu Cys Ala Met Lys Glu Ala Ala Cys Ser Ser
290                 295                 300
Gly Val Leu Leu Glu Val Lys His Ser Gly Ser Cys Asn Thr Gly Gly
305                 310                 315                 320
Gly Thr His Thr Cys Pro Cys Pro Ala Pro Glu Leu Leu Gly Gly
                325                 330                 335
Pro Ser Val Phe Leu Phe Pro Pro Lys Pro Lys Asp Thr Leu Met Ile
                340                 345                 350
Ser Arg Thr Pro Glu Val Thr Cys Val Val Val Asp Val Ser His Glu
                355                 360                 365
Asp Pro Glu Val Lys Phe Asn Trp Tyr Val Asp Gly Val Glu Val His
                370                 375                 380
Asn Ala Lys Thr Lys Pro Arg Glu Glu Gln Tyr Asn Ser Thr Tyr Arg
385                 390                 395                 400
Val Val Ser Val Leu Thr Val Leu His Gln Asp Trp Leu Asn Gly Lys
                405                 410                 415
Glu Tyr Lys Cys Lys Val Ser Asn Lys Ala Leu Pro Ala Pro Ile Glu
                420                 425                 430
Lys Thr Ile Ser Lys Ala Lys Gly Gln Pro Arg Glu Pro Gln Val Tyr
                435                 440                 445
Thr Leu Pro Pro Ser Arg Glu Glu Met Thr Lys Asn Gln Val Ser Leu
                450                 455                 460
Thr Cys Leu Val Lys Gly Phe Tyr Pro Ser Asp Ile Ala Val Glu Trp
465                 470                 475                 480
Glu Ser Asn Gly Gln Pro Glu Asn Asn Tyr Lys Thr Thr Pro Pro Val
                485                 490                 495
Leu Asp Ser Asp Gly Ser Phe Phe Leu Tyr Ser Lys Leu Thr Val Asp
                500                 505                 510
Lys Ser Arg Trp Gln Gln Gly Asn Val Phe Ser Cys Ser Val Met His
                515                 520                 525
Glu Ala Leu His Asn His Tyr Thr Gln Lys Ser Leu Ser Leu Ser Pro
                530                 535                 540
Gly Lys
545

<210> SEQ ID NO 165
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 165

Ala Gly Gly Gly Gly Ser Gly Gly Gly Gly Ser Gly Gly Gly Gly Ser
1               5                   10                  15

Gly Gly Gly Gly Ser Gly
            20

<210> SEQ ID NO 166
<211> LENGTH: 1641
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166

| | | |
|---|---|---|
| atggtccgcg cgaggcacca gccgggtggg ctttgcctcc tgctgctgct gctctgccag | 60 |
| ttcatggagg accgcagtgc ccaggctggg aactgctggc tccgtcaagc gaagaacggc | 120 |
| cgctgccagg tcctgtacaa gaccgaactg agcaaggagg agtgctgcag caccggccgg | 180 |
| ctgagcacct cgtggaccga ggaggacgtg aatgacaaca cactcttcaa gtggatgatt | 240 |
| ttcaacgggg gcgcccccaa ctgcatcccc tgtaaagaaa cgtgtgagaa cgtggactgt | 300 |
| ggacctggga aaaatgccg aatgaacaag aagaacaaac cccgctgcgt ctgcgccccg | 360 |
| gattgttcca acatcacctg gaagggtcca gtctgcgggc tggatgggaa acctaccgc | 420 |
| aatgaatgtg cactcctaaa ggcaagatgt aaagagcagc agaactggaa gtccagtac | 480 |
| caaggcagat gtaaaaagac ttgtcgggat gttttctgtc caggcagctc acatgtgtg | 540 |
| gtggaccaga ccaataatgc ctactgtgtg acctgtaatc ggatttgccc agagcctgct | 600 |
| tcctctgagc aatatctctg tgggaatgat ggagtcacct actccagtgc ctgccacctg | 660 |
| agaaaggcta cctgcctgct gggcagatct attggattag cctatgaggg aaagtgtatc | 720 |
| aaagcaaagt cctgtgaaga tatccagtgc actggtggga aaaaatgttt atgggattc | 780 |
| aaggttggga gaggccggtg ttccctctgt gatgagctgt gccctgacag taagtcggat | 840 |
| gagcctgtct gtgccagtga caatgccact tatgccagcg agtgtgccat gaaggaagct | 900 |
| gcctgctcct caggtgtgct actggaagta agcactccg gatcttgcaa caccggtggt | 960 |
| ggaactcaca catgcccacc gtgcccagca cctgaactcc tgggggggacc gtcagtcttc | 1020 |
| ctcttccccc caaaacccaa ggacaccctc atgatctccc ggacccctga ggtcacatgc | 1080 |
| gtggtggtgg acgtgagcca cgaagaccct gaggtcaagt tcaactggta cgtggacggc | 1140 |
| gtggaggtgc ataatgccaa gacaaagccg cgggaggagc agtacaacag cacgtaccgt | 1200 |
| gtggtcagcg tcctcaccgt cctgcaccag gactggctga atggcaagga gtacaagtgc | 1260 |
| aaggtctcca acaaagccct cccagccccc atcgagaaaa ccatctccaa agccaaaggg | 1320 |
| cagccccgag aaccacaggt gtacaccctg cccccatccc gggaggagat gaccaagaac | 1380 |
| caggtcagcc tgacctgcct ggtcaaaggc ttctatccca gcgacatcgc cgtggagtgg | 1440 |
| gagagcaatg ggcagccgga gaacaactac aagaccacgc ctcccgtgct ggactccgac | 1500 |
| ggctccttct cctctatag caagctcacc gtggacaaga gcaggtggca gcaggggaac | 1560 |
| gtcttctcat gctccgtgat gcatgaggct ctgcacaacc actacacgca gaagagcctc | 1620 |
| tccctgtctc cgggtaaatg a | 1641 |

<210> SEQ ID NO 167
<211> LENGTH: 120

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Met Gly Gly Tyr Asp Arg Tyr Tyr Phe Asp Tyr Trp Gly Gln
            100                 105                 110

Gly Thr Thr Leu Thr Val Ser Ser
        115                 120

<210> SEQ ID NO 168
<211> LENGTH: 329
<212> TYPE: PRT
<213> ORGANISM: Homo sapiens

<400> SEQUENCE: 168

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 169
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Gly Gly Ser Gly Gly Gly Ser Gly Gly Gly Ser Gly Gly
1               5                   10                  15

Gly Gly Ser Gly
            20

<210> SEQ ID NO 170
<211> LENGTH: 162
<212> TYPE: PRT
<213> ORGANISM: Homo sapiens

<400> SEQUENCE: 170

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr Asn Thr Ser Asn
145                 150                 155                 160
```

Pro Asp

<210> SEQ ID NO 171
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Thr Gly Gly Gly Gly Ser Gly
                325                 330                 335

Gly Gly Gly Ser Gly Gly Gly Gly Ser Gly Gly Gly Gly Ser Thr Ile
            340                 345                 350
```

```
Pro Pro His Val Gln Lys Ser Asp Val Glu Met Glu Ala Gln Lys Asp
            355                 360                 365

Glu Ile Ile Cys Pro Ser Cys Asn Arg Thr Ala His Pro Leu Arg His
370                 375                 380

Ile Asn Asp Met Ile Val Thr Asp Asn Asn Gly Ala Val Lys Phe
385                 390                 395                 400

Pro Gln Leu Cys Lys Phe Cys Asp Val Arg Phe Ser Thr Cys Asp Asn
                405                 410                 415

Gln Lys Ser Cys Met Ser Asn Cys Ser Ile Thr Ser Ile Cys Glu Lys
                420                 425                 430

Pro Gln Glu Val Cys Val Ala Val Trp Arg Lys Asn Asp Glu Asn Ile
            435                 440                 445

Thr Leu Glu Thr Val Cys His Asp Pro Lys Leu Pro Tyr His Asp Phe
        450                 455                 460

Ile Leu Glu Asp Ala Ala Ser Pro Lys Cys Ile Met Lys Glu Lys Lys
465                 470                 475                 480

Lys Pro Gly Glu Thr Phe Phe Met Cys Ser Cys Ser Ser Asp Glu Cys
                485                 490                 495

Asn Asp Asn Ile Ile Phe Ser Glu Glu Tyr Asn Thr Ser Asn Pro Asp
                500                 505                 510

<210> SEQ ID NO 172
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Met Gly Gly Tyr Asp Arg Tyr Tyr Phe Asp Tyr Trp Gly Gln
                100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Gly Gln Pro Arg Glu Pro Gln Val Tyr Thr
                340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Thr Gly Gly Gly Gly Ser Gly Gly Gly Gly Ser Gly Gly Gly Gly Ser
            450                 455                 460
Gly Gly Gly Gly Ser Thr Ile Pro Pro His Val Gln Lys Ser Asp Val
465                 470                 475                 480
Glu Met Glu Ala Gln Lys Asp Glu Ile Ile Cys Pro Ser Cys Asn Arg
                485                 490                 495
Thr Ala His Pro Leu Arg His Ile Asn Asn Asp Met Ile Val Thr Asp
                500                 505                 510
Asn Asn Gly Ala Val Lys Phe Pro Gln Leu Cys Lys Phe Cys Asp Val
            515                 520                 525
Arg Phe Ser Thr Cys Asp Asn Gln Lys Ser Cys Met Ser Asn Cys Ser
530                 535                 540
Ile Thr Ser Ile Cys Glu Lys Pro Gln Glu Val Cys Val Ala Val Trp
545                 550                 555                 560
Arg Lys Asn Asp Glu Asn Ile Thr Leu Glu Thr Val Cys His Asp Pro
                565                 570                 575
Lys Leu Pro Tyr His Asp Phe Ile Leu Glu Asp Ala Ala Ser Pro Lys
                580                 585                 590
Cys Ile Met Lys Glu Lys Lys Pro Gly Glu Thr Phe Phe Met Cys
            595                 600                 605
Ser Cys Ser Ser Asp Glu Cys Asn Asp Asn Ile Ile Phe Ser Glu Glu
610                 615                 620
```

```
Tyr Asn Thr Ser Asn Pro Asp
625                 630

<210> SEQ ID NO 173
<211> LENGTH: 651
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Gly Trp Ser Cys Ile Met Leu Phe Leu Ala Ala Thr Ala Thr Gly
1               5                   10                  15

Ala His Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Ser Tyr Trp Met Gln Trp Val Lys Gln Arg Pro Gly Gln Gly Leu
    50                  55                  60

Glu Trp Ile Gly Ala Ile Tyr Pro Gly Asp Gly Asp Thr Arg Tyr Thr
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Ala Ser Glu Asp Ser Ala Val
            100                 105                 110

Tyr Tyr Cys Ala Arg Met Gly Gly Tyr Asp Arg Tyr Tyr Phe Asp Tyr
        115                 120                 125

Trp Gly Gln Gly Thr Thr Leu Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350
```

```
Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Thr Gly Gly Gly Ser Gly Gly Gly Ser Gly
465                 470                 475                 480

Gly Gly Ser Gly Gly Gly Ser Thr Ile Pro Pro His Val Gln
                485                 490                 495

Lys Ser Asp Val Glu Met Glu Ala Gln Lys Asp Glu Ile Ile Cys Pro
            500                 505                 510

Ser Cys Asn Arg Thr Ala His Pro Leu Arg His Ile Asn Asn Asp Met
        515                 520                 525

Ile Val Thr Asp Asn Asn Gly Ala Val Lys Phe Pro Gln Leu Cys Lys
        530                 535                 540

Phe Cys Asp Val Arg Phe Ser Thr Cys Asp Asn Gln Lys Ser Cys Met
545                 550                 555                 560

Ser Asn Cys Ser Ile Thr Ser Ile Cys Glu Lys Pro Gln Glu Val Cys
                565                 570                 575

Val Ala Val Trp Arg Lys Asn Asp Glu Asn Ile Thr Leu Glu Thr Val
            580                 585                 590

Cys His Asp Pro Lys Leu Pro Tyr His Asp Phe Ile Leu Glu Asp Ala
        595                 600                 605

Ala Ser Pro Lys Cys Ile Met Lys Glu Lys Lys Pro Gly Glu Thr
        610                 615                 620

Phe Phe Met Cys Ser Cys Ser Ser Asp Glu Cys Asn Asp Asn Ile Ile
625                 630                 635                 640

Phe Ser Glu Glu Tyr Asn Thr Ser Asn Pro Asp
                645                 650

<210> SEQ ID NO 174
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ala Asn Gln Lys Asn Tyr Leu Ala Trp Tyr Gln Gln Lys Pro Gly Gln
        35                  40                  45
```

-continued

```
Ser Pro Lys Leu Leu Val Tyr Phe Ala Ser Thr Arg Glu Ser Gly Val
         50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
             85                  90                  95

His Tyr Asn Thr Pro Leu Thr Phe Gly Ala Gly Thr Lys Leu Glu Leu
            100                 105                 110

Lys

<210> SEQ ID NO 175
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 176
<211> LENGTH: 19
<212> TYPE: PRT
<213> ORGANISM: Unknown
<220> FEATURE:
<223> OTHER INFORMATION: Description of Unknown:
      Leader sequence

<400> SEQUENCE: 176

Met Gly Trp Ser Cys Ile Met Leu Phe Leu Ala Ala Thr Ala Thr Gly
1               5                   10                  15

Ala His Ser

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Asp Tyr Lys Asp Asp Asp Asp Lys
1               5

<210> SEQ ID NO 178
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 178

His His His His His His
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Tyr Pro Tyr Asp Val Pro Asp Tyr Ala
1               5

<210> SEQ ID NO 180
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220
```

```
Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
            245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Thr Gly Gly Gly Thr His Thr Cys Pro Pro Cys Pro Ala Pro Glu Leu
        290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
            325                 330                 335

Ser His Glu Asp Pro Glu Val Lys Phe Asn Trp Tyr Val Asp Gly Val
            340                 345                 350

Glu Val His Asn Ala Lys Thr Lys Pro Arg Glu Glu Gln Tyr Asn Ser
        355                 360                 365

Thr Tyr Arg Val Val Ser Val Leu Thr Val Leu His Gln Asp Trp Leu
        370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
            405                 410                 415

Gln Val Tyr Thr Leu Pro Pro Ser Arg Glu Glu Met Thr Lys Asn Gln
            420                 425                 430

Val Ser Leu Thr Cys Leu Val Lys Gly Phe Tyr Pro Ser Asp Ile Ala
        435                 440                 445

Val Glu Trp Glu Ser Asn Gly Gln Pro Glu Asn Asn Tyr Lys Thr Thr
450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
            485                 490                 495

Val Met His Glu Ala Leu His Asn His Tyr Thr Gln Lys Ser Leu Ser
            500                 505                 510

Leu Ser Pro Gly Lys Ala Gly Gly Gly Ser Gly Gly Gly Gly Gly Ser
        515                 520                 525

Gly Gly Gly Gly Ser Gly Gly Gly Gly Ser Gly Thr Ile Pro Pro His
        530                 535                 540

Val Gln Lys Ser Asp Val Glu Met Glu Ala Gln Lys Asp Glu Ile Ile
545                 550                 555                 560

Cys Pro Ser Cys Asn Arg Thr Ala His Pro Leu Arg His Ile Asn Asn
            565                 570                 575

Asp Met Ile Val Thr Asp Asn Asn Gly Ala Val Lys Phe Pro Gln Leu
            580                 585                 590

Cys Lys Phe Cys Asp Val Arg Phe Ser Thr Cys Asp Asn Gln Lys Ser
        595                 600                 605

Cys Met Ser Asn Cys Ser Ile Thr Ser Ile Cys Glu Lys Pro Gln Glu
        610                 615                 620

Val Cys Val Ala Val Trp Arg Lys Asn Asp Glu Asn Ile Thr Leu Glu
625                 630                 635                 640
```

```
Thr Val Cys His Asp Pro Lys Leu Pro Tyr His Asp Phe Ile Leu Glu
            645                 650                 655

Asp Ala Ala Ser Pro Lys Cys Ile Met Lys Glu Lys Lys Pro Gly
            660                 665                 670

Glu Thr Phe Phe Met Cys Ser Cys Ser Ser Asp Glu Cys Asn Asp Asn
            675                 680                 685

Ile Ile Phe Ser Glu Glu Tyr Asn Thr Ser Asn Pro Asp
            690                 695                 700

<210> SEQ ID NO 181
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
        50                  55                  60

Thr Cys Glu Asn Val Asp Cys Gly Pro Gly Lys Lys Cys Arg Met Asn
65              70                  75                  80

Lys Lys Asn Lys Pro Arg Cys Val Cys Ala Pro Asp Cys Ser Asn Ile
            85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
        130                 135                 140

Pro Gly Ser Ser Thr Cys Val Val Asp Gln Thr Asn Asn Ala Tyr Cys
145             150                 155                 160

Val Thr Cys Asn Arg Ile Cys Pro Glu Pro Ala Ser Ser Glu Gln Tyr
            165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
            195                 200                 205

Lys Cys Ile Lys Ala Lys Ser Cys Glu Asp Ile Gln Cys Thr Gly Gly
        210                 215                 220

Lys Lys Cys Leu Trp Asp Phe Lys Val Gly Arg Gly Arg Cys Ser Leu
225             230                 235                 240

Cys Asp Glu Leu Cys Pro Asp Ser Lys Ser Asp Glu Pro Val Cys Ala
            245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
            275                 280                 285
```

```
Thr Gly Gly Gly Thr His Thr Cys Pro Pro Cys Pro Ala Pro Glu Leu
    290                 295                 300
Leu Gly Gly Pro Ser Val Phe Leu Phe Pro Pro Lys Pro Lys Asp Thr
305                 310                 315                 320
Leu Met Ile Ser Arg Thr Pro Glu Val Thr Cys Val Val Val Asp Val
                325                 330                 335
Ser His Glu Asp Pro Glu Val Lys Phe Asn Trp Tyr Val Asp Gly Val
            340                 345                 350
Glu Val His Asn Ala Lys Thr Lys Pro Arg Glu Glu Gln Tyr Asn Ser
        355                 360                 365
Thr Tyr Arg Val Val Ser Val Leu Thr Val Leu His Gln Asp Trp Leu
    370                 375                 380
Asn Gly Lys Glu Tyr Lys Cys Lys Val Ser Asn Lys Ala Leu Pro Ala
385                 390                 395                 400
Pro Ile Glu Lys Thr Ile Ser Lys Ala Lys Gly Gln Pro Arg Glu Pro
                405                 410                 415
Gln Val Tyr Thr Leu Pro Pro Ser Arg Glu Glu Met Thr Lys Asn Gln
            420                 425                 430
Val Ser Leu Thr Cys Leu Val Lys Gly Phe Tyr Pro Ser Asp Ile Ala
        435                 440                 445
Val Glu Trp Glu Ser Asn Gly Gln Pro Glu Asn Asn Tyr Lys Thr Thr
    450                 455                 460
Pro Pro Val Leu Asp Ser Asp Gly Ser Phe Phe Leu Tyr Ser Lys Leu
465                 470                 475                 480
Thr Val Asp Lys Ser Arg Trp Gln Gln Gly Asn Val Phe Ser Cys Ser
                485                 490                 495
Val Met His Glu Ala Leu His Asn His Tyr Thr Gln Lys Ser Leu Ser
            500                 505                 510
Leu Ser Pro Gly Ala Gly Gly Gly Ser Gly Gly Gly Ser Gly
        515                 520                 525
Gly Gly Gly Ser Gly Gly Gly Ser Gly Thr Ile Pro Pro His Val
    530                 535                 540
Gln Lys Ser Asp Val Glu Met Glu Ala Gln Lys Asp Glu Ile Ile Cys
545                 550                 555                 560
Pro Ser Cys Asn Arg Thr Ala His Pro Leu Arg His Ile Asn Asn Asp
                565                 570                 575
Met Ile Val Thr Asp Asn Asn Gly Ala Val Lys Phe Pro Gln Leu Cys
            580                 585                 590
Lys Phe Cys Asp Val Arg Phe Ser Thr Cys Asp Asn Gln Lys Ser Cys
        595                 600                 605
Met Ser Asn Cys Ser Ile Thr Ser Ile Cys Glu Lys Pro Gln Glu Val
    610                 615                 620
Cys Val Ala Val Trp Arg Lys Asn Asp Glu Asn Ile Thr Leu Glu Thr
625                 630                 635                 640
Val Cys His Asp Pro Lys Leu Pro Tyr His Asp Phe Ile Leu Glu Asp
                645                 650                 655
Ala Ala Ser Pro Lys Cys Ile Met Lys Glu Lys Lys Pro Gly Glu
            660                 665                 670
Thr Phe Phe Met Cys Ser Cys Ser Ser Asp Glu Cys Asn Asp Asn Ile
        675                 680                 685
Ile Phe Ser Glu Glu Tyr Asn Thr Ser Asn Pro Asp
    690                 695                 700
```

<210> SEQ ID NO 182
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ala Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asn Thr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 183
<211> LENGTH: 550
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

Met Asp Ala Met Lys Arg Gly Leu Cys Cys Val Leu Leu Leu Cys Gly
1               5                   10                  15

Ala Val Phe Val Ser Pro Gly Ala Ile Leu Gly Arg Ser Glu Thr Gln
            20                  25                  30

Glu Cys Leu Phe Phe Asn Ala Asn Trp Glu Lys Asp Arg Thr Asn Gln
        35                  40                  45

Thr Gly Val Glu Pro Cys Tyr Gly Asp Lys Asp Lys Arg Arg His Cys
    50                  55                  60

Phe Ala Thr Trp Lys Asn Ile Ser Gly Ser Ile Glu Ile Val Lys Gln
65                  70                  75                  80

-continued

```
Gly Cys Trp Leu Asp Asp Ile Asn Cys Tyr Asp Arg Thr Asp Cys Val
                85                  90                  95
Glu Lys Lys Asp Ser Pro Glu Val Tyr Phe Cys Cys Glu Gly Asn
            100                 105                 110
Met Cys Asn Glu Lys Phe Ser Tyr Phe Pro Glu Met Glu Val Thr Gln
        115                 120                 125
Pro Thr Ser Asn Pro Val Thr Pro Lys Pro Pro Gly Gly Gly Thr His
    130                 135                 140
Thr Cys Pro Pro Cys Pro Ala Pro Glu Leu Leu Gly Gly Pro Ser Val
145                 150                 155                 160
Phe Leu Phe Pro Pro Lys Pro Lys Asp Thr Leu Met Ile Ser Arg Thr
                165                 170                 175
Pro Glu Val Thr Cys Val Val Val Asp Val Ser His Glu Asp Pro Glu
            180                 185                 190
Val Lys Phe Asn Trp Tyr Val Asp Gly Val Glu Val His Asn Ala Lys
        195                 200                 205
Thr Lys Pro Arg Glu Glu Gln Tyr Asn Ser Thr Tyr Arg Val Val Ser
    210                 215                 220
Val Leu Thr Val Leu His Gln Asp Trp Leu Asn Gly Lys Glu Tyr Lys
225                 230                 235                 240
Cys Lys Val Ser Asn Lys Ala Leu Pro Ala Pro Ile Glu Lys Thr Ile
                245                 250                 255
Ser Lys Ala Lys Gly Gln Pro Arg Glu Pro Gln Val Tyr Thr Leu Pro
            260                 265                 270
Pro Ser Arg Glu Glu Met Thr Lys Asn Gln Val Ser Leu Thr Cys Leu
        275                 280                 285
Val Lys Gly Phe Tyr Pro Ser Asp Ile Ala Val Glu Trp Glu Ser Asn
    290                 295                 300
Gly Gln Pro Glu Asn Asn Tyr Lys Thr Thr Pro Pro Val Leu Asp Ser
305                 310                 315                 320
Asp Gly Ser Phe Phe Leu Tyr Ser Lys Leu Thr Val Asp Lys Ser Arg
                325                 330                 335
Trp Gln Gln Gly Asn Val Phe Ser Cys Ser Val Met His Glu Ala Leu
            340                 345                 350
His Asn His Tyr Thr Gln Lys Ser Leu Ser Leu Ser Pro Gly Ala Gly
        355                 360                 365
Gly Gly Gly Ser Gly Gly Gly Ser Gly Gly Gly Ser Gly
    370                 375                 380
Gly Gly Ser Gly Thr Ile Pro Pro His Val Gln Lys Ser Asp Val Glu
385                 390                 395                 400
Met Glu Ala Gln Lys Asp Glu Ile Ile Cys Pro Ser Cys Asn Arg Thr
                405                 410                 415
Ala His Pro Leu Arg His Ile Asn Asn Asp Met Ile Val Thr Asp Asn
            420                 425                 430
Asn Gly Ala Val Lys Phe Pro Gln Leu Cys Lys Phe Cys Asp Val Arg
        435                 440                 445
Phe Ser Thr Cys Asp Asn Gln Lys Ser Cys Met Ser Asn Cys Ser Ile
    450                 455                 460
Thr Ser Ile Cys Glu Lys Pro Gln Glu Val Cys Val Ala Val Trp Arg
465                 470                 475                 480
Lys Asn Asp Glu Asn Ile Thr Leu Glu Thr Val Cys His Asp Pro Lys
                485                 490                 495
```

```
Leu Pro Tyr His Asp Phe Ile Leu Glu Asp Ala Ala Ser Pro Lys Cys
            500                 505                 510

Ile Met Lys Glu Lys Lys Pro Gly Glu Thr Phe Phe Met Cys Ser
        515                 520                 525

Cys Ser Ser Asp Glu Cys Asn Asp Asn Ile Ile Phe Ser Glu Glu Tyr
    530                 535                 540

Asn Thr Ser Asn Pro Asp
545                 550

<210> SEQ ID NO 184
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Asp Ala Met Lys Arg Gly Leu Cys Cys Val Leu Leu Leu Cys Gly
1               5                   10                  15

Ala Val Phe Val Ser Pro Gly Ala Ile Leu Gly Arg Ser Glu Thr Gln
            20                  25                  30

Glu Cys Leu Phe Phe Asn Ala Asn Trp Glu Lys Asp Arg Thr Asn Gln
        35                  40                  45

Thr Gly Val Glu Pro Cys Tyr Gly Asp Lys Asp Lys Arg Arg His Cys
    50                  55                  60

Phe Ala Thr Trp Lys Asn Ile Ser Gly Ser Ile Glu Ile Val Lys Gln
65                  70                  75                  80

Gly Cys Trp Leu Asp Asp Ile Asn Cys Tyr Asp Arg Thr Asp Cys Val
                85                  90                  95

Glu Lys Lys Asp Ser Pro Glu Val Tyr Phe Cys Cys Cys Glu Gly Asn
            100                 105                 110

Met Cys Asn Glu Lys Phe Ser Tyr Phe Pro Glu Met Glu Val Thr Gln
        115                 120                 125

Pro Thr Ser Asn Pro Val Thr Pro Lys Pro Pro Gly Gly Gly Thr His
    130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Cys Arg Glu Glu Met Thr Lys Asn Gln Val Ser Leu Trp Cys Leu
        275                 280                 285
```

Val Lys Gly Phe Tyr Pro Ser Asp Ile Ala Val Glu Trp Glu Ser Asn
290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
            325                 330                 335

Trp Gln Gln Gly Asn Val Phe Ser Cys Ser Val Met His Glu Ala Leu
        340                 345                 350

His Asn His Tyr Thr Gln Lys Ser Leu Ser Leu Ser Pro Gly Ala Gly
    355                 360                 365

Gly Gly Gly Ser Gly Gly Gly Gly Ser Gly Gly Gly Gly Ser Gly Gly
370                 375                 380

Gly Gly Ser Gly Thr Ile Pro Pro His Val Gln Lys Ser Asp Val Glu
385                 390                 395                 400

Met Glu Ala Gln Lys Asp Glu Ile Ile Cys Pro Ser Cys Asn Arg Thr
            405                 410                 415

Ala His Pro Leu Arg His Ile Asn Asn Asp Met Ile Val Thr Asp Asn
        420                 425                 430

Asn Gly Ala Val Lys Phe Pro Gln Leu Cys Lys Phe Cys Asp Val Arg
    435                 440                 445

Phe Ser Thr Cys Asp Asn Gln Lys Ser Cys Met Ser Asn Cys Ser Ile
450                 455                 460

Thr Ser Ile Cys Glu Lys Pro Gln Glu Val Cys Val Ala Val Trp Arg
465                 470                 475                 480

Lys Asn Asp Glu Asn Ile Thr Leu Glu Thr Val Cys His Asp Pro Lys
            485                 490                 495

Leu Pro Tyr His Asp Phe Ile Leu Glu Asp Ala Ala Ser Pro Lys Cys
        500                 505                 510

Ile Met Lys Glu Lys Lys Pro Gly Glu Thr Phe Phe Met Cys Ser
    515                 520                 525

Cys Ser Ser Asp Glu Cys Asn Asp Asn Ile Ile Phe Ser Glu Glu Tyr
530                 535                 540

Asn Thr Ser Asn Pro Asp
545                 550

<210> SEQ ID NO 185
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Asp Ala Met Lys Arg Gly Leu Cys Cys Val Leu Leu Leu Cys Gly
1               5                   10                  15

Ala Val Phe Val Ser Pro Gly Ala Ser Asn Thr Lys Val Asp Lys Arg
            20                  25                  30

Val Thr Gly Gly Gly Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

-continued

```
Val Ser His Glu Asp Pro Glu Val Lys Phe Asn Trp Tyr Val Asp Gly
                85                  90                  95
Val Glu Val His Asn Ala Lys Thr Lys Pro Arg Glu Glu Gln Tyr Asn
            100                 105                 110
Ser Thr Tyr Arg Val Val Ser Val Leu Thr Val Leu His Gln Asp Trp
        115                 120                 125
Leu Asn Gly Lys Glu Tyr Lys Cys Lys Val Ser Asn Lys Ala Leu Pro
    130                 135                 140
Ala Pro Ile Glu Lys Thr Ile Ser Lys Ala Lys Gly Gln Pro Arg Glu
145                 150                 155                 160
Pro Gln Val Cys Thr Leu Pro Pro Ser Arg Glu Glu Met Thr Lys Asn
                165                 170                 175
Gln Val Ser Leu Ser Cys Ala Val Lys Gly Phe Tyr Pro Ser Asp Ile
            180                 185                 190
Ala Val Glu Trp Glu Ser Asn Gly Gln Pro Glu Asn Asn Tyr Lys Thr
        195                 200                 205
Thr Pro Pro Val Leu Asp Ser Asp Gly Ser Phe Phe Leu Val Ser Lys
    210                 215                 220
Leu Thr Val Asp Lys Ser Arg Trp Gln Gln Gly Asn Val Phe Ser Cys
225                 230                 235                 240
Ser Val Met His Glu Ala Leu His Asn His Tyr Thr Gln Lys Ser Leu
                245                 250                 255
Ser Leu Ser Pro Gly Ala Gly Gly Gly Ser Gly Gly Gly Gly Ser
            260                 265                 270
Gly Gly Gly Gly Ser Gly Gly Gly Ser Gly Thr Ile Pro Pro His
        275                 280                 285
Val Gln Lys Ser Asp Val Glu Met Glu Ala Gln Lys Asp Glu Ile Ile
    290                 295                 300
Cys Pro Ser Cys Asn Arg Thr Ala His Pro Leu Arg His Ile Asn Asn
305                 310                 315                 320
Asp Met Ile Val Thr Asp Asn Asn Gly Ala Val Lys Phe Pro Gln Leu
                325                 330                 335
Cys Lys Phe Cys Asp Val Arg Phe Ser Thr Cys Asp Asn Gln Lys Ser
            340                 345                 350
Cys Met Ser Asn Cys Ser Ile Thr Ser Ile Cys Glu Lys Pro Gln Glu
        355                 360                 365
Val Cys Val Ala Val Trp Arg Lys Asn Asp Glu Asn Ile Thr Leu Glu
    370                 375                 380
Thr Val Cys His Asp Pro Lys Leu Pro Tyr His Asp Phe Ile Leu Glu
385                 390                 395                 400
Asp Ala Ala Ser Pro Lys Cys Ile Met Lys Glu Lys Lys Lys Pro Gly
                405                 410                 415
Glu Thr Phe Phe Met Cys Ser Cys Ser Ser Asp Glu Cys Asn Asp Asn
            420                 425                 430
Ile Ile Phe Ser Glu Glu Tyr Asn Thr Ser Asn Pro Asp
        435                 440                 445
```

<210> SEQ ID NO 186

<400> SEQUENCE: 186

000

<210> SEQ ID NO 187

```
<400> SEQUENCE: 187

000

<210> SEQ ID NO 188

<400> SEQUENCE: 188

000

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Asn Thr Lys Val Asp Lys Arg Val
1               5

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30
```

```
Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
            210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Ala Gly Gly Gly Ser Gly Gly Gly
            340                 345                 350

Ser Gly Gly Gly Ser Gly Gly Gly Ser Gly Thr Ile Pro Pro
            355                 360                 365

His Val Gln Lys Ser Asp Val Glu Met Glu Ala Gln Lys Asp Glu Ile
            370                 375                 380

Ile Cys Pro Ser Cys Asn Arg Thr Ala His Pro Leu Arg His Ile Asn
385                 390                 395                 400

Asn Asp Met Ile Val Thr Asp Asn Asn Gly Ala Val Lys Phe Pro Gln
                405                 410                 415

Leu Cys Lys Phe Cys Asp Val Arg Phe Ser Thr Cys Asp Asn Gln Lys
            420                 425                 430

Ser Cys Met Ser Asn Cys Ser Ile Thr Ser Ile Cys Glu Lys Pro Gln
            435                 440                 445
```

Glu Val Cys Val Ala Val Trp Arg Lys Asn Asp Glu Asn Ile Thr Leu
450                 455                 460

Glu Thr Val Cys His Asp Pro Lys Leu Pro Tyr His Asp Phe Ile Leu
465                 470                 475                 480

Glu Asp Ala Ala Ser Pro Lys Cys Ile Met Lys Glu Lys Lys Pro
                485                 490                 495

Gly Glu Thr Phe Phe Met Cys Ser Cys Ser Ser Asp Glu Cys Asn Asp
                500                 505                 510

Asn Ile Ile Phe Ser Glu Glu Tyr Asn Thr Ser Asn Pro Asp
                515                 520                 525

<210> SEQ ID NO 196
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro Gly Gly Gly Thr His Thr Cys Pro Pro Cys Pro Ala Pro
                115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
                180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
        210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Lys
                245                 250                 255

Asn Gln Val Ser Leu Trp Cys Leu Val Lys Gly Phe Tyr Pro Ser Asp
                260                 265                 270

Ile Ala Val Glu Trp Glu Ser Asn Gly Gln Pro Glu Asn Asn Tyr Lys
                275                 280                 285

```
Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Ala Gly Gly Gly Ser Gly Gly Gly Gly
            340                 345                 350

Ser Gly Gly Gly Gly Ser Gly Gly Gly Ser Gly Thr Ile Pro Pro
                355                 360                 365

His Val Gln Lys Ser Asp Val Glu Met Glu Ala Gln Lys Asp Glu Ile
    370                 375                 380

Ile Cys Pro Ser Cys Asn Arg Thr Ala His Pro Leu Arg His Ile Asn
385                 390                 395                 400

Asn Asp Met Ile Val Thr Asp Asn Asn Gly Ala Val Lys Phe Pro Gln
                405                 410                 415

Leu Cys Lys Phe Cys Asp Val Arg Phe Ser Thr Cys Asp Asn Gln Lys
            420                 425                 430

Ser Cys Met Ser Asn Cys Ser Ile Thr Ser Ile Cys Glu Lys Pro Gln
                435                 440                 445

Glu Val Cys Val Ala Val Trp Arg Lys Asn Asp Glu Asn Ile Thr Leu
450                 455                 460

Glu Thr Val Cys His Asp Pro Lys Leu Pro Tyr His Asp Phe Ile Leu
465                 470                 475                 480

Glu Asp Ala Ala Ser Pro Lys Cys Ile Met Lys Glu Lys Lys Pro
                485                 490                 495

Gly Glu Thr Phe Phe Met Cys Ser Cys Ser Ser Asp Glu Cys Asn Asp
                500                 505                 510

Asn Ile Ile Phe Ser Glu Glu Tyr Asn Thr Ser Asn Pro Asp
                515                 520                 525

<210> SEQ ID NO 197
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Asn Thr Lys Val Asp Lys Arg Val Thr Gly Gly Gly Thr His Thr Cys
1               5                   10                  15

Pro Pro Cys Pro Ala Pro Glu Leu Leu Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110
```

```
Val Ser Asn Lys Ala Leu Pro Ala Pro Ile Glu Lys Thr Ile Ser Lys
        115                 120                 125

Ala Lys Gly Gln Pro Arg Glu Pro Gln Val Cys Thr Leu Pro Pro Ser
        130                 135                 140

Arg Glu Glu Met Thr Lys Asn Gln Val Ser Leu Ser Cys Ala Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
                180                 185                 190

Ser Phe Phe Leu Val Ser Lys Leu Thr Val Asp Lys Ser Arg Trp Gln
                195                 200                 205

Gln Gly Asn Val Phe Ser Cys Ser Val Met His Glu Ala Leu His Asn
        210                 215                 220

His Tyr Thr Gln Lys Ser Leu Ser Leu Ser Pro Gly Ala Gly Gly Gly
225                 230                 235                 240

Gly Ser Gly Gly Gly Gly Ser Gly Gly Gly Gly Ser Gly Gly Gly Gly
                245                 250                 255

Ser Gly Thr Ile Pro Pro His Val Gln Lys Ser Asp Val Glu Met Glu
        260                 265                 270

Ala Gln Lys Asp Glu Ile Ile Cys Pro Ser Cys Asn Arg Thr Ala His
        275                 280                 285

Pro Leu Arg His Ile Asn Asn Asp Met Ile Val Thr Asp Asn Asn Gly
        290                 295                 300

Ala Val Lys Phe Pro Gln Leu Cys Lys Phe Cys Asp Val Arg Phe Ser
305                 310                 315                 320

Thr Cys Asp Asn Gln Lys Ser Cys Met Ser Asn Cys Ser Ile Thr Ser
                325                 330                 335

Ile Cys Glu Lys Pro Gln Glu Val Cys Val Ala Val Trp Arg Lys Asn
                340                 345                 350

Asp Glu Asn Ile Thr Leu Glu Thr Val Cys His Asp Pro Lys Leu Pro
                355                 360                 365

Tyr His Asp Phe Ile Leu Glu Asp Ala Ala Ser Pro Lys Cys Ile Met
        370                 375                 380

Lys Glu Lys Lys Lys Pro Gly Glu Thr Phe Phe Met Cys Ser Cys Ser
385                 390                 395                 400

Ser Asp Glu Cys Asn Asp Asn Ile Ile Phe Ser Glu Glu Tyr Asn Thr
                405                 410                 415

Ser Asn Pro Asp
        420

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 198

Gly Gly Gly Gly Ser Gly Gly Gly Gly Ser
1               5                   10
```

```
<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 199

Gly Gly Gly Gly Ser Gly Gly Gly Ser Gly Gly Gly Gly Ser
1               5                   10                  15

<210> SEQ ID NO 200
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 200

Gly Gly Gly Gly Ser Gly Gly Gly Gly Ser Gly Gly Gly Gly Ser Gly
1               5                   10                  15

Gly Gly Gly Ser
            20

<210> SEQ ID NO 201
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units
<220> FEATURE:
<223> OTHER INFORMATION: See specification as filed for detailed
      description of substitutions and preferred embodiments

<400> SEQUENCE: 201

Gly Gly Gly Gly Ser Gly Gly Gly Gly Ser Gly Gly Gly Gly Ser Gly
1               5                   10                  15

Gly Gly Gly Ser
            20

<210> SEQ ID NO 202
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Gly Gly Gly Ser Gly Gly Gly Gly Ser Gly Gly Gly Gly Ser Gly
1               5                   10                  15

Gly Gly Gly Ser Gly
            20
```

```
<210> SEQ ID NO 203
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Gly Gly Ser Gly Gly Gly Ser Gly Gly Gly Gly Ser Gly
1               5                   10                  15

Gly Gly Gly Ser
            20

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 204

Gly Gly Gly Gly Ser
1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Gly Gly Gly Ser
1               5

<210> SEQ ID NO 206
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asn Thr Ser Asn Pro Asp Thr Gly Gly Gly Thr His Thr Cys Pro Pro
1               5                   10                  15

Cys

<210> SEQ ID NO 207
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asn Thr Ser Asn Pro Asp Thr Gly Gly Gly Gly Ser Gly Gly Gly Gly
1               5                   10                  15

Ser Thr His Thr Cys Pro Pro Cys
            20
```

<210> SEQ ID NO 208
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asn Thr Ser Asn Pro Asp Thr Gly Gly Gly Ser Gly Gly Gly Gly
1               5                   10                  15

Ser Gly Gly Gly Gly Ser Thr His Thr Cys Pro Pro Cys
            20                  25

<210> SEQ ID NO 209
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Asn Thr Ser Asn Pro Asp Thr Gly Gly Gly Ser Gly Gly Gly Gly
1               5                   10                  15

Ser Gly Gly Gly Gly Ser Gly Gly Gly Gly Ser Thr His Thr Cys Pro
            20                  25                  30

Pro Cys

<210> SEQ ID NO 210
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asn Thr Ser Asn Pro Asp Thr Gly Gly Gly Pro Lys Ser Cys Asp Lys
1               5                   10                  15

Thr His Thr Cys Pro Pro Cys
            20

<210> SEQ ID NO 211
<211> LENGTH: 225
<212> TYPE: PRT
<213> ORGANISM: Homo sapiens

<400> SEQUENCE: 211

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

-continued

```
Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 212
<211> LENGTH: 115
<212> TYPE: PRT
<213> ORGANISM: Homo sapiens

<400> SEQUENCE: 212

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 213
<211> LENGTH: 115
<212> TYPE: PRT
<213> ORGANISM: Mus musculus

<400> SEQUENCE: 213

Ile Leu Gly Arg Ser Glu Thr Gln Glu Cys Leu Phe Phe Asn Ala Asn
1               5                   10                  15

Trp Glu Arg Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60
```

```
Cys Tyr Asp Arg Thr Asp Cys Ile Glu Lys Lys Asp Ser Pro Glu Val
 65                  70                  75                  80

Tyr Phe Cys Cys Cys Glu Gly Asn Met Cys Asn Glu Lys Phe Ser Tyr
                 85                  90                  95

Phe Pro Glu Met Glu Val Thr Gln Pro Thr Ser Asn Pro Val Thr Pro
                100                 105                 110

Lys Pro Pro
        115

<210> SEQ ID NO 214
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units
<220> FEATURE:
<223> OTHER INFORMATION: See specification as filed for detailed
      description of substitutions and preferred embodiments

<400> SEQUENCE: 214

Gly Gly Gly Gly Ser Gly Gly Gly Gly Ser Gly Gly Gly Gly Ser Gly
 1               5                  10                  15

Gly Gly Gly Ser
            20
```

MULTISPECIFIC BINDERS OF TGFBeta-SUPERFAMILY LIGANDS AND USES THEREOF

CROSS-REFERENCE TO RELATED APPLICATIONS

This application is a national stage filing under 35 U.S.C. § 371 of International Application No. PCT/US2019/030469, filed on May 2, 2019, which claims the benefit of and priority to U.S. Provisional Application No. 62/666,547, filed on May 3, 2018 and from U.S. Provisional Application No. 62/779,998, filed on Dec. 14, 2018. The specifications of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 28, 2020, is named 1848179-126-301_Seq.txt and is 386,366 bytes in size.

BACKGROUND OF THE INVENTION

The transforming growth factor-beta (TGFβ) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general phylogenetic clades: the more recently evolved members of the superfamily, which includes TGFβs, activins, and nodal and the Glade of more distantly related proteins of the superfamily, which includes a number of BMPs and GDFs [Hinck (2012) FEBS Letters 586:1860-1870]. TGFβ family members have diverse, often complementary biological effects. By manipulating the activity of a member of the TGFβ family, it is often possible to cause significant physiological changes in an organism. For example, the Piedmontese and Belgian Blue cattle breeds carry a loss-of-function mutation in the GDF8 (also called myostatin) gene that causes a marked increase in muscle mass [Grobet et al. (1997) Nat Genet 17(1):71-4]. Furthermore, in humans, inactive alleles of GDF8 are associated with increased muscle mass and, reportedly, exceptional strength [Schuelke et al. (2004) N Engl J Med 350:2682-8].

Changes in various tissues may be achieved by enhancing or inhibiting intracellular signaling (e.g., SMAD 1, 2, 3, 5, and/or 8) that is mediated by ligands of the TGFβ family. Thus, there is a need for agents that regulate the activity of various ligands of the TGFβ superfamily.

SUMMARY OF THE INVENTION

The TGFβ superfamily is comprised of over 30 secreted factors including TGFβs, activins, nodals, bone morphogenetic proteins (BMPs), growth and differentiation factors (GDFs), and anti-Mullerian hormone (AMH) [Weiss et al. (2013) Developmental Biology, 2(1): 47-63]. The TGFβ family can be divided into two phylogenetic branches based on the type I receptors they bind and the Smad proteins they activate. One is the more recently evolved branch, which includes, e.g., the TGFβs, activins, GDF8, GDF11, GDF9, BMP3 and nodal, which signal through type I receptors that activate Smads 2 and 3 [Hinck (2012) FEBS Letters 586: 1860-1870]. The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7, which signal through Smads 1, 5, and 8. In part, the present disclosure provides ActRIIA:TβRII heteromultimers that can antagonize a broad range of Smad 2/3 activating ligands. For example, the disclosure demonstrates that an ActRIIA:TβRII heterodimer inhibits TGFβ1, TGFβ3, activin A, activin B, and GDF11 signaling pathways in a cell-based assay. In contrast, ActRIIA and TβRII homodimers alone inhibit a smaller subset of Smad 2/3 activating ligands. Moreover, the data demonstrate that the ActRIIA:TβRII heterodimer is a surprisingly more selective Smad 2/3 ligand antagonists than merely combining the antagonistic profiles of ActRIIA and TβRII homodimer ligand traps. For example, the ActRIIA:TβRII heterodimer inhibited activin A, activin B, and GDF11 signaling pathways similarly to an ActRIIA homodimer. However, ActRIIA:TβRII heterodimer inhibition of BMP10 signaling pathways is significantly reduced compared to the ActRIIA homodimer. ActRIIA: TβRII heteromultimers therefore are more selective antagonists of Smad 2/3 activating ligands compared to ActRIIA homodimers. Accordingly, an ActRIIA:TβRII heteromultimer will be more useful than an ActRIIA or TβRII homodimer, or combination thereof, in certain applications where such broad, yet selective, Smad 2/3 antagonism is advantageous. Examples include therapeutic applications where it is desirable to antagonize one or more of TGFβ1, TGFβ3, activin (e.g., activin A, activin B, and activin AB), and GDF11 with decreased antagonism of BMP10.

In some embodiments, the disclosure provides for a multispecific binder of TGFβ-superfamily ligands. In some embodiments, the multispecific binder protein is capable of binding to a) at least one of TGFβ1 and TGFβ3, and b) at least one of activin A, activin B, activin AB, GDF11, and GDF8. In some embodiments, the multispecific binder comprises: a) a first portion that is capable of binding to TGFβ1 and/or TGFβ3; and b) a second portion that is capable of binding to at least one of activin A, activin B, activin AB, GDF11, and GDF8. In some embodiments, the multispecific binder is a heteromultimer comprising an ActRIIA polypeptide and a TβRII polypeptide. In some embodiments, the multispecific binder comprises a TβRII polypeptide and a follistatin or a follistatin-like protein domain. In some embodiments, the multispecific binder comprises a TβRII polypeptide and an antibody or antigen-binding fragment, wherein the antibody or antigen-binding fragment is capable of binding to one or more of activin A, activin B, activin AB, GDF11, and/or GDF8. In particular embodiments, the multispecific binder comprises a TβRII polypeptide and an antibody or antigen-binding fragment, wherein the antibody or antigen-binding fragment is capable of binding to GDF8.

In some embodiments, the disclosure provides for a heteromultimer comprising an ActRIIA polypeptide and a TβRII polypeptide. In some embodiments, the ActRIIA polypeptide comprises an amino acid sequence that is at least 75% identical to: a) a sequence beginning at any one of positions 21 to 30 of SEQ ID NO: 50, and ending at any one of positions 110 to 135 of SEQ ID NO: 50; b) a sequence beginning at position 21 of SEQ ID NO: 50, and ending at position 135 of SEQ ID NO: 50; c) a sequence beginning at position 30 of SEQ ID NO: 50 and ending at position 110 of SEQ ID NO: 50; d) the sequence of SEQ ID NO: 51; or e) the sequence of SEQ ID NO: 52. In some embodiments, the ActRIIA polypeptide comprises an amino acid sequence that is at least 90% identical to: a) a sequence beginning at any one of positions 21 to 30 of SEQ ID NO: 50, and ending at any one of positions 110 to 135 of SEQ ID NO: 50; b) a sequence beginning at position 21 of SEQ ID NO: 50, and ending at position 135 of SEQ ID NO: 50; c) a sequence beginning at position 30 of SEQ ID NO: 50 and ending at position 110 of SEQ ID NO: 50; d) the sequence of SEQ ID NO: 51; or e) the sequence of SEQ ID NO: 52. In some embodiments, the ActRIIA polypeptide comprises an amino acid sequence that is at least 95% identical to: a) sequence beginning at any one of positions 21 to 30 of SEQ ID NO: 50, and ending at any one of positions 110 to 135 of SEQ ID NO: 50; b) a sequence beginning at position 21 of SEQ ID NO: 50, and ending at position 135 of SEQ ID NO: 50; c) a sequence beginning at position 30 of SEQ ID NO: 50 and ending at position 110 of SEQ ID NO: 50; d) the sequence of SEQ ID NO: 51; or e) the sequence of SEQ ID NO: 52. In some embodiments, the ActRIIA polypeptide comprises a amino acid sequence is selected from: a) a sequence beginning at any one of positions 21 to 30 of SEQ ID NO: 50, and ending at any one of positions 110 to 135 of SEQ ID NO: 50; b) a sequence beginning at position 21 of SEQ ID NO: 50, and ending at position 135 of SEQ ID NO: 50; c) a sequence beginning at position 30 of SEQ ID NO: 50 and ending at position 110 of SEQ ID NO: 50; d) the sequence of SEQ ID NO: 51; and e) the sequence of SEQ ID NO: 52. In some embodiments, the ActRIIA polypeptide is a fusion protein comprising: a) a ActRIIA portion comprising an extracellular domain of ActRIIA; and b) a heterologous portion. In some embodiments, the ActRIIA portion comprises an amino acid sequence that is at least 75% identical to: a) a sequence beginning at any one of positions 21 to 30 of SEQ ID NO: 50, and ending at any one of positions 110 to 135 of SEQ ID NO: 50; b) a sequence beginning at position 21 of SEQ ID NO: 50, and ending at position 135 of SEQ ID NO: 50; c) a sequence beginning at position 30 of SEQ ID NO: 50 and ending at position 110 of SEQ ID NO: 50; d) the sequence of SEQ ID NO: 51; or e) the sequence of SEQ ID NO: 52. In some embodiments, the ActRIIA portion comprises an amino acid sequence that is at least 90% identical to: a) a sequence beginning at any one of positions 21 to 30 of SEQ ID NO: 50, and ending at any one of positions 110 to 135 of SEQ ID NO: 50; b) a sequence beginning at position 21 of SEQ ID NO: 50, and ending at position 135 of SEQ ID NO: 50; c) a sequence beginning at position 30 of SEQ ID NO: 50 and ending at position 110 of SEQ ID NO: 50; d) the sequence of SEQ ID NO: 51; or e) the sequence of SEQ ID NO: 52. In some embodiments, the ActRIIA portion comprises an amino acid sequence that is at least 95% identical to: a) a sequence beginning at any one of positions 21 to 30 of SEQ ID NO: 50, and ending at any one of positions 110 to 135 of SEQ ID NO: 50; b) a sequence beginning at position 21 of SEQ ID NO: 50, and ending at position 135 of SEQ ID NO: 50; c) a sequence beginning at position 30 of SEQ ID NO: 50 and ending at position 110 of SEQ ID NO: 50; d) the sequence of SEQ ID NO: 51; or e) the sequence of SEQ ID NO: 52. In some embodiments, the ActRIIA portion comprises an amino acid sequence selected from: a) a sequence beginning at any one of positions 21 to 30 of SEQ ID NO: 50, and ending at any one of positions 110 to 135 of SEQ ID NO: 50; b) a sequence beginning at position 21 of SEQ ID NO: 50, and ending at position 135 of SEQ ID NO: 50; c) a sequence beginning at position 30 of SEQ ID NO: 50 and ending at position 110 of SEQ ID NO: 50; d) the sequence of SEQ ID NO: 51; and e) the sequence of SEQ ID NO: 52. In some embodiments, the heterologous portion comprises a first or second member of an interaction pair. In some embodiments, the heterologous portion comprises one or more amino acid modifications that promotes heterodimer formation. In some embodiments, the heterologous portion is an immunoglobulin Fc domain. In some embodiments, the immunoglobulin Fc domain is a human immunoglobulin Fc domain. In some embodiments, the immunoglobulin Fc domain is an immunoglobulin G1Fc domain. In some embodiments, the immunoglobulin Fc domain comprises an amino acid sequence that is at least 75% identical to: a) the amino acid sequence of SEQ ID NO: 68, wherein the sequence comprises a lysine (K) at position 356 and a K at position 399 based on the amino acid positioning of the EU numbering scheme of Kabat; b) the amino acid sequence of SEQ ID NO: 69, wherein the sequence comprises a aspartic acid (D) at position 392 and a D at position 409 based on the amino acid positioning of the EU numbering scheme of Kabat; c) the amino acid sequence of SEQ ID NO: 72, wherein the sequence comprises a cysteine (C) at position 354 and a tryptophan (W) at position 366 based on the amino acid positioning of the EU numbering scheme of Kabat; or d) the amino acid sequence of SEQ ID NO: 73, wherein the sequence comprises a C at position 349, a serine (S) at position 366, an alanine (A) at position 368, and a valine at position 407 based on the amino acid positioning of the EU numbering scheme of Kabat. In some embodiments, the immunoglobulin Fc domain comprises an amino acid sequence that is at least 95% identical to: a) the amino acid sequence of SEQ ID NO: 68, wherein the sequence comprises a lysine (K) at position 356 and a K at position 399 based on the amino acid positioning of the EU numbering scheme of Kabat; b) the amino acid sequence of SEQ ID NO: 69, wherein the sequence comprises a aspartic acid (D) at position 392 and a D at position 409 based on the amino acid positioning of the EU numbering scheme of Kabat; c) the amino acid sequence of SEQ ID NO: 72, wherein the sequence comprises a cysteine (C) at position 354 and a tryptophan (W) at position 366 based on the amino acid positioning of the EU numbering scheme of Kabat; or d) the amino acid sequence of SEQ ID NO: 73, wherein the sequence comprises a C at position 349, a serine (S) at position 366, an alanine (A) at position 368, and a valine at position 407 based on the amino acid positioning of the EU numbering scheme of Kabat. In some embodiments, the immunoglobulin Fc domain comprises an amino acid sequence selected from: a) the amino acid sequence of SEQ ID NO: 68; b) the amino acid sequence of SEQ ID NO: 69; c) the amino acid sequence of SEQ ID NO: 72; and d) the amino acid sequence of SEQ ID NO: 73. In some embodiments, the fusion protein further comprises a linker domain portion positioned between the ActRIIA portion and the heterologous portion. In some embodiments, the linker is between 10 and 25 amino acids in length. In some embodiments, the linker comprises an amino acid sequence selected from: a) $(GGGGS)_n$, wherein n=≥2 (SEQ ID NO: 198); b) $(GGGGS)_n$, wherein n=≥3 (SEQ ID NO: 199); c) $(GGGGS)_n$, wherein n=≥4 (SEQ ID NO: 200); and d) the amino acid sequence of any one of SEQ ID Nos: 4-7, 19, 21, 25, 26, 40, and 63-67. In some embodiments, the linker comprises $(GGGGS)_n$, wherein n≠≥5 (SEQ ID NO: 201). In some embodiments, the ActRIIA fusion protein comprises an amino acid sequence that is at least 75%, 80%, 90%, 95%, or 99% identical to the amino acid sequence of SEQ ID NO: 84. In some embodiments, the ActRIIA fusion protein comprises the amino acid sequence of SEQ ID NO: 84. In some embodiments, the ActRIIA fusion protein comprises an amino acid sequence that is at least 75%, 80%, 90%, 95%, or 99% identical to the amino acid sequence of SEQ ID NO: 90. In some embodiments, the ActRIIA fusion protein comprises the amino acid sequence of SEQ ID NO: 90. In some embodiments, the ActRIIA polypeptide consists of or consists essentially of: a) an ActRIIA polypeptide portion comprising an amino acid sequence that is at least 85%, 90%, 95%, 97%, or 99% identical to the amino acid sequence of SEQ ID NO: 51 and no more than 10, 9, 8, 7, 6, 5, 4, 3, 2 or 1 additional amino acids; b) a linker portion comprising an amino acid sequence that is at least 85%, 90%, 95%, 97%, or 99% identical to the amino acid sequence of SEQ ID NO: 6 and no more than 5, 4, 3, 2 or 1 additional amino acids; c) a heterologous portion comprising an amino acid sequence that is at least 85%, 90%, 95%, 97%, or 99% identical to an amino acid sequence selected from SEQ ID NOs: 68, 69, 72, or 73 and no more than 25, 20, 15, 10, 5, 4, 3, 2, or 1 additional amino acids; and c) optionally a leader sequence (e.g., SEQ ID NO: 23). In some embodiments, the ActRIIA polypeptide consists of or consists essentially of: a) an ActRIIA polypeptide portion comprising the amino acid sequence of SEQ ID NO: 51 and no more than 10, 9, 8, 7, 6, 5, 4, 3, 2 or 1 additional amino acids; b) a linker portion comprising the amino acid sequence of SEQ ID NO: 6 and no more than 5, 4, 3, 2 or 1 additional amino acids; c) a heterologous portion comprising an amino acid sequence selected from SEQ ID NOs: 68, 69, 72, or 73 and no more than 25, 20, 15, 10, 5, 4, 3, 2, or 1 additional amino acids; and d) optionally a leader sequence (e.g., SEQ ID NO: 23). In some embodiments, the ActRIIA polypeptide comprises: a) an ActRIIA polypeptide portion comprising an amino acid sequence that is at least 85%, 90%, 95%, 97%, or 99% identical to the sequence of SEQ ID NO: 51; b) a heterologous portion, wherein the heterologous portion comprises an amino acid sequence that is at least 85%, 90%, 95%, 97%, or 99% identical to an amino acid sequence selected from SEQ ID NOs: 68, 69, 72, or 73; and c) a linker portion connecting the ActRIIA polypeptide portion and the heterologous portion; wherein the linker comprises an amino acid sequence that is at least 85%, 90%, 95%, 97%, or 99% identical to the amino acid sequence of SEQ ID NO: 6. In some embodiments, the ActRIIA polypeptide comprises: a) an ActRIIA polypeptide portion comprising the amino acid sequence of SEQ ID NO: 51; b) a heterologous portion comprising an amino acid sequence selected from SEQ ID NOs: 68, 69, 72, or 73; and c) a linker portion connecting the ActRIIA polypeptide portion and the heterologous portion; wherein the linker comprises the amino acid sequence of SEQ ID NO: 6. In some embodiments, the heteromultimer is soluble. In some embodiments, the heteromultimer is a recombinant protein. In some embodiments, the TβRII polypeptide comprises an amino acid sequence that is at least 75% identical to: a) a sequence beginning at any one of positions 23 to 35 of SEQ ID NO: 1, and ending at any one of positions 153 to 159 of SEQ ID NO: 1; b) a sequence beginning at any one of positions 23 to 60 of SEQ ID NO: 2, and ending at any one of positions 178 to 184 of SEQ ID NO: 2; c) the sequence of SEQ ID NO: 18; d) the sequence of SEQ ID NO: 27; or e) the sequence of any one of SEQ ID NOs: 28, 29, 30, 31, 32, 33, 34, 35, 36, 37, 38; and 39. In some embodiments, the TβRII polypeptide comprises an amino acid sequence that is at least 90% identical to: a) a sequence beginning at any one of positions 23 to 35 of SEQ ID NO: 1, and ending at any one of positions 153 to 159 of SEQ ID NO: 1; b) a sequence beginning at any one of positions 23 to 60 of SEQ ID NO: 2, and ending at any one of positions 178 to 184 of SEQ ID NO: 2; c) the sequence of SEQ ID NO: 18; d) the sequence of SEQ ID NO: 27; or e) the sequence of any one of SEQ ID NOs: 28, 29, 30, 31, 32, 33, 34, 35, 36, 37, 38; and 39. In some embodiments, the TβRII polypeptide comprises an amino acid sequence that is at least 95% identical to: a) a sequence beginning at any one of positions 23 to 35 of SEQ ID NO: 1, and ending at any one of positions 153 to 159 of SEQ ID NO: 1; b) a sequence beginning at any one of positions 23 to 60 of SEQ ID NO: 2, and ending at any one of positions 178 to 184 of SEQ ID NO: 2; c) the sequence of SEQ ID NO: 18; d) the sequence of SEQ ID NO: 27; or e) the sequence of any one of SEQ ID NOs: 28, 29, 30, 31, 32, 33, 34, 35, 36, 37, 38; and 39. In some embodiments, the TβRII polypeptide comprises a amino acid sequence is selected from: a) a sequence beginning at any one of positions 23 to 35 of SEQ ID NO: 1, and ending at any one of positions 153 to 159 of SEQ ID NO: 1; b) a sequence beginning at any one of positions 23 to 60 of SEQ ID NO: 2, and ending at any one of positions 178 to 184 of SEQ ID NO: 2; c) the sequence of SEQ ID NO: 18; d) the sequence of SEQ ID NO: 27; and e) the sequence of any one of SEQ ID NOs: 28, 29, 30, 31, 32, 33, 34, 35, 36, 37, 38; and 39. In some embodiments, the TβRII polypeptide comprises an amino acid sequence that is at least 85%, 90%, 95%, 97%, or 99% identical to the sequence of SEQ ID NO: 18. In some embodiments, the TβRII polypeptide comprises the amino acid sequence of SEQ ID NO: 18. In some embodiments, the TβRII polypeptide is a fusion protein comprising: a) a TβRII portion comprising an extracellular domain of TβRII; and b) a heterologous portion. In some embodiments, the TβRII portion comprises an amino acid sequence that is at least 75% identical to: a) a sequence beginning at any one of positions 23 to 35 of SEQ ID NO: 1, and ending at any one of positions 153 to 159 of SEQ ID NO: 1; b) a sequence beginning at any one of positions 23 to 60 of SEQ ID NO: 2, and ending at any one of positions 178 to 184 of SEQ ID NO: 2; c) the sequence of SEQ ID NO: 18; d) the sequence of SEQ ID NO: 27; or e) the sequence of any one of SEQ ID NOs: 28, 29, 30, 31, 32, 33, 34, 35, 36, 37, 38; and 39. In some embodiments, the TβRII portion comprises an amino acid sequence that is at least 90% identical to: a) a sequence beginning at any one of positions 23 to 35 of SEQ ID NO: 1, and ending at any one of positions 153 to 159 of SEQ ID NO: 1; b) a sequence beginning at any one of positions 23 to 60 of SEQ ID NO: 2, and ending at any one of positions 178 to 184 of SEQ ID NO: 2; c) the sequence of SEQ ID NO: 18; d) the sequence of SEQ ID NO: 27; or e) the sequence of any one of SEQ ID NOs: 28, 29, 30, 31, 32, 33, 34, 35, 36, 37, 38; and 39. In some embodiments, the TβRII portion comprises an amino acid sequence that is at least 95% identical to: a) a sequence beginning at any one of positions 23 to 35 of SEQ ID NO: 1, and ending at any one of positions 153 to 159 of SEQ ID NO: 1; b) a sequence beginning at any one of positions 23 to 60 of SEQ ID NO: 2, and ending at any one of positions 178 to 184 of SEQ ID NO: 2; c) the sequence of SEQ ID NO: 18; d) the sequence of SEQ ID NO: 27; or e) the sequence of any one of SEQ ID NOs: 28, 29, 30, 31, 32, 33, 34, 35, 36, 37, 38; and 39. In some embodiments, the TβRII portion comprises an amino acid sequence selected from: a) a sequence beginning at any one of positions 23 to 35 of SEQ ID NO: 1, and ending at any one of positions 153 to 159 of SEQ ID NO: 1; b) a sequence beginning at any one of positions 23 to 60 of SEQ ID NO: 2, and ending at any one of positions 178 to 184 of SEQ ID NO: 2; c) the sequence of SEQ ID NO: 18;

d) the sequence of SEQ ID NO: 27; and e) the sequence of any one of SEQ ID NOs: 28, 29, 30, 31, 32, 33, 34, 35, 36, 37, 38; and 39. In some embodiments, the heterologous portion comprises a first or second member of an interaction pair. In some embodiments, the heterologous portion comprises one or more amino acid modifications that promotes heterodimer formation. In some embodiments, the heterologous portion is an immunoglobulin Fc domain. In some embodiments, the immunoglobulin Fc domain is a human immunoglobulin Fc domain. In some embodiments, the immunoglobulin Fc domain is an immunoglobulin G1Fc domain. In some embodiments, the immunoglobulin Fc domain comprises an amino acid sequence that is at least 75% identical to: a) the amino acid sequence of SEQ ID NO: 68, wherein the sequence comprises a lysine (K) at position 356 and a K at position 399 based on the amino acid positioning of the EU numbering scheme of Kabat; b) the amino acid sequence of SEQ ID NO: 69, wherein the sequence comprises a aspartic acid (D) at position 392 and a D at position 409 based on the amino acid positioning of the EU numbering scheme of Kabat; c) the amino acid sequence of SEQ ID NO: 72, wherein the sequence comprises a cysteine (C) at position 354 and a tryptophan (W) at position 366 based on the amino acid positioning of the EU numbering scheme of Kabat; or d) the amino acid sequence of SEQ ID NO: 73, wherein the sequence comprises a C at position 349, a serine (S) at position 366, an alanine (A) at position 368, and a valine at position 407 based on the amino acid positioning of the EU numbering scheme of Kabat. In some embodiments, the immunoglobulin Fc domain comprises an amino acid sequence that is at least 95% identical to: a) the amino acid sequence of SEQ ID NO: 68, wherein the sequence comprises a lysine (K) at position 356 and a K at position 399 based on the amino acid positioning of the EU numbering scheme of Kabat; b) the amino acid sequence of SEQ ID NO: 69, wherein the sequence comprises a aspartic acid (D) at position 392 and a D at position 409 based on the amino acid positioning of the EU numbering scheme of Kabat; c) the amino acid sequence of SEQ ID NO: 72, wherein the sequence comprises a cysteine (C) at position 354 and a tryptophan (W) at position 366 based on the amino acid positioning of the EU numbering scheme of Kabat; or d) the amino acid sequence of SEQ ID NO: 73, wherein the sequence comprises a C at position 349, a serine (S) at position 366, an alanine (A) at position 368, and a valine at position 407 based on the amino acid positioning of the EU numbering scheme of Kabat. In some embodiments, the immunoglobulin Fc domain comprises an amino acid sequence selected from: a) the amino acid sequence of SEQ ID NO: 68; b) the amino acid sequence of SEQ ID NO: 69; c) the amino acid sequence of SEQ ID NO: 72; and d) the amino acid sequence of SEQ ID NO: 73. In some embodiments, the fusion protein further comprises a linker domain portion positioned between the TβRII portion and the heterologous portion. In some embodiments, the linker is between 10 and 25 amino acids in length. In some embodiments, the linker comprises an amino acid sequence selected from: a) (GGGGS)$_n$, wherein n=≥2 (SEQ ID NO: 198); b) (GGGGS)$_n$, wherein n=≥3 (SEQ ID NO: 199); c) (GGGGS)$_n$, wherein n=≥4 (SEQ ID NO: 200); and d) the amino acid sequence of any one of SEQ ID Nos: 4-7, 19, 21, 25, 26, 40, and 63-67. In some embodiments, the linker comprises (GGGGS)$_n$, wherein n≠≥5 (SEQ ID NO: 201). In some embodiments, the TβRII fusion protein comprises an amino acid sequence that is at least 75%, 80%, 90%, 95%, or 99% identical to the amino acid sequence of SEQ ID NO: 87. In some embodiments, the TβRII fusion protein comprises the amino acid sequence of SEQ ID NO: 87. In some embodiments, the TβRII fusion protein comprises an amino acid sequence that is at least 75%, 80%, 90%, 95%, or 99% identical to the amino acid sequence of SEQ ID NO: 93. In some embodiments, the TβRII fusion protein comprises the amino acid sequence of SEQ ID NO: 93. In some embodiments, the TβRII polypeptide consists of or consists essentially of: a) an TβRII polypeptide portion comprising an amino acid sequence that is at least 85%, 90%, 95%, 97%, or 99% identical to the amino acid sequence of SEQ ID NO: 18 and no more than 10, 9, 8, 7, 6, 5, 4, 3, 2 or 1 additional amino acids; b) a linker portion comprising an amino acid sequence that is at least 85%, 90%, 95%, 97%, or 99% identical to the amino acid sequence of SEQ ID NO: 6 and no more than 5, 4, 3, 2 or 1 additional amino acids; c) a heterologous portion comprising an amino acid sequence that is at least 85%, 90%, 95%, 97%, or 99% identical to an amino acid sequence selected from SEQ ID NOs: 68, 69, 72, or 73 and no more than 25, 20, 15, 10, 5, 4, 3, 2, or 1 additional amino acids; and c) optionally a leader sequence (e.g., SEQ ID NO: 23). In some embodiments, the TβRII polypeptide consists of or consists essentially of: a) an TβRII polypeptide portion comprising the amino acid sequence of SEQ ID NO: 18 and no more than 10, 9, 8, 7, 6, 5, 4, 3, 2 or 1 additional amino acids; b) a linker portion comprising the amino acid sequence of SEQ ID NO: 6 and no more than 5, 4, 3, 2 or 1 additional amino acids; c) a heterologous portion comprising an amino acid sequence selected from SEQ ID NOs: 68, 69, 72, or 73 and no more than 25, 20, 15, 10, 5, 4, 3, 2, or 1 additional amino acids; and d) optionally a leader sequence (e.g., SEQ ID NO: 23). In some embodiments, the TβRII polypeptide comprises: a) an TβRII polypeptide portion comprising an amino acid sequence that is at least 85%, 90%, 95%, 97%, or 99% identical to the sequence of SEQ ID NO: 18; b) a heterologous portion, wherein the heterologous portion comprises an amino acid sequence that is at least 85%, 90%, 95%, 97%, or 99% identical to an amino acid sequence selected from SEQ ID NOs: 68, 69, 72, or 73; and c) a linker portion connecting the TβRII polypeptide portion and the heterologous portion; wherein the linker comprises an amino acid sequence that is at least 85%, 90%, 95%, 97%, or 99% identical to the amino acid sequence of SEQ ID NO: 6. In some embodiments, the TβRII polypeptide comprises: a) an TβRII polypeptide portion comprising the amino acid sequence of SEQ ID NO: 18; b) a heterologous portion comprising an amino acid sequence selected from SEQ ID NOs: 68, 69, 72, or 73; and c) a linker portion connecting the TβRII polypeptide portion and the heterologous portion; wherein the linker comprises the amino acid sequence of SEQ ID NO: 6. In some embodiments, the heteromultimer comprises one or more modified amino acid residues selected from: a glycosylated amino acid, a PEGylated amino acid, a farnesylated amino acid, an acetylated amino acid, a biotinylated amino acid, and an amino acid conjugated to a lipid moiety. In some embodiments, the heteromultimer is glycosylated. In some embodiments, the heteromultimer has a glycosylation pattern characteristic of expression of the polypeptide in CHO cells. In some embodiments, the heteromultimer has a glycosylation pattern characteristic of expression of the polypeptide in CHO cells. In some embodiments, the heteromultimer binds to one or more of: GDF11, activin A, activin B, TGFβ1, and TGFβ3. In some embodiments, the heteromultimer inhibits on or more of GDF11, activin A, activin B, TGFβ1, and TGFβ3 signaling as determined using a reporter gene assay. In some embodiments, the heteromultimer is a heterodimer.

In some embodiments, the heteromultimer is isolated. In some embodiments, the heteromultimer is recombinant In some embodiments, the disclosure provides for an isolated polynucleotide comprising a coding sequence for any of the ActRIIA polypeptides or fusion proteins disclosed herein. In some embodiments, the disclosure provides for an isolated polynucleotide comprising a coding sequence for any of the TβRII polypeptides or fusion proteins disclosed herein. In some embodiments, the disclosure provides for an isolated polynucleotide comprising a coding sequence for any of the ActRIIA polypeptides or fusion proteins disclosed herein and any of the TβRII polypeptides or fusion proteins disclosed herein. In some embodiments, the disclosure provides for a recombinant polynucleotide comprising a promotor sequence operably linked to any of the polynucleotides disclosed herein. In some embodiments, the disclosure provides for a cell comprising any the polynucleotide disclosed herein. In some embodiments, the cell is a CHO cell. In some embodiments, the disclosure provides a pharmaceutical preparation comprising any of the polypeptides disclosed herein and a pharmaceutically acceptable excipient. In some embodiments, the disclosure provides a method of making a heteromultimer comprising an ActRIIA polypeptide and a TβRII polypeptide comprising culturing a cell under conditions suitable for expression of an ActRIIA polypeptide and a TβRII polypeptide, wherein the cell comprises any combination of the polynucleotides disclosed herein. In some embodiments, the disclosure provides a method of making a heteromultimer comprising an ActRIIA polypeptide and a TβRII polypeptide comprising culturing a cell under conditions suitable for expression of an ActRIIA polypeptide and a TβRII polypeptide, wherein the cell comprises the any of the recombinant polynucleotides disclosed herein. In some embodiments, the disclosure provides a method of making a heteromultimer comprising an TβRII polypeptide and an ActRIIA polypeptide comprising: a) culturing a first cell under conditions suitable for expression of an TβRII polypeptide, wherein the first cell comprises any of the polynucleotides disclosed herein; b) recovering the TβRII polypeptide so expressed; c) culturing a second cell under conditions suitable for expression of an ActRIIA polypeptide, wherein the second cell comprises any of the recombinant polynucleotides disclosed herein; d) recovering the ActRIIA polypeptide so expressed; and e) combining the recovered TβRII polypeptide and the recovered ActRIIA polypeptide under conditions suitable for ActRIIA:TβRII heteromultimer formation. In some embodiments, the disclosure provides a method of modulating the response of a cell to a TGFβ superfamily member, the method comprising exposing the cell to any of the heteromultimers disclosed herein. In some embodiments, the disclosure provides a method of treating a disease or condition associated with a TGFβ superfamily member in a patient in need thereof, the method comprising administering to the patient an effective amount of any of the heteromultimers disclosed herein or any of the pharmaceutical preparations disclosed herein. In some embodiments, the disclosure provides a method of treating a pulmonary-related disease or condition in a patient in need thereof, the method comprising administering to the patient an effective amount of a heteromultimer of any of the pharmaceutical preparations disclosed herein. In some embodiments, the pulmonary-related disease or condition is selected from pulmonary hypertension, pulmonary arterial hypertension, and idiopathic pulmonary fibrosis. In some embodiments, the disclosure provides a method of treating a cancer in a patient in need thereof, the method comprising administering to the patient an effective amount of any of the heteromultimers disclosed herein or any of the pharmaceutical preparations disclosed herein. In some embodiments, the disclosure provides a method of treating a kidney-related disease or condition in a patient in need thereof, the method comprising administering to the patient an effective amount of any of the heteromultimers disclosed herein or any of the pharmaceutical preparations disclosed herein. In some embodiments, the kidney-related disease or condition is selected from: Alport syndrome, chronic kidney disease, polycystic kidney disease and renal fibrosis. In some embodiments, the disclosure provides a method of treating a anemia or an anemia-related disease or condition in a patient in need thereof, the method comprising administering to the patient an effective amount of any of the heteromultimers disclosed herein or any of the pharmaceutical preparations disclosed herein. In some embodiments, the anemia-related disease or condition is selected from: thalassemia, myelodysplastic syndrome, myelofibrosis, and sickle cell disease.

In some embodiments, the disclosure provides for a multispecific binder protein comprising a TβRII polypeptide and a follistatin polypeptide. In some embodiments, the TβRII polypeptide comprises an amino acid sequence that is at least 80%, 85%, 90%, 91%, 92%, 93%, 94%, 95%, 96%, 97%, 98%, 99%, or 100% identical to the amino acid sequence of SEQ ID NO: 170, or a biologically active fragment thereof. In some embodiments, the follistatin polypeptide comprises an amino acid sequence that is at least 80%, 85%, 90%, 91%, 92%, 93%, 94%, 95%, 96%, 97%, 98%, 99%, or 100% identical to the amino acid sequence of SEQ ID NO: 111, or a biologically active fragment thereof. In some embodiments, the binder protein further comprises a heterologous portion. In some embodiments, the heterologous portion is an Fc domain. In some embodiments, the Fc domain comprises an amino acid sequence that is at least 80%, 85%, 90%, 91%, 92%, 93%, 94%, 95%, 96%, 97%, 98%, 99%, or 100% identical to the amino acid sequence of SEQ ID NO: 163. In some embodiments, the heterologous portion is between the follistatin polypeptide and the TβRII polypeptide. In some embodiments, the heterologous portion is conjugated to the follistatin polypeptide directly. In some embodiments, the heterologous portion is conjugated to the follistatin polypeptide by means of a linker. In some embodiments, the linker comprises the amino acid sequence of SEQ ID NO: 3. In some embodiments, the heterologous portion is conjugated to the TβRII polypeptide directly. In some embodiments, the heterologous portion is conjugated to the TβRII polypeptide by means of a linker. In some embodiments, the linker conjugating the heterologous portion to the TβRII polypeptide comprises an amino acid sequence that is at least 80%, 85%, 90%, 91%, 92%, 93%, 94%, 95%, 96%, 97%, 98%, 99%, or 100% identical to the amino acid sequence of SEQ ID NO: 165. In some embodiments, the protein comprises, from N-terminus to C-terminus: the follistatin polypeptide, the heterologous domain, and the TβRII polypeptide. In some embodiments, the protein comprises a leader sequence. In some embodiments, the leader sequence comprises an amino acid sequence that is at least 80%, 85%, 90%, 91%, 92%, 93%, 94%, 95%, 96%, 97%, 98%, 99%, or 100% identical to the amino acid sequence of SEQ ID NO: 23. In some embodiments, the binder protein comprises an amino acid sequence that is at least 80%, 85%, 90%, 91%, 92%, 93%, 94%, 95%, 96%, 97%, 98%, 99%, or 100% identical to the amino acid sequence of SEQ ID NO: 164. In some embodiments, the binder protein comprises an amino acid sequence that is at least 80%, 85%, 90%, 91%, 92%, 93%, 94%, 95%, 96%, 97%, 98%, 99%, or 100% identical to the amino acid sequence of SEQ ID NO: 180 or 181.

In some embodiments, the disclosure provides for a multispecific binder protein comprising a TβRII polypeptide and an antibody or antigen-binding fragment capable of binding to GDF8. In some embodiments, the TβRII polypeptide comprises an amino acid sequence that is at least 80%, 85%, 90%, 91%, 92%, 93%, 94%, 95%, 96%, 97%, 98%, 99%, or 100% identical to the amino acid sequence of SEQ ID NO: 170, or a biologically active fragment thereof. In some embodiments, the antibody or antigen-binding fragment comprises a variable heavy chain and a variable light chain. In some embodiments, the variable heavy chain comprises CDRs having the amino acid sequence of SEQ ID NOs: 151-153. In some embodiments, the variable light chain comprises CDRs having the amino acid sequence of SEQ ID NOs: 154-156. In some embodiments, the variable heavy chain comprises an amino acid sequence that is at least 80%, 85%, 90%, 91%, 92%, 93%, 94%, 95%, 96%, 97%, 98%, 99%, or 100% identical to the amino acid sequence of SEQ ID NO: 167. In some embodiments, the variable light chain comprises an amino acid sequence that is at least 80%, 85%, 90%, 91%, 92%, 93%, 94%, 95%, 96%, 97%, 98%, 99%, or 100% identical to the amino acid sequence of SEQ ID NO: 174. In some embodiments, the antibody or antigen-binding fragment comprises an amino acid sequence that is at least 80%, 85%, 90%, 91%, 92%, 93%, 94%, 95%, 96%, 97%, 98%, 99%, or 100% identical to the amino acid sequence of SEQ ID NO: 168, or a biologically active fragment thereof. In some embodiments, the antibody or antigen-binding fragment comprises an amino acid sequence that is at least 80%, 85%, 90%, 91%, 92%, 93%, 94%, 95%, 96%, 97%, 98%, 99%, or 100% identical to the amino acid sequence of SEQ ID NO: 167, or a biologically active fragment thereof. In some embodiments, the antibody or antigen-binding fragment comprises an amino acid sequence that is at least 80%, 85%, 90%, 91%, 92%, 93%, 94%, 95%, 96%, 97%, 98%, 99%, or 100% identical to the amino acid sequence of SEQ ID NO: 171, or a biologically active fragment thereof. In some embodiments, the protein comprises an amino acid sequence that is at least 80%, 85%, 90%, 91%, 92%, 93%, 94%, 95%, 96%, 97%, 98%, 99%, or 100% identical to the amino acid sequence of SEQ ID NO: 172. In some embodiments, the protein comprises an amino acid sequence that is at least 80%, 85%, 90%, 91%, 92%, 93%, 94%, 95%, 96%, 97%, 98%, 99%, or 100% identical to the amino acid sequence of SEQ ID NO: 175. In some embodiments, the protein comprises an amino acid sequence that is at least 80%, 85%, 90%, 91%, 92%, 93%, 94%, 95%, 96%, 97%, 98%, 99%, or 100% identical to the amino acid sequence of SEQ ID NO: 182. In some embodiments, the protein comprises an amino acid sequence that is at least 80%, 85%, 90%, 91%, 92%, 93%, 94%, 95%, 96%, 97%, 98%, 99%, or 100% identical to the amino acid sequence of SEQ ID NO: 172, and wherein the protein further comprises an amino acid sequence that is at least 80%, 85%, 90%, 91%, 92%, 93%, 94%, 95%, 96%, 97%, 98%, 99%, or 100% identical to the amino acid sequence of SEQ ID NO: 182. In some embodiments, the protein comprises a leader sequence. In some embodiments, the leader sequence comprises an amino acid sequence that is at least 80%, 85%, 90%, 91%, 92%, 93%, 94%, 95%, 96%, 97%, 98%, 99%, or 100% identical to the amino acid sequence of SEQ ID NO: 176. In some embodiments, the antibody or antigen-binding fragment is also capable of binding to GDF11 and/or activin.

In some embodiments, the disclosure provides for a polynucleotide or collection of polynucleotides capable of expressing any of the multispecific binder proteins disclosed herein. In some embodiments, the disclosure provides for a vector or collection of vectors comprising any of the polynucleotides disclosed herein. In some embodiments, the disclosure provides for a host cell comprising and capable of expressing any of the polynucleotides or vectors disclosed herein. In some embodiments, the disclosure provides for a pharmaceutical composition comprising any of the multispecific binders disclosed herein and a pharmaceutically acceptable carrier.

In some embodiments, the disclosure provides for a method of treating a subject having a muscle disorder with any of the multispecific binders disclosed herein. In some embodiments, the subject has muscular dystrophy. In some embodiments, the subject has Duchenne Muscular Dystrophy. In some embodiments, the subject has Becker Muscular Dystrophy. In some embodiments, the disorder is associated with muscle fibrosis. In some embodiments, the disorder is associated with muscle loss or muscle wasting.

In some embodiments, the disclosure provides for a fusion protein comprising an ActRIIA polypeptide and a TβRII polypeptide. In some embodiments, the ActRIIA polypeptide comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 51 or 52. In some embodiments, the TβRII polypeptide comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 170. In some embodiments, the ActRIIA polypeptide portion is N-terminal to the TβRII polypeptide portion. In some embodiments, the ActRIIA polypeptide portion is C-terminal to the TβRII polypeptide portion. In some embodiments, a heterologous portion and/or one or more linker portions separate the ActRIIA and TβRII polypeptide portions in the fusion protein. In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 163. In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 72 or 73 (which may optionally lack the C-terminal lysine residue). In some embodiments, the TβRII polypeptide portion is fused to the Fc portion by means of a linker. In some embodiments, the TβRII polypeptide portion is fused to the Fc portion by means of a glycine-serine-rich linker. In some embodiments, the linker comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 165. In some embodiments, the ActRIIA polypeptide portion is fused to the Fc portion by means of a linker. In some embodiments, the ActRIIA polypeptide portion is fused to the Fc portion by means of a linker comprising a GGG linker (SEQ ID NO: 63). In some embodiments, the fusion protein comprises a signal sequence. In some embodiments, the signal sequence comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 23. In some embodiments, the fusion protein comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 183 or 195. In some embodiments, the fusion protein is a unit of a multimer. In some embodiments, the multimer is a homodimer. In some embodiments, the multimer is a heteromultimer, wherein the fusion protein is one unit of the heteromultimer, and wherein the heteromultimer comprises a second protein unit. In some embodiments, the second protein unit comprises an ActRIIA polypeptide portion but lacks a TβRII polypeptide portion. In some embodiments, the second protein unit comprises a TβRII polypeptide portion but lacks an ActRIIA polypeptide portion. In some embodiments, each unit of the heteromultimer comprises a member of an interaction pair. In some embodiments, the members of the interaction pair comprise an Fc domain. In some embodiments, the Fc domains comprise amino acid modifications that promote heteromultimer formation and/or to inhibit homomultimer formation. In some embodiments, the Fc domains have been modified to include one or more "knob-in-hole" mutations. In some embodiments, the fusion protein comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 184 or 196. In some embodiments, the second unit of the heteromultimer comprises a TβRII polypeptide portion but lacks an ActRIIA polypeptide portion, wherein the second protein unit comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 185 or 197. In some embodiments, the fusion protein comprises the amino acid sequence of SEQ ID NO: 184 or 196 and wherein the second protein unit comprises the amino acid sequence of SEQ ID NO: 185 or 197.

In some embodiments, the disclosure provides for an isolated polynucleotide encoding any of the fusion proteins disclosed herein.

In some embodiments, the disclosure provides for a recombinant polynucleotide comprising a promotor sequence operably linked to any of the polynucleotides disclosed herein.

In some embodiments, the disclosure provides for a cell comprising any of the polynucleotides disclosed herein. In some embodiments, the cell is a CHO cell.

In some embodiments, the disclosure provides for a pharmaceutical preparation comprising any of the fusion proteins disclosed herein and a pharmaceutically acceptable excipient.

In some embodiments, the disclosure provides for a method of modulating the response of a cell to a TGFβ superfamily member, the method comprising exposing the cell to any of the fusion proteins disclosed herein.

In some embodiments, the disclosure provides for a method of treating a disease or condition associated with a TGFβ superfamily member in a patient in need thereof, the method comprising administering to the patient an effective amount of any of the fusion proteins disclosed herein.

In some embodiments, the disclosure provides for a method of treating a muscle-related disease or condition in a patient in need thereof, the method comprising administering to the patient an effective amount of any of the fusion proteins disclosed herein. In some embodiments, the muscle-related disease or condition is selected from: muscular dystrophy, Duchene muscular dystrophy, Becker muscular dystrophy, Charcot-Marie-Tooth, facioscapulohumeral muscular dystrophy, amyotrophic lateral sclerosis, and sarcopenia.

In some embodiments, the disclosure provides for a method of treating a pulmonary-related disease or condition in a patient in need thereof, the method comprising administering to the patient an effective amount of any of the fusion proteins disclosed herein. In some embodiments, the pulmonary-related disease or condition is selected from interstitial lung disease, pulmonary hypertension, pulmonary arterial hypertension, and idiopathic pulmonary fibrosis.

In some embodiments, the disclosure provides for a method of treating a cancer in a patient in need thereof, the method comprising administering to the patient an effective amount of the fusion protein of any of the fusion proteins disclosed herein.

In some embodiments, the disclosure provides for a method of treating a kidney-related disease or condition in a patient in need thereof, the method comprising administering to the patient an effective amount of any of the fusion proteins disclosed herein. In some embodiments, the kidney-related disease or condition is selected from: Alport syndrome, chronic kidney disease, polycystic kidney disease and renal fibrosis.

In some embodiments, the disclosure provides for a method of treating an anemia or an anemia-related disease or condition in a patient in need thereof, the method comprising administering to the patient an effective amount of any of the fusion proteins disclosed herein. In some embodiments, the anemia-related disease or condition is selected from: thalassemia, myelodysplastic syndrome, myelofibrosis, and sickle cell disease.

In some embodiments, the disclosure provides for a method of treating a fibrotic or sclerotic disease or condition in a patient in need thereof, the method comprising administering to the patient an effective amount of any of the fusion proteins disclosed herein. In some embodiments, the fibrotic or sclerotic disease or condition is any one or more of systemic sclerosis, diffuse systemic sclerosis, systemic sclerosis-interstitial lung disease, myelofibrosis, progressive systemic sclerosis (PSS), or idiopathic pulmonary fibrosis.

BRIEF DESCRIPTION OF THE DRAWINGS

FIG. 1 shows the amino acid sequence of native precursor for the B (short) isoform of human TGFβ receptor type II (hTβRII) (NP_003233.4) (SEQ ID NO: 1). Solid underline indicates the processed extracellular domain (ECD) (residues 23-159), and double underline indicates valine that is replaced in the A (long) isoform. Dotted underline denotes leader (residues 1-22).

FIG. 2 shows the amino acid sequence of native precursor for the A (long) isoform of human TβRII (NP_001020018.1) (SEQ ID NO: 2). Solid underline indicates the processed ECD (residues 23-184), and double underline indicates the splice-generated isoleucine substitution. Dotted underline denotes leader (residues 1-22).

FIG. 3 discloses SEQ ID NOS 206-210, respectively, in order of appearance.

FIGS. 4A and 4B show in tabular form the binding affinity between TGFβ1 and TGFβ3 and one of several different TβRII-Fc fusion protein constructs.

FIGS. 5E and 5F provide $IC_{50}$ data from these same experiments in tabular form.

FIG. 6 shows multiple sequence alignment of Fc domains from human IgG isotypes using Clustal 2.1. Hinge regions are indicated by dotted underline. Double underline indicates examples of positions engineered in IgG1 (SEQ ID NO: 211) Fc to promote asymmetric chain pairing and the corresponding positions with respect to other isotypes IgG2 (SEQ ID NO: 42), IgG3 (SEQ ID NO: 60) and IgG4 (SEQ ID NO: 62).

FIG. 7 shows an alignment of extracellular domains of human ActRIIA (SEQ ID NO: 51) and human ActRIIB (SEQ ID NO: 212) with the residues that are deduced herein, based on composite analysis of multiple ActRIIB and ActRIIA crystal structures, to directly contact ligand indicated with boxes.

Figure 9A:
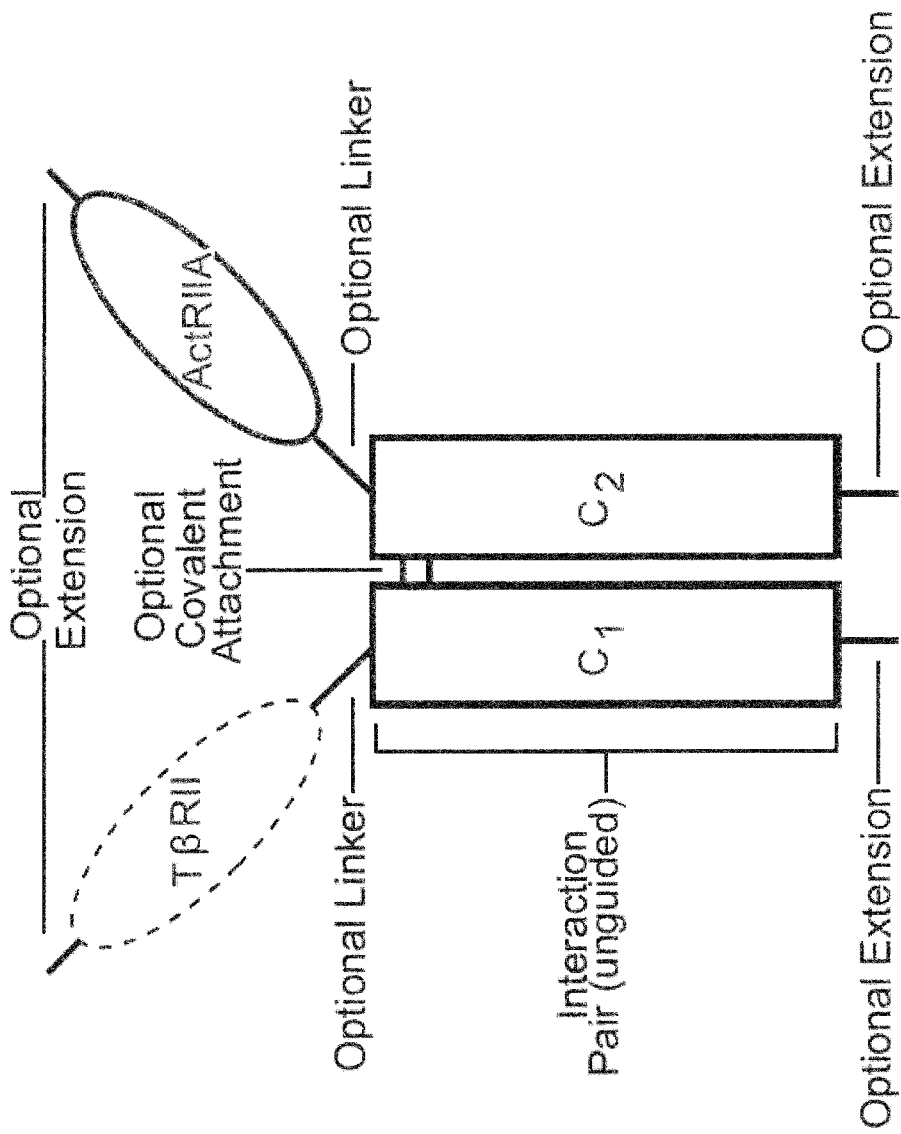
FIGS. 9A-9D show schematic examples of heteromeric protein complexes comprising an TβRII polypeptide (e.g. a polypeptide that is at least 70%, 75%, 80%, 85%, 90%, 91%, 92%, 93%, 94%, 95%, 97%, 98%, 99% or 100% identical to an extracellular domain of an TβRII protein from humans or other species such as those described herein, e.g., SEQ ID Nos: 18, 27, and 28-39) and an ActRIIA polypeptide (e.g. a polypeptide that is at least 70%, 75%, 80%, 85%, 90%, 91%, 92%, 93%, 94%, 95%, 97%, 98%, 99% or 100% identical to an extracellular domain of an ActRIIA protein from humans or other species such as those described herein, e.g., SEQ ID Nos: 51 and 52).
Figure 9B:
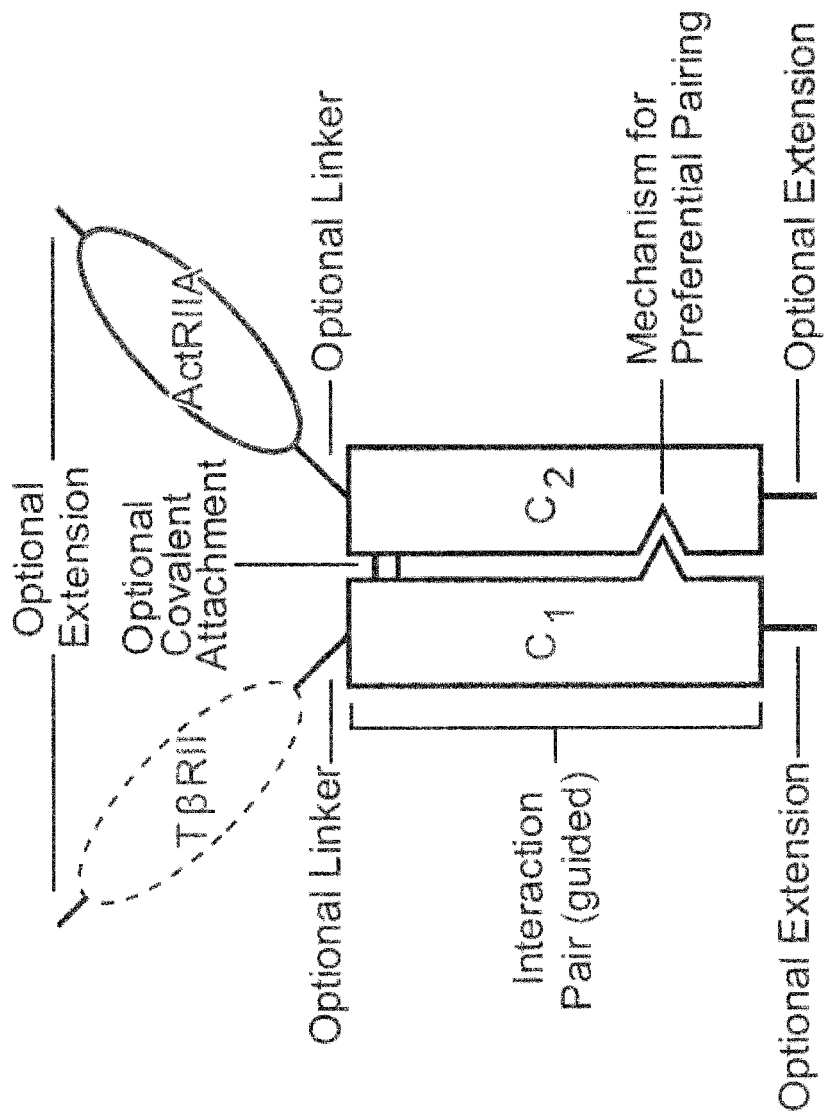
Figure 9C:
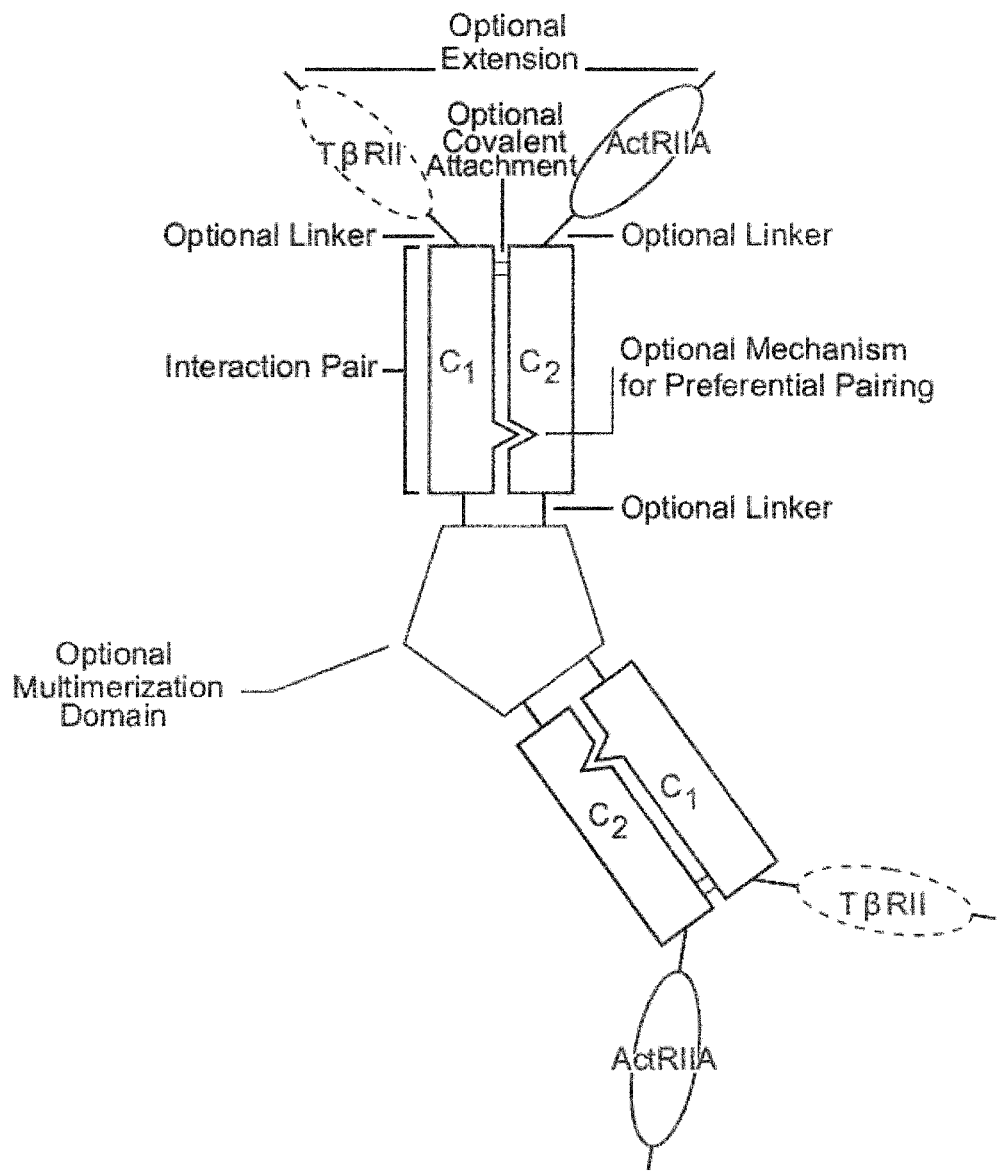
Figure 9D:
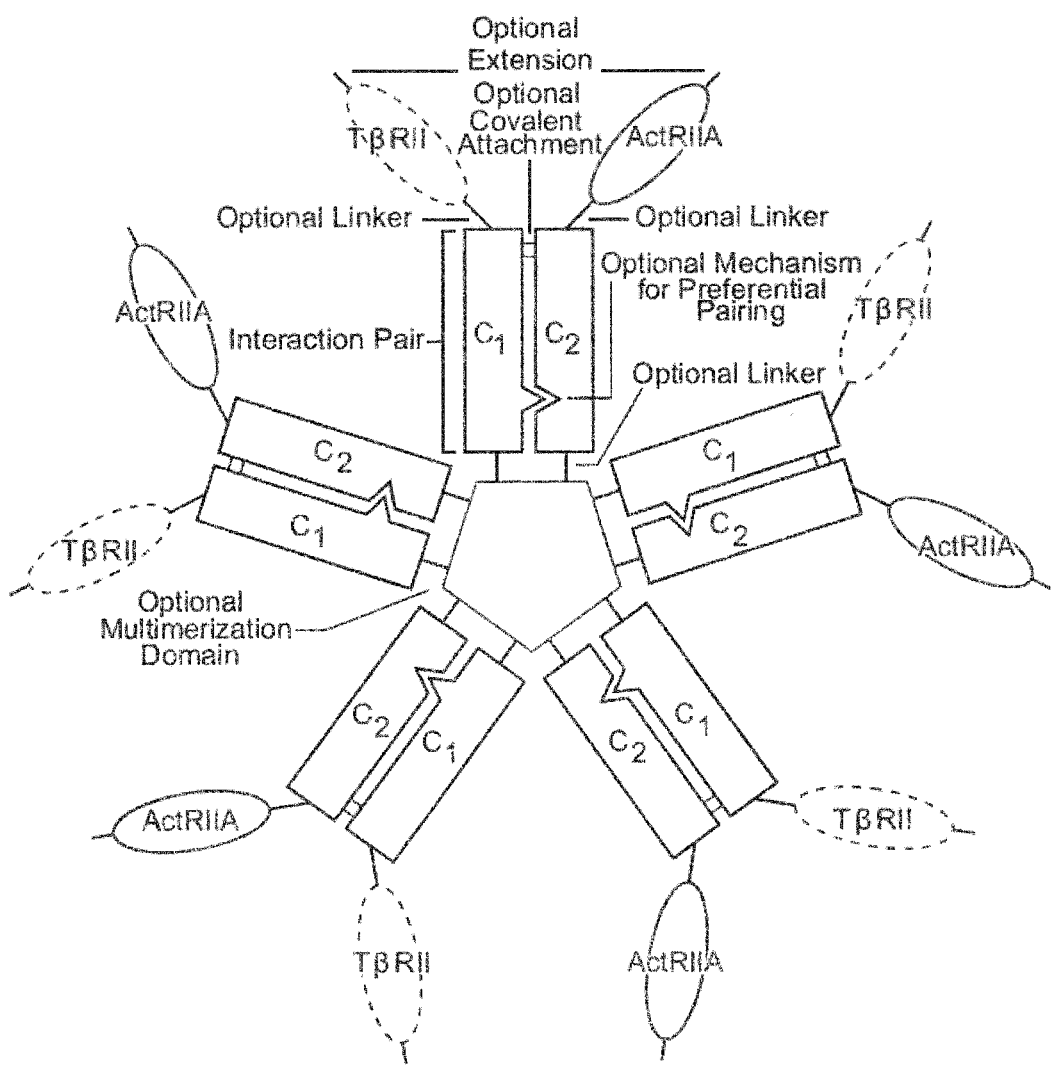

In the illustrated embodiments, the TβRII polypeptide (from left to right) is part of a fusion polypeptide that comprises a first member of an interaction pair ("$C_1$"), and the ActRIIA polypeptide is part of a fusion polypeptide that comprises a second member of an interaction pair ("$C_2$"). Suitable interaction pairs included, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the TβRII or ActRIIA polypeptide and the corresponding member of the interaction pair. The first and second members of the interaction pair may be unguided, meaning that the members of the pair may associate with each other or self-associate without substantial preference, and they may have the same or different amino acid sequences. See FIG. 9A. Alternatively, the interaction pair may be a guided (asymmetric) pair, meaning that the members of the pair associate preferentially with each other rather than self-associate. See FIG. 9B. Complexes of higher order can be envisioned. See FIGS. 9C and 9D.

FIGS. 10A-10G show schematic examples of heteromeric protein complexes comprising two TβRII polypeptides (e.g. polypeptide that are independently at least 70%, 75%, 80%, 85%, 90%, 91%, 92%, 93%, 94%, 95%, 97%, 98%, 99% or 100% identical to an extracellular domain of an TβRII protein from humans or other species such as those described herein, e.g., SEQ ID Nos: 18, 27, and 28-39) and two ActRIIA polypeptides (e.g. two polypeptides that are independently at least 70%, 75%, 80%, 85%, 90%, 91%, 92%, 93%, 94%, 95%, 97%, 98%, 99% or 100% identical to an extracellular domain of an ActRIIA protein from humans or other species such as those described herein, e.g., SEQ ID Nos: 51 and 52.

Figure 10A:
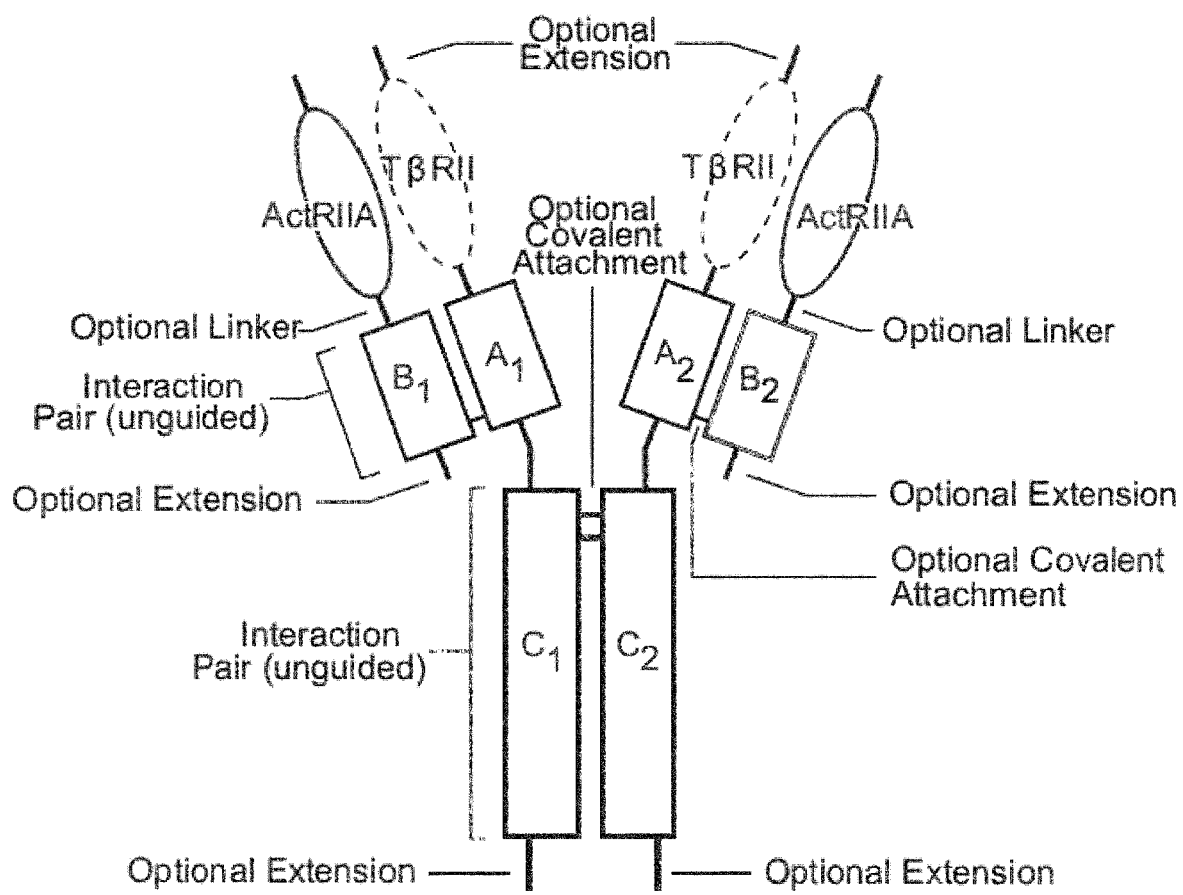

In the illustrated embodiment 10A, the first TβRII polypeptide (from left to right) is part of a fusion polypeptide that comprises a first member of an interaction pair ("$C_1$") and further comprises an additional first member of an interaction pair ("$A_1$"); and the second TβRII polypeptide is part of a fusion polypeptide that comprises a second member of an interaction pair ("$C_2$") and further comprises an first member of an interaction pair ("$A_2$"). The first ActRIIA polypeptide (from left to right) is part of a fusion polypeptide that comprises a second member of an interaction pair ("$B_1$"); and the second ActRIIA polypeptide is part of a fusion polypeptide that comprises a second member of an interaction pair ("$B_2$"). $A_1$ and $A_2$ may be the same or different; $B_1$ and $B_2$ may be the same or different, and $C_1$ and $C_2$ may be the same or different. In each fusion polypeptide, a linker may be positioned between the TβRII or ActRIIA polypeptide and the corresponding member of the interaction pair as well as between interaction pairs. FIG. 10A is an example of an association of unguided interaction pairs, meaning that the members of the pair may associate with each other or self-associate without substantial preference and may have the same or different amino acid sequences.

Figure 10B:
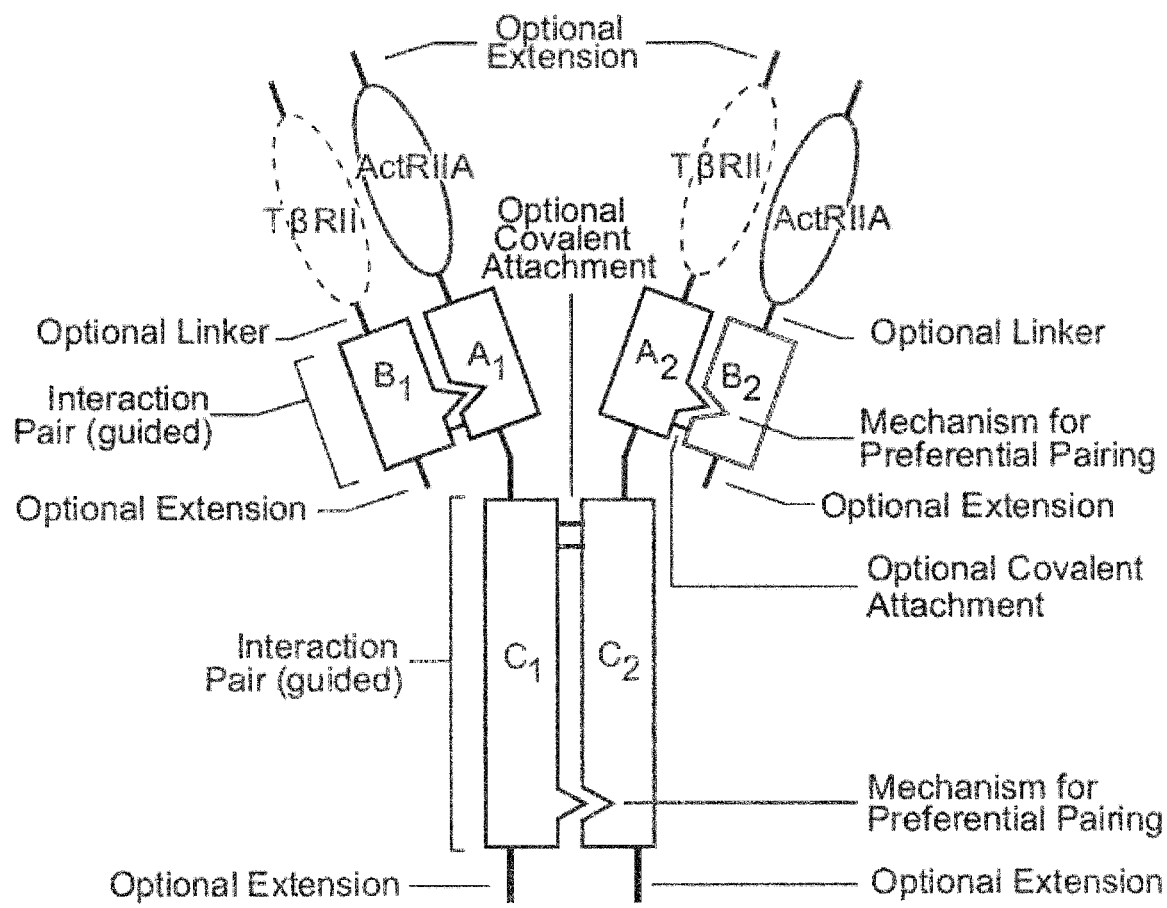
Figure 10C:
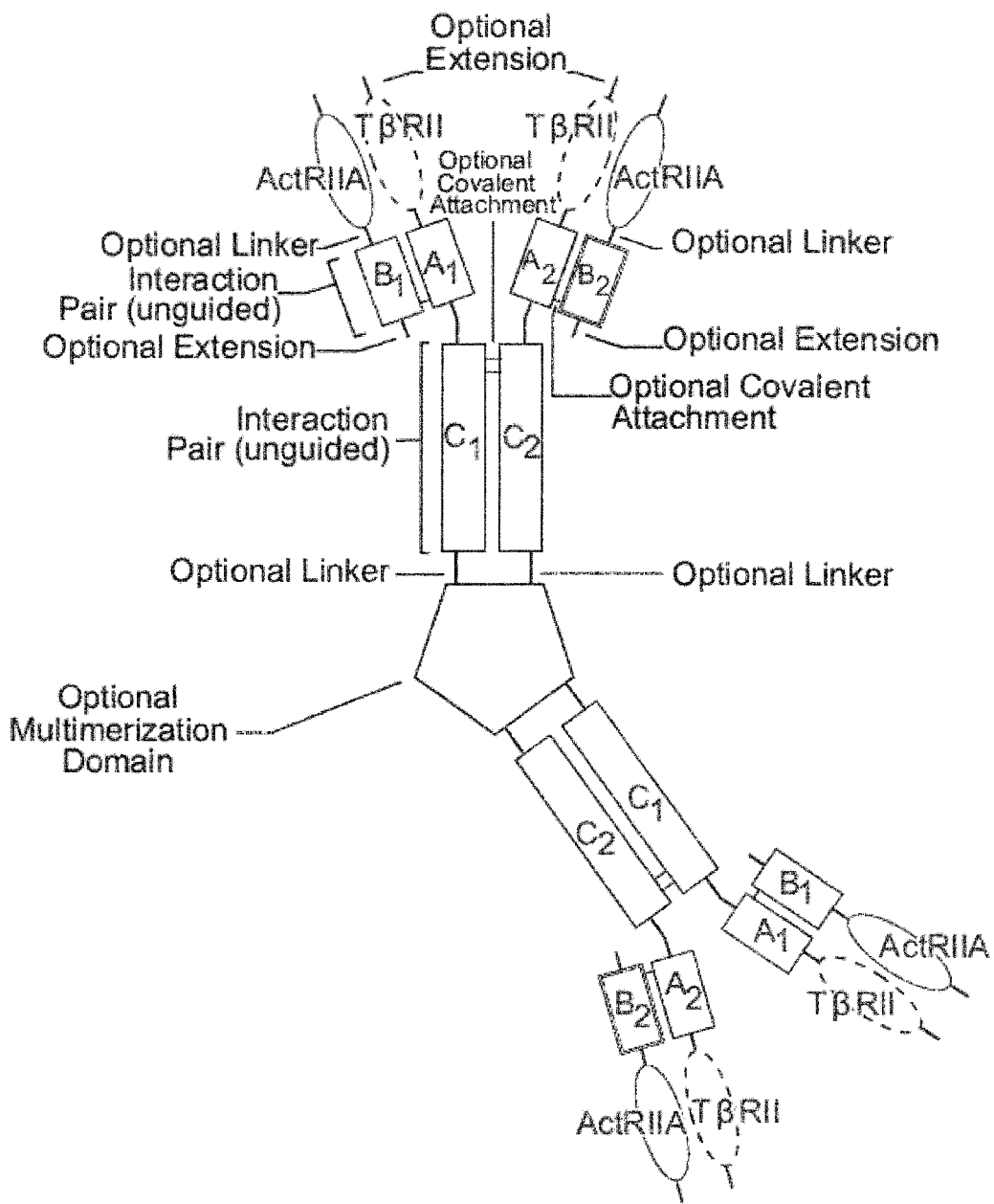
Figure 10D:
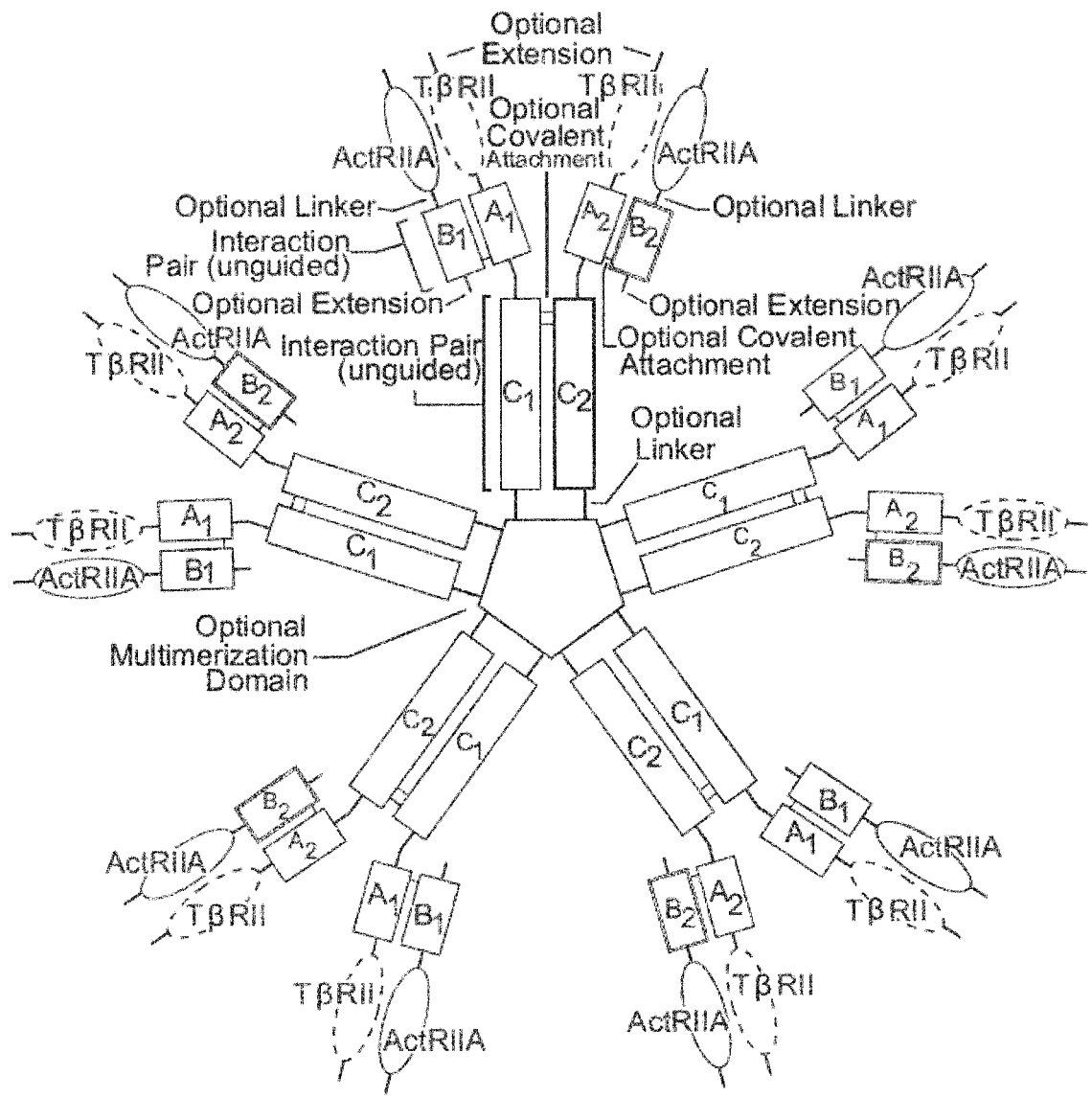
Figure 10E:
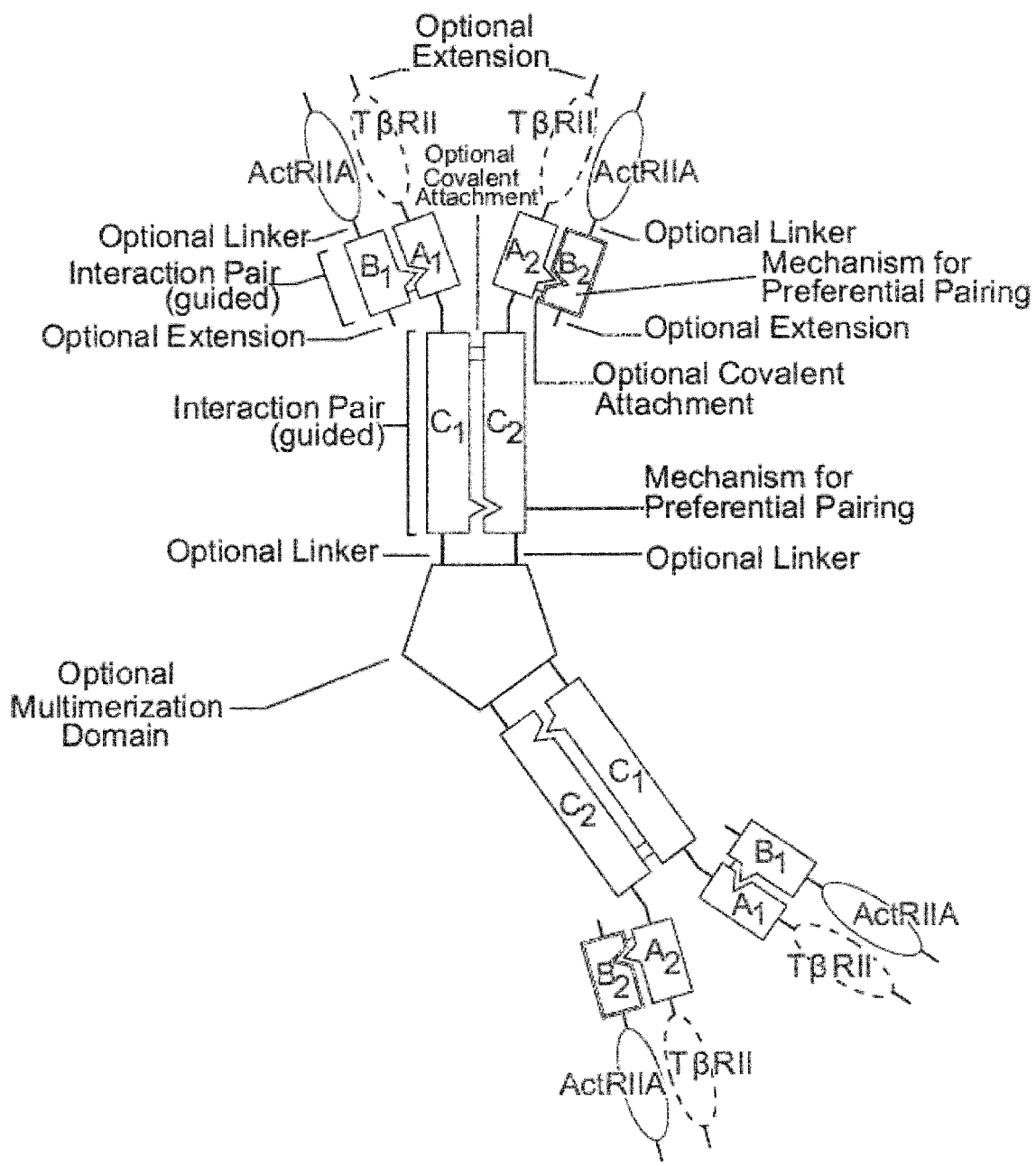
Figure 10F:
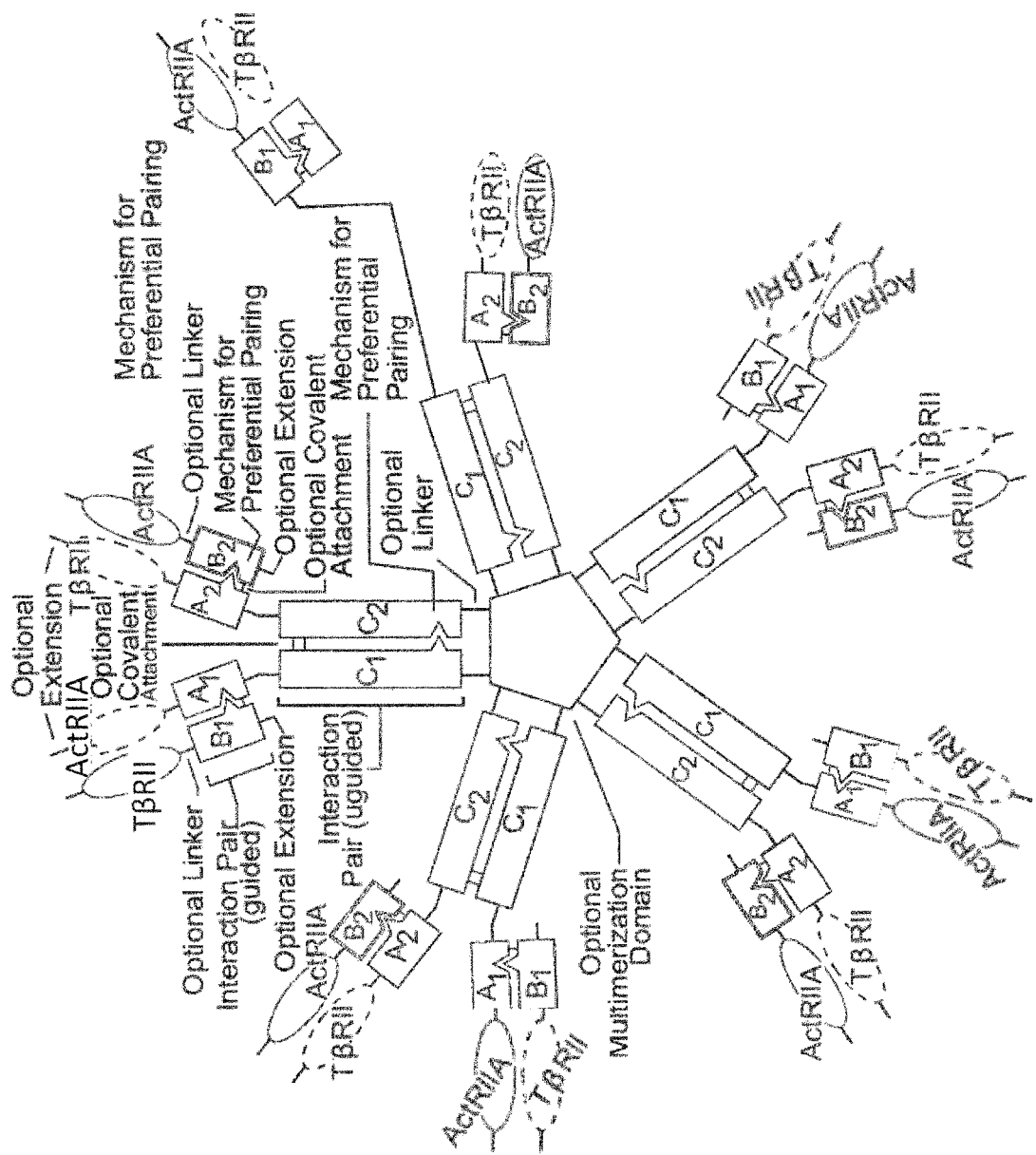
Figure 10G:
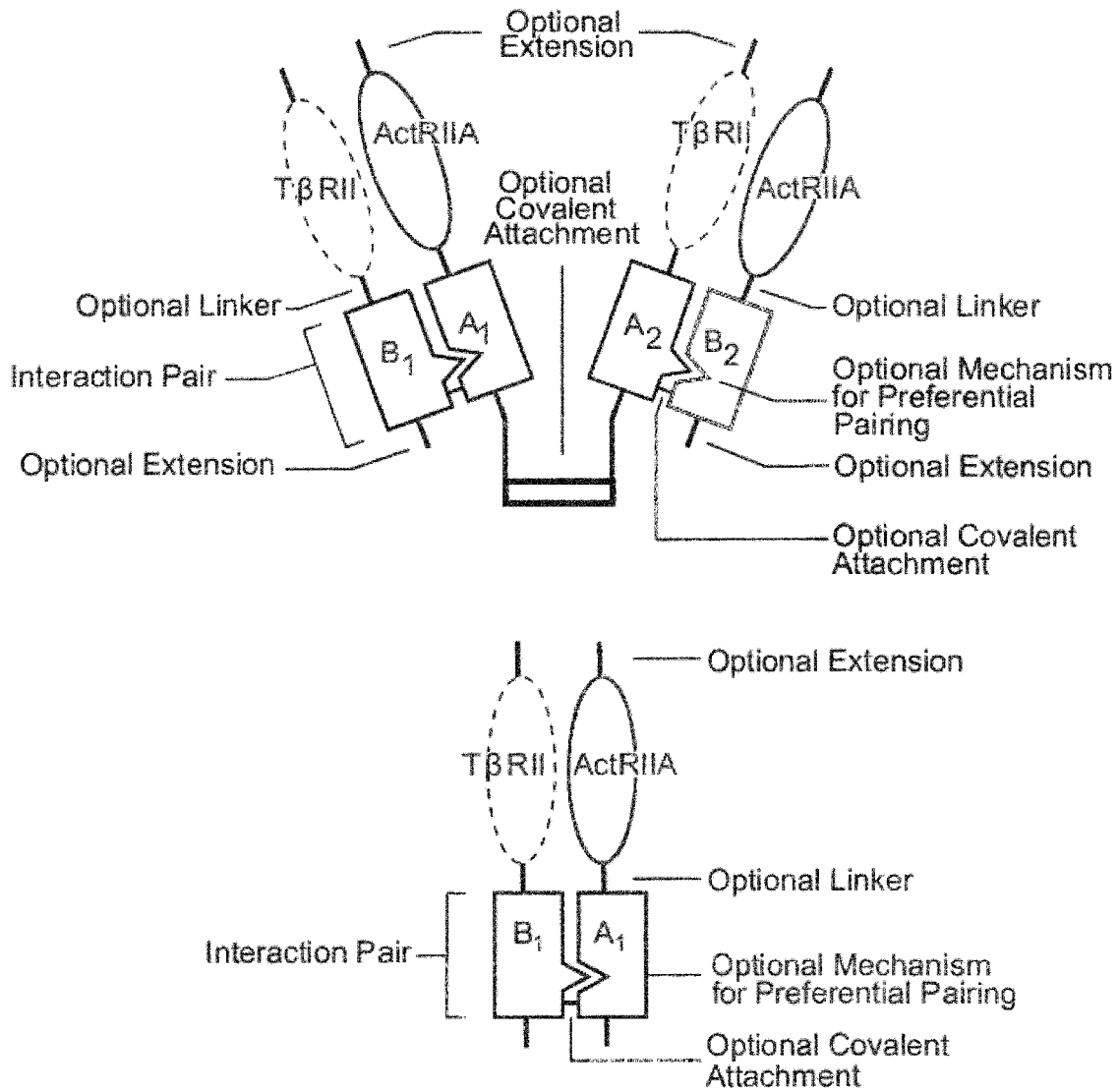

In the illustrated embodiment 10B, the first ActRIIA polypeptide (from left to right) is part of a fusion polypeptide that comprises a first member of an interaction pair ("$C_1$") and further comprises an additional first member of an interaction pair ("$A_1$"); and the second ActRIIA polypeptide is part of a fusion polypeptide that comprises a second member of an interaction pair ("$B_2$"). The first TβRII polypeptide (from left to right) is part of a fusion polypeptide that comprises a second member of an interaction pair ("$B_1$"); and the second TβRII polypeptide is part of a fusion polypeptide that comprises a second member of an interaction pair ("$C_2$") and further comprises a first member of an interaction pair ("$A_2$"). In each fusion polypeptide, a linker may be positioned between the TβRII or ActRIIA polypeptide and the corresponding member of the interaction pair as well as between interaction pairs. FIG. 10B is an example of an association of guided (asymmetric) interaction pairs, meaning that the members of the pair associate preferentially with each other rather than self-associate.

Suitable interaction pairs included, for example, heavy chain and/or light chain immunoglobulin interaction pairs, truncations, and variants thereof as described herein [e.g., Spiess et al (2015) Molecular Immunology 67(2A): 95-106]. Complexes of higher order can be envisioned. See FIG. 10C-10F. Using similar methods (particularly those that employ light and/or heavy chain immunoglobulins, truncations, or variants thereof), interaction pairs may be used to produce ActRIIA:TβRII heterodimers that resemble antibody Fab and F(ab')$_2$ complexes [e.g., Spiess et al (2015) Molecular Immunology 67(2A): 95-106]. See FIG. 10G.

Figure 11A:
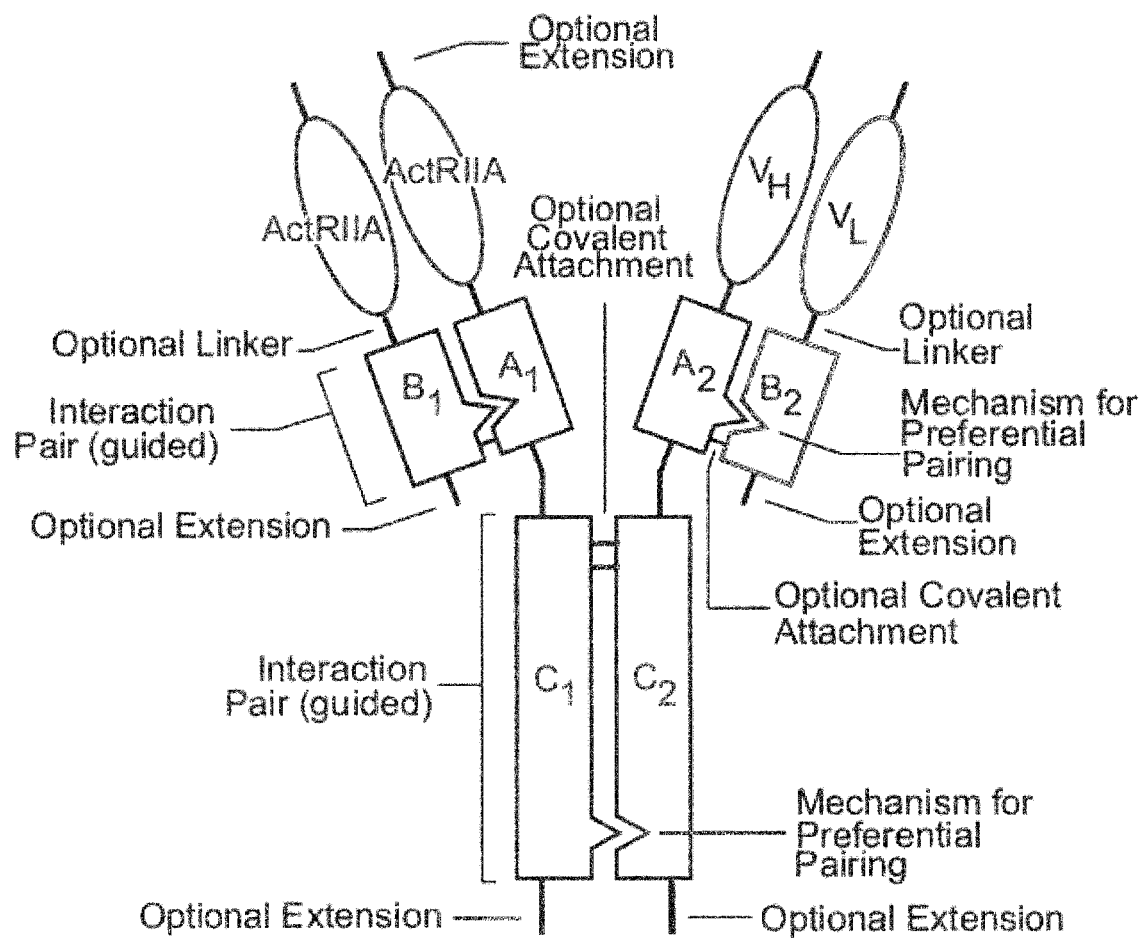
Figure 11B:
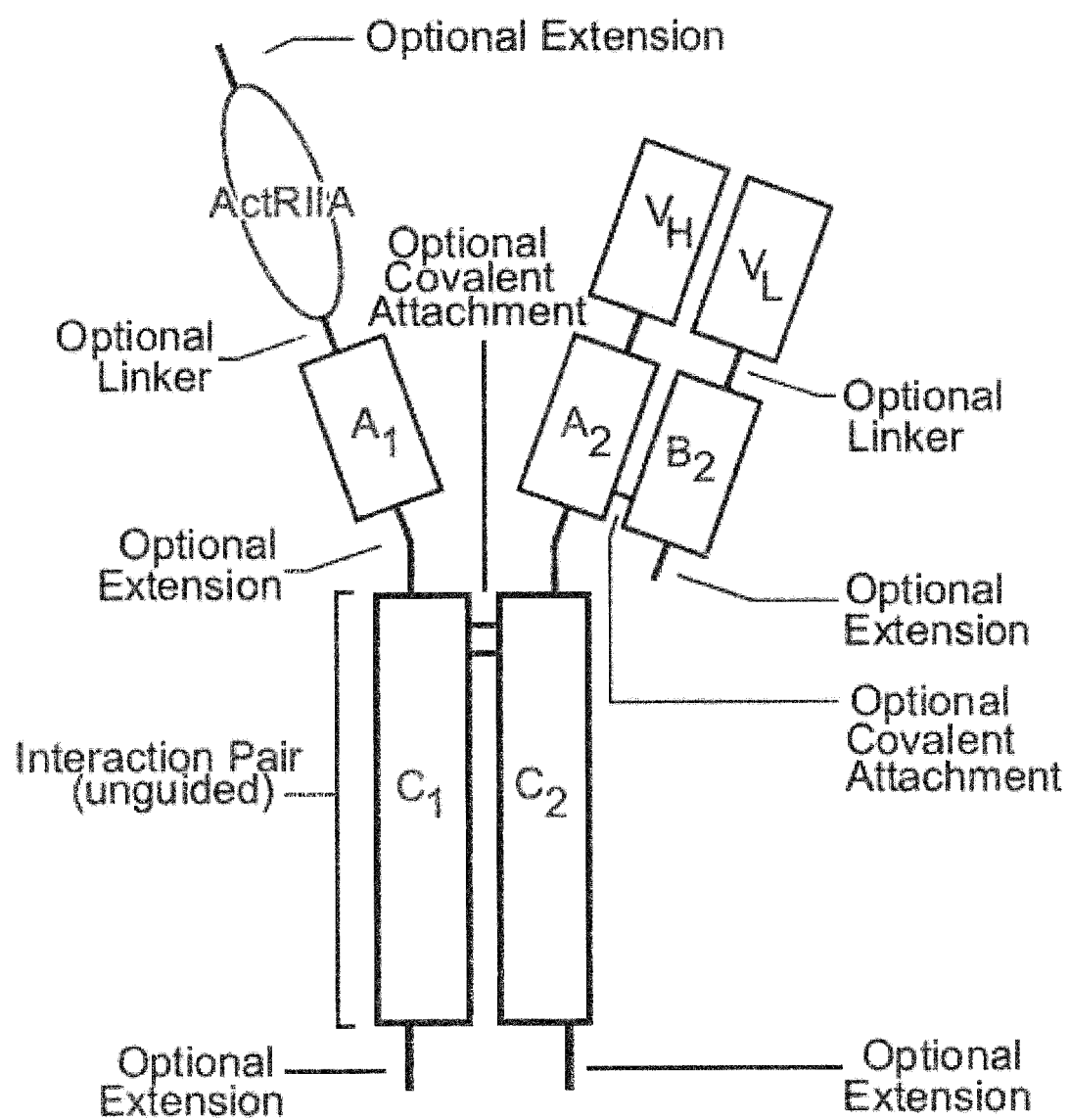
Figure 13A:
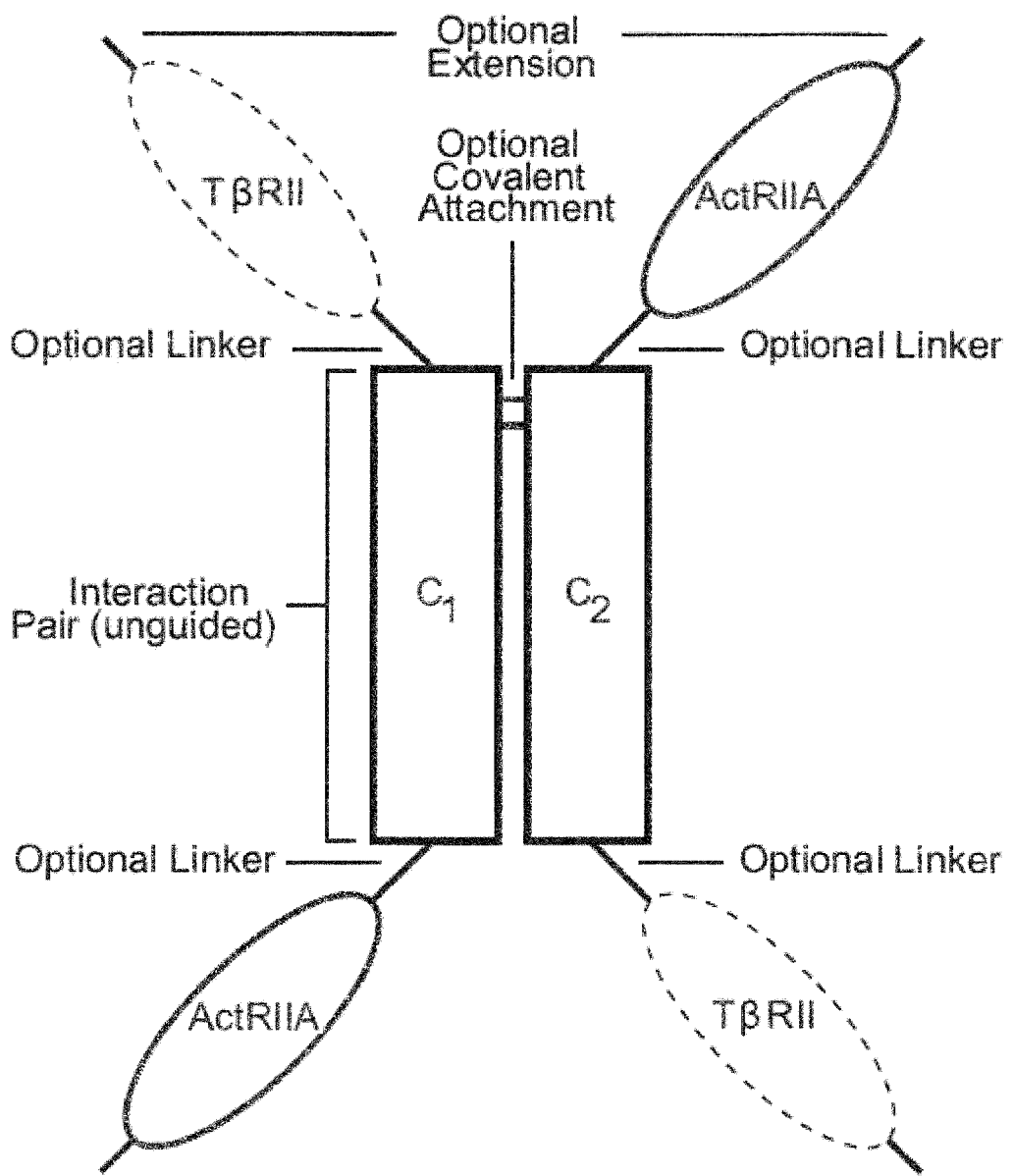
Figure 13B:
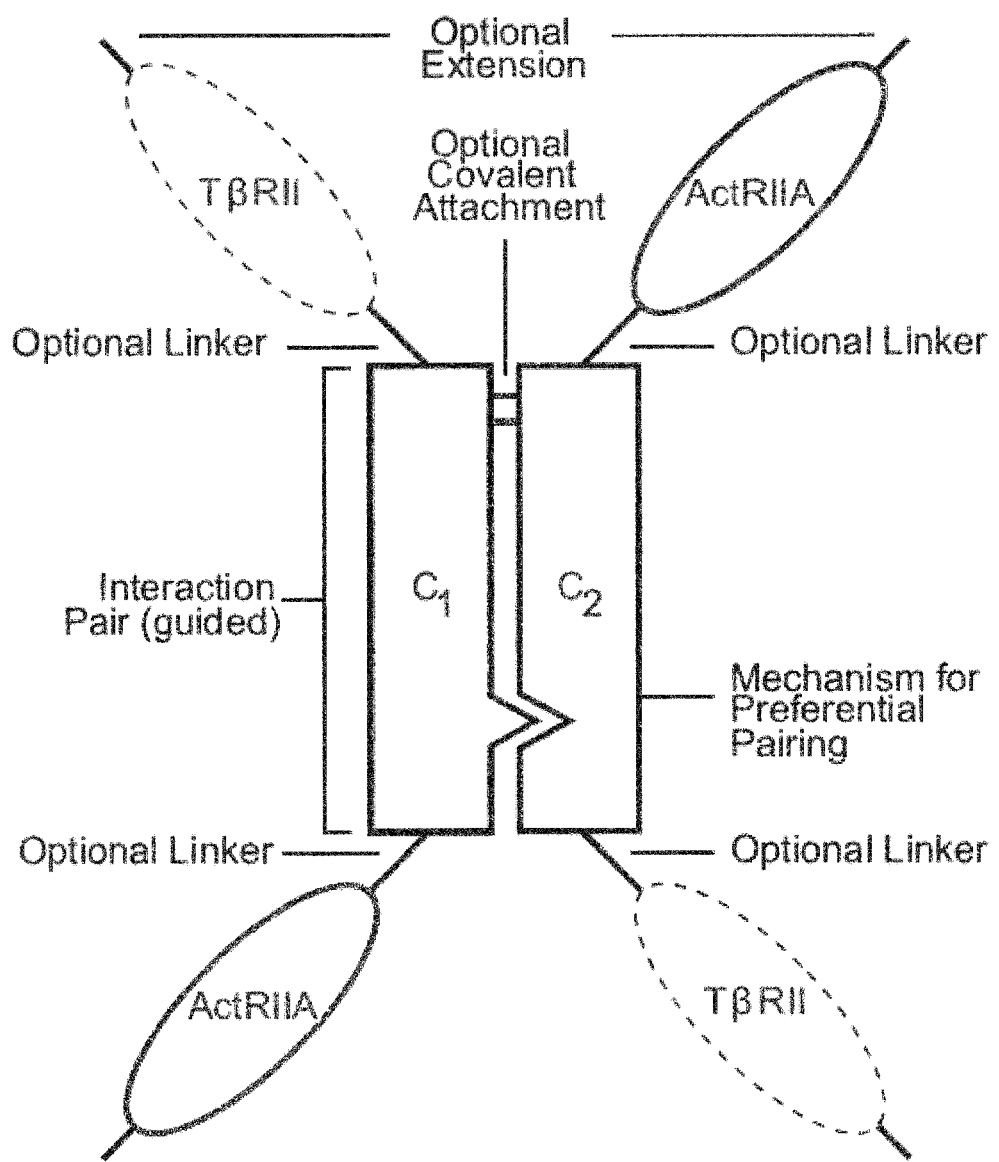
Figure 13C:
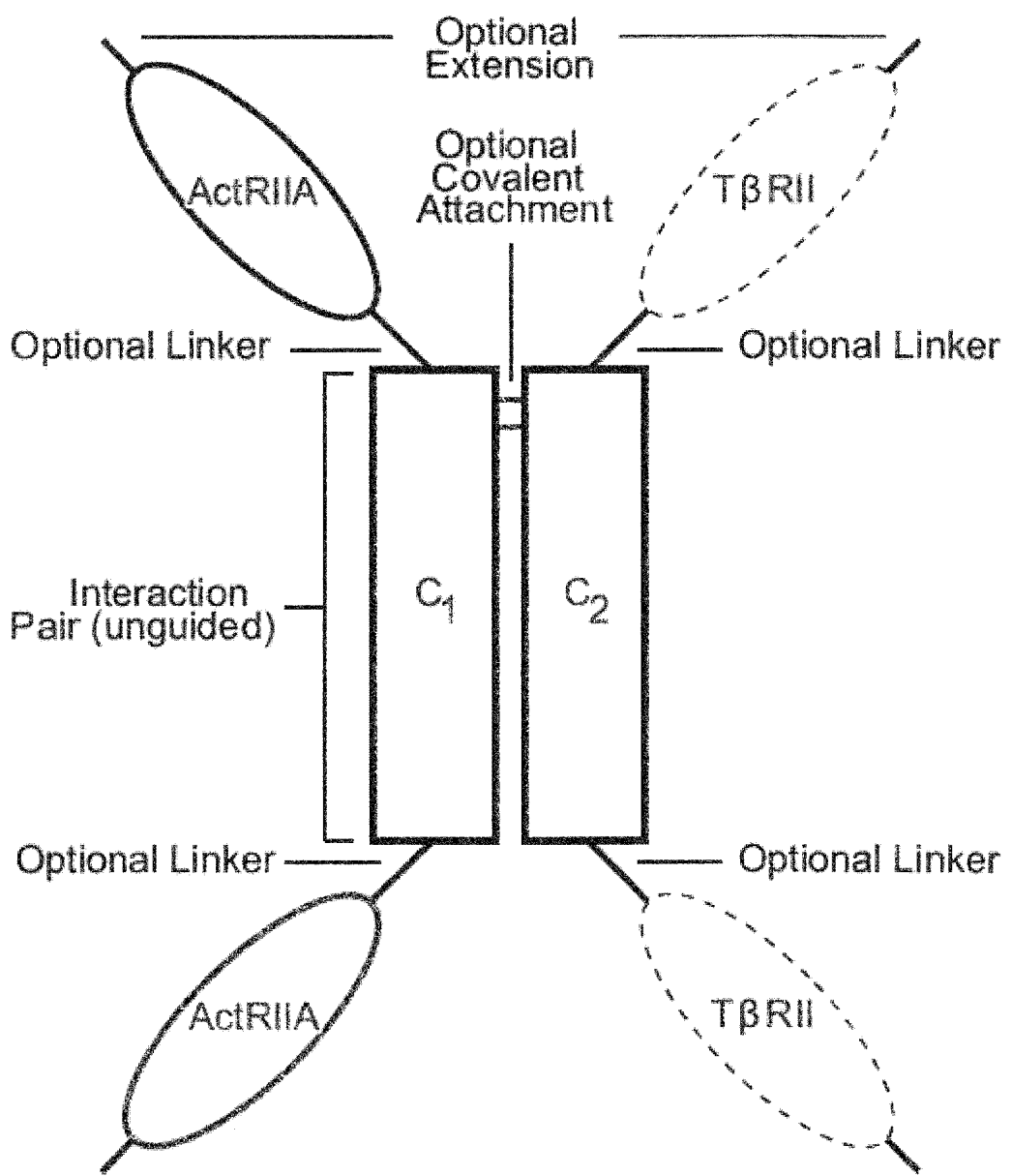
Figure 13D:
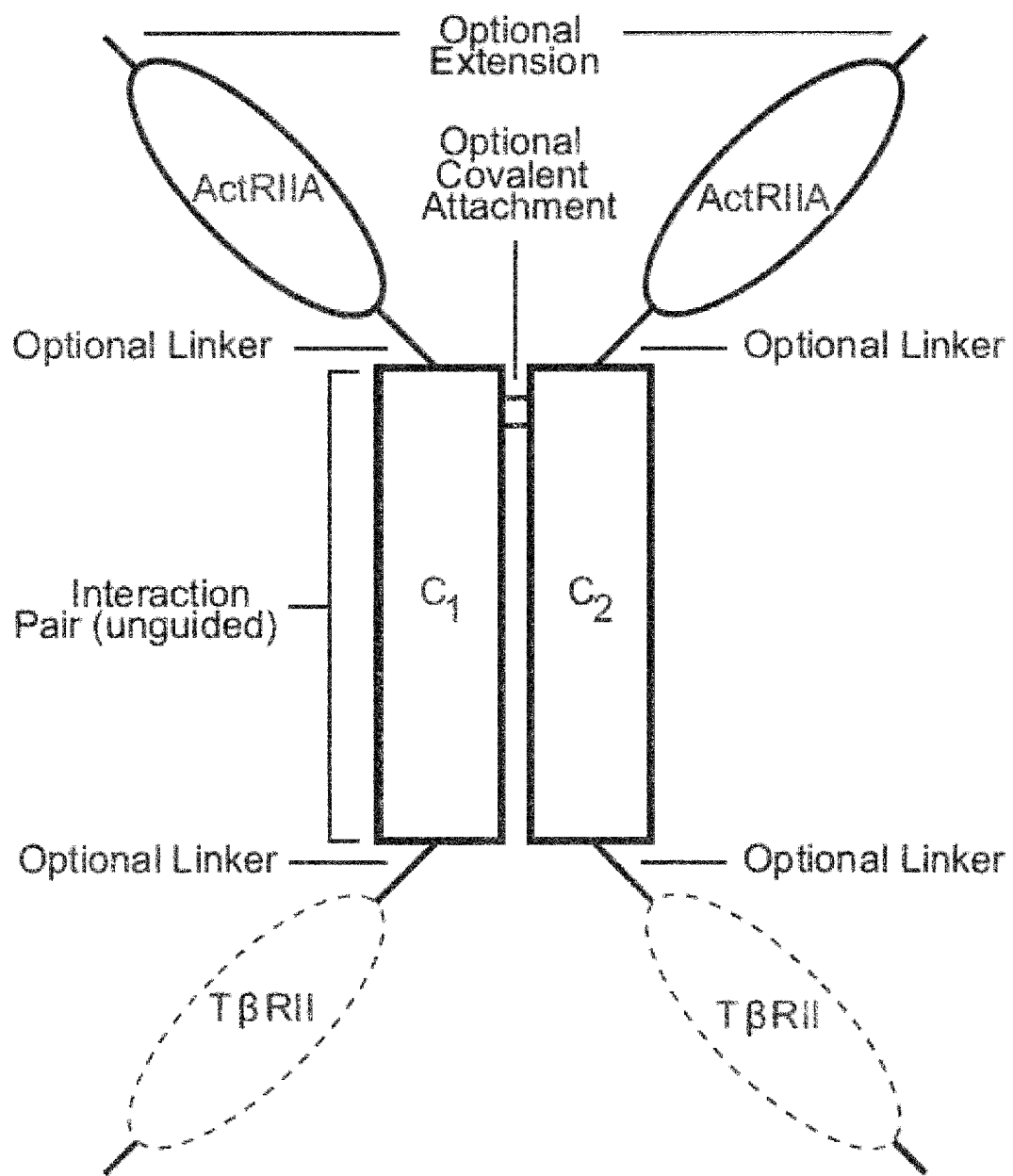

FIGS. 11A and 11B show schematic examples of a heteromeric protein complex comprising an antigen-binding domain of antibody that binds to one or more of TGFβ1, TGFβ2, TGFβ3 and at least one ActRIIA polypeptide domain (e.g. a polypeptide that is at least 70%, 75%, 80%, 85%, 90%, 91%, 92%, 93%, 94%, 95%, 97%, 98%, 99% or 100% identical to an extracellular domain of an ActRIIA protein from humans or other species as such as those described herein, e.g., SEQ ID Nos: 51 or 52). In the illustrated embodiments, the first ActRIIA polypeptide is part of a fusion polypeptide that comprises a first member of an interaction pair ("$C_1$"), and further comprises an additional first member of an interaction pair ("$A_1$"). The second ActRIIA polypeptide is part of a fusion polypeptide that comprises a second member of an interaction pair ("$B_1$").

The variable heavy chain ($V_H$) polypeptide is part of a fusion polypeptide that comprises a second member of an interaction pair ("$C_2$"), and further comprises a first member of an interaction pair ("$A_2$"). The variable light chain ($V_L$) polypeptide is part of a fusion polypeptide that comprises a second member of an interaction pair ("$B_2$"). In each fusion polypeptide, a linker may be positioned between the first or second ActRIIA polypeptide and the corresponding member of the interaction pair, between interaction pairs, and between the $V_H$ and $V_L$ polypeptides and a member of the interaction pair. $A_1$ and $A_2$ may be the same or different; $B_1$ and $B_2$ may be the same or different, and $C_1$ and $C_2$ may be the same or different. Suitable interaction pairs included, for example, constant heavy chain and/or light chain immunoglobulin interaction pairs, truncations, and variants thereof as described herein [e.g., Spiess et al (2015) Molecular Immunology 67(2A): 95-106]. FIG. 11A is an example of a heterodimer comprising a first and second ActRIIA extracellular domain. FIG. 11B is an example of a heteromultimer comprising a single ActRIIA extracellular domain.

FIG. 12 shows comparative ActRIIA-Fc:TβRII-Fc heterodimer compared to an ActRIIA-Fc:ActRIIA-Fc homodimer and TβRII-Fc:TβRII-Fc homodimer. $IC_{50}$ data was determined by an A-204 Reporter Gene Assay as described herein. ActRIIA-Fc:TβRII-Fc heterodimer inhibits activin A, activin B, and GDF11 signaling pathways similarly to the ActRIIA-Fc:ActRIIA-Fc homodimer. However, ActRIIA-Fc:TβRII-Fc heterodimer inhibition of BMP10 signaling pathways is significantly reduced compared to the ActRIIA-Fc:ActRIIA-Fc homodimer. These data demonstrate that ActRIIA-Fc:TβRII-Fc heterodimers are more selective antagonists of activin A, activin B, and GDF11 compared to corresponding ActRIIA-Fc:ActRIIA-Fc homodimers. In addition the ActRIIA-Fc:TβRII-Fc heterodimer inhibits TGFβ1 and TGFβ3 signaling pathways similarly to the TβRII-Fc:TβRII-Fc homodimer.

FIGS. 13A-13D show schematic examples of heteromeric protein complexes comprising an TβRII polypeptide (e.g., a polypeptide that is at least 70%, 75%, 80%, 85%, 90%, 91%, 92%, 93%, 94%, 95%, 97%, 98%, 99% or 100% identical to an extracellular domain of an TβRII protein from humans or other species such as those described herein, e.g., SEQ ID Nos: 18, 27, and 28-39) and an ActRIIA polypeptide (e.g. a polypeptide that is at least 70%, 75%, 80%, 85%, 90%, 91%, 92%, 93%, 94%, 95%, 97%, 98%, 99% or 100% identical to an extracellular domain of an ActRIIA protein from humans or other species such as those described herein, e.g., SEQ ID Nos: 51 and 52).

In the illustrated embodiments, the TβRII:ActRIIA single-chain polypeptide (is part of a fusion polypeptide that comprises a first member of an interaction pair ("$C_1$"), and the ActRIIA:TβRII polypeptide is part of a fusion polypeptide that comprises a second member of an interaction pair ("$C_2$"). Suitable interaction pairs included, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the TβRII and/or ActRIIA polypeptide and the corresponding member of the interaction pair. The first and second members of the interaction pair may be unguided, meaning that the members of the pair may associate with each other or self-associate without substantial preference, and they may have the same or different amino acid sequences. See FIG. 13A. Alternatively, the interaction pair may be a guided (asymmetric) pair, meaning that the members of the pair associate preferentially with each other rather than self-associate. See FIG. 13B. Additional protein complexes can be envisioned. See FIGS. 13C and 13D.

Figure 14B:
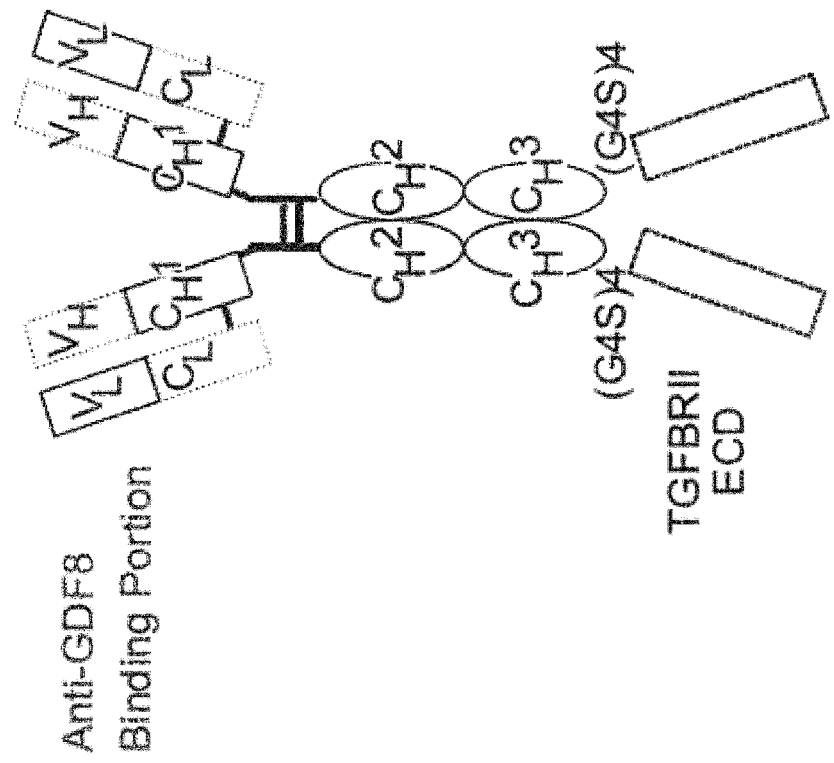
Figure 14A:
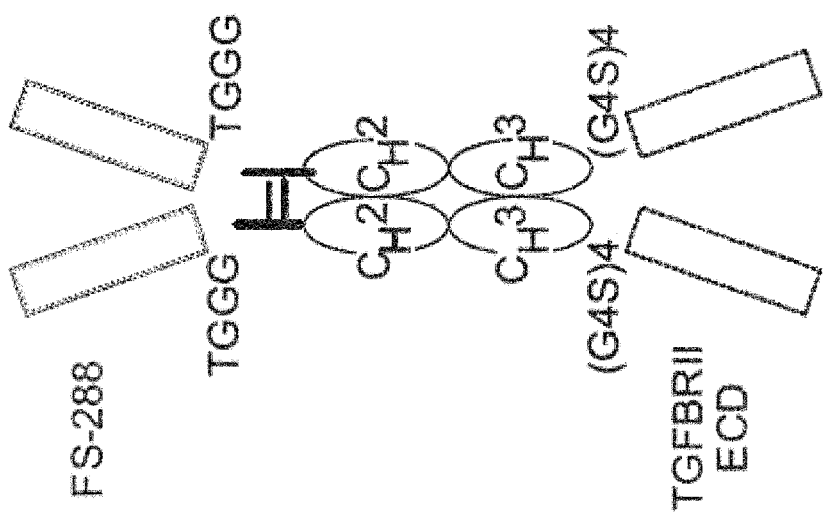

FIG. 14A shows a schematic example of a representative multispecific binder comprising a TβRII (referred to here as a TGFBRII) polypeptide (e.g., a polypeptide that is at least 70%, 75%, 80%, 85%, 90%, 91%, 92%, 93%, 94%, 95%, 97%, 98%, 99% or 100% identical to SEQ ID NO: 170) and a follistatin polypeptide (e.g. a polypeptide that is at least 70%, 75%, 80%, 85%, 90%, 91%, 92%, 93%, 94%, 95%, 97%, 98%, 99% or 100% identical to SEQ ID NO: 111). FIG. 14A discloses "TGGG" as SEQ ID NO: 3 and "(G4S) 4" as SEQ ID NO: 203. FIG. 14B shows a schematic example of multispecific binder comprising a TβRII polypeptide (e.g., a polypeptide that is at least 70%, 75%, 80%, 85%, 90%, 91%, 92%, 93%, 94%, 95%, 97%, 98%, 99% or 100% identical to SEQ ID NO: 170) and a GDF8 antigen binding fragment (e.g. a polypeptide comprising the heavy chain and light chain CDRs of SEQ ID NOs: 151-156). FIG. 14B discloses "(G4S)4" as SEQ ID NO: 203.

Figure 15B:
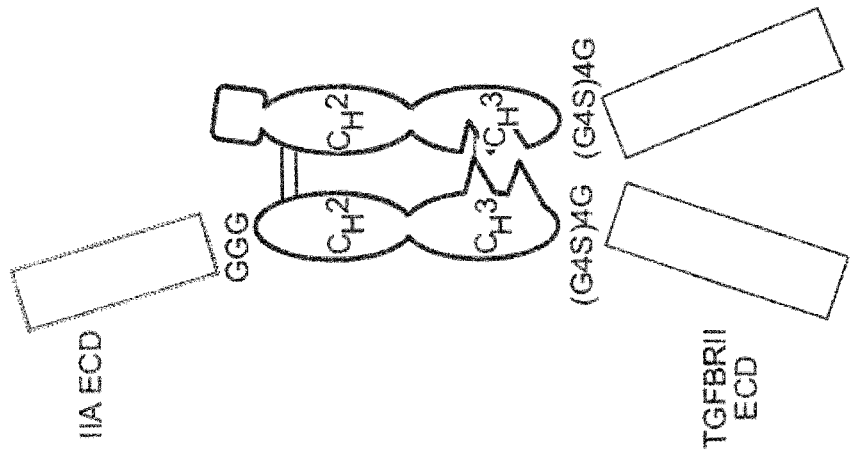
Figure 15A:
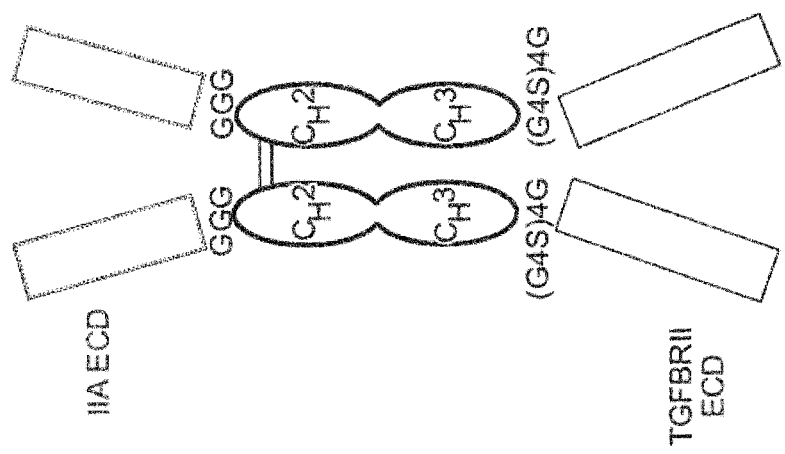

FIG. 15A shows a simplified schematic of a representative "four arm" homodimer comprising two fusion proteins, with each fusion protein comprising an ActRIIA extracellular domain (IIB ECD), a GGG linker (SEQ ID NO: 63), an Fc portion comprising CH2-CH3 Fc domains, a (G4S)4G linker (SEQ ID NO: 202), and a TGFβRII extracellular domain (TGFβRII ECD). FIG. 15B shows a simplified schematic of a representative "three-arm" heteromultimer comprising two fusion proteins, where the first fusion protein comprises an ActRIIA extracellular domain (IIB ECD), a GGG linker (SEQ ID NO: 63), an Fc portion comprising CH2-CH3 Fc domains with "knob substitutions", a (G4S)4G linker (SEQ ID NO: 202), and a TGFβRII extracellular domain (TGFβRII ECD); and where the second fusion protein comprises an Fc portion comprising CH2-CH3 Fc domains with "hole substitutions", a (G4S)4G linker (SEQ ID NO: 202), and a TGFβRII extracellular domain (TGFβRII ECD).

DETAILED DESCRIPTION OF THE INVENTION

1. Overview

In some embodiments, the disclosure provides for a multispecific binder of TGFβ-superfamily ligands. In some embodiments, the multispecific binder protein is capable of binding to a) at least one of TGFβ1 and TGFβ3, and b) at least one of activin A, activin B, activin AB, GDF11, and GDF8. In some embodiments, the multispecific binder comprises: a) a first portion that is capable of binding to TGFβ1 and/or TGFβ3; and b) a second portion that is capable of binding to at least one of activin A, activin B, activin AB, GDF11, and GDF8. In some embodiments, the multispecific binder is a heteromultimer comprising an ActRIIA polypeptide and a TβRII polypeptide. In some embodiments, the multispecific binder comprises a TβRII polypeptide and a follistatin or a follistatin-like protein domain. In some embodiments, the multispecific binder comprises a TβRII polypeptide and an antibody or antigen-binding fragment, wherein the antibody or antigen-binding fragment is capable of binding to one or more of activin A, activin B, activin AB, GDF11, and/or GDF8. In particular embodiments, the multispecific binder comprises a TβRII polypeptide and an antibody or antigen-binding fragment, wherein the antibody or antigen-binding fragment is capable of binding to GDF8.

In some embodiments, the disclosure provides heteromultimers that comprise an ActRIIA polypeptide and a TβRII polypeptide. Preferably, such ActRIIA polypeptides comprise a ligand-binding domain of an ActRIIA receptor and such TβRII polypeptides comprise a ligand-binding domain of a TβRII receptor. In certain preferred embodiments, ActRIIA:TβRII heteromultimers of the disclosure are soluble. In certain preferred embodiments, ActRIIA:TβRII heteromultimers of the disclosure have an altered TGFβ superfamily ligand specificity compared to a corresponding sample of a homomultimer (e.g., an ActRIIA:TβRII heterodimer compared to an ActRIIA:ActRIIA homodimer or an TβRII:TβRII homodimer).

The TGFβ superfamily is comprised of over 30 secreted factors including TGFβs, activins, nodals, bone morphogenetic proteins (BMPs), growth and differentiation factors (GDFs), and anti-Mullerian hormone (AMH) [Weiss et al. (2013) Developmental Biology, 2(1): 47-63]. Members of the superfamily, which are found in both vertebrates and invertebrates, are ubiquitously expressed in diverse tissues and function during the earliest stages of development throughout the lifetime of an animal. Indeed, TGFβ superfamily proteins are key mediators of stem cell self-renewal, gastrulation, differentiation, organ morphogenesis, and adult tissue homeostasis. Consistent with this ubiquitous activity, aberrant TGFβ superfamily signaling is associated with a wide range of human pathologies including, for example, autoimmune disease, cardiovascular disease, fibrotic disease, and cancer.

Ligands of the TGFβ superfamily share the same dimeric structure in which the central 3-1/2 turn helix of one monomer packs against the concave surface formed by the beta-strands of the other monomer. The majority of TGFβ family members are further stabilized by an intermolecular disulfide bond. This disulfide bonds traverses through a ring formed by two other disulfide bonds generating what has been termed a 'cysteine knot' motif [Lin et al. (2006) Reproduction 132: 179-190; and Hinck et al. (2012) FEBS Letters 586: 1860-1870].

TGFβ superfamily signaling is mediated by heteromeric complexes of type I and type II serine/threonine kinase receptors, which phosphorylate and activate downstream SMAD proteins (e.g., SMAD proteins 1, 2, 3, 5, and 8) upon ligand stimulation [Massagué (2000) Nat. Rev. Mol. Cell Biol. 1:169-178]. These type I and type II receptors are transmembrane proteins, composed of a ligand-binding extracellular domain with cysteine-rich region, a transmembrane domain, and a cytoplasmic domain with predicted serine/threonine kinase specificity. In general, type I receptors mediate intracellular signaling while the type II receptors are required for binding TGFβ superfamily ligands. Type I and II receptors form a stable complex after ligand binding, resulting in phosphorylation of type I receptors by type II receptors.

The TGFβ family can be divided into two phylogenetic branches based on the type I receptors they bind and the Smad proteins they activate. One is the more recently evolved branch, which includes, e.g., the TGFβs, activins, GDF8, GDF9, GDF11, BMP3 and nodal, which signal through type I receptors that activate Smads 2 and 3 [Hinck (2012) FEBS Letters 586:1860-1870]. The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7, which signal through Smads 1, 5, and 8.

TGFβ isoforms are the founding members of the TGFβ superfamily, of which there are 3 known isoforms in mammals designated as TGFβ1, TGFβ2 and TGFβ3. Mature bioactive TGFβ ligands function as homodimers and predominantly signal through the type I receptor ALK5, but have also been found to additionally signal through ALK1 in endothelial cells [Goumans et al. (2003) Mol Cell 12(4): 817-828]. TGFβ1 is the most abundant and ubiquitously expressed isoform. TGFβ1 is known to have an important role in wound healing, and mice expressing a constitutively active TGFβ1 transgene develop fibrosis [Clouthier et al. (1997) J Clin. Invest. 100(11): 2697-2713]. TGFβ1 is also involved in T cell activation and maintenance of T regulatory cells [Li et al. (2006) Immunity 25(3): 455-471]. TGFβ2 expression was first described in human glioblastoma cells, and is occurs in neurons and astroglial cells of the embryonic nervous system. TGFβ2 is known to suppress interleukin-2-dependent growth of T lymphocytes. TGFβ3 was initially isolated from a human rhabdomyosarcoma cell line and since has been found in lung adenocarcinoma and kidney carcinoma cell lines. TGFβ3 is known to be important for palate and lung morphogenesis [Kubiczkova et al. (2012) Journal of Translational Medicine 10:183].

Activins are members of the TGFβ superfamily and were initially discovered as regulators of secretion of follicle-stimulating hormone, but subsequently various reproductive and non-reproductive roles have been characterized. There are three principal activin forms (A, B, and AB) that are homo/heterodimers of two closely related β subunits ($β_Aβ_A$, $β_Bβ_B$, and $β_Aβ_B$, respectively). The human genome also encodes an activin C and an activin E, which are primarily expressed in the liver, and heterodimeric forms containing $β_C$ or $β_E$ are also known. In the TGFβ superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos [DePaolo et al. (1991) Proc Soc Ep Biol Med. 198:500-512; Dyson et al. (1997) Curr Biol. 7:81-84; and Woodruff (1998) Biochem Pharmacol. 55:953-963]. In several tissues, activin signaling is antagonized by its related heterodimer, inhibin. For example, in the regulation of follicle-stimulating hormone (FSH) secretion from the pituitary, activin promotes FSH synthesis and secretion, while inhibin reduces FSH synthesis and secretion. Other proteins that may regulate activin bioactivity and/or bind to activin include follistatin (FS), follistatin-related protein (FSRP, also known as FLRG or FSTL3), and $α_2$-macroglobulin.

As described herein, agents that bind to "activin A" are agents that specifically bind to the $β_A$ subunit, whether in the context of an isolated $β_A$ subunit or as a dimeric complex (e.g., a $β_Aβ_A$ homodimer or a $β_Aβ_B$ heterodimer). In the case of a heterodimer complex (e.g., a $β_Aβ_B$ heterodimer), agents that bind to "activin A" are specific for epitopes present within the $β_A$ subunit, but do not bind to epitopes present within the non-$β_A$ subunit of the complex (e.g., the $β_B$ subunit of the complex). Similarly, agents disclosed herein that antagonize (inhibit) "activin A" are agents that inhibit one or more activities as mediated by a $β_A$ subunit, whether in the context of an isolated $β_A$ subunit or as a dimeric complex (e.g., a $β_Aβ_A$ homodimer or a $β_Aβ_B$ heterodimer). In the case of $β_Aβ_B$ heterodimers, agents that inhibit "activin A" are agents that specifically inhibit one or more activities of the $β_A$ subunit, but do not inhibit the activity of the non-$β_A$ subunit of the complex (e.g., the $β_B$ subunit of the complex). This principle applies also to agents that bind to and/or inhibit "activin B", "activin C", and "activin E". Agents disclosed herein that antagonize "activin AB" are agents that inhibit one or more activities as mediated by the $β_A$ subunit and one or more activities as mediated by the $β_B$ subunit.

The same principle also applies to agent that bind to and/or inhibit "activin AC", "activin BC", "activin AE", and "activin BE".

The BMPs and GDFs together form a family of cysteine-knot cytokines sharing the characteristic fold of the TGFβ superfamily [Rider et al. (2010) Biochem J., 429(1):1-12]. This family includes, for example, BMP2, BMP4, BMP6, BMP7, BMP2a, BMP3, BMP3b (also known as GDF10), BMP4, BMP5, BMP6, BMP7, BMP8, BMP8a, BMP8b, BMP9 (also known as GDF2), BMP10, BMP11 (also known as GDF11), BMP12 (also known as GDF7), BMP13 (also known as GDF6), BMP14 (also known as GDF5), BMP15, GDF1, GDF3 (also known as VGR2), GDF8 (also known as myostatin), GDF9, GDF15, and decapentaplegic. Besides the ability to induce bone formation, which gave the BMPs their name, the BMP/GDFs display morphogenetic activities in the development of a wide range of tissues. BMP/GDF homo- and hetero-dimers interact with combinations of type I and type II receptor dimers to produce multiple possible signaling complexes, leading to the activation of one of two competing sets of SMAD transcription factors. BMP/GDFs have highly specific and localized functions. These are regulated in a number of ways, including the developmental restriction of BMP/GDF expression and through the secretion of several specific BMP antagonist proteins that bind with high affinity to the cytokines. Curiously, a number of these antagonists resemble TGFβ superfamily ligands.

Growth and differentiation factor-8 (GDF8) is also known as myostatin. GDF8 is a negative regulator of skeletal muscle mass and is highly expressed in developing and adult skeletal muscle. The GDF8 null mutation in transgenic mice is characterized by a marked hypertrophy and hyperplasia of skeletal muscle [McPherron et al. Nature (1997) 387:83-90]. Similar increases in skeletal muscle mass are evident in naturally occurring mutations of GDF8 in cattle and, strikingly, in humans [Ashmore et al. (1974) Growth, 38:501-507; Swatland and Kieffer, J. Anim. Sci. (1994) 38:752-757; McPherron and Lee, Proc. Natl. Acad. Sci. USA (1997) 94:12457-12461; Kambadur et al. Genome Res. (1997) 7:910-915; and Schuelke et al. (2004) N Engl J Med, 350:2682-8]. Studies have also shown that muscle wasting associated with HIV-infection in humans is accompanied by increases in GDF8 protein expression [Gonzalez-Cadavid et al., PNAS (1998) 95:14938-43]. In addition, GDF8 can modulate the production of muscle-specific enzymes (e.g., creatine kinase) and modulate myoblast cell proliferation [International Patent Application Publication No. WO 00/43781]. The GDF8 propeptide can noncovalently bind to the mature GDF8 domain dimer, inactivating its biological activity [Miyazono et al. (1988) J. Biol. Chem., 263: 6407-6415; Wakefield et al. (1988) J. Biol. Chem., 263; 7646-7654; and Brown et al. (1990) Growth Factors, 3: 35-43]. Other proteins which bind to GDF8 or structurally related proteins and inhibit their biological activity include follistatin, and potentially, follistatin-related proteins [Gamer et al. (1999) Dev. Biol., 208: 222-232].

GDF11, also known as BMP11, is a secreted protein that is expressed in the tail bud, limb bud, maxillary and mandibular arches, and dorsal root ganglia during mouse development [McPherron et al. (1999) Nat. Genet., 22: 260-264; and Nakashima et al. (1999) Mech. Dev., 80: 185-189]. GDF11 plays a unique role in patterning both mesodermal and neural tissues [Gamer et al. (1999) Dev Biol., 208:222-32]. GDF11 was shown to be a negative regulator of chondrogenesis and myogenesis in developing chick limb [Gamer et al. (2001) Dev Biol., 229:407-20]. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium [Wu et al. (2003) Neuron., 37:197-207]. Hence, inhibitors GDF11 may have in vitro and in vivo applications in the treatment of diseases such as muscle diseases and neurodegenerative diseases (e.g., amyotrophic lateral sclerosis).

BMP7, also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and ActRIIB. However, BMP7 and activin recruit distinct type I receptors into heteromeric receptor complexes. The major BMP7 type I receptor observed was ALK2, while activin bound exclusively to ALK4 (ActRIIB). BMP7 and activin elicited distinct biological responses and activated different SMAD pathways [Macias-Silva et al. (1998) J Biol Chem. 273:25628-36].

As described herein, comparative inhibition data demonstrated that an ActRIIA:TβRII heterodimer can antagonize a broad range of Smad 2/3 activating ligands. For example, the disclosure demonstrates that an ActRIIA:TβRII heterodimer inhibits TGFβ1, TGFβ3, activin A, activin B, and GDF11 signaling pathways in a cell-based assay. In contrast, ActRIIA and TβRII homodimers alone inhibit a smaller subset of Smad 2/3 activating ligands. Moreover, the data demonstrate that the ActRIIA:TβRII heterodimer is a surprisingly more selective Smad 2/3 ligand antagonists that merely combining the antagonistic profiles of ActRIIA and TβRII homodimer ligand traps. For example, the ActRIIA:TβRII heterodimer inhibited activin A, activin B, and GDF ii signaling pathways similarly to an ActRIIA homodimer. However, ActRIIA:TβRII heterodimer inhibition of BMP10 signaling pathways is significantly reduced compared to the ActRIIA homodimer. ActRIIA:TβRII heteromultimers therefore are more selective antagonists of Smad 2/3 activating ligands compared to ActRIIA homodimers. Accordingly, an ActRIIA:TβRII heterodimer will be more useful than an ActRIIA or TβRII homodimer, or combination thereof, in certain applications where such broad, yet selective, Smad 2/3 antagonism is advantageous.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin. However, in common usage and in the instant application, the term "homologous," when modified with an adverb such as "highly," may refer to sequence similarity and may or may not relate to a common evolutionary origin.

"Percent (%) sequence identity" or "percent (%) identical" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif, or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers. As used herein, the term "comprises" also encompasses the use of the narrower terms "consisting" and "consisting essentially of."

The term "consisting essentially of" is limited to the specified materials or steps and those that do not materially affect the basic and novel characteristics of the invention(s) disclosed herein.

The term "appreciable affinity" as used herein means binding with a dissociation constant ($K_D$) of less than 50 nM.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

The terms "heteromer" or "heteromultimer" is a complex comprising at least a first polypeptide chain and a second polypeptide chain, wherein the second polypeptide chain differs in amino acid sequence from the first polypeptide chain by at least one amino acid residue. The heteromer can comprise a "heterodimer" formed by the first and second polypeptide chains or can form higher order structures where one or more polypeptide chains in addition to the first and second polypeptide chains are present. Exemplary structures for the heteromultimer include heterodimers, heterotrimers, heterotetramers and further oligomeric structures. Heterodimers are designated herein as X:Y or equivalently as X-Y, where X represents a first polypeptide chain and Y represents a second polypeptide chain. Higher-order heteromers and oligomeric structures are designated herein in a corresponding manner. In certain embodiments a heteromultimer is recombinant (e.g., one or more polypeptide components may be a recombinant protein), isolated and/or purified.

As used herein, the term "capable of" (e.g., capable of binding to) means that something has the ability to perform a particular action, but does not necessarily need to be performing that action at any particular point in time. For example, if a protein is "capable of binding to a ligand", this would mean that the protein has the capability to bind to the ligand under physiological conditions, but is not required to be binding to the ligand at any particular point in time. Unless explicitly indicated otherwise herein, the term "binds to" means that something is "capable of binding to."

2. Multispecific Binder of TGFβ-Superfamily Ligands

In some embodiments, the disclosure provides for a multispecific binder of TGFβ-superfamily ligands. In some embodiments, the multispecific binder is capable of binding to a) at least one of TGFβ1 and TGFβ3, and b) at least one of activin A, activin B, activin AB, GDF11, and GDF8. In some embodiments, the multispecific binder comprises: a) a first portion that is capable of binding to TGFβ1 and/or TGFβ3; and b) a second portion that is capable of binding to at least one of activin A, activin B, activin AB, GDF11, and GDF8. In some embodiments, the multispecific binder is a heteromultimer comprising an ActRIIA polypeptide and a TβRII polypeptide. In some embodiments, the multispecific binder comprises a TβRII polypeptide and a follistatin or a follistatin-like protein domain. In some embodiments, the multispecific binder comprises a TβRII polypeptide and an antibody or antigen-binding fragment, wherein the antibody or antigen-binding fragment is capable of binding to one or more of activin A, activin B, activin AB, GDF11, and/or GDF8. In particular embodiments, the multispecific binder comprises a TβRII polypeptide and an antibody or antigen-binding fragment, wherein the antibody or antigen-binding fragment is capable of binding to GDF8.

A. ActRIIA and TβRII Polypeptides and Heteromultimers Thereof

In certain aspects, the present disclosure relates to heteromultimers comprising one or more ActRIIA receptor polypeptides (e.g., SEQ ID NOs: 51, 52, 82, 84, 88, and 90) and one or more TβRII receptor polypeptides (e.g., SEQ ID NOs: 9, 11, 13, 15, 17, 18, 27, 28, 29, 30, 31, 32, 33, 34, 35, 36, 37, 38, 39, 44, 45, 85, 87, 91, 93, 94, 95, 96, 97, 98, 99, and 100) which are generally referred to herein as "ActRIIA:TβRII heteromultimer complexes" or "ActRIIA:TβRII heteromultimers". Preferably, ActRIIA:TβRII heteromultimers of the disclosure are soluble, for example, a heteromultimer may comprises a soluble portion (domain) of a TβRII receptor and a soluble portion (domain) of an ActRIIA receptor. In general, the extracellular domains of TβRII and ActRIIA correspond to a soluble portion of these receptors. Therefore, in some embodiments, heteromultimers of the disclosure comprise an extracellular domain of a TβRII receptor and an extracellular domain of an ActRIIA receptor. Example extracellular domains TβRII and ActRIIA receptors are disclosed herein and such sequences, as well as fragments, functional variants, and modified forms thereof, may be used in accordance with the inventions of the disclosure (e.g., ActRIIA:TβRII heteromultimer compositions and uses thereof). ActRIIA:TβRII heteromultimers of the disclosure include, e.g., heterodimers, heterotrimers, heterotetramers and higher order oligomeric structures. See, e.g., FIGS. 9 and 10. In certain preferred embodiments, heteromultimers of the disclosure are ActRIIA:TβRII heterodimers. Preferably, ActRIIA:TβRII heteromultimers of the disclosure bind to one or more TGFβ superfamily ligands. In some embodiments, ActRIIA:TβRII heteromultimers may bind to one or more of activin (e.g., activin A, activin B, activin C, activin E, activin AC, activin AB, activin BC, activin AE, and activin BE), GDF11, TGFβ1, and TGFβ3. In some embodiments, ActRIIA:TβRII heteromultimers do not bind to, or no not substantially bind to BMP10 (e.g., have indeterminate $K_a$ or $K_d$ due to the transient nature of the interaction between BMP10 and an ActRIIA:TβRII heteromultimer). In some embodiments, ActRIIA:TβRII heteromultimers may be used to inhibit (antagonize) signaling (e.g., Smad 2/3) mediated by one or more TGFβ superfamily ligands. In particular, ActRIIA:TβRII heteromultimers of the disclosure may be used to inhibit intracellular signaling by one or more TGFβ superfamily ligands in, for example, a cell-based assay such as those described herein. For example, ActRIIA:TβRII heteromultimers may inhibit signaling mediated by one or more of activin (e.g., activin A, activin B, activin C, activin E, activin AC, activin AB, activin BC, activin AE, and activin BE), GDF11, TGFβ1, and TGFβ3 in a cell-based assay.

As used herein, the term "TβRII" refers to a family of transforming growth factor beta receptor II (TβRII) proteins from any species and variants derived from such TβRII proteins by mutagenesis or other modification. Reference to TβRII herein is understood to be a reference to any one of the currently identified forms. Members of the TβRII family are generally transmembrane proteins, composed of a ligand-binding extracellular domain comprising a cysteine-rich region, a transmembrane domain, and a cytoplasmic domain with predicted serine/threonine kinase activity. The term "TβRII polypeptide" includes polypeptides comprising any naturally occurring polypeptide of an TβRII family member as well as any variants thereof (including mutants, fragments, fusions, and peptidomimetic forms) that retain a useful activity.

As described above, human TβRII occurs naturally in at least two isoforms—A (long) and B (short)—generated by alternative splicing in the extracellular domain (ECD) (FIGS. 1 and 2 and SEQ ID NOS: 1 and 2). SEQ ID NO: 27, which corresponds to residues 23-159 of SEQ ID NO: 1, depicts the native full-length extracellular domain of the short isoform of TβRII. SEQ ID NO: 18, which corresponds to residues 23-184 of SEQ ID NO: 2, depicts the native full-length extracellular domain of the long isoform of TβRII. Unless noted otherwise, amino acid position numbering with regard to variants based on the TβRII short and long isoforms refers to the corresponding position in the native precursors, SEQ ID NO: 1 and SEQ ID NO: 2, respectively.

In certain embodiments, the disclosure provides variant TβRII polypeptides. A TβRII polypeptide of the disclosure may bind to and inhibit the function of a TGFβ superfamily member, such as but not limited to, TGFβ1 or TGFβ3. TβRII polypeptides may include a polypeptide consisting of, or comprising, an amino acid sequence at least 70% identical, and optionally at least 70%, 75%, 80%, 85%, 90%, 91%, 92%, 93%, 94%, 95%, 96%, 97%, 98%, 99%, or 100% identical to a truncated ECD domain of a naturally occurring TβRII polypeptide, whose C-terminus occurs at any of amino acids 153-159 of SEQ ID NO: 1. TβRII polypeptides may include a polypeptide consisting of, or comprising, an amino acid sequence at least 70% identical, and optionally at least 70%, 75%, 80%, 85%, 90%, 91%, 92%, 93%, 94%, 95%, 96%, 97%, 98%, 99%, or 100% identical to a truncated ECD domain of a naturally occurring TβRII polypeptide, whose C-terminus occurs at any of amino acids 178-184 of SEQ ID NO: 2. In particular embodiments, the TβRII polypeptides comprise an amino acid sequence at least 70% identical, and optionally at least 70%, 75%, 80%, 85%, 90%, 91%, 92%, 93%, 94%, 95%, 96%, 97%, 98%, 99%, or 100% identical to the amino acid sequence of SEQ ID NO: 18. Optionally, a TβRII polypeptide does not include more than 5 consecutive amino acids, or more than 10, 20, 30, 40, 50, 52, 60, 70, 80, 90, 100, 150 or 200 or more consecutive amino acids from a sequence consisting of amino acids 160-567 of SEQ ID NO: 1 or from a sequence consisting of amino acids 185-592 of SEQ ID NO: 2. In some embodiments, the TβRII polypeptide does not include amino acids 160-567 of SEQ ID NO: 1. In some embodiments, the TβRII polypeptide does not include amino acids 1-22 of SEQ ID NO: 1. In some embodiments, the TβRII polypeptide does not include amino acids 1-22 and 160-567 of SEQ ID NO: 1. In some embodiments, the TβRII polypeptide does not include amino acids 185-592 of SEQ ID NO: 2. In some embodiments, the TβRII polypeptide does not include amino acids 1-22 of SEQ ID NO: 2. In some embodiments, the TβRII polypeptide does not include amino acids 1-22 and 185-592 of SEQ ID NO: 2. The unprocessed TβRII polypeptide may either include or exclude any signal sequence, as well as any sequence N-terminal to the signal sequence. As elaborated herein, the N-terminus of the processed TβRII polypeptide may occur at any of amino acids 23-35 of SEQ ID NO: 1 or 23-60 of SEQ ID NO: 2. Examples of processed TβRII polypeptides include, but are not limited to, amino acids 23-159 of SEQ ID NO: 1 (set forth in SEQ ID NO: 27), amino acids 29-159 of SEQ ID NO: 1 (set forth in SEQ ID NO: 28), amino acids 35-159 of SEQ ID NO: 1 (set forth in SEQ ID NO: 29), amino acids 23-153 of SEQ ID NO: 1 (set forth in SEQ ID NO: 30), amino acids 29-153 of SEQ ID NO: 1 (set forth in SEQ ID NO: 31), amino acids 35-153 of SEQ ID NO: 1 (set forth in SEQ ID NO: 32), amino acids 23-184 of SEQ ID NO: 2 (set forth in SEQ ID NO: 18), amino acids 29-184 of SEQ ID NO: 2 (set forth in SEQ ID NO: 33), amino acids 60-184 of SEQ ID NO: 2 (set forth in SEQ ID NO: 29), amino acids 23-178 of SEQ ID NO: 2 (set forth in SEQ ID NO: 34), amino acids 29-178 of SEQ ID NO: 2 (set forth in SEQ ID NO: 35), and amino acids 60-178 of SEQ ID NO: 2 (set forth in SEQ ID NO: 32). It will be understood by one of skill in the art that corresponding variants based on the long isoform of TβRII will include nucleotide sequences encoding the 25-amino acid insertion along with a conservative Val-Ile substitution at the flanking position C-terminal to the insertion. The TβRII polypeptides accordingly may include isolated extracellular portions of TβRII polypeptides, including both the short and the long isoforms, variants thereof (including variants that comprise, for example, no more than 2, 3, 4, 5, 10, 15, 20, 25, 30, or 35 amino acid substitutions in the sequence corresponding to amino acids 23-159 of SEQ ID NO: 1 or amino acids 23-184 of SEQ ID NO: 2), fragments thereof, and fusion proteins comprising any of the foregoing, but in each case preferably any of the foregoing TβRII polypeptides will retain substantial affinity for at least one of, or both of, TGFβ1 or TGFβ3. Generally, a TβRII polypeptide will be designed to be soluble in aqueous solutions at biologically relevant temperatures, pH levels, and osmolarity.

In some embodiments, the variant TβRII polypeptides of the disclosure comprise one or more mutations in the extracellular domain that confer an altered ligand binding profile. A TβRII polypeptide may include one, two, five or more alterations in the amino acid sequence relative to the corresponding portion of a naturally occurring TβRII polypeptide. In some embodiments, the mutation results in a substitution, insertion, or deletion at the position corresponding to position 70 of SEQ ID NO: 1. In some embodiments, the mutation results in a substitution, insertion, or deletion at the position corresponding to position 110 of SEQ ID NO: 1. Examples include, but are not limited to, an N to D substitution or a D to K substitution in the positions corresponding to positions 70 and 110, respectively, of SEQ ID NO: 1. Examples of such variant TβRII polypeptides include, but are not limited to, the sequences set forth in SEQ ID NOs: 36-39. A TβRII polypeptide may comprise a polypeptide or portion thereof that is encoded by any one of SEQ ID NOs: 8, 10, 12, 14, 16, 46 or 47, or silent variants thereof or nucleic acids that hybridize to the complement thereof under stringent hybridization conditions. In particular embodiments, a TβRII polypeptide may comprise a polypeptide or portion thereof that is encoded by any one of SEQ ID NO: 12, or silent variants thereof or nucleic acids that hybridize to the complement thereof under stringent hybridization conditions.

In some embodiments, the variant TβRII polypeptides of the disclosure further comprise an insertion of 36 amino acids (SEQ ID NO: 41) between the pair of glutamate residues (positions 151 and 152 of SEQ ID NO: 1, or positions 176 and 177 of SEQ ID NO: 2) located near the C-terminus of the human TβRII ECD, as occurs naturally in the human TβRII isoform C (Konrad et al., BMC Genomics 8:318, 2007).

It has been demonstrated that TβRII polypeptides can be modified to selectively antagonize TβRII ligands. The N70 residue represents a potential glycosylation site. In some embodiments, the TβRII polypeptides are aglycosylated. In some embodiments, the TβRII polypeptides are aglycosylated or have reduced glycosylation at position Asn157. In some embodiments, the TβRII polypeptides are aglycosylated or have reduced glycosylation at position Asn73.

In certain embodiments, a TβRII polypeptide binds to TGFβ1, and the TβRII polypeptide does not show substantial binding to TGFβ3. In certain embodiments, a TβRII polypeptide binds to TGFβ3, and the TβRII polypeptide does not show substantial binding to TGFβ1. Binding may be assessed using purified proteins in solution or in a surface plasmon resonance system, such as a Biacore™ system.

In certain embodiments, a TβRII polypeptide inhibits TGFβ1 cellular signaling, and the TβRII polypeptide has an intermediate or limited inhibitory effect on TGFβ3 signaling. In certain embodiments, a TβRII polypeptide inhibits TGFβ3 cellular signaling, and the TβRII polypeptide has an intermediate or limited inhibitory effect on TGFβ1 signaling. Inhibitory effect on cell signaling can be assayed by methods known in the art.

Taken together, an active portion of a TβRII polypeptide may comprise amino acid sequences 23-153, 23-154, 23-155, 23-156, 23-157, or 23-158 of SEQ ID NO: 1, as well as variants of these sequences starting at any of amino acids 24-35 of SEQ ID NO: 1. Similarly, an active portion of a TβRII polypeptide may comprise amino acid sequences 23-178, 23-179, 23-180, 23-181, 23-182, or 23-183 of SEQ ID NO: 2, as well as variants of these sequences starting at any of amino acids 24-60 of SEQ ID NO: 2. Exemplary TβRII polypeptides comprise amino acid sequences 29-159, 35-159, 23-153, 29-153 and 35-153 of SEQ ID NO: 1 or amino acid sequences 29-184, 60-184, 23-178, 29-178 and 60-178 of SEQ ID NO: 2. Variants within these ranges are also contemplated, particularly those having at least 70%, 75%, 80%, 85%, 90%, 91%, 92%, 93%, 94%, 95%, 96%, 97%, 98%, or 99% identity to the corresponding portion of SEQ ID NO: 1 or SEQ ID NO: 2. A TβRII polypeptide may be selected that does not include the sequence consisting of amino acids 160-567 of SEQ ID NO: 1 or amino acids 185-592 of SEQ ID NO: 2. In particular embodiments, the TβRII polypeptides comprise an amino acid sequence at least 70% identical, and optionally at least 70%, 75%, 80%, 85%, 90%, 91%, 92%, 93%, 94%, 95%, 96%, 97%, 98%, 99%, or 100% identical to the amino acid sequence of SEQ ID NO: 18.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication Nos. WO 2006/012627 and WO 2007/062188, which are incorporated herein by reference in their entirety. Numbering of amino acids for all ActRIIA-related polypeptides described herein is based on the numbering of the human ActRIIA precursor protein sequence provided below (SEQ ID NO: 50), unless specifically designated otherwise.

The human ActRIIA precursor protein sequence is as follows:

(SEQ ID NO: 50)
```
  1 MGAAAKLAFA VFLISCSSGA ILGRSETQEC LFFNANWEKD
    RTNQTGVEPC

51 YGDKDKRRHC FATWKNISGS IEIVKQGCWL DDINCYDRTD
    CVEKKDSPEV

101 YFCCCEGNMC NEKFSYFPEM EVTQPTSNPV TPKPPYYNIL
    LYSLVPLMLI

151 AGIVICAFWV YRHHKMAYPP VLVPTQDPGP PPPSPLLGLK
    PLQLLEVKAR

201 GRFGCVWKAQ LLNEYVAVKI FPIQDKQSWQ NEYEVYSLPG
    MKHENILQFI

251 GAEKRGTSVD VDLWLITAFH EKGSLSDFLK ANVVSWNELC
    HIAETMARGL

301 AYLHEDIPGL KDGHKPAISH RDIKSKNVLL KNNLTACIAD
    FGLALKFEAG

351 KSAGDTHGQV GTRRYMAPEV LEGAINFQRD AFLRIDMYAM
    GLVLWELASR

401 CTAADGPVDE YMLPFEEEIG QHPSLEDMQE VVVHKKKRPV
    LRDYWQKHAG

451 MAMLCETIEE CWDHDAEARL SAGCVGERIT QMQRLTNIIT
    TEDIVTVVTM

501 VTNVDFPPKE SSL
```

The signal peptide is indicated by a single underline; the extracellular domain is indicated in bold font; and the potential, endogenous N-linked glycosylation sites are indicated by a double underline.

A processed extracellular human ActRIIA polypeptide sequence is as follows:

(SEQ ID NO: 51)
ILGRSETQECLFFNANWEKDRTNQTGVEPCYGDKDKRRHCFATWKNISGSIEIVKQGCWLDD

INCYDRTDCVEKKDSPEVYFCCCEGNMCNEKFSYFPEMEVTQPTSNPVTPKPP

The C-terminal "tail" of the extracellular domain is indicated by a single underline. The sequence with the "tail" deleted (a Δ15 sequence) is as follows:

(SEQ ID NO: 52)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

A nucleic acid sequence encoding the human ActRIIA precursor protein is shown below (SEQ ID NO: 56), corresponding to nucleotides 159-1700 of Genbank Reference Sequence NM_001616.4. The signal sequence is underlined.

(SEQ ID NO: 56)
```
  1 ATGGGAGCTG CTGCAAAGTT GGCGTTTGCC GTCTTTCTTA TCTCCTGTTC

51 TTCAGGTGCT ATACTTGGTA GATCAGAAAC TCAGGAGTGT CTTTTCTTTA

101 ATGCTAATTG GGAAAAAGAC AGAACCAATC AAACTGGTGT TGAACCGTGT

151 TATGGTGACA AAGATAAACG CGGCATTGT TTTGCTACCT GGAAGAATAT

201 TTCTGGTTCC ATTGAAATAG TGAAACAAGG TTGTTGGCTG GATGATATCA

251 ACTGCTATGA CAGGACTGAT TGTGTAGAAA AAAAGACAG CCCTGAAGTA

301 TATTTTTGTT GCTGTGAGGG CAATATGTGT AATGAAAAGT TTTCTTATTT

351 TCCGGAGATG GAAGTCACAC AGCCCACTTC AAATCCAGTT ACACCTAAGC

401 CACCCTATTA CAACATCCTG CTCTATTCCT TGGTGCCACT TATGTTAATT

451 GCGGGGATTG TCATTTGTGC ATTTTGGGTG TACAGGCATC ACAAGATGGC

501 CTACCCTCCT GTACTTGTTC CAACTCAAGA CCCAGGACCA CCCCCACCTT

551 CTCCATTACT AGGTTTGAAA CCACTGCAGT TATTAGAAGT GAAAGCAAGG
```

```
                        -continued
 601  GGAAGATTTG GTTGTGTCTG GAAAGCCCAG TTGCTTAACG AATATGTGGC

651  TGTCAAAATA TTTCCAATAC AGGACAAACA GTCATGGCAA AATGAATACG

701  AAGTCTACAG TTTGCCTGGA ATGAAGCATG AGAACATATT ACAGTTCATT

751  GGTGCAGAAA AACGAGGCAC CAGTGTTGAT GTGGATCTTT GGCTGATCAC

801  AGCATTTCAT GAAAAGGGTT CACTATCAGA CTTTCTTAAG GCTAATGTGG

851  TCTCTTGGAA TGAACTGTGT CATATTGCAG AAACCATGGC TAGAGGATTG

901  GCATATTTAC ATGAGGATAT ACCTGGCCTA AAAGATGGCC ACAAACCTGC

951  CATATCTCAC AGGGACATCA AAAGTAAAAA TGTGCTGTTG AAAAACAACC

1001  TGACAGCTTG CATTGCTGAC TTTGGGTTGG CCTTAAAATT TGAGGCTGGC

1051  AAGTCTGCAG GCGATACCCA TGGACAGGTT GGTACCCGGA GGTACATGGC

1101  TCCAGAGGTA TTAGAGGGTG CTATAAACTT CCAAAGGGAT GCATTTTTGA

1151  GGATAGATAT GTATGCCATG GGATTAGTCC TATGGGAACT GGCTTCTCGC

1201  TGTACTGCTG CAGATGGACC TGTAGATGAA TACATGTTGC CATTTGAGGA

1251  GGAAATTGGC CAGCATCCAT CTCTTGAAGA CATGCAGGAA GTTGTTGTGC

1301  ATAAAAAAAA GAGGCCTGTT TTAAGAGATT ATTGGCAGAA ACATGCTGGA

1351  ATGGCAATGC TCTGTGAAAC CATTGAAGAA TGTTGGGATC ACGACGCAGA

1401  AGCCAGGTTA TCAGCTGGAT GTGTAGGTGA AAGAATTACC CAGATGCAGA

1451  GACTAACAAA TATTATTACC ACAGAGGACA TTGTAACAGT GGTCACAATG

1501  GTGACAAATG TTGACTTTCC TCCCAAAGAA TCTAGTCTA
```

The nucleic acid sequence encoding processed extracellular ActRIIA polypeptide is as follows:

```
                                                 (SEQ ID NO: 57)
  1  ATACTTGGTA GATCAGAAAC TCAGGAGTGT CTTTTCTTTA ATGCTAATTG

51  GGAAAAAGAC AGAACCAATC AAACTGGTGT TGAACCGTGT TATGGTGACA

101  AAGATAAACG GCGGCATTGT TTTGCTACCT GGAAGAATAT TTCTGGTTCC

151  ATTGAAATAG TGAAACAAGG TTGTTGGCTG GATGATATCA ACTGCTATGA

201  CAGGACTGAT TGTGTAGAAA ALALAGACAG CCCTGAAGTA TATTTTTGTT

251  GCTGTGAGGG CAATATGTGT AAIGAAAAGT TTTCTTATTT TCCGGAGATG

302  GAAGTCACAC AGCCCACTTC AAATCCAGTT ACACCTAAGC CACCC
```

Figure 8:
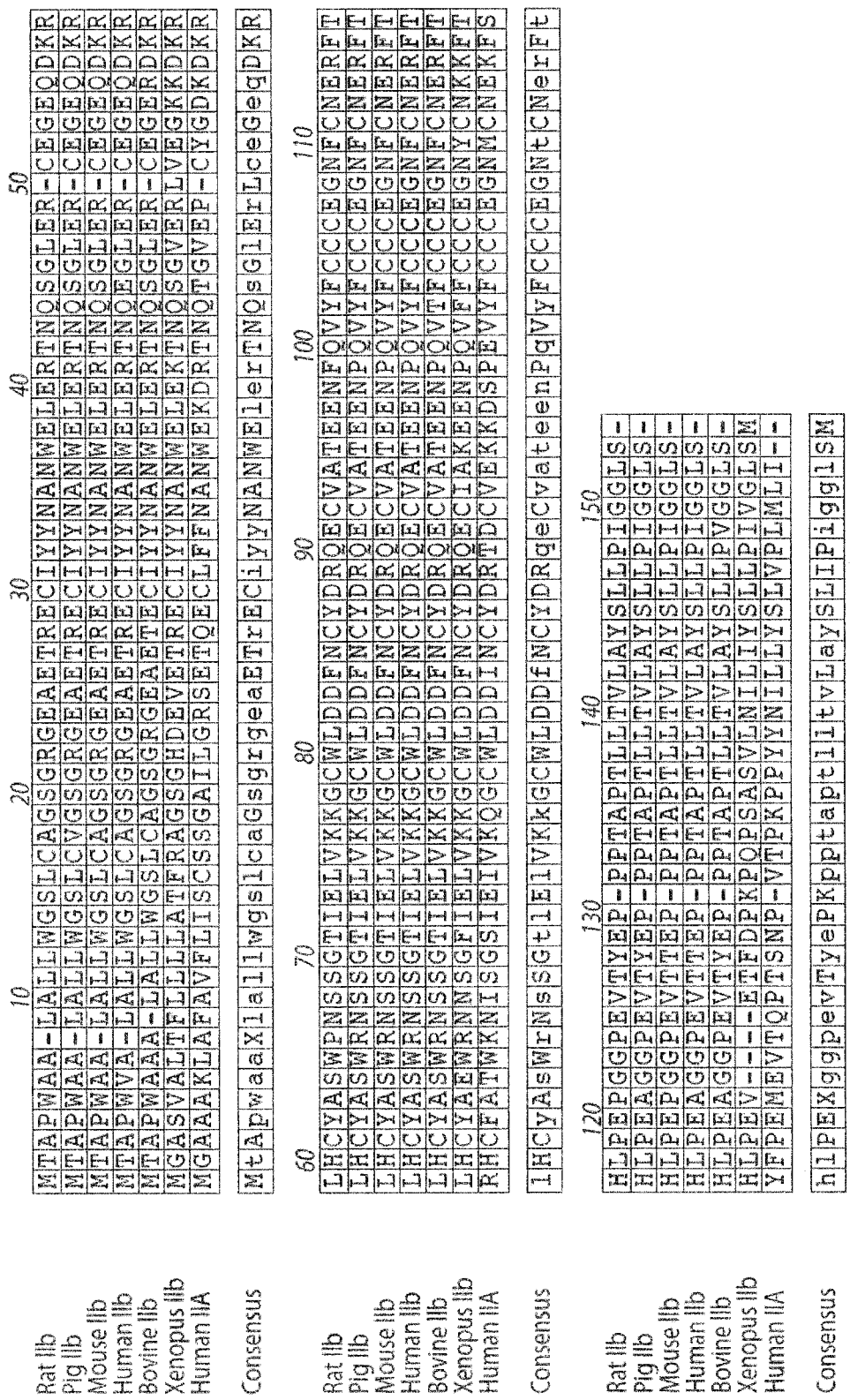
FIG. 8 shows a multiple sequence alignment of various vertebrate ActRIIA proteins (SEQ ID Nos: 101-102, 106, 213, 104-105, 107 and 103, respectively, in order of appearance) without their intracellular domains.

ActRIIA is well-conserved among vertebrates, with large stretches of the extracellular domain completely conserved. For example, FIG. 8 depicts a multi-sequence alignment of a human ActRIIA extracellular domain compared to various ActRIIA orthologs. Many of the ligands that bind to ActRIIA are also highly conserved. Accordingly, from these alignments, it is possible to predict key amino acid positions within the ligand-binding domain that are important for normal ActRIIA-ligand binding activities as well as to predict amino acid positions that are likely to be tolerant to substitution without significantly altering normal ActRIIA-ligand binding activities. Therefore, an active, human ActRIIA variant polypeptide useful in accordance with the presently disclosed methods may include one or more amino acids at corresponding positions from the sequence of another vertebrate ActRIIA, or may include a residue that is similar to that in the human or other vertebrate sequences.

Without meaning to be limiting, the following examples illustrate this approach to defining an active ActRIIA variant. As illustrated in FIG. 8, F13 in the human extracellular domain is Y in *Ovis aries* (sheep) (SEQ ID NO: 102), *Gallus gallus* (chicken) (SEQ ID NO: 104), *Bos taurus* (cow) (SEQ ID NO: 105), *Tyto alba* (owl) (SEQ ID NO: 107), and *Myotis davidii* (bat) (SEQ ID NO: 103) ActRIIA, indicating that aromatic residues are tolerated at this position, including F, W, and Y. Q24 in the human extracellular domain is R in *Bos taurus* ActRIIA, indicating that charged residues will be tolerated at this position, including D, R, K, H, and E. S95 in the human extracellular domain is F in *Gallus gallus* and *Tyto alba* ActRIIA, indicating that this site may be tolerant of a wide variety of changes, including polar residues, such as E, D, K, R, H, S, T, P, G, Y, and probably hydrophobic residue such as L, I, or F. E52 in the human extracellular domain is D in *Ovis aries* ActRIIA, indicating that acidic residues are tolerated at this position, including D and E. P29 in the human extracellular domain is relatively poorly conserved, appearing as S in *Ovis aries* ActRIIA and L in *Myotis davidii* ActRIIA, thus essentially any amino acid should be tolerated at this position.

Moreover, as discussed above, ActRII proteins have been characterized in the art in terms of structural/functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103 (20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide ample guidance for how to generate ActRIIA variants that retain one or more desired activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIA, as demarcated by the outermost of these conserved cysteines, corresponds to positions 30-110 of SEQ ID NO: 50 (ActRIIA precursor). Therefore, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, 28, or 29 residues at the N-terminus and by about 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ActRIIA extracellular domains include SEQ ID NOs: 51 and 52.

Accordingly, a general formula for an active portion (e.g., ligand binding) of ActRIIA is a polypeptide that comprises, consists essentially of, or consists of amino acids 30-110 of SEQ ID NO: 50. Therefore ActRIIA polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99% or 100% identical to a portion of ActRIIA beginning at a residue corresponding to any one of amino acids 21-30 (e.g., beginning at any one of amino acids 21, 22, 23, 24, 25, 26, 27, 28, 29, or 30) of SEQ ID NO: 50 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, 134, or 135) of SEQ ID NO: 50. Other examples include constructs that begin at a position selected from 21-30 (e.g., beginning at any one of amino acids 21, 22, 23, 24, 25, 26, 27, 28, 29, or 30), 22-30 (e.g., beginning at any one of amino acids 22, 23, 24, 25, 26, 27, 28, 29, or 30), 23-30 (e.g., beginning at any one of amino acids 23, 24, 25, 26, 27, 28, 29, or 30), 24-30 (e.g., beginning at any one of amino acids 24, 25, 26, 27, 28, 29, or 30) of SEQ ID NO: 50, and end at a position selected from 111-135 (e.g., ending at any one of amino acids 111, 112, 113, 114, 115, 116, 117, 118, 119, 120, 121, 122, 123, 124, 125, 126, 127, 128, 129, 130, 131, 132, 133, 134 or 135), 112-135 (e.g., ending at any one of amino acids 112, 113, 114, 115, 116, 117, 118, 119, 120, 121, 122, 123, 124, 125, 126, 127, 128, 129, 130, 131, 132, 133, 134 or 135), 113-135 (e.g., ending at any one of amino acids 113, 114, 115, 116, 117, 118, 119, 120, 121, 122, 123, 124, 125, 126, 127, 128, 129, 130, 131, 132, 133, 134 or 135), 120-135 (e.g., ending at any one of amino acids 120, 121, 122, 123, 124, 125, 126, 127, 128, 129, 130, 131, 132, 133, 134 or 135), 130-135 (e.g., ending at any one of amino acids 130, 131, 132, 133, 134 or 135), 111-134 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 134), 111-133 (e.g., ending at any one of amino acids 110, 111, 112, 113, 114, 115, 116, 117, 118, 119, 120, 121, 122, 123, 124, 125, 126, 127, 128, 129, 130, 131, 132, or 133), 111-132 (e.g., ending at any one of amino acids 110, 111, 112, 113, 114, 115, 116, 117, 118, 119, 120, 121, 122, 123, 124, 125, 126, 127, 128, 129, 130, 131, or 132), or 111-131 (e.g., ending at any one of amino acids 110, 111, 112, 113, 114, 115, 116, 117, 118, 119, 120, 121, 122, 123, 124, 125, 126, 127, 128, 129, 130, or 131) of SEQ ID NO: 50. Variants within these ranges are also contemplated, particularly those comprising, consisting essentially of, or consisting of an amino acid sequence that has at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 50. Thus, in some embodiments, an ActRIIA polypeptide may comprise, consists essentially of, or consist of a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 50. Optionally, ActRIIA polypeptides comprise a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 50, and comprising no more than 1, 2, 5, 10 or 15 conservative amino acid changes in the ligand-binding pocket.

As described above, the disclosure provides TβRII or ActRIIA polypeptides sharing a specified degree of sequence identity or similarity to a naturally occurring TβRII or ActRIIA polypeptide. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, the percent identity between two amino acid sequences is determined using the Needleman and Wunsch (J Mol. Biol. (48):444-453 (1970)) algorithm which has been incorporated into the GAP program in the GCG software package (available at http://www.gcg.com). In a specific embodiment, the following parameters are used in the GAP program: either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)) (available at http://www.gcg.com). Exemplary parameters include using a NWSgapdna.CMP matrix and a gap weight of 40, 50, 60, 70, or 80 and a length weight of 1, 2, 3, 4, 5, or 6. Unless otherwise specified, percent identity between two amino acid sequences is to be determined using the GAP program using a Blosum 62 matrix, a GAP weight of 10 and a length weight of 3, and if such algorithm cannot compute the desired percent identity, a suitable alternative disclosed herein should be selected.

In another embodiment, the percent identity between two amino acid sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

Another embodiment for determining the best overall alignment between two amino acid sequences can be determined using the FASTDB computer program based on the algorithm of Brutlag et al. (Comp. App. Biosci., 6:237-245 (1990)). In a sequence alignment the query and subject sequences are both amino acid sequences. The result of said global sequence alignment is presented in terms of percent identity. In one embodiment, amino acid sequence identity is performed using the FASTDB computer program based on the algorithm of Brutlag et al. (Comp. App. Biosci., 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

Polypeptides of the disclosure (e.g., TβRII or ActRIIA polypeptides) may additionally include any of various leader sequences at the N-terminus. Such a sequence would allow the peptides to be expressed and targeted to the secretion pathway in a eukaryotic system. See, e.g., Ernst et al., U.S. Pat. No. 5,082,783 (1992). Alternatively, a native signal sequence (e.g., native TβRII or ActRIIA signal sequence) may be used to effect extrusion from the cell. Possible leader sequences include native leaders, tissue plasminogen activator (TPA) and honeybee mellitin (SEQ ID NOs. 22-24, respectively). Examples of TβRII-Fc and ActRIIA-Fc fusion proteins incorporating a TPA leader sequence include SEQ ID NOs: 11, 13, 15, 17, 82, 85, 88, and 91. Processing of signal peptides may vary depending on the leader sequence chosen, the cell type used and culture conditions, among other variables, and therefore actual N-terminal start sites for processed polypeptides may shift by 1, 2, 3, 4 or 5 amino acids in either the N-terminal or C-terminal direction. It will be understood by one of skill in the art that corresponding variants based on the long isoform of TβRII will include the 25-amino acid insertion along with a conservative Val-Ile substitution at the flanking position C-terminal to the insertion.

In certain embodiments, the present disclosure contemplates specific mutations of the polypeptides (e.g., TβRII or ActRIIA polypeptides) so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagine-X-serine) (where "X" is any amino acid) which is specifically recognized by appropriate cellular glycosylation enzymes. The alteration may also be made by the addition of, or substitution by, one or more serine or threonine residues to the sequence of the wild-type polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a polypeptide may be accomplished chemically and/or enzymatically. Chemical deglycosylation may involve, for example, exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on polypeptides can be achieved by the use of a variety of endo- and exo-glycosidases as described by Thotakura et al. (1987) Meth. Enzymol. 138:350. The sequence of a polypeptide may be adjusted, as appropriate, depending on the type of expression system used, as mammalian, yeast, insect and plant cells may all introduce differing glycosylation patterns that can be affected by the amino acid sequence of the peptide. In general, polypeptides (e.g., TβRII or ActRIIA polypeptides) for use in humans will be expressed in a mammalian cell line that provides proper glycosylation, such as HEK293 or CHO cell lines, although other mammalian expression cell lines, yeast cell lines with engineered glycosylation enzymes, and insect cells are expected to be useful as well.

This disclosure further contemplates a method of generating mutants, particularly sets of combinatorial mutants of a polypeptide (e.g., TβRII or ActRIIA polypeptides as well as heteromultimers thereof), as well as truncation mutants; pools of combinatorial mutants are especially useful for identifying functional variant sequences. The purpose of screening such combinatorial libraries may be to generate, for example, polypeptide variants which can act as either agonists or antagonist, or alternatively, which possess novel activities all together. A variety of screening assays are provided below, and such assays may be used to evaluate variants. For example, a ActRIIA:TβRII heteromultimer comprising an ActRIIA and/or TβRII polypeptide variant may be screened for ability to bind to an AcRIIA or TβRII ligand, to prevent binding of an ActRIIA or TβRII ligand to an ActRIIA or TβRII polypeptide or to interfere with signaling caused by an ActRIIA or TβRII ligand.

Combinatorially-derived variants can be generated which have a selective or generally increased potency relative to a polypeptide (e.g., TβRII or ActRIIA polypeptides) comprising an extracellular domain of a naturally occurring polypeptide. Likewise, mutagenesis can give rise to variants which have serum half-lives dramatically different than the corresponding wild-type polypeptide. For example, the altered protein can be rendered either more stable or less stable to proteolytic degradation or other processes which result in destruction of, or otherwise elimination or inactivation of, a native TβRII polypeptide. Such variants, and the genes which encode them, can be utilized to alter TβRII polypeptide levels by modulating the half-life of the TβRII polypeptides. For instance, a short half-life can give rise to more transient biological effects and can allow tighter control of recombinant polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential polypeptide (e.g., TβRII or ActRIIA polypeptides) sequences. For instance, a mixture of synthetic oligonucleotides can be enzymatically ligated into gene sequences such that the degenerate set of potential polypeptide nucleotide sequences are expressible as individual polypeptides, or alternatively, as a set of larger fusion proteins (e.g., for phage display).

There are many ways by which the library of potential polypeptide (e.g., TβRII or ActRIIA polypeptide) variants can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, polypeptide (e.g., TβRII or ActRIIA polypeptide) variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268: 2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, NY; and Greener et al., (1994) Strategies in Mol Biol 7:32-34). Linker scanning mutagenesis, particularly in a combinatorial setting, is an attractive method for identifying truncated (bioactive) forms of polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of polypeptides (e.g., TβRII or ActRIIA polypeptides). The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include ligand binding assays and ligand-mediated cell signaling assays.

In certain embodiments, the polypeptides (e.g., TβRII or ActRIIA polypeptides) of the disclosure may further comprise post-translational modifications in addition to any that are naturally present in the native polypeptides. Such modifications include, but are not limited to, acetylation, carboxylation, glycosylation, phosphorylation, lipidation, pegylation (polyethylene glycol) and acylation. As a result, the modified polypeptides may contain non-amino acid elements, such as polyethylene glycols, lipids, mono- or poly-saccharides, and phosphates. Effects of such non-amino acid elements on the functionality of a polypeptide may be tested as described herein for other polypeptide variants. When a polypeptide is produced in cells by cleaving a nascent form of the polypeptide, post-translational processing may also be important for correct folding and/or function of the protein. Different cells (such as CHO, HeLa, MDCK, 293, WI38, NIH-3T3 or HEK-293) have specific cellular machinery and characteristic mechanisms for such post-translational activities and may be chosen to ensure the correct modification and processing of the polypeptides.

In certain aspects, the disclosure provides for fusion proteins (e.g., TβRII or ActRIIA fusion proteins), and in some embodiments, a first portion (e.g., a TβRII or ActRIIA polypeptide portion) is connected to a heterologous portion (e.g., Fc portion) by means of a linker. In some embodiments, the linkers are glycine and serine rich linkers. Other near neutral amino acids, such as, but not limited to, Thr, Asn, Pro and Ala, may also be used in the linker sequence. In some embodiments, the linker comprises various permutations of amino acid sequences containing Gly and Ser. In some embodiments, the linker is greater than 10 amino acids in length. In further embodiments, the linkers have a length of at least 12, 15, 20, 21, 25, 30, 35, 40, 45 or 50 amino acids. In some embodiments, the linker is less than 40, 35, 30, 25, 22 or 20 amino acids. In some embodiments, the linker is 10-50, 10-40, 10-30, 10-25, 10-21, 10-15, 10, 15-25, 17-22, 20, or 21 amino acids in length. In some preferred embodiments, the linker comprises the amino acid sequence GlyGlyGlyGlySer (GGGGS) (SEQ ID NO: 19), or repetitions thereof (GGGGS)$_n$, where n≥2 (SEQ ID NO: 198). In particular embodiments n≥3, or n=3-10. The application teaches the surprising finding that proteins comprising a TβRII portion and a heterologous portion fused together by means of a (GGGGS)$_4$ linker (SEQ ID NO: 203) were associated with a stronger affinity for TGFβ1 and TGFβ3 as compared to a TβRII fusion protein where n<4. As such, in preferred embodiments, n≥4, or n=4-10. The application also teaches that proteins comprising (GGGGS)$_n$ linkers ("GGGGS" disclosed as SEQ ID NO: 204) in which n>4 had similar inhibitory properties as proteins having the (GGGGS)$_4$ linker (SEQ ID NO: 203). As such, in some embodiments, n is not greater than 4 in a (GGGGS)n linker (SEQ ID NO: 214). In some embodiments, n=4-10, 4-9, 4-8, 4-7, 4-6, 4-5, 5-8, 5-7, or 5-6. In some embodiments, n=3, 4, 5, 6, or 7. In particular embodiments, n=4. In some embodiments, a linker comprising a (GGGGS)$_n$ (SEQ ID NO: 205) sequence also comprises an N-terminal threonine. In some embodiments, the linker is any one of the following:

```
GGGGSGGGGS                                      (SEQ ID NO: 21)

TGGGGSGGGGS                                     (SEQ ID NO: 4)

TGGGGSGGGGSGGGGS                                (SEQ ID NO: 5)

TGGGGSGGGGSGGGGSGGGGS                           (SEQ ID NO: 6)

TGGGGSGGGGSGGGGSGGGGSGGGGS                      (SEQ ID NO: 25)

TGGGGSGGGGSGGGGSGGGGSGGGGSGGGGS                 (SEQ ID NO: 26)
or

TGGGGSGGGGSGGGGSGGGGSGGGGSGGGGSGGGGS.           (SEQ ID NO: 40)
```

In some embodiments, the linker comprises the amino acid sequence of TGGGPKSCDK (SEQ ID NO: 7). In some embodiments, the linker is any one of SEQ ID NOs: 21, 4-7, 25-26 or 40 lacking the N-terminal threonine. In some embodiments, a linker may be rich in glycine (e.g., 2-10, 2-5, 2-4, 2-3 glycine residues) and may, for example, contain a single sequence of threonine/serine and glycines or repeating sequences of threonine/serine and/or glycines, e.g., GGG (SEQ ID NO: 63), GGGG (SEQ ID NO: 64), TGGGG (SEQ ID NO: 65), SGGGG (SEQ ID NO: 66), or SGGG (SEQ ID NO: 67) singlets, or repeats. In some embodiments, the linker does not comprise the amino acid sequence of SEQ ID NO: 26 or 40.

In some embodiments, the TβRII polypeptides comprise an amino acid sequence that is at least 80%, 85%, 90%, 92%, 94%, 95%, 97%, 99% or 100% identical to the amino acid sequence of any one of SEQ ID NOs: 94-100. In some embodiments, the TβRII polypeptides comprise an amino acid sequence that is at least 80%, 85%, 90%, 92%, 94%, 95%, 97%, 99% or 100% identical to the amino acid sequence of SEQ ID NO: 94. In some embodiments, the TβRII polypeptides comprise an amino acid sequence that is at least 80%, 85%, 90%, 92%, 94%, 95%, 97%, 99% or 100% identical to the amino acid sequence of SEQ ID NO: 98.

In certain aspects, functional variants or modified forms of the TβRII or ActRIIA polypeptides include fusion proteins having at least a portion of the TβRII or ActRIIA polypeptides and one or more heterologous portions. Well-known examples of such heterologous portions include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A heterologous portion may be selected so as to confer a desired property. For example, some heterologous portions are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$ (SEQ ID NO: 178)) fusion partners. As another example, a heterologous portion may be selected so as to facilitate detection of the TβRII or ActRIIA polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the heterologous portions have a protease cleavage site, such as for Factor Xa or Thrombin, which allows the relevant protease to partially digest the fusion proteins and thereby liberate the recombinant proteins therefrom. The liberated proteins can then be isolated from the heterologous portion by subsequent chromatographic separation. In certain preferred embodiments, a TβRII or ActRIIA polypeptide is fused with a domain that stabilizes the TβRII or ActRIIA polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of heterologous portions that may be selected include multimerizing (e.g., dimerizing, tetramerizing) domains and functional domains.

It is understood that different elements of the fusion proteins may be arranged in any manner that is consistent with the desired functionality. For example, a TβRII or ActRIIA polypeptide may be placed C-terminal to a heterologous domain, or, alternatively, a heterologous domain may be placed C-terminal to a TβRII or ActRIIA polypeptide. The TβRII or ActRIIA polypeptide domain and the heterologous domain need not be adjacent in a fusion protein, and additional domains or amino acid sequences may be included C- or N-terminal to either domain or between the domains.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In some embodiments, the immunoglobulin Fc region is a human immunoglobulin Fc region.

In one embodiment, the class of immunoglobulin from which the heavy chain constant region is derived is IgG (Igγ) (γ subclasses 1, 2, 3, or 4).

An example of a native amino acid sequence that may be used for the Fc portion of human IgG1 (G1Fc) is shown below (SEQ ID NO: 58). Dotted underline indicates the hinge region, and solid underline indicates positions with naturally occurring variants. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 58. Naturally occurring variants in G1Fc would include E134D and M136L according to the numbering system used in SEQ ID NO: 58 (see Uniprot P01857).

```
                                                       (SEQ ID NO: 58)
  1   THTCPPCPAP   ELLGGPSVFL   FPPKPKDTLM   ISRTPEVTCV   VVDVSHEDPE

51   VKFNWYVDGV   EVHNAKTKPR   EEQYNSTYRV   VSVLTVLHQD   WLNGKEYKCK

101   VSNKALPAPI   EKTISKAKGQ   PREPQVYTLP   PSREEMTKNQ   VSLTCLVKGF

151   YPSDIAVEWE   SNGQPENNYK   TTPPVLDSDG   SFFLYSKLTV   DKSRWQQGNV

201   FSCSVMHEAL   HNHYTQKSLS   LSPGK
```

Optionally, the IgG1 Fc domain has one or more mutations at residues such as Asp-265, lysine 322, and Asn-434. In certain cases, the mutant IgG1 Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the MHC class I-related Fc-receptor (FcRN) relative to a wild-type IgG1 Fc domain.

An example of a native amino acid sequence that may be used for the Fc portion of human IgG2 (G2Fc) is shown below (SEQ ID NO: 59). Dotted underline indicates the hinge region and double underline indicates positions where there are data base conflicts in the sequence (according to UniProt P01859). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99% or 100% identity to SEQ ID NO: 59.

```
                                                       (SEQ ID NO: 59)
  1   VECPPCPAPP   VAGPSVELFP   PKPKDTLMIS   RTPEVTCVVV   DVSHEDPEVQ

51   FNWYVDGVEV   HNAKTKPREE   QFNSTFRVVS   VLTVVHQDWL   NGKEYKCKVS

101   NKGLPAPIEK   TISKTKGQPR   EPQVYTLPPS   REEMTKNQVS   LTCLVKGFYP

151   SDIAVEWESN   GQPENNYKTT   PPMLDSDGSF   FLYSKLTVDK   SRWQQGNVFS

201   CSVMHEALHN   HYTQKSLSLS   PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 60) contains a short hinge region consisting of a single 15-residue segment, whereas the second G3Fc sequence (SEQ ID NO: 61) contains a full-length hinge region. In each case, dotted underline indicates the hinge region, and solid underline indicates positions with naturally occurring variants according to UniProt P01859. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NOs: 60 or 61.

```
                                                         (SEQ ID NO: 60)
  1  EPKSCDTPPP CPRCPAPELL GGPSVFLFPP KPKDTLMISR TPEVTCVVVD

51  VSHEDPEVQF KWYVDGVEVH NAKTKPREEQ YNSTFRVVSV LTVLHQDWLN

101  GKEYKCKVSN KALPAPIEKT ISKTKGQPRE PQVYTLPPSR EEMTKNQVSL

151  TCLVKGFYPS DIAVEWESSG QPENNYNTTP PMLDSDGSFF LYSKLTVDKS

201  RWQQGNIFSC SVMHEALHNR FTQKSLSLSP GK
                                                         (SEQ ID NO: 61)
  1  ELKTPLGDTT HTCPRCPEPK SCDTPPPCPR CPEPKSCDTP PPCPRCPEPK

51  SCDTPPPCPR CPAPELLGGP SVFLFPPKPK DTLMISRTPE VTCVVVDVSH

101  EDPEVQFKWY VDGVEVHNAK TKPREEQYNS TFRVVSVLTV LHQDWLNGKE

151  YKCKVSNKAL PAPIEKTISK TKGQPREPQV YTLPPSREEM TKNQVSLTCL

201  VKGFYPSDIA VEWESSGQPE NNYNTTPPML DSDGSFFLYS KLTVDKSRWQ

251  QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 60, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 62). Dotted underline indicates the hinge region. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 62.

```
                                                         (SEQ ID NO: 62)
  1  ESKYGPPCPS CPAPEFLGGP SVFLFPPKPK DTLMISRTPE VTCVVVDVSQ

51  EDPEVQFNWY VDGVEVHNAK TKPREEQFNS TYRVVSVLTV LHQDWLNGKE

101  YKCKVSNKGL PSSIEKTISK AKGQPREPQV YTLPPSQEEM TKNQVSLTCL
```

```
-continued
151 VKGFYPSDIA VEWESNGQPE NNYKTTPPVL DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 58), and analogous mutations in G2Fc, G3Fc, and G4Fc can be derived from their alignment with G1Fc in FIG. 6. Due to unequal hinge lengths, analogous Fc positions based on isotype alignment (FIG. 6) possess different amino acid numbers in SEQ ID NOs: 58, 59, 60, 61, and 62. It can also be appreciated that a given amino acid position in an immunoglobulin sequence consisting of hinge, $C_H2$, and $C_H3$ regions (e.g., SEQ ID NOs: 58, 59, 60, 61, and 62) will be identified by a different number than the same position when numbering encompasses the entire IgG1 heavy-chain constant domain (consisting of the $C_H1$, hinge, $C_H2$, and $C_H3$ regions) as in the Uniprot database.

Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087 and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a CH3 domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

For example, the application further provides Fc fusion proteins with engineered or variant Fc regions. Such antibodies and Fc fusion proteins may be useful, for example, in modulating effector functions, such as, antigen-dependent cytotoxicity (ADCC) and complement-dependent cytotoxicity (CDC). Additionally, the modifications may improve the stability of the antibodies and Fc fusion proteins. Amino acid sequence variants of the antibodies and Fc fusion proteins are prepared by introducing appropriate nucleotide changes into the DNA, or by peptide synthesis. Such variants include, for example, deletions from, and/or insertions into and/or substitutions of, residues within the amino acid sequences of the antibodies and Fc fusion proteins disclosed herein. Any combination of deletion, insertion, and substitution is made to arrive at the final construct, provided that the final construct possesses the desired characteristics. The amino acid changes also may alter post-translational processes of the antibodies and Fc fusion proteins, such as changing the number or position of glycosylation sites.

Antibodies and Fc fusion proteins with reduced effector function may be produced by introducing changes in the amino acid sequence, including, but are not limited to, the Ala-Ala mutation described by Bluestone et al. (see WO 94/28027 and WO 98/47531; also see Xu et al. 2000 Cell Immunol 200; 16-26). Thus, in certain embodiments, Fc fusion proteins of the disclosure with mutations within the constant region including the Ala-Ala mutation may be used to reduce or abolish effector function. According to these embodiments, antibodies and Fc fusion proteins may comprise a mutation to an alanine at position 234 or a mutation to an alanine at position 235, or a combination thereof. In one embodiment, the antibody or Fc fusion protein comprises an IgG4 framework, wherein the Ala-Ala mutation would describe a mutation(s) from phenylalanine to alanine at position 234 and/or a mutation from leucine to alanine at position 235. In another embodiment, the antibody or Fc fusion protein comprises an IgG1 framework, wherein the Ala-Ala mutation would describe a mutation(s) from leucine to alanine at position 234 and/or a mutation from leucine to alanine at position 235. The antibody or Fc fusion protein may alternatively or additionally carry other mutations, including the point mutation K322A in the CH2 domain (Hezareh et al. 2001 J Virol. 75: 12161-8).

In particular embodiments, the antibody or Fc fusion protein may be modified to either enhance or inhibit complement dependent cytotoxicity (CDC). Modulated CDC activity may be achieved by introducing one or more amino acid substitutions, insertions, or deletions in an Fc region (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. Nos. 5,648,260; 5,624,821; and WO94/29351.

In certain preferred embodiments, heteromultimers described herein comprise at least one TβRII polypeptide associated, covalently or non-covalently, with at least one ActRIIA polypeptide. Preferably, polypeptides disclosed herein form heterodimeric complexes, although higher order heteromultimeric complexes are also included such as, but not limited to, heterotrimers, heterotetramers, and further oligomeric structures (see, e.g., FIGS. 9 and 10). In some embodiments, TβRII and/or ActRIIA polypeptides comprise at least one multimerization domain. As disclosed herein, the term "multimerization domain" refers to an amino acid or sequence of amino acids that promote covalent or non-covalent interaction between at least a first polypeptide and at least a second polypeptide. Polypeptides disclosed herein may be joined covalently or non-covalently to a multimerization domain. Preferably, a multimerization domain promotes interaction between a first polypeptide (e.g., a TβRII polypeptide) and a second polypeptide (e.g., an ActRIIA polypeptide) to promote heteromultimer formation (e.g., heterodimer formation), and optionally hinders or otherwise disfavors homomultimer formation (e.g., homodimer formation), thereby increasing the yield of desired heteromultimer (see, e.g., FIGS. 9 and 10).

Many methods known in the art can be used to generate ActRIIA:TβRII heteromultimers. For example, non-naturally occurring disulfide bonds may be constructed by replacing on a first polypeptide (e.g., a TβRII polypeptide) a naturally occurring amino acid with a free thiol-containing residue, such as cysteine, such that the free thiol interacts with another free thiol-containing residue on a second polypeptide (e.g., an ActRIIA polypeptide) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S.20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of a TβRII polypeptide and the amino acid sequence of a first member of an interaction pair; and the second polypeptide comprises the amino acid sequence of an ActRIIA polypeptide and the amino acid sequence of a second member of an interaction pair. The interaction pair may be any two polypeptide sequences that interact to form a complex, particularly a heterodimeric complex although operative embodiments may also employ an interaction pair that can form a homodimeric complex. One member of the interaction pair may be fused to a TβRII or ActRIIA polypeptide as described herein, including for example, a polypeptide sequence comprising, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of any one of SEQ ID NOs: 18, 27, 28, 29, 30, 31, 32, 33, 34, 35, 36, 37, 38, 39, 51, and 52. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric complex (see, e.g., FIGS. 9 and 10). Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

A problem that arises in large-scale production of asymmetric immunoglobulin-based proteins from a single cell line is known as the "chain association issue". As confronted prominently in the production of bispecific antibodies, the chain association issue concerns the challenge of efficiently producing a desired multichain protein from among the multiple combinations that inherently result when different heavy chains and/or light chains are produced in a single cell line [Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), "knobs-into-holes" steric pairing, SEEDbody pairing, and leucine zipper-based pairing [Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605]. As described herein, these methods may be used to generate ActRIIA-Fc:TβRII-Fc heteromultimer. See FIGS. 9 and 10.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The table below lists possible charge change mutations that can be used, alone or in combination, to enhance ActRIIA:TβRII heteromultimer formation.

Examples of Pair-Wise Charged Residue Mutations to Enhance Heterodimer Formation

| Position in first chain | Mutation in first chain | Interacting position in second chain | Corresponding mutation in second chain |
|---|---|---|---|
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positive-charged amino acid in the interface (e.g., a lysine, arginine, or histidine) is replaced with a negatively charged amino acid (e.g., aspartic acid or glutamic acid). Alternatively, or in combination with the forgoing substitution, a negative-charged amino acid in the interface is replaced with a positive-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarily can be arbitrarily fused to the TβRII or ActRIIA polypeptide of the construct, with or without an optional linker, to generate an ActRIIA:TβRII heteromultimer. This single chain can be coexpressed in a cell of choice along with the Fc sequence complementary to the first Fc to favor generation of the desired multichain construct (e.g., ActRIIA:TβRII heteromultimer). In this example based on electrostatic steering, SEQ ID NO: 68 [human G1Fc(E356K/D399K)] and SEQ ID NO: 69 [human G1Fc(K392D/K409D)] are examples of complementary Fc sequences in which the engineered amino acid substitutions are double underlined, and the TGFβ superfamily type I or type II receptor polypeptide of the construct can be fused to either SEQ ID NO: 68 or SEQ ID NO: 69, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 6) will generate complementary Fc pairs which may be used instead of the complementary hG1Fc pair below (SEQ ID NOs: 68 and 69).

```
                                                    (SEQ ID NO: 68)
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PREPQVYTLP  PSRKEMTKNQ  VSLTCLVKGF

151  YPSDIAVEWE  SNGQPENNYK  TTPPVLKSDG  SFFLYSKLTV  DKSRWQQGNV

201  FSCSVMHEAL  HNHYTQKSLS  LSPGK (SEQ ID NO: 69)
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PREPQVYTLP  PSREEMTKNQ  VSLTCLVKGF
```

-continued

```
151 YPSDIAVEWE SNGQPENNYD TTPPVLDSDG SFFLYSDLTV DKSRWQQGNV

201 FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to the TβRII or ActRIIA polypeptide of the construct, with or without an optional linker, to generate an ActRIIA:TβRII heteromultimer. This single chain can be co-expressed in a cell of choice along with the Fc sequence complementary to the first Fc to favor generation of the desired multi-chain construct. In this example based on knobs-into-holes pairing, SEQ ID NO: 70 [human G1Fc(T144Y)] and SEQ ID NO: 71 [human G1Fc(Y185T)] are examples of complementary Fc sequences in which the engineered amino acid substitutions are double underlined, and the TβRII or ActRIIA polypeptide of the construct can be fused to either SEQ ID NO: 70 or SEQ ID NO: 71, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 6) will generate complementary Fc pairs which may be used instead of the complementary hG1Fc pair below (SEQ ID NOs: 70 and 71).

```
                                                      (SEQ ID NO: 70)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLYCLVKGF

151 YPSDIAVEWE SNGQPENNYK TTPPVLDSDG SFFLYSKLTV DKSRWQQGNV

201 FSCSVMHEAL HNHYTQKSLS LSPGK (SEQ ID NO: 71)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLTSKLTV DKSRWQQGNV

201 FSCSVMHEAL HNHYTQKSLS LSPGK
```

An example of Fc complementarity based on knobs-into-holes pairing combined with an engineered disulfide bond is disclosed in SEQ ID NO: 72 [hG1Fc(S132C/T144W)] and SEQ ID NO: 73 [hG1Fc(Y127C/T144S/L146A/Y185V)]. The engineered amino acid substitutions in these sequences are double underlined, and the TGFβ superfamily type I or type II polypeptide of the construct can be fused to either SEQ ID NO: 72 or SEQ ID NO: 73, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 6) will generate complementary Fc pairs which may be used instead of the complementary hG1Fc pair below (SEQ ID NOs: 72 and 73).

```
                                                      (SEQ ID NO: 72)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTKNQ VSLWCLVKGF

151 YPSDIAVEWE SNGQPENNYK TTPPVLDSDG SFFLYSKLTV DKSRWQQGNV

201 FSCSVMHEAL HNHYTQKSLS LSPGK
```

```
                                                     (SEQ ID NO: 73)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVCTLP PSREEMTKNQ VSLSCAVKGF

151 YPSDIAVEWE SNGQPENNYK TTPPVLDSDG SFFLVSKLTV DKSRWQQGNV

201 FSCSVMHEAL HNHYTQKSLS LSPGK
```

In part, the disclosure provides desired pairing of asymmetric Fc-containing polypeptide chains using Fc sequences engineered to generate interdigitating β-strand segments of human IgG and IgA C$_H$3 domains. Such methods include the use of strand-exchange engineered domain (SEED) C$_H$3 heterodimers allowing the formation of SEEDbody fusion proteins [Davis et al. (2010) Protein Eng Design Sel 23:195-202]. One of a pair of Fc sequences with SEEDbody complementarity can be arbitrarily fused to the TβRII or ActIIA of the construct, with or without an optional linker, to generate a TβRII or ActRIIA fusion polypeptide. This single chain can be co-expressed in a cell of choice along with the Fc sequence complementary to the first Fc to favor generation of the desired multi-chain construct. In this example based on SEEDbody (Sb) pairing, SEQ ID NO: 74 [hG1Fc(Sb$_{AG}$)] and SEQ ID NO: 75 [hG1Fc(Sb$_{GA}$)] are examples of complementary IgG Fc sequences in which the engineered amino acid substitutions from IgA Fc are double underlined, and the TβRII or ActRIIA polypeptide of the construct can be fused to either SEQ ID NO: 74 or SEQ ID NO: 75, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 6) will generate an Fc monomer which may be used in the complementary IgG-IgA pair below (SEQ ID NOs: 74 and 75).

In part, the disclosure provides desired pairing of asymmetric Fc-containing polypeptide chains with a cleavable leucine zipper domain attached at the C-terminus of the Fc C$_H$3 domains. Attachment of a leucine zipper is sufficient to cause preferential assembly of heterodimeric antibody heavy chains [Wranik et al (2012) J Biol Chem 287:43331-43339]. As disclosed herein, one of a pair of Fc sequences attached to a leucine zipper-forming strand can be arbitrarily fused to the TβRII or ActRIIA polypeptide of the construct, with or without an optional linker, to generate a TβRII or ActRIIA fusion polypeptide. This single chain can be co-expressed in a cell of choice along with the Fc sequence attached to a complementary leucine zipper-forming strand to favor generation of the desired multi-chain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 76 [hG1Fc-Ap1 (acidic)] and SEQ ID NO: 77 [hG1Fc-Bp1 (basic)] are examples of complementary IgG Fc sequences in which the engineered complimentary leucine zipper sequences are underlined, and the TβRII or ActRIIA polypeptide of the construct can be fused to either SEQ ID NO: 76 or SEQ ID NO: 77, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc, or hG4Fc (see FIG. 6) will generate an Fc monomer which may be used in the complementary leucine zipper-forming pair below (SEQ ID NOs: 76 and 77).

```
                                                     (SEQ ID NO: 74)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PFRPEVHLLP PSREEMTKNQ VSLTCLARGF

151 YPKDIAVEWE SNGQPENNYK TTPSRQEPSQ GTTTFAVTSK LTVDKSRWQQ

201 GNVFSCSVMH EALHNHYTQK TISLSPGK (SEQ ID NO: 75)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PPSEELALNE LVTLTCLVKG

151 FYPSDIAVEW ESNGQELPRE KYLTWAPVLD SDGSFFLYSI LRVAAEDWKK

201 GDTFSCSVMH EALHNHYTQK SLDRSPGK
```

```
  1 THTCPPCPAP ELLGGPSVFL FPPKPKDTLM ISRTPEVTCV VVDVSHEDPE
 51 VKFNWYVDGV EVHNAKTKPR EEQYNSTYRV VSVLTVLHQD WLNGKEYKCK
101 VSNKALPAPI EKTISKAKGQ PREPQVYTLP PSREEMTKNQ VSLTCLVKGF
151 YPSDIAVEWE SNGQPENNYK TTPPVLDSDG SFFLYSKLTV DKSRWQQGNV
201 FSCSVMHEAL HNHYTQKSLS LSPGKGGSAQ LEKELQALEK ENAQLEWELQ
251 ALEKELAQGA T (SEQ ID NO: 76)

1 THTCPPCPAP ELLGGPSVFL FPPKPKDTLM ISRTPEVTCV VVDVSHEDPE
 51 VKFNWYVDGV EVHNAKTKPR EEQYNSTYRV VSVLTVLHQD WLNGKEYKCK
101 VSNKALPAPI EKTISKAKGQ PREPQVYTLP PSREEMTKNQ VSLTCLVKGF
151 YPSDIAVEWE SNGQPENNYK TTPPVLDSDG SFFLYSKLTV DKSRWQQGNV
201 FSCSVMHEAL HNHYTQKSLS LSPGKGGSAQ LKKKLQALKK KNAQLKWKLQ
251 ALKKKLAQGA T (SEQ ID NO: 77)
```

In certain aspects, the disclosure relates to TβRII polypeptides (e.g., TβRII-Fc fusion proteins) comprising one or more amino acid modifications that alter the isoelectric point (pI) of the TβRII polypeptide and/or ActRIIA polypeptides (e.g., ActRIIA-Fc fusion proteins) comprising one or more amino acid modifications that alter the isoelectric point of the ActRIIA polypeptide. In some embodiments, one or more candidate domains that have a pI value higher than about 5.0, 5.5, 6.0, 6.5, 7.0, 7.5, 8.0, 8.5, or 9.0 are selected for construction of the full multidomain protein. In other embodiments, one or more candidate domains that have a pI value less than about 9.0, 8.5, 8.0, 7.5, 7.0, 6.5, 6.0, 5.5, or 5.0 are selected for construction of the full multidomain protein. It will be understood by one skilled in the art that a single protein will have multiple charge forms. Without wishing to be bound by any particular theory, the charge of a protein can be modified by a number of different mechanisms including but not limited to, amino acid substitution, cationization, deamination, carboxyl-terminal amino acid heterogeneity, phosphorylation and glycosylation.

The pI of a protein may be determined by a variety of methods including but not limited to, isoelectric focusing and various computer algorithms (see for example Bjellqvist et al., 1993, Electrophoresis 14:1023). In one embodiment, pI is determined using a Pharmacia Biotech Multiphor 2 electrophoresis system with a multi temp refrigerated bath recirculation unit and an EPS 3501 XL power supply. Pre-cast ampholine gels (e.g., Amersham Biosciences, pI range 2.5-10) are loaded with protein samples. Broad range pI marker standards (e.g., Amersham, pI range 3-10, 8 .mu.L) are used to determine relative pI for the proteins. Electrophoresis may be performed, for example, at 1500 V, 50 mA for 105 minutes. The gel is fixed using, for example, a Sigma fixing solution (5×) diluted with purified water to 1×. Staining is performed, for example, overnight at room temperature using Simply Blue stain (Invitrogen). Destaining is carried out, for example, with a solution that consisted of 25% ethanol, 8% acetic acid and 67% purified water. Isoelectric points are determined using, for example, a Bio-Rad Densitometer relative to calibration curves of the standards. The one or more metrics may further include metrics characterizing stability of the domain under one or more different conditions selected from the group consisting of different pH values, different temperatures, different shear stresses, and different freeze/thaw cycles.

In part, the disclosure provides desired pairing of asymmetric Fc-containing polypeptide chains by methods described above in combination with additional mutations in the Fc domain which facilitate purification of the desired heteromeric species. An example is complementarity of Fc domains based on knobs-into-holes pairing combined with an engineered disulfide bond, as disclosed in SEQ ID NOs: 72-73, plus additional substitution of two negatively charged amino acids (aspartic acid or glutamic acid) in one Fc-containing polypeptide chain and two positively charged amino acids (e.g., arginine) in the complementary Fc-containing polypeptide chain (SEQ ID NOs: 78-79). These four amino acid substitutions facilitate selective purification of the desired heteromeric fusion protein from a heterogeneous polypeptide mixture based on differences in isoelectric point or net molecular charge. The engineered amino acid substitutions in these sequences are double underlined below, and the TβRII or ActRIIA polypeptide of the construct can be fused to either SEQ ID NO: 78 or SEQ ID NO: 79, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 6) will generate complementary Fc pairs which may be used instead of the complementary hG1Fc pair below (SEQ ID NOs: 78-79).

```
                                                      (SEQ ID NO: 78)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTENQ VSLWCLVKGF

151 YPSDIAVEWE SNGQPENNYK TTPPVLDSDG SFFLYSKLTV DKSRWQQGNV

201 FSCSVMHEAL HNHYTQDSLS LSPGK
                                                      (SEQ ID NO: 79)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK
```

```
-continued
101  VSNKALPAPI EKTISKAKGQ PREPQVCTLP PSREEMTKNQ VSLSCAVKGF

151  YPSDIAVEWE SRGQPENNYK TTPPVLDSRG SFFLVSKLTV DKSRWQQGNV

201  FSCSVMHEAL HNHYTQKSLS LSPGK
```

Another example involves complementarity of Fc domains based on knobs-into-holes pairing combined with an engineered disulfide bond, as disclosed in SEQ ID NOs: 72-73, plus a histidine-to-arginine substitution at position 213 in one Fc-containing polypeptide chain (SEQ ID NO: 80). This substitution (denoted H435R in the numbering system of Kabat et al.) facilitates separation of desired heteromer from undesirable homodimer based on differences in affinity for protein A. The engineered amino acid substitution is indicated by double underline, and the TβRII or ActRIIA polypeptide of the construct can be fused to either SEQ ID NO: 80 or SEQ ID NO: 73, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 6) will generate complementary Fc pairs which may be used instead of the complementary hG1Fc pair of SEQ ID NO: 80 (below) and SEQ ID NO: 73.

chains to heterodimerize with light chains. In particular, heterodimerization of a heavy and light chain occurs between the $C_H1$ with the $C_L$, which is generally stabilized by covalent linking of the two domains via a disulfide bridge. Constructs employing the full-length heavy chain, or at least a portion of the heavy chain comprising the hinge region, could give rise to antibody-like molecules comprising two "light chains" and two "heavy chains". See FIG. 10. A potential advantage of this design is that it may more closely mimic the naturally occurring TβRII-ligand-ActRIIA complex and may display higher affinity for the ligand than comparable single heterodimers. In some embodiments, this design may be modified by incorporating various heavy chain truncations including, for example, truncations that comprise the $C_H1$ domain and some or all of the hinge domain (giving rise to F(ab')$_2$-like molecules) as well as truncations that only comprise the $C_H1$ domain or a fragment thereof (giving rise to Fab-like molecules). See FIG. 10G. Various methods for designing such heteromultimer

```
                                            (SEQ ID NO: 80)
  1  THTCPPCPAP ELLGGPSVFL FPPKPKDTLM ISRTPEVTCV VVDVSHEDPE

51  VKFNWYVDGV EVHNAKTKPR EEQYNSTYRV VSVLTVLHQD WLNGKEYKCK

101  VSNKALPAPI EKTISKAKGQ PREPQVYTLP PCREEMTKNQ VSLWCLVKGF

151  YPSDIAVEWE SNGQPENNYK TTPPVLDSDG SFFLYSKLTV DKSRWQQGNV

201  FSCSVMHEAL HNRYTQKSLS LSPGK
```

As described above, various methods are known in the art that increase desired pairing of Fc-containing fusion polypeptide chains in a single cell line to produce a preferred asymmetric fusion protein at acceptable yields [Klein et al (2012) mAbs 4:653-663; and Spiess et al (2015) Molecular Immunology 67(2A): 95-106]. In addition, ActRIIA:TβRII heteromultimers may be generated using a combination of heavy and light chain fusion proteins comprising either an TβRII or ActRIIA polypeptide. For example, in some embodiments, a TβRII polypeptide may be fused, with or without a linker domain, to an immunoglobulin heavy chain (IgG1, IgG2, IgG3, IgG4, IgM, IgA1, or IgA2) that comprises at least a portion of the $C_H1$ domain. Similarly, an ActRIIA polypeptide may be fused, with or without a linker domain, to an immunoglobulin light chain (kappa or lambda) that comprises at least a portion of the light chain constant domain ($C_L$). In alternative embodiments, an ActRIIA polypeptide may be fused, with or without a linker domain, to an immunoglobulin heavy chain (IgG1, IgG2, IgG3, IgG4, IgM, IgA1, or IgA2) that comprises at least a portion of the $C_H1$ domain, and an TβRII polypeptide may be fused, with or without a linker domain, to an immunoglobulin light chain (kappa or lambda) that comprises at least a portion of the light chain constant domain ($C_L$). This design takes advantage of the natural ability of the heavy constructs are described in US 2009/0010879, Klein et al [(2012) mAbs 4:653-663], and Spiess et al [(2015) Molecular Immunology 67(2A): 95-106] the contents of which are incorporated in their entirety herein.

In some embodiments, it is desirable to generate antibody-like ActRIIA:TβRII heterodimers comprising at least one branch of the complex comprising an TβRII-$C_L$:ActRIIA-$C_H1$ heterodimer pair and at least a second branch comprising an ActRIIA-$C_L$:TβRII-$C_H1$ heterodimer pair. See, e.g., FIG. 10B. Such heterodimer complexes can be generated, for example, using combinations of heavy chain and light chain asymmetrical pairing technologies [Spiess et al (2015) Molecular Immunology 67(2A): 95-106]. For example, in CrossMab technology, [Schaefer et al (2011). Proc. Natl. Acad. Sci. U.S.A. 108: 11187-11192] light chain mispairing is overcome using domain crossovers and heavy chains heterodimerized using knobs-into-holes [Merchant et al (1998) Nat. Biotechnol. 16: 677-681]. For the domain crossovers either the variable domains or the constant domains are swapped between light and heavy chains to create two asymmetric Fab arms that drive cognate light chain pairing while preserving the structural and functional integrity of the variable domain [Fenn et al (2013) PLoS ONE 8: e61953]. An alternative approach for overcoming light chain mispairing is designing heavy and light chains with orthogonal Fab inter-faces [Lewis (2014) Nat. Biotechnol. 32: 191-198]. This has been accomplished by computational modeling [Das et al (2008) Annu. Rev. Biochem. 77: 363-382] in combination with X-ray crystallography to identify mutations at the $V_H/V_L$ and $C_H1/C_L$ interfaces. For the heterodimers generated using this methodology, it may be necessary to engineer mutations into both $V_H/V_L$ and $C_H1/C_L$ interfaces to minimize heavy/light chain mispairing. The designed orthogonal Fab interface may be used in conjunction with a heavy chain heterodimerization strategy to facilitate efficient IgG production in a single host cell. Electrostatic steering may also be used to generate orthogonal Fab interfaces to facilitate the construction of such heterodimers. Peptide linkers may be used to ensure cognate pairing of light and heavy chains in a format known as "LUZ-Y" [Wranik et al (2012) J. Biol. Chem. 287: 43331-43339], wherein heavy chain heterodimerization is accomplished using leucine zippers which may be subsequently removed by proteolysis in vitro.

In some embodiments, the disclosure provides for TβRII polypeptides fusion proteins, as well as ActRIIA:TβRII heteromultimers comprising the same, comprising an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NOs: 11, 13, 15, 17, 18, 27, 85, 87, 91, and 93 or biologically active fragments thereof. In some embodiments, the TβRII polypeptides fusion proteins, as well as ActRIIA:TβRII heteromultimers comprising the same, comprise an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NOs: 85, 87, 91, and 93, or biologically active fragments thereof. In some embodiments, the TβRII polypeptides fusion proteins, as well as ActRIIA:TβRII heteromultimers comprising the same, comprise an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NO: 87, or a biologically active fragment thereof. In some embodiments, the TβRII polypeptides fusion protein, as well as ActRIIA:TβRII heteromultimers comprising the same, comprises an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 93, or a biologically active fragment thereof.

In some embodiments, the disclosure provides for ActRIIA polypeptides fusion proteins, as well as ActRIIA:TβRII heteromultimers comprising the same, comprising an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NOs: 51, 52, 82, 84, 88, and 90 or biologically active fragments thereof. In some embodiments, the ActRIIA polypeptides fusion proteins, as well as ActRIIA:TβRII heteromultimers comprising the same, comprise an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NOs: 82, 84, 88, and 90, or biologically active fragments thereof. In some embodiments, the ActRIIA polypeptides fusion proteins, as well as ActRIIA:TβRII heteromultimers comprising the same, comprise an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NO: 84, or a biologically active fragment thereof. In some embodiments, the ActRIIA polypeptides fusion protein, as well as ActRIIA:TβRII heteromultimers comprising the same, comprises an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 90, or a biologically active fragment thereof.

In some embodiments, the TβRII fusion proteins described herein have improved binding affinity for TGFβ1 and TGFβ3. In some embodiments, a TβRII fusion protein comprising a linker at least 10 amino acids in length (e.g., a fusion protein having the amino acid sequence of any one of SEQ ID NOs: 11, 13 and 15) has improved binding affinity for TGFβ1 and TGFβ3 as compared to a reference TβRII fusion protein (e.g., a TβRII fusion protein having the amino acid sequence of SEQ ID NO: 9). In some embodiments, the TβRII fusion protein binds to TGFβ1 with a $K_D$ of less than 200 pM, less than 150 pM, less than 100 pM, less than 75 pM, less than 50 pM or less than 25 pM. In some embodiments, the fusion protein binds to TGFβ3 with a $K_D$ of less than 75 pM, less than 70 pM, less than 60 pM, less than 50 pM, less than 40 pM, less than 35 pM, less than 25 pM, less than 15, less than 10, or less than 5 pM.

In some embodiments any of the TβRII polypeptides, as well as ActRIIA:TβRII heteromultimers comprising the same, disclosed herein inhibits one or more of activin (e.g., activin A, activin B, activin C, activin E, activin AC, activin AB, activin BC, activin AE, and activin BE), GDF11, TGFβ1, and TGFβ3 in a measurable assay. In some embodiments, the reporter gene assay is a CAGA reporter assay. In some embodiments, the CAGA assay is based on a human lung carcinoma cell line transfected with a pGL3(CAGA)12 reporter plasmid (Dennler et al, 1998, EMBO 17: 3091-3100) as well as a Renilla reporter plasmid (pRLCMV) to control for transfection efficiency. The CAGA motif is present in the promoters of TGFβ-responsive genes (for example, PAI-1), so this vector is of general use for factors signaling through SMAD2 and SMAD3. See, e.g., Example 2.

In some embodiments, any of the fusion polypeptides disclosed herein comprises the following components: a) any of the TβRII or ActRIIA polypeptides disclosed herein ("A"), b) any of the linkers disclosed herein ("B"), c) any of the heterologous portions disclosed herein ("C"), and optionally a linker ("X"). In such embodiments, the fusion polypeptide may be arranged in a manner as follows (N-terminus to C-terminus): A-B-C or C-B-A. In such embodiments, the fusion polypeptide may be arranged in a manner as follows (N-terminus to C-terminus): X-A-B-C or X-C-B-A. In some embodiments, the fusion polypeptide comprises each of A, B and C (and optionally a leader sequence such as the amino acid sequence of SEQ ID NO: 23), and comprises no more than 100, 90, 80, 70, 60, 50, 40, 30, 20, 10, 5, 4, 3, 2 or 1 additional amino acids (but which may include further post-translational modifications, such as PEGylation).

In some embodiments, the fusion polypeptide comprises a leader sequence (e.g., SEQ ID NO: 23) positioned in a manner as follows (N-terminus to C-terminus): X-A-B-C, and the fusion polypeptide comprises 1, 2, 3, 4, or 5 amino acids between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises 1, 2, 3, 4, or 5 amino acids between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises an alanine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises an alanine between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises a glycine and an alanine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises a glycine and an alanine between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises a threonine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises a threonine between X and C.

In some embodiments, the TβRII fusion polypeptide, as well as ActRIIA:TβRII heteromultimers comprising the same, comprises an amino acid sequence that is at least 70%, 75%, 80%, 85%, 90%, 91%, 92%, 93%, 94%, 95%, 96%, 97%, 98%, or 99% identical to any of the TβRII polypeptide amino acid sequences disclosed herein (e.g., SEQ ID NO: 18 or 27), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation and/or glycosylation). In some embodiments, the TβRII fusion polypeptide, as well as ActRIIA:TβRII heteromultimers comprising the same, comprises an amino acid sequence that is at least 70%, 75%, 80%, 85%, 90%, 91%, 92%, 93%, 94%, 95%, 96%, 97%, 98%, or 99% identical to any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation and/or glycosylation). In some embodiments, the TβRII fusion polypeptide, as well as ActRIIA:TβRII heteromultimers comprising the same, comprises an amino acid sequence that is at least 70%, 75%, 80%, 85%, 90%, 91%, 92%, 93%, 94%, 95%, 96%, 97%, 98%, or 99% identical to any of the heterologous portion sequences disclosed herein (e.g., SEQ ID NOs: 68, 69, 72, or 73), wherein the heterologous portion of the fusion polypeptide comprises no more than 25, 20, 15, 10, 5, 4, 3, 2, or 1 additional amino acids (but which may include further post-translational modifications, such as PEGylation and/or glycosylation). In some embodiments, the TβRII fusion polypeptide, as well as ActRIIA:TβRII heteromultimers comprising the same, comprises any of the TβRII polypeptide amino acid sequences disclosed herein (e.g., SEQ ID NO: 18 or 27), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation and/or glycosylation). In some embodiments, the TβRII fusion polypeptide, as well as ActRIIA:TβRII heteromultimers comprising the same, comprises any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation and/or glycosylation). In some embodiments, the TβRII fusion polypeptide, as well as ActRIIA:TβRII heteromultimers comprising the same, comprises any of the heterologous portion sequences disclosed herein (e.g., SEQ ID NO: 68, 69, 72, or 73), wherein the heterologous portion of the fusion polypeptide comprises no more than 25, 20, 15, 10, 5, 4, 3, 2, or 1 additional amino acids (but which may include further post-translational modifications, such as PEGylation and/or glycosylation).

In some embodiments, the ActRIIA fusion polypeptide, as well as ActRIIA:TβRII heteromultimers comprising the same, comprises an amino acid sequence that is at least 70%, 75%, 80%, 85%, 90%, 91%, 92%, 93%, 94%, 95%, 96%, 97%, 98%, or 99% identical to any of the ActRIIA polypeptide amino acid sequences disclosed herein (e.g., SEQ ID NO: 51 or 52 wherein the ActRIIA polypeptide portion of the fusion polypeptide comprises no more than 10, 9, 8, 7, 6, 5, 4, 3, 2 or 1 additional amino acids (but which may include further post-translational modifications, such as PEGylation and/or glycosylation). In some embodiments, the ActRIIA fusion polypeptide, as well as ActRIIA:TβRII heteromultimers comprising the same, comprises an amino acid sequence that is at least 70%, 75%, 80%, 85%, 90%, 91%, 92%, 93%, 94%, 95%, 96%, 97%, 98%, or 99% identical to any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation and/or glycosylation). In some embodiments, the ActRIIA fusion polypeptide, as well as ActRIIA:TβRII heteromultimers comprising the same, comprises an amino acid sequence that is at least 70%, 75%, 80%, 85%, 90%, 91%, 92%, 93%, 94%, 95%, 96%, 97%, 98%, or 99% identical to any of the heterologous portion sequences disclosed herein (e.g., SEQ ID NOs: 68, 69, 72, or 73), wherein the heterologous portion of the fusion polypeptide comprises no more than 25, 20, 15, 10, 5, 4, 3, 2, or 1 additional amino acids (but which may include further post-translational modifications, such as PEGylation and/or glycosylation). In some embodiments, the ActRIIA fusion polypeptide, as well as ActRIIA:TβRII heteromultimers comprising the same, comprises any of the ActRIIA polypeptide amino acid sequences disclosed herein (e.g., SEQ ID NO: 51 or 52), wherein the ActRIIA polypeptide portion of the fusion polypeptide comprises no more than 10, 9, 8, 7, 6, 5, 4, 3, 2 or 1 additional amino acids (but which may include further post-translational modifications, such as PEGylation and/or glycosylation). In some embodiments, the ActRIIA fusion polypeptide, as well as ActRIIA:TβRII heteromultimers comprising the same, comprises any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation and/or glycosylation). In some embodiments, the ActRIIA fusion polypeptide, as well as ActRIIA:TβRII heteromultimers comprising the same, comprises any of the heterologous portion sequences disclosed herein (e.g., SEQ ID NO: 68, 69, 72, or 73), wherein the heterologous portion of the fusion polypeptide comprises no more than 25, 20, 15, 10, 5, 4, 3, 2, or 1 additional amino acids (but which may include further post-translational modifications, such as PEGylation and/or glycosylation).

In some embodiments, the disclosure provides for a TβRII fusion polypeptide, as well as ActRIIA:TβRII heteromultimers comprising the same, wherein the fusion polypeptide consists or consists essentially of (and not necessarily in the following order): a) an amino acid sequence that is at least 70%, 75%, 80%, 85%, 90%, 91%, 92%, 93%, 94%, 95%, 96%, 97%, 98%, or 99% identical to any of the TβRII polypeptide amino acid sequences disclosed herein (e.g., SEQ ID NO: 18 or 27), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation and/or glycosylation); b) an amino acid sequence that is at least 70%, 75%, 80%, 85%, 90%, 91%, 92%, 93%, 94%, 95%, 96%, 97%, 98%, or 99% identical to any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation and/or glycosylation); and c) an amino acid sequence that is at least 70%, 75%, 80%, 85%, 90%, 91%, 92%, 93%, 94%, 95%, 96%, 97%, 98%, or 99% identical to any of the heterologous portion sequences disclosed herein (e.g., SEQ ID NO: 68, 69, 72, or 73), wherein the heterologous portion of the fusion polypeptide comprises no more than 25, 20, 15, 10, 5, 4, 3, 2, or 1 additional amino acids (but which may include further post-translational modifications, such as PEGylation and/or glycosylation); and d) optionally a leader sequence (e.g., SEQ ID NO: 23). In some embodiments, the disclosure provides for a TβRII fusion polypeptide, as well as ActRIIA:TβRII heteromultimers comprising the same, wherein the fusion polypeptide consists or consists essentially of (and not necessarily in the following order): a) any of the TβRII polypeptide amino acid sequences disclosed herein (e.g., SEQ ID NO: 18 or 27), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation and/or glycosylation); b) any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation and/or glycosylation); and c) any of the heterologous portion sequences disclosed herein (e.g., SEQ ID NO: 68, 69, 72, 73), wherein the heterologous portion of the fusion polypeptide comprises no more than 25, 20, 15, 10, 5, 4, 3, 2, or 1 additional amino acids (but which may include further post-translational modifications, such as PEGylation and/or glycosylation); and d) optionally a leader sequence (e.g., SEQ ID NO: 23).

In some embodiments, the disclosure provides for a ActRIIA fusion polypeptide, as well as ActRIIA:TβRII heteromultimers comprising the same, wherein the fusion polypeptide consists or consists essentially of (and not necessarily in the following order): a) an amino acid sequence that is at least 70%, 75%, 80%, 85%, 90%, 91%, 92%, 93%, 94%, 95%, 96%, 97%, 98%, or 99% identical to any of the ActRIIA polypeptide amino acid sequences disclosed herein (e.g., SEQ ID NO: 51 or 52), wherein the ActRIIA polypeptide portion of the fusion polypeptide comprises no more than 10, 9, 8, 7, 6, 5, 4, 3, 2 or 1 additional amino acids (but which may include further post-translational modifications, such as PEGylation and/or glycosylation); b) an amino acid sequence that is at least 70%, 75%, 80%, 85%, 90%, 91%, 92%, 93%, 94%, 95%, 96%, 97%, 98%, or 99% identical to any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation and/or glycosylation); and c) an amino acid sequence that is at least 70%, 75%, 80%, 85%, 90%, 91%, 92%, 93%, 94%, 95%, 96%, 97%, 98%, or 99% identical to any of the heterologous portion sequences disclosed herein (e.g., SEQ ID NO: 68, 69, 72, or 73), wherein the heterologous portion of the fusion polypeptide comprises no more than 25, 20, 15, 10, 5, 4, 3, 2, or 1 additional amino acids (but which may include further post-translational modifications, such as PEGylation and/or glycosylation); and d) optionally a leader sequence (e.g., SEQ ID NO: 23). In some embodiments, the disclosure provides for a ActRIIA fusion polypeptide, as well as ActRIIA:TβRII heteromultimers comprising the same, wherein the fusion polypeptide consists or consists essentially of (and not necessarily in the following order): a) any of the ActRIIA polypeptide amino acid sequences disclosed herein (e.g., SEQ ID NO: 51 or 52), wherein the ActRIIA polypeptide portion of the fusion polypeptide comprises no more than 10, 9, 8, 7, 6, 5, 4, 3, 2 or 1 additional amino acids (but which may include further post-translational modifications, such as PEGylation and/or glycosylation); b) any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation and/or glycosylation); and c) any of the heterologous portion sequences disclosed herein (e.g., SEQ ID NO: 68, 69, 72, 73), wherein the heterologous portion of the fusion polypeptide comprises no more than 25, 20, 15, 10, 5, 4, 3, 2, or 1 additional amino acids (but which may include further post-translational modifications, such as PEGylation and/or glycosylation); and d) optionally a leader sequence (e.g., SEQ ID NO: 23).

In some embodiments, the disclosure provides for a TβRII fusion polypeptide, as well as ActRIIA:TβRII heteromultimers comprising the same, consisting of or consisting essentially of (and not necessarily in the following order): a) a TβRII polypeptide portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 18 and no more than 10, 9, 8, 7, 6, 5, 4, 3, 2 or 1 additional amino acids (but which may include further post-translational modifications, such as PEGylation and/or glycosylation); b) a linker portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 6 and no more than 5, 4, 3, 2 or 1 additional amino acids (but which may include further post-translational modifications, such as PEGylation and/or glycosylation); and c) a heterologous portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 69 or 73 and no more than 25, 20, 15, 10, 5, 4, 3, 2, or 1 additional amino acids (but which may include further post-translational modifications, such as PEGylation and/or glycosylation); and d) optionally a leader sequence (e.g., SEQ ID NO: 23). In some embodiments, the disclosure provides for a TβRII fusion polypeptide, as well as ActRIIA:TβRII heteromultimers comprising the same, consisting or consisting essentially of (and not necessarily in the following order): a) a TβRII polypeptide portion consisting of the amino acid sequence of SEQ ID NO: 18 and no more than 10, 9, 8, 7, 6, 5, 4, 3, 2 or 1 additional amino acids (but which may include further post-translational modifications, such as PEGylation and/or glycosylation); b) a linker portion consisting of the amino acid sequence of SEQ ID NO: 6 and no more than 5, 4, 3, 2 or 1 additional amino acids (but which may include further post-translational modifications, such as PEGylation and glycosylation); and c) a heterologous portion consisting of the amino acid sequence of SEQ ID NO: 69 or 73 and no more than 25, 20, 15, 10, 5, 4, 3, 2, or 1 additional amino acids (but which may include further post-translational modifications, such as PEGylation); and d) optionally a leader sequence (e.g., SEQ ID NO: 23).

In some embodiments, the disclosure provides for an ActRIIA fusion polypeptide, as well as ActRIIA:TβRII heteromultimers comprising the same, consisting of or consisting essentially of (and not necessarily in the following order): a) a ActRIIA polypeptide portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 51 and no more than 10, 9, 8, 7, 6, 5, 4, 3, 2 or 1 additional amino acids (but which may include further post-translational modifications, such as PEGylation and/or glycosylation); b) a linker portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 6 and no more than 5, 4, 3, 2 or 1 additional amino acids (but which may include further post-translational modifications, such as PEGylation and/or glycosylation); and c) a heterologous portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 68 or 72 and no more than 25, 20, 15, 10, 5, 4, 3, 2, or 1 additional amino acids (but which may include further post-translational modifications, such as PEGylation and/or glycosylation); and d) optionally a leader sequence (e.g., SEQ ID NO: 23). In some embodiments, the disclosure provides for a ActRIIA fusion polypeptide, as well as ActRIIA:TβRII heteromultimers comprising the same, consisting or consisting essentially of (and not necessarily in the following order): a) a ActRIIA polypeptide portion consisting of the amino acid sequence of SEQ ID NO: 51 and no more than 10, 9, 8, 7, 6, 5, 4, 3, 2 or 1 additional amino acids (but which may include further post-translational modifications, such as PEGylation and/or glycosylation); b) a linker portion consisting of the amino acid sequence of SEQ ID NO: 6 and no more than 5, 4, 3, 2 or 1 additional amino acids (but which may include further post-translational modifications, such as PEGylation and glycosylation); and c) a heterologous portion consisting of the amino acid sequence of SEQ ID NO: 68 or 72 and no more than 25, 20, 15, 10, 5, 4, 3, 2, or 1 additional amino acids (but which may include further post-translational modifications, such as PEGylation); and d) optionally a leader sequence (e.g., SEQ ID NO: 23).

In some embodiments, the disclosure provides for a heteromultimer comprising an antigen-binding domain of an antibody that binds to one or more of TGFβ1, TGFβ2, TGFβ3 and at least one ActRIIA polypeptide domain (e.g. a polypeptide that is at least 70%, 75%, 80%, 85%, 90%, 91%, 92%, 93%, 94%, 95%, 97%, 98%, 99% or 100% identical to an extracellular domain of an ActRIIA protein from humans or other species as such as those described herein, e.g., SEQ ID Nos: 51 or 52). In some embodiments, the first ActRIIA polypeptide is part of a fusion polypeptide that comprises a first member of an interaction pair ("$C_1$"), and further comprises an additional first member of an interaction pair ("$A_1$"). The second ActRIIA polypeptide is part of a fusion polypeptide that comprises a second member of an interaction pair ("$B_1$"). The variable heavy chain ($V_H$) polypeptide is part of a fusion polypeptide that comprises a second member of an interaction pair ("$C_2$"), and further comprises a first member of an interaction pair ("$A_2$"). The variable light chain ($V_L$) polypeptide is part of a fusion polypeptide that comprises a second member of an interaction pair ("$B_2$"). In each fusion polypeptide, a linker may be positioned between the first or second ActRIIA polypeptide and the corresponding member of the interaction pair, between interaction pairs, and between the $V_H$ and $V_L$ polypeptides and a member of the interaction pair. $A_1$ and $A_2$ may be the same or different; $B_1$ and $B_2$ may be the same or different, and $C_1$ and $C_2$ may be the same or different. Suitable interaction pairs included, for example, constant heavy chain and/or light chain immunoglobulin interaction pairs, truncations, and variants thereof as described herein [e.g., Spiess et al (2015) Molecular Immunology 67(2A): 95-106]. FIG. 11A is an example of a heterodimer comprising a first and second ActRIIA extracellular domain. FIG. 11B is an example of a heteromultimer comprising a single ActRIIA extracellular domain. In some embodiments, the disclosure provides for a heteromultimer comprising an interaction pair, wherein one member of the interaction pair comprises a TGFβ-binding portion wherein the TGFβ-binding portion is an antibody or antigen-binding fragment thereof that binds any one or more of TGFβ1, TGFβ2, or TGFβ3; and wherein the second member of the interaction pair comprises an ActRIIA polypeptide portion that is at least 70%, 75%, 80%, 85%, 90%, 91%, 92%, 93%, 94%, 95%, 97%, 98%, 99% or 100% identical to any of the ActRIIA sequences disclosed herein. In some embodiments, the antibody or antigen-binding fragment thereof binds to TGFβ1 and TGFβ3 with significantly greater affinity than to TGFβ1. In some embodiments, the antibody or antigen-binding fragment thereof binds to TGFβ1 with significantly greater affinity than to TGFβ1 or TGFβ2. In some embodiments, the antibody or antigen-binding fragment thereof binds to TGFβ1. In some embodiments, the antibody or antigen-binding fragment thereof does not bind to TGFβ2 or does not bind to TGFβ2 with appreciable affinity. In some embodiments, the antibody or antigen-binding fragment thereof does not bind to TGFβ2 or TGFβ3, or does not bind to TGFβ2 or TGFβ3 with appreciable affinity. In some embodiments, the second member comprises a dimer of any two ActRIIA polypeptide portions disclosed herein. In some embodiments, the ActRIIA polypeptide dimerizes with a TβRII polypeptide portion that is at least 70%, 75%, 80%, 85%, 90%, 91%, 92%, 93%, 94%, 95%, 97%, 98%, 99% or 100% identical to any of the TβRII sequences disclosed herein. In some embodiments, the ActRIIA polypeptide portion is a monomeric or "single-arm" ActRIIA polypeptide portion. In some embodiments, the interaction pair comprises a heterologous moiety that facilitates the interaction. In some embodiments, the heterologous moiety is any of the Fc portions disclosed herein. In some embodiments, the ActRIIA polypeptide portion is fused to a first heterologous moiety (e.g., a first Fc portion) and the antibody or antigen-binding fragment thereof portion is fused to a second heterologous moiety (e.g., a first Fc portion). In some embodiments, the ActRIIA polypeptide portion is fused to the N-terminus of the first Fc portion, and the antibody or antigen-binding fragment thereof portion is fused to the N-terminus of the second Fc portion. In some embodiments, the ActRIIA polypeptide portion is fused to the N-terminus of the first Fc portion, and the antibody or antigen-binding fragment thereof portion is fused to the C-terminus of the second Fc portion. In some embodiments, the ActRIIA polypeptide portion is fused to the C-terminus of the first Fc portion, and the antibody or antigen-binding fragment thereof portion is fused to the N-terminus of the second Fc portion. In some embodiments, the ActRIIA polypeptide portion is fused to the N-terminus of the first Fc portion, and the antibody or antigen-binding fragment thereof portion is fused to the N-terminus of the second Fc portion; and the ActRIIA polypeptide portion is a heterodimer with any of the TβRII polypeptides disclosed herein. In some embodiments, the ActRIIA polypeptide portion is fused to the N-terminus of the first Fc portion, and the antibody or antigen-binding fragment thereof portion is fused to the C-terminus of the second Fc portion; and the ActRIIA polypeptide portion is a heterodimer with any of the TβRII polypeptides disclosed herein. In some embodiments, the ActRIIA polypeptide portion is fused to the C-terminus of the first Fc portion, and the antibody or antigen-binding fragment thereof portion is fused to the N-terminus of the second Fc portion; and the ActRIIA polypeptide portion is a heterodimer with any of the TβRII polypeptides disclosed herein. In embodiments comprising an ActRIIA polypeptide portion and a TβRII polypeptide, the ActRIIA polypeptide may be fused to the Fc portion, or the TβRII polypeptide may be fused to the Fc portion. In some embodiments, the $V_L$ portion of the antibody or antigen-binding fragment thereof is fused to the Fc portion, and in some embodiments, the $V_H$ of the antibody or antigen-binding fragment thereof is fused to the Fc portion. The disclosure contemplates linkers to facilitate the fusion between any of the components in the interaction pair. In some embodiments, the interaction pair comprises a second interaction pair that facilitates that interaction between the TβRII polypeptide and the ActRIIA polypeptide. FIG. 11A provides an illustrative example of an interaction pair comprising an ActRIIA polypeptide portion that is fused to the N-terminus of the first Fc portion, and the antibody or antigen-binding fragment thereof portion is fused to the N-terminus of the second Fc portion; and wherein the ActRIIA polypeptide portion is a heterodimer with a TβRII polypeptide.

In some embodiments, the disclosure provides for a fusion protein comprising any of the ActRIIA polypeptides disclosed herein (e.g., an ActRIIA polypeptide comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 51 or 52) fused to any of the TβRII polypeptides disclosed herein (e.g., a TβRII polypeptide comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 170). In some embodiments, the ActRIIA polypeptide portion is N-terminal to the TβRII polypeptide portion. In some embodiments, the ActRIIA polypeptide portion is C-terminal to the TβRII polypeptide portion. In some embodiments, the ActRIIA polypeptide portion of the fusion protein is fused directly to the TβRII polypeptide portion of the fusion protein. In some embodiments, a heterologous portion (e.g., any of the Fc portions disclosed herein) and/or one or more linker portions separate the ActRIIA and TβRII polypeptide portions in the fusion protein. In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 163. In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 72 (which may optionally lack the C-terminal lysine residue). In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 73 (which may optionally lack the C-terminal lysine residue). In some embodiments, the TβRII polypeptide portion is fused to the Fc portion by means of a linker (e.g., any of the linkers disclosed herein). In some embodiments, the TβRII polypeptide portion is fused to the Fc portion by means of a glycine-serine-rich linker, such as a linker comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 165. In some embodiments, the ActRIIA polypeptide portion is fused to the Fc portion by means of a linker (e.g., any of the linkers disclosed herein). In some embodiments, the ActRIIA polypeptide portion is fused to the Fc portion by means of a linker comprising a glycine linker, such as a linker comprising a GGG amino acid sequence (SEQ ID NO: 63). In some embodiments, the fusion protein comprises any of the signal sequences disclosed herein. In some embodiments, the signal sequence comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 23. In some embodiments, the fusion protein comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 183. In some embodiments, the fusion protein comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 195.

(SEQ ID NO: 183)

```
MDAMKRGLCC VLLLCGAVFV SPGAILGRS ETQECLFFNA NWEKDRTNQT

GVEPCYGDKD KRRHCFATWK NISGSIEIVK QGCWLDDINC YDRTDCVEKK

DSPEVYFCCC EGNMCNEKFS YFPEMEVTQP TSNPVTPKPP GGGTHTCPPC

PAPELLGGPS VFLFPPKPKD TLMISRTPEV TCVVVDVSHE DPEVKFNWYV

DGVEVHNAKT KPREEQYNST YRVVSVLTVL HQDWLNGKEY KCKVSNKALP

APIEKTISKA KGQPREPQVY TLPPSREEMT KNQVSLTCLV KGFYPSDIAV

EWESNGQPEN NYKTTPPVLD SDGSFFLYSK LTVDKSRWQQ GNVFSCSVMH
```

```
EALHNHYTQK SLSLSPGAGG GGSGGGGSGG GGSGGGGSGT IPPHVQKSDV

EMEAQKDEII CPSCNRTAHP LRHINNDMIV TDNNGAVKFP QLCKFCDVRK

STCDNQKSCM SNCSITSICE KPQEVCVAVW RKNDENITLE TVCHDPKLPY

HDFILEDAAS PKCIMKEKKK PGETFFMCSC SSDECNDNII FSEEYNTSNPD (SEQ ID NO: 195)
ILGRS ETQECLFFNA NWEKDRTNQT GVEPCYGDKD KRRHCFATWK NISGSIEIVK

QGCWLDDINC YDRTDCVEKK DSPEVYFCCC EGNMCNEKFS YFPEMEVTQP TSNPVTPKPP

GGGTHTCPPC PAPELLGGPS VFLFPPKPKD TLMISRTPEV TCVVVDVSHE DPEVKFNWYV

DGVEVHNAKT KPREEQYNST YRVVSVLTVL HQDWLNGKEY KCKVSNKALP APIEKTISKA

KGQPREPQVY TLPPSREEMT KNQVSLTCLV KGFYPSDIAV EWESNGQPEN NYKTTPPVLD

SDGSFFLYSK LTVDKSRWQQ GNVFSCSVMH EALHNHYTQK SLSLSPGAGG GGSGGGGSGG

GGSGGGGSGT IPPHVQKSDV EMEAQKDEII CPSCNRTAHP LRHINNDMIV TDNNGAVKFP

QLCKFCDVRF STCDNQKSCM SNCSITSICE KPQEVCVAVW RKNDENITLE TVCHDPKLPY

HDFILEDAAS PKCIMKEKKK PGETFFMCSC SSDECNDNII FSEEYNTSNPD
```

In some embodiments, any of the ActRIIA and TβRII polypeptide fusion proteins disclosed herein multimerize with another protein. In some embodiments, any of the ActRIIA and TβRII polypeptide fusion proteins disclosed herein homomultimerize (e.g., homodimerize). For example, in some embodiments, the disclosure contemplates a homomultimer comprising two or more fusion proteins comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 183. For example, in some embodiments, the disclosure contemplates a homomultimer comprising two or more fusion proteins comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 195.

In some embodiments, any of the ActRIIA and TβRII polypeptide fusion proteins disclosed herein heteromultimerize with one or more different proteins/polypeptides. In some embodiments, any of the ActRIIA and TβRII polypeptide fusion proteins disclosed herein heteromultimerize with a protein/polypeptide comprising an ActRIIA polypeptide portion but lacking a TβRII polypeptide portion. In such embodiments, the resulting fusion protein would comprise two ActRIIA polypeptide portion "arms," but a single TβRII polypeptide portion arm. In some embodiments, each unit of the heteromultimer comprises a member of an interaction pair. In some embodiments, the member of the interaction pair is any of the Fc portions disclosed herein. In some embodiments, the Fc portions have been modified to promote heteromultimer formation and/or to inhibit homomultimer formation. In some embodiments, the Fc portions have been modified to promote heterodimer formation and/or to inhibit homodimer formation. In some embodiments, the Fc portions have been modified to include any of the "knob-in-hole" mutations disclosed herein. In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 72 (which may optionally lack the C-terminal lysine residue). In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 73 (which may optionally lack the C-terminal lysine residue).

In some embodiments, any of the ActRIIA and TβRII polypeptide fusion proteins disclosed herein heteromultimerize with a protein/polypeptide comprising a TβRII polypeptide portion but lacking an ActRIIA polypeptide portion. In such embodiments, the resulting fusion protein would comprise two TβRII polypeptide portion "arms," but a single ActRIIA polypeptide portion arm. In some embodiments, each unit of the heteromultimer comprises a member of an interaction pair. In some embodiments, the member of the interaction pair is any of the Fc portions disclosed herein. In some embodiments, the Fc portions have been modified to promote heteromultimer formation and/or to inhibit homomultimer formation. In some embodiments, the Fc portions have been modified to promote heterodimer formation and/or to inhibit homodimer formation. In some embodiments, the Fc portions have been modified to include any of the "knob-in-hole" mutations disclosed herein. In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 72 (which may optionally lack the C-terminal lysine residue). In some embodiments, the heterologous portion is an Fc polypeptide portion comprising an amino acid sequence that is at least 70%, 75%, 80%, 85%, 90%, 91%, 92%, 93%, 94%, 95%, 97%, 98%, 99% or 100% identical to the amino acid sequence of SEQ ID NO: 73 (which may optionally lack the C-terminal lysine residue). In some embodiments, the ActRIIA and TβRII polypeptide fusion protein in such heteromultimers comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 184. In some embodiments, the protein/polypeptide comprising the TβRII polypeptide portion but lacking the ActRIIA polypeptide portion comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 185. In some embodiments, the heteromultimer is a heterodimer comprising a first fusion protein comprising the amino acid sequence of SEQ ID NO: 184 and a second fusion protein comprising the amino acid sequence of SEQ ID NO: 185. In some embodiments, the ActRIIA and TβRII polypeptide fusion protein in such heteromultimers comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 196. In some embodiments, the protein/polypeptide comprising the TβRII polypeptide portion but lacking the ActRIIA polypeptide portion comprises an amino acid sequence that is at least 70%, 75%, 80%, 85%, 90%, 91%, 92%, 93%, 94%, 95%, 97%, 98%, 99% or 100% identical to the amino acid sequence of SEQ ID NO: 197. In some embodiments, the heteromultimer is a heterodimer comprising a first fusion protein comprising the amino acid sequence of SEQ ID NO: 196 and a second fusion protein comprising the amino acid sequence of SEQ. ID NO: 197.

```
                                                       (SEQ ID NO: 184)
MDAMKRGLCC VLLLCGAVFV SPGAILGRS ETQECLFFNA NWEKDRTNQT

GVEPCYGDKD KRRHCFATWK NISGSIEIVK QGCWLDDINC YDRTDCVEKK

PAPELLGGPS VFLFPPKPKD TLMISRTPEV TCVVVDVSHE DPEVKFNWYV

DGVEVHNAKT KPREEQYNST YRVVSVLTVL HQDWLNGKEY KCKVSNKALP

APIEKTISKA KGQPREPQVY TLPPCREEMT KNQVSLWCLV KGFYPSDIAV

EWESNGQPEN NYKTTPPVLD SDGSFFLYSK LTVDKSRWQQ GNVFSCSVMH

EALHNHYTQK SLSLSPGAGG GGSGGGGSGG GGSGGGGSGT IPPHVQKSDV

EMEAQKDEII CPSCNRTAHP LRHINNDMIV TDNNGAVKFP QLCKFCDVRF

STCDNQKSCM SNCSITSICE KPQEVCVAVW RKNDENITLE TVCHDPKLPY

HDFILEDAAS PKCIMKEKKK PGETFFMCSC SSDECNDNII FSEEYNTSNPD
                                                       (SEQ ID NO: 185)
  1 MDAMKRGLCC VLLLCGAVFV SPGASNTKVD KRVTGGGTHT CPPCPAPELL

51 GGPSVFLFPP KPKDTLMISR TPEVTCVVVD VSHEDPEVKF NWYVDGVEVH

101 NAKTKPREEQ YNSTYRVVSV LTVLHQDWLN GKEYKCKVSN KALPAPIEKT

151 ISKAKGQPRE PQVCTLPPSR EEMTKNQVSL SCAVKGFYPS DIAVEWESNG

201 QPENNYKTTP PVLDSDGSFF LVSKLTVDKS RWQQGNVFSC SVMHEALHNH

251 YTQKSLSLSP GAGGGGSGGG GSGGGGSGGG GSGTIPPHVQ KSDVEMEAQK

301 DEIICPSCNR TAHPLRHINN DMIVTDNNGA VKFPQLCKFC DVRFSTCDNQ

351 KSCMSNCSIT SICEKPQEVC VAVWRKNDEN ITLETVCHDP KLPYHDFILE

401 DAASPKCIMK EKKKPGETFF MCSCSSDECN DNIIFSEEYN TSNPD
                                                       (SEQ ID NO: 196)
ILGRS ETQECLFFNA NWEKDRTNQT GVEPCYGDKD KRRHCFATWK NISGSIEIVK

QGCWLDDINC YDRTDCVEKK DSPEVYFCCC EGNMCNEKFS YFPEMEVTQP TSNPVTPKPP

GGGTHTCPPC PAPELLGGPS VFLFPPKPKD TLMISRTPEV TCVVVDVSHE DPEVKFNWYV

DGVEVHNAKT KPREEQYNST YRVVSVLTVL HQDWLNGKEY KCKVSNKALP APIEKTISKA

KGQPREPQVY TLPPCREEMT KNQVSLWCLV KGFYPSDIAV EWESNGQPEN NYKTTPPVLD

SDGSFFLYSK LTVDKSRWQQ GNVFSCSVMH EALHNHYTQK SLSLSPGAGG GGSGGGGSGG

GGSGGGGSGT IPPHVQKSDV EMEAQKDEII CPSCNRTAHP LRHINNDMIV TDNNGAVKFP

QLCKFCDVRF STCDNQKSCM SNCSITSICE KPQEVCVAVW RKNDENITLE TVCHDPKLPY

HDFILEDAAS PKCIMKEKKK PGETFFMCSC SSDECNDNII FSEEYNTSNPD
```

-continued (SEQ ID NO: 197)
NTKVD KRVIGGGTHT CPPCPAPELL GGPSVFLFPP KPKDTLMISR TPEVTCVVVD

VSHEDPEVKF NWYVDGVEVH NAKTKPREEQ YNSTYRVVSV LTVLHQDWLN GKEYKCKVSN

KALPAPIEKT ISKAKGQPRE PQVCTLPPSR EEMTKNQVSL SCAVKGFYPS DIAVEWESNG

QPENNYKTTP PVLDSDGSFF LVSKLTVDKS RWQQGNVFSC SVMHEALHNH YTQKSLSLSP

GAGGGGSGGG GSGGGGSGGG GSGTIPPHVQ KSDVEMEAQK DEIICPSCNR TAHPLRNHINN

DMIVTDNNGA VKFPQLCKFC DVRFSTCDNQ KSCMSNCSIT SICEKPQEVC VAVWRKNDEN

ITLETVCHDP KLPYHDFILE DAASPKCIMK EKKKPGETFF MCSCSSDECN DNIIFSEEYN

TSNPD

In some embodiments, the heteromultimers disclosed herein do not bind with appreciable affinity to CD4, CD8, CD25, CTLA-4, IL-10, TGFβ Receptor, PD-1, PD-L1, PD-L2, RANK, RANKL, HER2/neu, EGFR1, CD20, VEGF, TNF-α, TNFR2, FoxP3, CD80, CD86, IFN-α, IFN-β, IFN-γ, GITR, 4-1BB, OX-40, TLR1-10, ErbB-1, HER1, ErbB-3/HER3, ErbB-4/HER4, IGFR, IGFBP, IGF-1R, PDGFR, FGFR, VEGFR, HGFR, TRK receptor, ephrin receptors, AXL receptors, LTK receptors, TIE receptors, angiopoietin1, 2, ROR receptor, DDR receptor, RET receptor, KLG receptor, RYK receptor, MuSK receptor, ILβR, IlαR, TNTRSF, TRAIL receptor, ARTC1, alpha-actinin-4, Bcr-abl, B-RAF, caspases, beta-catenin, fibronectin, GPNMB, GDP-L, LDLR, HLA-A2, MLA-A11, HSP70, KIAA205, MART2, MUM-1, 2, 3, PAP, neo-PAP, NFYC, OGT, OS-9, pml-RARalpha fusion protein, PRDX5, PTPRK, KRAS2, NRAS, HRAS, RBAF600, SIRT2. SNRPD1, SYT-SSX1 or -SSX2 fusion protein, Triosephosphate Isomerase, BAGE, BAGE-1. BAGE-2, 3, 4, 5, GAGE-1,2,3,4, 5, 6, 7, 8, GnT-V, HERV-K MEL, KK-LC, KM-HN-1, LAGE, LAGE-1, CAMEL, MAGE-1, MAGE-A2, MAGE-A3, MAGE-A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikfein 4, mammaglobm-A, OA1, prostate specific antigen (PSA), prostate specific membrane antigen, TRP-1/, 75. TRP-2, AIM-2. BING-4, CPSF, cyclin D1, Ep-CAM, EpbA3, FGF-5, gp250, iCE), AFP, M-CSF, mdm-2, MUCI, p53 (TP53), PBF, FRAME, PSMA, RAGE-1. RNF43, RU2AS, SOX10, STEAP1, survivin (BIRCS), hTERT, telomerase, WT1, SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, estrogen receptors (ER), androgen receptors (AR), CD40, CD30, CD20, CD19, CD33, CD4, CD25, CD3, CA 72-4, CA 15-3, CA 27-29, CA 125, CA 19-9, beta-human chorionic gonadotropin, 1-2 microglobulin, squamous cell carcinoma antigen, neuron-specific enoJase, heat shock protein gp96, GM2, sargramostim, CTLA-4, 707-AP, ART-4, CAP-1, CLCA2, Cyp-B, HST-2, HPV proteins, EBV proteins, Hepatitis B or C virus proteins, and/or HIV proteins.

In some embodiments, the disclosure provides for a TβRII fusion polypeptide wherein the polypeptide does not comprise an additional ligand binding domain in addition to the TβRII domain in the same linear sequence. In some embodiments, the polypeptide comprises a linear amino acid sequence comprising a TβRII domain and a heterologous portion (e.g., an Fc portion), but the linear amino acid sequence does not comprise any additional ligand binding domains. In some embodiments, the polypeptide comprises a linear amino acid sequence comprising a TβRII domain and an Fc portion, but the linear amino acid sequence does not comprise any additional ligand binding domains. In some embodiments, the disclosure provides for a TβRII fusion polypeptide wherein the polypeptide does not comprise multiple ligand binding domains in a single linear amino acid sequence. In some embodiments, the disclosure provides for a TβRII fusion polypeptide wherein the polypeptide does not comprise more than one continuous linker sequence in a single linear amino acid sequence. In some embodiments, the polypeptide does not comprise multiple continuous glycine and/or serine linkers (e.g., a linker comprising (GGGGS)n ("GGGGS" disclosed as SEQ ID NO: 204), wherein n=≥4) in a single linear amino acid sequence. In some embodiments, the disclosure provides for a TβRII fusion polypeptide wherein the heterologous portion is an Fc domain, and wherein only one continuous linker is covalently bound to the Fc domain. In some embodiments, the only one continuous linker comprises or consists of a (GGGGS)n linker ("GGGGS" disclosed as SEQ ID NO: 204), wherein n=≥4.

B. Alternative Multispecific Binders

In some embodiments, the disclosure provides for a multispecific binder of TGFβ-superfamily ligands. In some embodiments, the multispecific binder is capable of binding to a) at least one of TGFβ1 and TGFβ3, and b) at least one of activin A, activin B, activin AB, GDF11, and GDF8. In some embodiments, the multispecific binder comprises: a) a first portion that is capable of binding to TGFβ1 and/or TGFβ3; and b) a second portion that is capable of binding to at least one of activin A, activin B, activin AB, GDF11, and GDF8. In some embodiments, the multispecific binder comprises a TβRII polypeptide and a follistatin or a follistatin-like protein domain. In some embodiments, the multispecific binder comprises a TβRII polypeptide and an antibody or antigen-binding fragment, wherein the antibody or antigen-binding fragment is capable of binding to one or more of activin A, activin B, activin AB, GDF11, and/or GDF8. In particular embodiments, the multispecific binder comprises a TβRII polypeptide and an antibody or antigen-binding fragment, wherein the antibody or antigen-binding fragment is capable of binding to GDF8.

i. Follistatin and Follistatin-Like Polypeptides

In some embodiments, the disclosure provides for a multispecific binder comprising any of the TβRII polypeptides disclosed herein and a follistatin or follistatin-like polypeptide. As used herein, the term "follistatin" refers to a family of follistatin (FST) proteins and follistatin-related proteins, derived from any species. Follistatin is an autocrine glycoprotein that is expressed in nearly all tissues of higher animals. It was initially isolated from follicular fluid and was identified as a protein fraction that inhibited follicle-stimulating hormone (FSH) secretion from the anterior pituitary, and therefore was designated as FSH-suppressing protein (FSP). Subsequently, its primary function has been determined to be the binding and neutralization of members of the TGF-β superfamily including, for example, activin, a paracrine hormone that enhances secretion of FSH in the anterior pituitary.

The term "follistatin polypeptide" is used to refer to polypeptides comprising any naturally occurring polypeptide of the follistatin family as well as any variants thereof (including mutants, fragments, fusions, and peptidomimetic forms) that retain a useful activity, including, for example, ligand binding (e.g., myostatin (GDF8), GDF11, activin A, activin B) or heparin binding. For example, follistatin polypeptides include polypeptides comprising an amino acid sequence derived from the sequence of any known follistatin having a sequence at least about 80% identical to the sequence of a follistatin polypeptide, and preferably at least 85%, 90%, 95%, 97%, 99% or greater identity. The term "follistatin polypeptide" may refer to fusion proteins that comprise any of the polypeptides mentioned above along with a heterologous (non-follistatin) portion. An amino acid sequence is understood to be heterologous to follistatin if it is not uniquely found in the long (315 amino acid) form of human follistatin, represented by SEQ ID NO: 112. Many examples of heterologous portions are provided herein, and such heterologous portions may be immediately adjacent, by amino acid sequence, to the follistatin polypeptide portion of a fusion protein, or separated by intervening amino acid sequence, such as a linker or other sequence.

Follistatin is a single-chain polypeptide with a range of molecular weights from 31 to 49 kDa based on alternative mRNA splicing and variable glycosylation of the protein. The alternatively spliced mRNAs encode two proteins of 315 amino acids (i.e., FST315) and 288 amino acids (i.e., FST288); follistatin 315 can be further proteolytically degraded to follistatin 303 (FST303). Analysis of the amino acid sequence has revealed that the native human follistatin polypeptide comprises five domains (from the N-terminal side): a signal sequence peptide (amino acids 1-29 of SEQ ID NO: 110), an N-terminal domain (FSN) (amino acids 30-94 of SEQ ID NO: 110), follistatin domain I (FSDI) (amino acids 95-164 of SEQ ID NO: 110), follistatin domain II (FSDII) (amino acids (168-239 of SEQ ID NO: 110), and follistatin domain III (FSDIII) (amino acids 245-316 of SEQ ID NO: 110). See PNAS, U.S.A., 1988, Vol. 85, No 12, pp 4218-4222. In some embodiments, any of the follistatin polypeptides disclosed herein comprises any one or more of the follistatin polypeptide domains disclosed herein.

The human follistatin-288 (FST288) precursor has the following amino acid sequence, with the signal peptide indicated in bold, the N-terminal domain (FSN) indicated by single underlining, and the follistatin domains I-III (FSI, FSII, FSIII) indicated by double underlining.

(SEQ ID NO: 110)
MVRARHQPGGLCLLLLLLCQFMEDRSAQA<u>GNCWLRQAKNGRCQVLYKTEL</u>

<u>SKEECCSTGRLSTSWTEEDVNDNTLFKWMIFNGGAPNCIPCKETCENVDC</u>

<u>GPGKKCRMNKKNKPRCVCAPDCSNITWKG</u>PVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCN

The processed (mature) human follistatin variant FST (288) has the following amino acid sequence with the N-terminal domain indicated by single underlining, and the follistatin domains I-III indicated by double underlining. Moreover, it will be appreciated that any of the initial amino acids G or N, prior to the first cysteine may be removed by processing or intentionally eliminated without any consequence, and polypeptides comprising such slightly smaller polypeptides are further included.

(SEQ ID NO: 111)
<u>GNCWLRQAKNGRCQVLYKTELSKEECCSTGRLSTSWTEEDVNDNTLFKWM</u>

<u>IFNGGAPNCIPCKETCENVDC</u>GPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCN

The human follistatin-315 (FST315) precursor has the following amino acid sequence, with the signal peptide indicated in bold, the N-terminal domain (FSN) indicated by single underlining, and the follistatin domains I-III (FSI, FSII, FSIII) indicated by double underlining (NCBI Accession Number AAH04107.1; 344 amino acids).

(SEQ ID NO: 112)
MVRARHQPGGLCLLLLLLCQFMEDRSAQA<u>GNCWLRQAKNGRCQVLYKTEL</u>

<u>SKEECCSTGRLSTSWTEEDVNDNTLFKWMIFNGGAPNCIPCKETCENVDC</u>

<u>GPGKKCRMNKKNKPRCVCAPDCSNITWKG</u>PVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCNSISEDTEEEEEDEDQDYSFPISSILEW

The processed (mature) human FST(315) has the following amino acid sequence with the N-terminal domain indicated by single underlining, and the follistatin domains I-III indicated by double underlining. Moreover, it will be appreciated that any of the initial amino acids G or N, prior to the first cysteine may be removed by processing or intentionally eliminated without any consequence, and polypeptides comprising such slightly smaller polypeptides are further included.

(SEQ ID NO: 113)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEW

Follistatin proteins herein may be referred to as FST. If followed by a number, such as FST(288), this indicates that the protein is the 288 form of follistatin. If presented as FST(288)-Fc, this indicates a C-terminal Fc fusion to the FST(288), which may or may not include an intervening linker. The Fc in this instance may be any immunoglobulin Fc portion as that term is defined herein. If presented as FST(288)-IgG2, this indicates a C-terminal Fc fusion to the FST(288) of the Fc portion of human IgG2.

The term "biologically active", in all its grammatical forms, when used in the context of a follistatin polypeptide or variant or fragment thereof, refers to a polypeptide with the ability to bind a ligand from at least one of the (1) activin or (2) bone morphogenic protein (BMP) class of ligands. In some embodiments, the "biologically active" follistatin is capable of binding to GDF8. In some embodiments, a biologically active polypeptide or fragment thereof inhibits the activity of a ligand from at least one of the (1) activin or (2) bone morphogenic protein (BMP) class of ligands. In some embodiments, a biologically active follistatin polypeptide or variant or fragment thereof inhibits GDF8, activin A and/or GDF-11 in a cell-based reporter gene assay with a lower $IC_{50}$ than the $IC_{50}$ of a follistatin polypeptide comprising the amino acid sequence of SEQ ID NO: 111. In some embodiments, a biologically active follistatin polypeptide or variant or fragment thereof inhibits GDF8, activin A and/or GDF-11 in a cell-based reporter gene assay with an equal $IC_{50}$ as compared to the $IC_{50}$ of a follistatin polypeptide comprising the amino acid sequence of SEQ ID NO: 111. In some embodiments, a biologically active follistatin polypeptide or variant or fragment thereof binds to one or more ligands selected from the group consisting of: GDF8 (myostatin), GDF11, activin A and activin B with a $K_D$ less than 1 nM, 100 pM, 50 pM or 10 pM. In some embodiments, a biologically active follistatin polypeptide or variant or fragment thereof binds heparin with a greater affinity as compared to a follistatin polypeptide comprising the amino acid sequence of SEQ ID NO: 113. In some embodiments, a biologically active follistatin polypeptide or variant or fragment thereof binds heparin with an equal binding affinity to a follistatin polypeptide comprising the amino acid sequence of SEQ ID NO: 113. In some embodiments, the follistatin proteins are truncated forms exemplified by polypeptides comprising SEQ ID NO: 111, 116, 117, 118, 119, 120, 121, 122, 123, 124 or 125, and variants thereof. In some embodiments, any of the follistatin polypeptides, fragments, functional variants, and modified forms disclosed herein may have similar, the same or improved biological activities as compared to a wild-type follistatin polypeptide (e.g., a polypeptide having the amino acid sequence of SEQ ID NO: 111 or 113). For example, in some embodiments, a follistatin variant of the disclosure may bind to and inhibit function of a follistatin ligand (e.g., activin A, activin AB, activin B, and GDF8). In some embodiments, a follistatin polypeptide modulates growth of tissues, particularly muscle. Examples of follistatin polypeptides include polypeptides comprising, consisting essentially of or consisting of the amino acid sequences by any of SEQ ID NOs: 110-125, 135, 137-139, and 141-148 or biologically active fragments thereof, as well as polypeptides comprising, consisting essentially of or consisting of amino acid sequences that are at least 80%, 81%, 82%, 83%, 84%, 85%, 86%, 87%, 88%, 89%, 90%, 91%, 92%, 93%, 94%, 95%, 96%, 97%, 98%, 99% or 100% identical to an amino acid sequence of any of SEQ ID NOs: 110-125, 135, 137-139, and 141-148, or biologically active fragments thereof. In particular embodiments, the follistatin polypeptide comprises, consists or consists essentially of an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 111. Variations on these polypeptides may be prepared according to the following guidance. Unless stated otherwise, the numbering of amino acids in the follistatin polypeptides is based on the sequence of SEQ ID NO: 110, regardless of whether the native leader sequence is used. As described above, follistatin is characterized by three cysteine-rich regions (i.e., FS domains I-III) that are believed to mediate follistatin-ligand binding. Furthermore, researchers have demonstrated that polypeptide constructs comprising only one of the three FS-binding domains (e.g., FSDI) retains strong affinity towards certain follistatin-ligands (e.g., myostatin) and is biologically active in vivo. See Nakatani et al., The FASEB Journal, Vol. 22477-487 (2008). Therefore, variant follistatin polypeptides of the disclosure may comprise one or more active portions of a follistatin protein. For example, constructs of the disclosure may begin at a residue corresponding to amino acids 30-95 of SEQ ID NO: 112 and end at a position corresponding to amino acids 316-344 of SEQ ID NO: 112. Other examples include constructs that begin at a position from 30-95 of SEQ ID NO: 110 and end at a position corresponding to amino acids 164-167 or 238-244 of SEQ ID NO: 110. Others may include any of SEQ ID Nos. 116-125. Further examples include constructs that end at a position corresponding to an amino acid selected from the group consisting of the amino acid corresponding to amino acid 289, 290, 291, 292, 293, 294, 295, 296, 297, 298, 299, 300, 301, 302, 303, 304, and 305 of SEQ ID NO: 113. In some embodiments, follistatin polypeptides and constructs of the disclosure may comprise follistatin polypeptides which do not include residues corresponding to the amino acids selected from the group consisting of amino acids 289-315, 290-315, 291-315, 292-315, 293-315, 294-315, 295-315, 296-315, 297-315, 298-315, 299-315, 300-315, 301-315, 302-315, 303-315, 304-315, and 305-315 of SEQ ID NO: 113.

Follistatin polypeptides of the disclosure may include any naturally occurring domain of a follistatin protein as well as variants thereof (e.g., mutants, fragments, and peptidomimetic forms) that retain a useful activity. For example, it is well-known that FST(315) and FST(288) have high affinity for both activin (activin A and activin B) and myostatin (and the closely related GDF11) and that the follistatin domains (e.g., FSN and FSD I-III) are thought to be involved in the binding of such TGF-β ligands. However, it believed that each of these three domains may have a different affinity for these TGF-β ligands. For example, a recent study has demonstrated that polypeptide constructs comprising only the N-terminal domain (FSN) and two FSDI domains in tandem retained high affinity for myostatin, demonstrated little or no affinity for activin and promoted systemic muscle growth when introduced into a mouse by gene expression (Nakatani et al., The FASEB Journal, Vol. 22477-487 (2008)).

Additionally, the FSDI domain contains the heparin binding domain of human follistatin, which has the amino acid sequence of KKCRMNKKNKPR (SEQ ID NO: 114). This heparin binding domain can be represented as BBXBXXBBXBXB (SEQ ID NO: 115) wherein "B" means a basic amino acid, particularly lysine (K) or arginine (R). Accordingly, the present disclosure encompasses, in part, variant follistatin proteins that demonstrate selective binding and/or inhibition of a given TGF-β ligand relative to the naturally occurring FST protein (e.g., maintaining high-affinity for myostatin while having a significantly reduced affinity for activin).

In certain aspects, the disclosure includes polypeptides comprising the FSN domain, as set forth below, and, for example, one or more heterologous polypeptide, and moreover, it will be appreciated that any of the initial amino acids G or N, prior to the first cysteine may be deleted, as in the example shown below (SEQ ID NO:117).

(SEQ ID NO: 116)
GNCWLRQAKNGRCQVLYKTELSKEECCSTGRLSTSWTEEDVNDNTLFKW

MIFNGGAPNCIPCKET (SEQ ID NO: 117)
CWLRQAKNGRCQVLYKTELSKEECCSTGRLSTSWTEEDVNDNTLFKWMI

FNGGAPNCIPCKET

In certain aspects, the disclosure includes polypeptides comprising the FSDI domain which contains the minimal core activities of myostatin (and/or GDF11) binding along with heparin binding as set forth below, and, for example, one or more heterologous polypeptide.

(SEQ ID NO: 118)
CENVDCGPGKKCRMNKKNKPRCVCAPDCSNITWKGPVCGLDGKTYRNEC

ALLKARCKEQPELEVQYQGRC

An FSDI sequence may be advantageously maintained in structural context by expression as a polypeptide further comprising the FSN domain. Accordingly, the disclosure includes polypeptides comprising the FSN-FSDI sequence, as set forth below (SEQ ID NO: 119), and, for example, one or more heterologous polypeptide, and moreover, it will be appreciated that any of the initial amino acids G or N, prior to the first cysteine may be removed by processing or intentionally eliminated without any consequence, and polypeptides comprising such slightly smaller polypeptides are further included.

(SEQ ID NO: 119)
CWLRQAKNGRCQVLYKTELSKEECCSTGRLSTSWTEEDVNDNTLFKWMI

FNGGAPNCIPCKETCENVDCGPGKKCRMNKKNKPRCVCAPDCSNITWKG

PVCGLDGKTYRNECALLKARCKEQELEVQYQGRC

As demonstrated by Nakani et al., an FSN-FSDI-FSDI construct is sufficient to confer systemic muscle growth when genetically expressed in a mouse, and accordingly the disclosure includes polypeptides comprising the amino acid sequences below and, for example, one or more heterologous polypeptide.

(SEQ ID NO: 120)
CWLRQAKNGRCQVLYKTELSKEECCSTGRLSTSWTEEDVNDNTLFKWMI

FNGGAPNCIPCKETCENVDCGPGKKCRMNKKNKPRCVCAPDCSNITWKG

PVCGLDGKTYRNECALLKARCKEQPELEVQYQGRCKKTCENVDCGPGKK

CRMNKKNKPRCVCAPDCSNITWKGPVCGLDGKTYRNECALLKARCKEQE

LEVQYQGRC

The FSDI sequence confers myostatin and GDF11 binding. It has been demonstrated that activins, particularly activin A but also activin B, are also negative regulators of muscle, and therefore a follistatin polypeptide that inhibits both the myostatin/GDF11 group and the activin A/activin B group may provide a more potent muscle effect. Moreover, in view of the findings herein demonstrating the low systemic availability of certain follistatin polypeptides, particularly those comprising a heparin binding domain, and more particularly in a homodimeric form, such as an Fc fusion, safety concerns associated with the known effects of activin inhibition on the reproductive axis and other tissues are alleviated. Given that FSDII confers activin A and B binding, the disclosure provides polypeptides comprising FSDI and FSDII (SEQ ID NO: 121), as well as FSN-FSDI-FSDII constructs (SEQ ID NO: 122) and, for example, one or more heterologous polypeptide.

(SEQ ID NO: 121)
CENVDCGPGKKCRMNKKNKPRCVCAPDCSNITWKGPVCGLDGKTYRNEC

ALLKARCKEQPELEVQYQGRCKKTCRDVFCPGSSTCVVDQTNNAYCVTC

NRICPEPASSEQYLCGNDGVTYSSACHLRKATCLLGRSIGLAYEGKC (SEQ ID NO: 122)
CWLRQAKNGROQVLYKTELSKEECCSTGRLSTSWTEEDVNDNTLFKWMI

FNGGAPNCIPCKETCENVDCGPGKKCRMNKKNKPRCVCAPDCSNITWKG

PVCGLDGKTYRNECALLKARCKEQPELEVQYQGRCKKTCRDVFCPGSST

CVVDQTNNAYCVTCNRICPEPASSEQYLCGNDGVTYSSACHLRKATCLL

GRSIGLAYEGKC

As described in the Examples, a follistatin polypeptide of 291 amino acids (representing a truncation of the naturally occurring FST-315) has advantageous properties. Accordingly, unprocessed (SEQ ID NO: 123) and mature FST(291) (SEQ ID NO: 124) polypeptides are included in the disclosure and may be combined with heterologous proteins. Moreover, it will be appreciated that any of the initial amino acids G or N, prior to the first cysteine may be removed by processing or intentionally eliminated without any consequence, and polypeptides comprising such slightly smaller polypeptides are further included, such as the example shown below (SEQ ID NO: 125).

(SEQ ID NO: 123)
MVRARHQPGGLCLLLLLLCQFMEDRSAQAGNCWLRQAKNGRCQVLYKTE

LSKEECCSTGRLSTSWTEEDVNDNTLFKWMIFNGGAPNCIPCKETCENV

DCGPGKKCRMNKKNKPRCVCAPDCSNITWKGPVCGLDGKTYRNECALLK

ARCKEQPELEVQYQGRCKKTCRDVFCPGSSTCVVDQTNNAYCVTCNRIC

PEPASSEQYLCGNDGVTYSSACHLRKATCLLGRSIGLAYEGKCIKAKSC

AMKEAEDIQCTGGKKCLWDFKVGRGRCSLCDELCPDSKSDEPVCASDNA

TYASECACSSGVLLEVKHSGSCNSIS (SEQ ID NO: 124)
GNCWLRQAKNGRCQVLYKTELSKEECCSTGRLSTSWTEEDVNDNTLFKW

MTENGGAPNCIPCKETCENVDCGPGKKCRMNKKNKPRCVCAPDCSNITW

KGPVCGLDGKTYRNECALLKARCKEQPELEVQYQGRCKKTCRDVFCPGS

STCVVDQTNNAYCVTCNRICPEPASSEQYLCGNDGVTYSSACHLRKATC

LLGRSIGLAYEGKCIKAKSCEDIQCTGGKKCLWDFKVGRGRCSLCDELC

PDSKSDEPVCASDNATYASECAMKEAACSSGVLLEVKHSGSCNSIS (SEQ ID NO: 125)
CWLRQAKNGRCQVLYKTELSKEECCSTGRLSTSWTEEDVNDNTLFKWMI

FNGGAPNCIPCKETCENVDCGPGKKCRMNKKNKPRCVCAPDCSNITWKG

PVCGLDGKTYRNECALLKARCKEQPELEVQYQGRCKKTCRDVFCPGSST

CVVDQTNNAYCVTCNRICPEPASSEQYLCGNDGVTYSSACHLRKATCLL

GRSIGLAYEGKCIKAKSCEDIQCTGGKKCLWDFKVGRGRCSLCDELCPD

SKSDEPVCASDNATYASECAMKEAACSSGVLLEVKHSGECNSIS

In certain embodiments, the present invention relates to antagonizing a ligand of follistatin (also referred to as a follistatin ligand) with a subject follistatin polypeptide (e.g., an FST-IgG fusion polypeptide). Thus, compositions and methods of the present disclosure are useful for treating disorders associated with abnormal activity of one or more ligands of follistatin. Exemplary ligands of follistatin include some TGF-β family members, such as activin A, activin B, myostatin (GDF8) and GDF11.

The follistatin variations described herein may be combined in various ways with each other or with heterologous amino acid sequences. For example, variant follistatin proteins of the disclosure include polypeptides that comprise one or more FS domains selected from FSDI (amino acids 95-164 of SEQ ID NO: 110), FSDII (amino acids 168-239 of SEQ ID NO: 110), or FSDIII (amino acids 245-316 of SEQ ID NO: 110) as well as proteins that comprise one or more FS domains selected from a sequence at least 80%, 85%, 90%, 92%, 95%, 96%, 97%, 98% or 99% identical to FSDI (amino acids 95-164 of SEQ ID NO: 110), FSDII (amino acids 168-239 of SEQ ID NO: 110), or FSDIII (amino acids 245-316 of SEQ ID NO: 110). In some embodiments, any of the follistatin polypeptides disclosed herein comprises any of the FS domains disclosed herein. These FS domains may be combined in any order within a variant follistatin polypeptide of the disclosure provided that such recombinant proteins maintain the desired activity including, for example, follistatin ligand-binding activity (e.g., myostatin) and biological activity (e.g., inducing muscle mass and/or strength). Examples of such follistatin variant polypeptides include, for example, polypeptides having domain structures such as FSDI-FSDII-FSDIII, FSDI-FSDIII, FSDI-FSDI-FSDIII, FSDI-FSDII, FSDI-FSDI, FSN-FSDI-FSDII-FSDIII, FSN-FSDI-FSDII, FSN-FSDI-FSDI, FSN-FSDI-FSDIII, FSN-FSDI-FSDI-FSDIII, and polypeptides obtained by fusing other heterologous polypeptides to the N-termini or the C-termini of these polypeptides. These domains may be directly linked or liked via a linker polypeptide. Optionally, polypeptide linkers may be any sequence and may comprise 1-50, preferably 1-10, and more preferably 1-5 amino acids. In certain aspects, preferred linkers contain no cysteine amino acids.

As referenced herein, "follistatin variants" includes follistatin polypeptides that are fragments and/or mutants/modified polypeptides as compared to a reference wildtype follistatin protein (e.g., a follistatin protein having the amino acid sequence of any of SEQ ID NOs: 110-113). In some embodiments, follistatin variants of the disclosure have reduced or abolished binding affinity for one or more follistatin ligands as compared to a wildtype follistatin polypeptide (e.g., a polypeptide having the amino acid sequence of SEQ ID NO: 113). In certain aspects, the disclosure provides follistatin variants that have reduced or abolished binding affinity for activin as compared to a wildtype follistatin polypeptide (e.g., a polypeptide having the amino acid sequence of SEQ ID NO: 113). In certain aspects, the disclosure provides follistatin variants that have reduced or abolished binding affinity for activin but retain high affinity for myostatin as compared to a wildtype follistatin polypeptide (e.g., a polypeptide having the amino acid sequence of SEQ ID NO: 113). In certain aspects, the disclosure provides follistatin variants that have reduced or abolished binding affinity for GDF11 as compared to a wildtype follistatin polypeptide (e.g., a polypeptide having the amino acid sequence of SEQ ID NO: 113).

In some embodiments, follistatin fragments or variants of the disclosure have increased binding affinity for heparin. In some embodiments, follistatin fragments or variants of the disclosure have a binding affinity for heparin which is equivalent to the binding affinity of a follistatin polypeptide comprising SEQ ID NO: 111. In some embodiments, follistatin fragments or variants have a binding affinity for heparin that is at least 20%, 30%, 40%, 50%, 60%, 70%, 80%, 90% or 95% of the binding affinity for heparin of a follistatin polypeptide comprising SEQ ID NO: 111. In some embodiments, follistatin fragments or variants of the disclosure have a binding affinity for heparin which is greater than the binding affinity of a follistatin polypeptide comprising SEQ ID NO: 111. In some embodiments, follistatin fragments or variants of the disclosure have a binding affinity for heparin which is greater than the binding affinity of a follistatin polypeptide comprising SEQ ID NO: 113. In some embodiments, follistatin fragments or variants of the disclosure have an unmasked heparin binding domain. In some embodiments, follistatin fragments or variants of the disclosure comprise a heparin binding domain which comprises the endogenous follistatin heparin binding sequence. In some embodiments, follistatin fragments or variants of the disclosure comprise a heparin binding domain which comprises the endogenous follistatin heparin binding sequence (e.g., SEQ ID NO: 114). In some embodiments, follistatin fragments or variants of the disclosure comprise a heterologous heparin binding sequence.

In certain aspects, the disclosure provides follistatin fragments or variants that do not comprise a sequence corresponding to the FSDII domain or functionally active FSDII domain. For example, follistatin polypeptides of the disclosure may include a variant obtained through partial or complete deletion of the FSDII domain. In certain aspects, such follistatin variants include the deletion of one or more cysteine residues within the FSDII region or substitution with non-cysteine amino acids.

The follistatin proteins of the disclosure may comprise a signal sequence. The signal sequence can be a native signal sequence of a follistatin protein (e.g., amino acids 1-29 of SEQ ID NO: 110) or a signal sequence from another protein, such as tissue plasminogen activator (TPA) signal sequence or a honey bee melatin (HBM) signal sequence. In some embodiments, the signal sequence is removed during processing of the follistatin protein.

Further N-linked glycosylation sites (N-X-S/T) may be added to a follistatin polypeptide, and may increase the serum half-life of an FST-Fc fusion protein. N-X-S/T sequences may be generally introduced at positions outside the ligand-binding pocket. N-X-S/T sequences may be introduced into the linker between the follistatin sequence and the Fc or other fusion component. Such a site may be introduced with minimal effort by introducing an N in the correct position with respect to a pre-existing S or T, or by introducing an S or T at a position corresponding to a pre-existing N. Any S that is predicted to be glycosylated may be altered to a T without creating an immunogenic site, because of the protection afforded by the glycosylation. Likewise, any T that is predicted to be glycosylated may be altered to an S. Accordingly, a follistatin variant may include one or more additional, non-endogenous N-linked glycosylation consensus sequences.

In certain embodiments, the present disclosure contemplates making functional variants by modifying the structure of a follistatin polypeptide for such purposes as enhancing therapeutic efficacy, or stability (e.g., ex vivo shelf life and resistance to proteolytic degradation in vivo). Modified follistatin polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a follistatin polypeptide results in a functional homolog can be readily determined by assessing the ability of the variant follistatin polypeptide to produce a response in cells in a fashion similar to the wild-type follistatin polypeptide, or to bind to one or more ligands, such as activin or myostatin in a fashion similar to wild-type follistatin.

In certain embodiments, the present invention contemplates specific mutations of the follistatin polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type follistatin polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a follistatin polypeptide is by chemical or enzymatic coupling of glycosides to the follistatin polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIA polypeptide may be accomplished chemically and/or enzymatically. Chemical deglycosylation may involve, for example, exposure of the follistatin polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on follistatin polypeptides can be achieved by the use of a variety of endo- and exo-glycosidases as described by Thotakura et al. (1987) Meth. Enzymol. 138:350. The sequence of a follistatin polypeptide may be adjusted, as appropriate, depending on the type of expression system used, as mammalian, yeast, insect and plant cells may all introduce differing glycosylation patterns that can be affected by the amino acid sequence of the peptide. In some embodiments, follistatin proteins for use in humans will be expressed in a cell line (e.g., a mammalian cell line) that provides proper glycosylation, such as HEK293 or CHO cell lines, although other expression cell lines are expected to be useful as well.

This disclosure further contemplates a method of generating variants, particularly sets of combinatorial variants of an follistatin polypeptide, including, optionally, truncation variants; pools of combinatorial mutants are especially useful for identifying functional variant sequences. The purpose of screening such combinatorial libraries may be to generate, for example, follistatin polypeptide variants that have altered properties, such as altered pharmacokinetics, or altered ligand binding as compared to a wildtype follistatin polypeptide (e.g., a polypeptide having the amino acid sequence of SEQ ID NO: 111 or 113). A variety of screening assays are provided below, and such assays may be used to evaluate variants. For example, a follistatin polypeptide variant may be screened for its ability to bind to a follistatin ligand, and/or to prevent binding of a follistatin ligand to a follistatin polypeptide.

The activity of a follistatin polypeptide or its variants may also be tested in a cell-based or in vivo assay. For example, the effect of a follistatin polypeptide variant on the expression of genes involved in muscle production may be assessed. This may, as needed, be performed in the presence of one or more recombinant follistatin ligand proteins (e.g., activin A), and cells may be transfected so as to produce a follistatin polypeptide and/or variants thereof, and optionally, a follistatin ligand. Likewise, a follistatin polypeptide may be administered to a mouse or other animal, and one or more muscle properties, such as muscle mass or strength may be assessed. In some embodiments, any of the follistatin polypeptides disclosed herein may be administered to an animal model of muscle contractures, and the effects of the follistatin polypeptide on the animal model may be assessed (see, e.g., Example 8). Such assays are either described in the application or are well known and routine in the art. A responsive reporter gene may be used in such cell lines to monitor effects on downstream signaling.

Combinatorially-derived variants can be generated which have a selective potency relative to a naturally occurring follistatin polypeptide. Such variant proteins, when expressed from recombinant DNA constructs, can be used in gene therapy protocols. Likewise, mutagenesis can give rise to variants which have intracellular half-lives dramatically different than the corresponding a wild-type follistatin polypeptide. For example, the altered protein can be rendered either more stable or less stable to proteolytic degradation or other processes which result in destruction of, or otherwise inactivation of a native follistatin polypeptide. Such variants, and the genes which encode them, can be utilized to alter follistatin polypeptide levels by modulating the half-life of the follistatin polypeptides. For instance, a short half-life can give rise to more transient biological effects and, when part of an inducible expression system, can allow tighter control of recombinant follistatin polypeptide levels within the cell.

In certain embodiments, the follistatin polypeptides of the disclosure may further comprise post-translational modifications in addition to any that are naturally present in the follistatin polypeptides. Such modifications include, but are not limited to, acetylation, carboxylation, glycosylation, phosphorylation, lipidation, and acylation. As a result, the modified follistatin polypeptides may contain non-amino acid elements, such as polyethylene glycols, lipids, poly- or mono-saccharide, and phosphates. Effects of such non-amino acid elements on the functionality of a follistatin polypeptide may be tested as described herein for other follistatin polypeptide variants. When a follistatin polypeptide is produced in cells by cleaving a nascent form of the follistatin polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the follistatin polypeptides.

In certain aspects, functional variants or modified forms of the follistatin polypeptides include fusion proteins having at least a portion of a follistatin polypeptide and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$ (SEQ ID NO: 178)) fusion partners. As another example, a fusion domain may be selected so as to facilitate detection of the follistatin polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a follistatin polypeptide is fused with a domain that stabilizes the follistatin polypeptide in vivo (a "stabilizer" domain). By "stabilizing" is meant anything that increases serum half-life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

As specific examples, the present disclosure provides fusion proteins comprising follistatin polypeptides fused to a polypeptide comprising a heterologous moiety/domain. In some embodiments, the heterologous moiety is serum albumin. In some embodiments, the heterologous moiety is a constant domain of an immunoglobulin, such as a CH1, CH2 or CH3 domain of an immunoglobulin or an Fc. Fc domains derived from human IgG1 and IgG2 are provided below (SEQ ID NO: 126 and SEQ ID NO: 127, respectively). As described herein, an IgG2, IgG4 or IgG2/4 Fc domain is particularly advantageous for fusion with follistatin polypeptides that retain heparin binding activity because these Fc species have reduced CDC and/or ADCC activity which may be harmful to the cells to which these heparin binding polypeptides may adhere. Other mutations are known that decrease either CDC or ADCC activity, and collectively, any of these variants are included in the disclosure and may be used as advantageous components of a follistatin fusion protein. In some embodiments, any of the follistatin polypeptides disclosed herein is conjugated to an Fc domain comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 126, or fragments thereof. In some embodiments, any of the follistatin polypeptides disclosed herein is conjugated to an Fc domain comprising an amino acid sequence that is at least 81%, 82%, 83%, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 127, or fragments thereof. Optionally, the Fc domain of SEQ ID NO: 126 (or variant or fragment thereof) has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

Examples of human IgG1 and IgG2 amino acid sequences that may be employed are shown below:

IgG1
(SEQ ID NO: 126)
THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNV

FSCSVMHEALHNHYTQKSLSLSPGK

IgG2
(SEQ ID NO: 127)
VECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVS

NKGLPAPIEKTISKTKGQPREPQVYTLPPSREEMTKNQVSLTCLVKGFYP

SDIAVEWESNGQPENNYKTTPPMLDSDGSFFLYSKLTVDKSRWQQGNVES

CSVMHEALHNHYTQKSLSLSPGK

It is understood that different elements of the fusion proteins may be arranged in any manner that is consistent with the desired functionality. For example, a follistatin polypeptide may be placed C-terminal to a heterologous moiety/domain, or, alternatively, a heterologous moiety/domain may be placed C-terminal to a follistatin polypeptide. The follistatin polypeptide domain and the heterologous domain need not be adjacent in a fusion protein, and additional domains or amino acid sequences may be included C- or N-terminal to either domain or between the domains. In some embodiments, the follistatin polypeptide is conjugated directly to the heterologous moiety/domain. In other embodiments, the follistatin polypeptide is conjugated to the heterologous moiety/domain by means of a linker. In some embodiments, the linker is a glycine, threonine and/or serine rich linker. Other near neutral amino acids, such as, but not limited to, Asn, Pro and Ala, may also be used in the linker sequence. In some embodiments, the linker comprises various permutations of amino acid sequences containing Gly and Thr. In some embodiments, the linker comprises various permutations of amino acid sequences containing Gly and Ser. In some embodiments, the linker has a length of at least 3, 4, 5, 7, 10, 12, 15, 20, 21, 25, 30, 35, 40, 45 or 50 amino acids. In some embodiments, the linker comprises GlyGlyGly (GGG (SEQ ID NO: 63)), or repetitions thereof. In some embodiments, the linker comprises the amino acid sequence of ThrGlyGlyGly (TGGG) (SEQ ID NO: 128) or repetitions thereof. In some embodiments, the linker is 1-5, 1-10 or 1-15 amino acids in length. In some embodiments, the linker consists of ThrGlyGlyGly (TGGG) (SEQ ID NO: 128). In some embodiments, the linker is greater than 10 amino acids in length. In some embodiments, the linker comprises between 10-100, 10-90, 10-80, 10-70, 10-60, 10-50, 10-40, 10-30, 10-20, 10-15 amino acids. In some embodiments, the linker comprises at least 10, 15, 20, 25, 30, 35, 40, 45, 50, 55, 60, 65, 70, 75, 80, 85, 90, or 95 amino acids. In some embodiments, the linker comprises an amino acid sequence that is at least 80%, 85%, 90%, 95%, 96%, 97%, 98%, 99% or 100% identical to GAPGGGG-GAAAAAGGGGGAP (SEQ ID NO: 129) or fragments thereof. In some embodiments, the linker comprises an amino acid sequence that is at least 80%, 85%, 90%, 95%, 96%, 97%, 98%, 99% or 100% identical to GAPGGGG-GAAAAAGGGGGAPGGGGGAAAAAGGGGGAP (SEQ ID NO: 130), or fragments thereof. In some embodiments, the linker comprises a sequence at least 80%, 85%, 90%, 95%, 96%, 97%, 98%, 99% or 100% identical to GAPGGGGGAAAAAGGGGGGAPGGGG-GAAAAAGGGGGGAPGGGGGAAAAAGGG GG GAP (SEQ ID NO: 131), or fragments thereof. In some embodiments, the linker comprises the amino acid sequence of ALEVLFQGP (SEQ ID NO: 132). In some embodiments, the linker does not consist of or comprise the amino acid sequence of any one of SEQ ID NOs 129-132).

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. It is also understood that a follistatin polypeptide may comprise only a domain of an immunoglobulin, such as a CH1 domain, a CH2 domain or a CH3 domain. Many of these domains confer desirable pharmacokinetic properties as well as dimerization or higher order multimerization.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087 and 5,726,044. The choice of particular immunoglobulin heavy chain constant region sequences from certain immunoglobulin classes and subclasses to achieve a particular result is considered to be within the level of skill in the art. In certain embodiments, the constant domain of an IgG immunoglobulin has reduced or no substantial ADCC and/or CDC activity relative to native human IgG1. The portion of the DNA construct encoding the immunoglobulin Fc region preferably comprises at least a portion of a hinge domain, and preferably at least a portion of a $CH_3$ domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613). Additionally, in many instances, the C-terminal lysine, or K, will be removed and thus any of the polypeptides described herein may omit the C-terminal K that is found in an Fc domain, such as those shown in SEQ ID NO: 126 or SEQ ID NO: 127.

In certain embodiments, the final (carboxy-terminal) lysine, or K, of the follistatin polypeptide is absent. For example, the protein may comprise an amino acid sequence that is at least 80%, 81%, 82%, 83%, 84%, 85%, 86%, 87%, 88%, 89%, 90%, 91%, 92%, 93% 94%, 95%, 96%, 97%, 98%, 99% or 100% identical to the sequence of SEQ ID NOs: 144 or 145, wherein the final (carboxy-terminal) lysine (K) of SEQ ID NO: 144 or 145, respectively, is optionally absent.

In certain embodiments, the follistatin polypeptides of the present disclosure contain one or more modifications that are capable of stabilizing the follistatin polypeptides. For example, such modifications enhance the in vitro half-life of the follistatin polypeptides, enhance circulatory half-life of the follistatin polypeptides or reducing proteolytic degradation of the follistatin polypeptides. Such stabilizing modifications include, but are not limited to, fusion proteins (including, for example, fusion proteins comprising a follistatin polypeptide and a stabilizer domain), modifications of a glycosylation site (including, for example, addition of a glycosylation site to a follistatin polypeptide), and modifications of carbohydrate moiety (including, for example, removal of carbohydrate moieties from a follistatin polypeptide). In the case of fusion proteins, a follistatin polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

A representative follistatin-Fc fusion protein is FST(288)-IgG2 fusion has the unprocessed and mature amino acid sequences shown below.

```
Unprocessed FST(288)-IgG2
                               (SEQ ID NO: 135)
MVRARHQPGGLCLLLLLLCQFMEDRSAQAGNCWLRQAKNGRCQVLYKTE

LSKEECCSTGRLSTSWTEEDVNDNTLEKWMIFNGGAPNCIPCKETCENV

DCGPGKKCRMNKKNKPRCVCAPDCSNITWKGPVCGLDGKTYRNECALLK

ARCKEQPELEVQYQGRCKKTCRDVFCPGSSTCVVDQTNNAYCVTCNRIC

PEPASSEQYLCGNDGVTYSSACHLRKATCLLGRSIGLAYEGKCIKAKSC

EDIQCTGGKKCLWDEKVGRGRCSLCDELCPDSKSDEPVCASDNATLASE

CAMKEAACSSGVLLEVKHSGSCNTGGGVECPPCPAPPVAGPSVFLFPPK

PKDTLMISRTPEVTCVVVDVSHEDPEVQFNWYVDGVEVHNAKTKPREEQ

FNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKT

TPPMLDSDGSFFLYSKLTVDKSRWQQGNVFSCSVMHEALHNHYTQKSLS

LSPGK

Which is encoded by the following nucleic acid
sequence
                               (SEQ ID NO: 136)
atggtccgcgcgaggcaccagccgggtgggctttgcctcctgctgctga ctgcagttcatggaggaccgcagtgcccaggctgggaactgctggctcc gtcaagcgaagaacggccgctgccaggtcctgtacaagaccgaactgag caaggaggagtgctgcagcaccggccggctgagcacctcgtggaccgag gaggacgtgaatgacaacacactcttcaagtggatgattttcaacgggg gcgcccccaactgcatccctgtaaagaaacgtgtgagaacgtggactt ggacctgggaaaaaatgccgaatgaacaagaagaacaaacccgctgcg tctgcgccccggattgttccaacatcacctggaagggtccagtctgcgg gctggatgggaaaacctaccgcaatgaatgtgcactcctaaaggcaaga tgtaaagagcagccagaactggaagtccagtaccaaggcagatgtaaaa
```

```
agacttgtcgggatgttttctgtccaggcagctccacatgtgtggtgga ccagaccaataatgcctactgtgtgacctgtaatcggatttgcccagag cctgcttcctctgagcaatatctagtgggaatgatggagtcacctactc cagtgcctgccacctgagaaaggctacctgcctgctgggcagatctatt ggattagcctatgagggaaagtgtatcaaagcaaagtcctgtgaagata tccagtgcactggtgggaaaaaatgtttatgggatttcaaggttgggag aggccggtgttccctctgtgatgagctgtgccctgacagtaagtcggat gagcctgtagtgccagtgacaatgccacttatgccagcgagtgtgccat gaaggaagctgcctgctcctcaggtgtgctactggaagtaaagcactcc ggatcttgcaacaccggtggtggagtcgagtgcccaccgtgcccagcac cacctgtggcaggaccgtcagtatcctcttccccccaaaacccaaggac accctcatgatacccgaccctgaggtcacgtgcgtggtggtggacgt gagccacgaagaccccgaggtccagttcaactggtacgtggacggcgtg gaggtgcataatgccaagacaaagccacgggaggagcagttcaacagca cgttccgtgtggtcagcgtcctcaccgtcgtgcaccaggactggctgaa cggcaaggagtacaagtgcaaggtctccaacaaaggcctcccagccccc atcgagaaaaccatctccaaaaccaaagggcagccccgagaaccacagg tgtacaccctgcccccatcccgggaggagatgaccaagaaccaggtcag cctgacctgcctggtcaaaggcttctaccccagcgacatcgccgtggag tgggagagcaatgggcagccggagaacaactacaagaccacacctccca tgctggactccgacggctccttcttcctctacagcaagctcaccgtgga caagagcaggtggcagcaggggaacgtcttctcatgctccgtgatgcat gaggctctgcacaaccactacacgcagaagagcctctccctgtctccgg gtaaatgagaattc Mature FST(288)-IgG2
                               (SEQ ID NO: 137)
GNCWLRQAKNGRCQVLYKTELSKEECCSTGRLSTSWTEEDVNDNTLFKW

MIFNGGAPNCIPCKETCENVDCGPGKKCRMNKKNKPRCVCAPDCSNITW

KGPVCGLDGKTYRNECALLKARCKEQPELEVQYQGRCKKTCRDVFCPGS

STCVVDQTNNAYCVTCNRICPEPASSEQYLCGNDGVTYSSACHLRKATC

LLGRSIGLAYEGKCIKAKSCEDIQCTGGKKCLWDFKVGRGRCSLCDELC

PDSKSDEPVCASDNATYASECAMKEAACSSGVLLEVKHSGSCNTGGGVE

CPPCPAPPVAGPSVELFPPKPKDTLMISRTPEVTCVVVDVSHEDPEVQF

NWYVDGVEVHNAKTKPREEQFNSTFRVVSVLTVVHQDWLNGKEYKCKVS

NKGLPAPIEKTISKTKGQPREPQVYTLPPSREEMTKNQVSLTCLVKGFY

PSDIAVEWESNGQPENNYKTTPPMLDSDGSFFLYSKLTVDKSRWQQGNV

FSCSVMHEALHNHYTQKSLSLSPGK
```

The initial "GN" sequence may be removed, yielding the following polypeptide.

```
                                            (SEQ ID NO: 138)
CWLRQAKNGRCQVLTYKTELSKEEGCSTGRLSTWTEEDVNDNTLEKWMI
FNGGAPNCIPCKETGENVDCGPGKKCRMNKKNKPRCVCAPDCSNITWKG
PVCGLDGKTYRNECALLKARCKEQPELEVQYQGRCKKTCRDVFCPGSST
CVVDQTNNAYCVTCNRICPEPASSEQYLCGNDGVTYSSACHLRKATCLL
GRSIGLAYEGKCIKAKSCEDIQCTGGKKCLWDFKVGRGRCSLCDELCPD
SKSDEPVCASDNATYASECAMKEAACSSGVLLEVRHSGSCNTGGVECP
PCPAPPVAGPSVFLEPPKPKDTLMISRTPEVTCVVVDVSHEDPEVQFNW
YVDGVEVHNAKTKPREEQFNSTERVVSVLTVVHQDWLNGKEYKCKVSNK
GLPAPIEKTISKTKGQPREPQVYTLPPSREEMTKNQVSLTCLVKGFYPS
DIAVEWESNGQPENNYKTTPPMLDSDGSFFLYSKLTVDKSRWQQGNVFS
CSVMHEALHNHYTQKSLSLSPGK
```

A further representative follistatin-Fc fusion protein is FST(315)-IgG2 fusion, which has the unprocessed and mature amino acid sequences shown below.

```
Unprocessed FST(315)-IgG2
                                            (SEQ ID NO: 139)
MVRARHQPGGLCLLLLLLCQFMEDRSAQAGNCWLRQAKNGRCQVLYKTE
LSKEECCSTGRLSTSWTEEDVNDNTLFKWMIFNGGAPNCIPCKETCENV
DCGPGKKCRMNKKNKPRCVCAPDCSNITWKGPVCGLDGKTYRNECALLK
ARCKEQPELEVQYQGRCKKTCRDVFCPGSSTCVVDQTNNAYCVTCNRIC
PEPASSEQYLCGNDGVTYSSACHLRKATCLLGRSIGLAYEGKCIKAKSC
EDIQCTGGKKCLWDFKVGRGRCSLCDELCPDSKSDEPVCASDNATYASE
CAMKEAACSSGVLLEVKHSGSCNSISEDTEEEEEDEDQDYSFPISSILE
WTGGGVECPPCPAPPVAGPSVFLFPPKPKDTLMISRTPEVTCVVVDVSH
EDPEVQFNWYVDGVEVHNAKTKPREEQFNSTFRVVSVLTVVHQDWLNGK
EYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDKS
RWQQGNVFSCSVMHEALHNHYTQKSLSLSPGK Which is encoded by the following nucleic acid
sequence
                                            (SEQ ID NO: 140)
atggtccgcgcgaggcaccagccgggtgggctttgcctcctgctgctgc
tgctctgccagttcatggaggaccgcagtgcccaggctgggaactgctg
gctccgtcaagcgaagaacggccgctgccaggtcctgtacaagaccgaa
ctgagcaaggaggagtgctgcagcaccggccggctgagcacctcgtgga
ccgaggaggacgtgaatgacaacacactcttcaagtggatgatttttcaa
cgggggtgcccccaactgcatccctgtaaagaaacgtgtgagaacgtg
gactgtggacctgggaaaaaatgccgaatgaacaagaagaacaaacccc
gctgcgtctgcgccccggattgttccaacatcacctggaagggtccagt
ctgcgggctggatgggaaaacctaccgcaatgaatgtgcactcctaaag
gcaagatgtaaagagcagccagaactggaagtccagtaccaaggcagat
```

```
gtaaaaagacttgtcgggatgttttctgtccaggcagctccacatgtgt
ggtggaccagaccaataatgcctactgtgtgacctgtaatcggatttgc
ccagagcctgcttcctctgagcaatatctctgtgggaatgatggagtca
cctactccagtgcctgccacctgagaaaggctacctgcctgctgggcag
atctattggattagcctatgagggaaagtgtatcaaagcaaagtcctgt
gaagatatccagtgcactggtgggaaaaaatgtttatgggatttcaagg
ttgggagaggccggtgttccctctgtgatgagctgtgccctgacagtaa
gtcggatgagcctgtctgtgccagtgacaatgccacttatgccagcgag
tgtgccatgaaggaagctgcctgctcctcaggtgtgctactggaagtaa
agcactccggatcttgcaactccatttcggaagacaccgaggaagagga
ggaagatgaagaccaggactacagctttcctatatcttctattctagag
tggaccggtggtggagtcgagtgcccaccgtgcccagcaccacctgtgg
caggaccgtcagtcttcctcttcccccaaaacccaaggacaccctcat
gatctcccggacccctgaggtcacgtgcgtggtggtggacgtgagcca
cgaagaccccgaggtccagttcaactggtacgtggacggcgtggaggtg
cataatgccaagacaaagccacgggaggagcagttcaacagcacgttcc
gtgtggtcagcgtcctcaccgtcgtgcaccaggactggctgaacggcaa
ggagtacaagtgcaaggtctccaacaaaggcctcccagcccccatcgag
aaaaccatctccaaaaccaaagggcagccccgagaaccacaggtgtaca
ccctgcccccatcccgggaggagatgaccaagaaccaggtcagcctgac
ctgcctggtcaaaggcttctaccccagcgacatcgccgtggagtgggag
agcaatgggcagccggagaacaactacaagaccacacctcccatgctgg
actccgacggctccttcttcctctacagcaagctcaccgtggacaagag
caggtggcagcaggggaacgtcttctcatgctccgtgatgcatgaggct
ctgcacaaccactacacgcagaagagcctctccctgtctccgggtaaat
gagaattc Mature FST(315)-IgG2
                                            (SEQ ID NO: 141)
GNCWLRQAKNGRCQVLYKTELSKEECCSTGRLSTSWTEEDVNDNTLFKW
MIFNGGAPNCIPCKETCENVDCGPGKKCRMNKKNKPRCVCAPDCSNITW
KGPVCGLDGKTYRNECALLKARCKEQPELEVQYQGRCKKTCRDVFCPGS
STCVVDQTNNAYCVTCNRICPEPASSEQYLCGNDGVTYSSACHLRKATC
LLGRSIGLAYEGKCIKAKSCEDIQCTGGKKCLWDFKVGRGRCSLCDELC
PDSKSDEPVCASDNATYASECAMKEAACSSGVLLEVKHSGSCNSISEDT
EEEEEDEDQDYSFPISSILEWTGGGVECPPCPAPPVAGPSVFLFPPKPK
DTLMISRTPEVTCVVVDVSHEDPEVQFNWYVDGVEVHNAKTKPREEQFN
STFRVVSVLTVVHQDWLNGKEYKCKVSNKGLPAPIEKTISKTKGQPREP
QVYTLPPSREEMTKNQVSLTCLVKGFYPSDIAVEWESNGQPENNYKTTP
PMLDSDGSFFLYSKLTVDKSRWQQGNVFSCSVMHEALHNHYTQKSLSLS
PGK
```

The initial "GN" sequence may be removed, yielding the following polypeptide.

(SEQ ID NO: 142)
CWLRQAKNGRCQVLYKTELSKEECCSTGRLSTSWTEEDVNDNTLFKWMIFN
GGAPNCIPCKETCENVDCGPGKKCRMNKKNKPRCVCAPDCSNITWKGPVCG
LDGKTYRNECALLKARCKEQPELEVQYQGRCKKTCRDVFCPGSSTCVVDQT
NNAYCVTCNRICPEPASSEQYLCGNDGVTYSSACHLRKATCLLGRSIGLAY
EGKCIKAKSCEDIQCTGGKKCLWDFKVGRGRCSLCDELCPDSKSDEPVCAS
DNATYASECAMKEAACSSGVLLEVKHSGSCNSISEDTEEEEDEDQDYSFP
ISSILEWTGGGVECPPCPAPPVAGPSVFLFPPKPKDTLMISRTPEVTCVVV
DVSHEDPEVQFNWYVDGVEVHNAKTKPREEQFNSTFRVVSVLTVVHQDWLN
GKEYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDKSRW
QQGNVFSCSVMHEALHNHYTQKSLSLSPGK

A further representative follistatin-Fc fusion is the FST (291)-IgG1 fusion, which has the unprocessed and mature amino acid sequences shown below.

Unprocessed FST(291)-IgG1
(SEQ ID NO: 143)
MVRARHQPGGLCLLLLLLCQFMEDRSAQAGNCWLRQAKNGRCQVLYKTELS
KEECCSTGRLSTSWTEEDVNDNTLFKWMIFNGGAPNCIPCKETCENVDCGP
GKKCRMNKKNKPRCVCAPDCSNITWKGPVCGLDGKTYRNECALLKARCKEQ
PELEVQYQGRCKKTCRDVFCPGSSTCVVDQTNNAYCVTCNRICPEPASSEQ
YLCGNDGVTYSSACHLRKATCLLGRSIGLAYEGKCIKAKSCEDIQCTGGKK
CLWDFKVGRGRCSLCDELCPDSKSDEPVCASDNATYASECAMKEAACSSGV
LLEVKHSGSCNSISTGGGTHTCPPCPAPELLGGPSVFLFPPKPKDTLMISR
TPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYS
KLTVDKSRWQQGNVFSCSVMREALHNHYTQKSLSLSPGK Mature FST(291)-IgG1
(SEQ ID NO: 144)
GNCWLRQAKNGRCQVLYKTELSKEECCSTGRLSTSWTEEDVNDNTLFKWMI
FNGGAPNCIPCKETCENVDCGPGKKCRMNKKNKPRCVCAPDCSNITWKGPV
CGLDGKTYRNECALLKARCKEQPELEVQYQGRCKKTCRDVFCPGSSTCVVD
QTNNAYCVTCNRICPEPASSEQYLCGNDGVTYSSACHLRKATCLLGRSIGL
AYEGKCIKAKSCEDIQCTGGKKCLWDFKVGRGRCSLCDELCPDSKSDEPVC
ASDNATYASECAMKEAACSSGVLLEVKHSGSCNSISTGGGTHTCPPCPAPE
LLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYT
QKSLSLSPGK The initial "GN" sequence may be removed, yielding the following polypeptide (SEQ ID NO: 145)
CWLRQAKNGRCQVLYKTELSKEECCSTGRLSTSWTEEDVNDNTLFKWMIFN
GGAPNCIPCKETCENVDCGPGKKCRMNKKNKPRCVCAPDCSNITWKGPVCG
LDGKTYRNECALLKARCKEQPELEVQYQGRCKKTCRDVFCPGSSTCVVDQT
NNAYCVTCNRICPEPASSEQYLCGNDGVTYSSACHLRKATCLLGRSIGLAY
EGKCIKAKSCEDIQCTGGKKCLWDFKVGRGRCSLCDELCPDSKSDEPVCAS
DNATYASECAMKEAACSSGVLLEVKHSGSCNSISTGGGTHTCPPCPAPELL
GGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQK
SLSLSPGK The FST(291)-IgG2 fusion has the unprocessed and mature amino acid sequences shown below.

Unprocessed FST(291)-IgG2
(SEQ ID NO: 146)
MVRARHQPGGLCLLLLLLCQFMEDRSAQAGNCWLRQAKNGRCQVLYKTELS
KEECCSTGRLSTSWTEEDVNDNTLFKWMIFNGGAPNCIPCKETCENVDCGP
GKKCRMNKKNKPRCVCAPDCSNITWKGPVCGLDGKTYRNECALLKARCKEQ
PELEVQYQGRCKKTCRDVFCPGSSTCVVDQTNNAYCVTCNRICPEPASSEQ
YLCGNDGVTYSSACHLRKATCLLGRSIGLAYEGKCIKAKSCEDIQCTGGKK
CLWDFKVGRGRCSLCDELCPDSKSDEPVCASDNATYASECAMKEAACSSGV
LLEVKHSGSCNSISTGGGVECPPCPAPPVAGPSVFLFPPKPKDTLMISRTP
EVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREEMT
KNQVSLTCLVKGFYPSDIAVEWESNGQPENNYKTTPPMLDSDGSFFLYSKL
TVDKSRWQQGNVFSCSVMHEALHNHYTQKSLSLSPGK Mature FST(291)-IgG2
(SEQ ID NO: 147)
GNCWLRQAKNGRCQVLYKTELSKEECCSTGRLSTSWTEEDVNDNTLFKWMI
FNGGAPNCIPCKETCENVDCGPGKKCRMNKKNKPRCVCAPDCSNITWKGPV
CGLDGKTYRNECALLKARCKEQPELEVQYQGRCKKTCRDVFCPGSSTCVVD
QTNNAYCVTCNRICPEPASSEQYLCGNDGVTYSSACHLRKATCLLGRSIGL
AYEGKCIKAKSCEDIQCTGGKKCLWDFKVGRGRCSLCDELCPDSKSDEPVC
ASDNATYASECAMKEAACSSGVLLEVKHSGSCNSISTGGGVECPPCPAPPV
AGPSVFLFPPKPKDTLMISRTPEVTCVVVDVSHEDPEVQFNWYVDGVEVHN
AKTKPREEQFNSTFRVVSVLTVVHQDWLNGKEYKCKVSNKGLPAPIEKTIS
KTKGQPREPQVYTLPPSREEMTKNQVSLTCLVKGFYPSDIAVEWESNGQPE
NNYKTTPPMLDSDGSFFLYSKLTVDKSRWQQGNVFSCSVMHEALHNHYTQK
SLSLSPGK The initial "GN" sequence may be removed, yielding the following polypeptide.

(SEQ ID NO: 148)
CWLRQAKNGRCQVLYKTELSKEECCSTGRLSTSWTEEDVNDNTLEKWMIF
NGGAPNCIPCKETCENVDCGPGKKCRMNKKNKPRCVCAPDCSNITWKGPV
CGLDGKTYRNECALLKARCKEQPELEVQYQGRCKKTCRDVFCPGSSTCVV
DQTNNAYCVTCNRICPEPASSEQYLCGNDGVTYSSACHLRKATCLLGRSI
GLAYEGKCIKAKSCEDIQCTGGKKCLWDFKVGRGRCSLCDELCPDSKSDE
PVCASDNATYASECAMKEAACSSGVLLEVKHSGSCNSISTGGGVECPPCP
APPVAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGLPAP
IEKTISKTKGQPREPQVYTLPPSREEMTKNQVSLTCLNKGFYPSDIAVEW
ESNGQPENNYKTTPPMLDSDGSFFLYSKLTVDKSRWQQGNVFSCSVMHEA
LHNHYTQKSLSLSPGK

In certain embodiments, the present invention makes available isolated and/or purified forms of the follistatin polypeptides, which are isolated from, or otherwise substantially free of, other proteins.

In certain embodiments, follistatin polypeptides (unmodified or modified) of the disclosure can be produced by a variety of art-known techniques. For example, such follistatin polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the follistatin polypeptides, fragments or variants thereof may be recombinantly produced using various expression systems (e.g., E. coli, Chinese Hamster Ovary cells, COS cells, baculovirus) as is well known in the art (also see below). In a further embodiment, the modified or unmodified follistatin polypeptides may be produced by digestion of naturally occurring or recombinantly produced full-length follistatin polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such follistatin polypeptides may be produced from naturally occurring or recombinantly produced full-length follistatin polypeptides such as standard techniques known in the art, such as by chemical cleavage (e.g., cyanogen bromide, hydroxylamine).

In some embodiments, any of the follistatin or follistatin-like polypeptides disclosed herein is conjugated to any of the TβRII polypeptides disclosed herein. In some embodiments, the follistatin or follistatin-like polypeptide is directly fused to the TβRII polypeptide. In some embodiments, the follistatin or follistatin-like polypeptide is fused to the TβRII polypeptide by means of a linker. In some embodiments, the multi-specific binder is laid out in a format similar to that shown in FIG. 14A. In some embodiments, the multi-specific binder comprises a follistatin amino acid sequence that is at least 80%, 85%, 90%, 91%, 92%, 93%, 94%, 95%, 96%, 97%, 98%, 99% or 100% identical to the amino acid sequence of SEQ ID NO: 111. In some embodiments, the multi-specific binder comprises a heterologous domain. In some embodiments, the heterologous domain is an Fc domain. In some embodiments, the multispecific binder comprises an amino acid sequence that is at least 80%, 85%, 90%, 91%, 92%, 93%, 94%, 95%, 96%, 97%, 98%, 99% or 100% identical to the amino acid sequence of SEQ ID NO: 163.

(SEQ ID NO: 163)
```
  1 THTCPPCPAP ELLGGPSVFL FPPKPKDTLM ISRTPEVTCV VVDVSHEDPE
 51 VKFNWYVDGV EVHNAKTKPR EEQYNSTYRV VSVLTVLHQD WLNGKEYKCK
101 VSNKALPAPI EKTISKAKGQ PREPQVYTLP PSREEMTKNQ VSLTCLVKGF
151 YPSDIAVEWE SNGQPENNYK TTPPVLDSDG SFFLYSKLTV DKSRWQQGNV
201 FSCSVMHEAL HNHYTQKSLS LSPG
```

In some embodiments, the multispecific binder comprises a linker between the follistatin polypeptide portion and the Fc portion. In some embodiments, the linker comprises the amino acid sequence of GGG (SEQ ID NO: 63) or the amino acid sequence of SEQ ID NO: 3.

In some embodiments, the multi-specific binder comprises an amino acid sequence that is at least 80%, 85%, 90%, 91%, 92%, 93%, 94%, 95%, 96%, 97%, 98%, 99% or 100% identical to the amino acid sequence of SEQ ID NO: 164.

(SEQ ID NO: 164)
```
  1 MVRARHQPGG LCLLLLLLCQ FMEDRSAQAG NCWLRQAKNG
    RCQVLYKTEL
 51 SKEECCSTGR LSTSWTEEDV NDNTLFKWMI FNGGAPNCIP
    CKETCENVDC
101 GPGKKCRMNK KNKPRCVCAP DCSNITWKGP VCGLDGKTYR
    NECALLKARC
151 KEQPELEVQY QGRCKKTCRD VFCPGSSTCV VDQTNNAYCV
    TCNRICPEPA
201 SSEQYLCGND GVTYSSACHL RKATCLLGRS IGLAYEGKCI
    KAKSCEDIQC
251 TGGKKCLWDF KVGRGRCSLC DELCPDSKSD EPVCASDNAT
    YASECAMKEA
301 ACSSGVLLEV KHSGSCNTGG GTHTCPPCPA PELLGGPSVF
    LFPPKPKDTL
351 MISRTPEVTC VVVDVSHEDP EVKFNWYVDG VEVHNAKTKP
    REEQYNSTYR
```

```
401 VVSVLTVLHQ DWLNGKEYKC KVSNKALPAP IEKTISKAKG
    QPREPQVYTL

451 PPSREEMTKN QVSLTCLVKG FYPSDIAVEW ESNGQPENNY
    KTTPPVLDSD

501 GSFFLYSKLT VDKSRWQQGN VFSCSVMHEA LHNHYTQKSL
    SLSPGK
```

In some embodiments, the multispecific binder comprises a TβRII polypeptide portion that is at least 80%, 85%, 90%, 91%, 92%, 93%, 94%, 95%, 96%, 97%, 98%, 99% or 100% identical to the amino acid sequence of SEQ ID NO: 170. In some embodiments, the TβRII polypeptide portion is fused to the follistatin polypeptide portion or the Fc portion by means of a linker. In some embodiments, the TβRII polypeptide portion is fused to the C-terminus of the Fc portion (e.g., the C-terminus of an amino acid sequence that is at least 80%, 85%, 90%, 91%, 92%, 93%, 94%, 95%, 96%, 97%, 98%, 99% or 100% identical to the amino acid sequence of SEQ ID NO: 164) by means of a linker. In some embodiments, the linker used to fuse the follistatin polypeptide portion or Fc portion to the TβRII polypeptide portion comprises an amino acid sequence that is at least 80%, 85%, 90%, 91%, 92%, 93%, 94%, 95%, 96%, 97%, 98%, 99% or 100% identical to the amino acid sequence of SEQ ID NO: 165.

```
                                    (SEQ ID NO: 165)
        AGGGGSGGGGSGGGGSGGGGSG
```

A representative nucleotide encoding a portion of a multispecific binder may comprise a nucleotide sequence that is at least 80%, 85%, 90%, 91%, 92%, 93%, 94%, 95%, 96%, 97%, 98%, 99% or 100% identical to the nucleotide sequence of SEQ ID NO: 166.

```
                                        (SEQ ID NO: 166)
  1 ATGGTCCGCG CGAGGCACCA GCCGGGTGGG CTTTGCCTCC
    TGCTGCTGCT

51 GCTCTGCCAG TTCATGGAGG ACCGCAGTGC CCAGGCTGGG
    AACTGCTGGC

101 TCCGTCAAGC GAAGAACGGC CGCTGCCAGG TCCTGTACAA
    GACCGAACTG

151 AGCAAGGAGG AGTGCTGCAG CACCGGCCGG CTGAGCACCT
    CGTGGACCGA

201 GGAGGACGTG AATGACAACA CACTCTTCAA GTGGATGATT
    TTCAACGGGG

251 GCGCCCCCAA CTGCATCCCC TGTAAAGAAA CGTGTGAGAA
    CGTGGACTGT

301 GGACCTGGGA AAAAATGCCG AATGAACAAG AAGAACAAAC
    CCCGCTGCGT

351 CTGCGCCCCG GATTGTTCCA ACATCACCTG GAAGGGTCCA
    GTCTGCGGGC

401 TGGATGGGAA AACCTACCGC AATGAATGTG CACTCCTAAA
    GGCAAGATGT

451 AAAGAGCAGC CAGAACTGGA AGTCCAGTAC CAAGGCAGAT
    GTAAAAAGAC

501 TTGTCGGGAT GTTTTCTGTC CAGGCAGCTC CACATGTGTG
    GTGGACCAGA

551 CCAATAATGC CTACTGTGTG ACCTGTAATC GGATTTGCCC
    AGAGCCTGCT

601 TCCTCTGAGC AATATCTCTG TGGGAATGAT GGAGTCACCT
    ACTCCAGTGC

651 CTGCCACCTG AGAAAGGCTA CCTGCCTGCT GGGCAGATCT
    ATTGGATTAG

701 CCTATGAGGG AAAGTGTATC AAAGCAAAGT CCTGTGAAGA
    TATCCAGTGC

751 ACTGGTGGGA AAAAATGTTT ATGGGATTTC AAGGTTGGGA
    GAGGCCGGTG

801 TTCCCTCTGT GATGAGCTGT GCCCTGACAG TAAGTCGGAT
    GAGCCTGTCT

851 GTGCCAGTGA CAATGCCACT TATGCCAGCG AGTGTGCCAT
    GAAGGAAGCT

901 GCCTGCTCCT CAGGTGTGCT ACTGGAAGTA AAGCACTCCG
    GATCTTGCAA

951 CACCGGTGGT GGAACTCACA CATGCCCACC GTGCCCAGCA
    CCTGAACTCC

1001 TGGGGGGACC GTCAGTCTTC CTCTTCCCCC CAAAACCCAA
     GGACACCCTC

1051 ATGATCTCCC GGACCCCTGA GGTCACATGC GTGGTGGTGG
     ACGTGAGCCA

1101 CGAAGACCCT GAGGTCAAGT TCAACTGGTA CGTGGACGGC
     GTGGAGGTGC

1151 ATAATGCCAA GACAAAGCCG CGGGAGGAGC AGTACAACAG
     CACGTACCGT

1201 GTGGTCAGCG TCCTCACCGT CCTGCACCAG GACTGGCTGA
     ATGGCAAGGA

1251 GTACAAGTGC AAGGTCTCCA ACALAGCCCT CCCAGCCCCC
     ATCGAGAAAA

1301 CCATCTCCAA AGCCAAAGGG CAGCCCCGAG AACCACAGGT
     GTACACCCTG

1351 CCCCCATCCC GGGAGGAGAT GACCAAGAAC CAGGTCAGCC
     TGACCTGCCT

1401 GGTCAAAGGC TTCTATCCCA GCGACATCGC CGTGGAGTGG
     GAGAGCAATG

1451 GGCAGCCGGA GAACAACTAC AAGACCACGC CTCCCGTGCT
     GGACTCCGAC

1501 GGCTCCTTCT TCCTCTATAG CAAGCTCACC GTGGACAAGA
     GCAGGTGGCA

1551 GCAGGGGAAC GTCTTCTCAT GCTCCGTGAT GCATGAGGCT
     CTGCACAACC

1601 ACTACACGCA GAAGAGCCTC TCCCTGTCTC CGGGTAAATG A
```

In some embodiments, any of the multispecific binders disclosed herein comprise an amino acid sequence that is at least 80%, 85%, 90%, 91%, 92%, 93%, 94%, 95%, 96%, 97%, 98%, 99% or 100% identical to the amino acid sequence of SEQ ID NO: 180.

GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

WDQTNNAYCVTCNRICPEPASSEQYLCGNDGVTYSSACHLRKATCLLGRS

-continued

IGLAYEGKCIKAKSCEDIQCTGGKKCLWDFKVGRGRCSLCDELCPDSKSD

EPVCASDNATYASECAMKEAACSSGVLLEVKHSGSCNTGGGTHTCPPCPA

PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVEW

ESNGQPENNYKTTPPVLDSDGSFFLYSKLTVDKSRVVQQGNVFSCSVMHE

ALHNHYTQKSLSLSPGKAGGGGSGGGGSGGGGSGGGGSGTIPPHVQKSDV

EMEAQKDEUCPSCNRTAHPLRHINNDMIVTDNNGAVKFPQLCKFCDVRFS

TCDNQKSCMSNCSITSICEKPQEVCVAVWRKNDENITLETVCHDPKLPYH

DFILEDAASPKCIMKEKKKPGETFFMCSCSSDECNDNIIFSEEYNTSNPD

In some embodiments, any of the multispecific binders disclosed herein comprise an amino acid sequence that is at least 80%, 85%, 90%, 91%, 92%, 93%, 94%, 95%, 96%, 97%, 98%, 99% or 100% identical to the amino acid sequence of SEQ ID NO: 181.

GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

WDQTNNAYCVTCNRICPEPASSEQYLCGNDGVTYSSACHLRKATCIXGRS

IGLAYEGKCIKAKSCEDIQCTGGKKCLWDFKVGRGRCSLCDELCPDSKSD

EPVCASDNATYASECAMKEAACSSGVLLEVKHSGSCNTGGGTHTCPPCPA

PELLGGPSVFLFPPKPKDTLMISRTPEVTCVVVDVSHEDPEVKFNWYVDG

VEVHNAKTKPREEQYNSTYRWSVLTVLHQDWLNGKEYKCKVSNKALPAPI

EKTISKAKGQPREPQVYTLPPSREEMTKNQVSLTCLVKGFYPSDIAVEWE

SNGQPENNYKTTPPVLDSDGSFFLYSRLTVDKSRWQQGNVFSCSVMHEAL

HNHYTQKSLSLSPGAGGGGSGGGGSGGGGSGGGGSGTIPPHVQKSDVEME

AQKDEIICPSCNRTAHPLRHINNDMIVTDNNGAVKFPQLCKFCDVRFSTC

DNQKSCMSNCSITSICEKPQEVCVAVWRKNPENITLETVCHPPKLPYHPF

ILEDAASPKCIMKEKKKPGETFFMCSCSSDECNDNIIFSEEYNTSNPD ii. Antibodies and Antigen-Binding Fragments Thereof In some embodiments, the disclosure provides for a multispecific binder comprising any of the TβRII polypeptides disclosed herein and an antibody or antigen-binding fragment thereof. In some embodiments, the multispecific binder comprises a TβRII polypeptide and an antibody or antigen-binding fragment, wherein the antibody or antigen-binding fragment is capable of binding to one or more of activin A, activin B, activin AB, GDF11, and/or GDF8. In particular embodiments, the multispecific binder comprises a TβRII polypeptide and an antibody or antigen-binding fragment, wherein the antibody or antigen-binding fragment is capable of binding to GDF8.

As used herein, the term "antibody" (Ab), which is synonymous with the term "immunoglobulin" (Ig), means a tetramer comprising two heavy (H) chains (about 50-70 kDa) and two light (L) chains (about 25 kDa) inter-connected by disulfide bonds. There are two types of light chain: λ and K. In humans they are similar, but only one type is present in each antibody. Heavy chains are classified as mu, delta, gamma, alpha, or epsilon, and define the antibody's isotype as IgM, IgD, IgG, IgA, and IgE1 respectively. See generally, Fundamental Immunology Ch. 7 (Paul, W., ed., 2nd ed. Raven Press, N.Y. (1989)). Each heavy chain (herein sometimes referred to as H-chain or Hc) is comprised of a heavy chain variable domain (VH, or H-variable domain) and a heavy chain constant region (CH). The heavy chain constant region is comprised of three domains, CH1, CH2 and CH3. Each light chain (herein sometimes referred to as L-chain or $L_C$) is comprised of a light chain variable domain (VL, or L-variable domain) and a light chain constant region. The light chain constant region is comprised of one domain, CL. Within light and heavy chains, the variable and constant regions are joined by a "J" region of about 12 or more amino acids, with the heavy chain also including a "D" region of about 3 or more amino acids. The VH and VL regions can be further subdivided into regions of hypervariability, termed "complementarity determining regions" (CDR), interspersed with regions that are more conserved, termed "framework regions" (FR). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. In some embodiments, the assignment of amino acids to each domain is in accordance with the definitions of Kabat, Sequences of Proteins of Immunological Interest (National Institutes of Health, Bethesda, MD (1987 and 1991)), or Chothia & Lesk, J. Mol. Biol. 196:901-917 (1987); Chothia et al., Nature 342:878-883 (1989).

As used herein, the term "antigen-binding fragment" refers to one or more fragments of an antibody that retain the ability to specifically bind to an antigen. It has been shown that the antigen-binding function of an antibody can be performed by fragments of a full-length antibody. Non-limiting examples of binding fragments encompassed within the term "antigen-binding fragment" include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fab' fragment which is obtained by cleaving a disulfide bond of the hinge region of the F(ab')2; (iv) a Fd fragment consisting of the VH and CH1 domains; (v) a Fv fragment consisting of the $V_L$ and VH domains of a single arm of an antibody, (vi) a dAb fragment (Ward et al., (1989) Nature 341:544-546), which consists of a VH domain; (vii) an isolated complementarity determining region (CDR); and (viii) a dsFv, which consists of a VH::VL heterodimer stabilized by a disulfide bond. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al. Proc. Natl. Acad. Sci. USA 85:5879-5883 (1988)). Also within the scope of this disclosure are antigen-binding molecules comprising a VH and/or a VL, In the case of a VH, the molecule may also comprise one or more of a CH 1, hinge, CH2 or CH3 region. Such single chain antibodies are also intended to be encompassed within the term "antigen-binding fragment" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al. Structure 2:1121-1123 (1994)).

As used herein, the term "antigen-binding fragment" also includes, e.g., single domain antibodies such as camelized single domain antibodies. See, e.g., Muyldermans et al. (2001) Trends Biochem Sci 26:230-235; Nuttall et al. (2000) Curr Pharm Biotech 1:253-263; Reichmann et al. (1999) J Immunol Meth 231:25-38; PCT application publication nos. WO 94/04678 and WO 94/25591; and U.S. Pat. No. 6,005, 079, all of which are incorporated herein by reference in their entireties. In some embodiments, the disclosure provides single domain antibodies comprising two VH domains with modifications such that single domain antibodies are formed.

As used herein, the terms "anti-ligand antibody" or "anti-ligand antigen-binding fragment" and the like are used to reference an antibody that is capable of binding/targeting a TGF-β superfamily ligand (e.g., activin A, activin B, activin AB, nodal, GDF11, GDF8). In some embodiments, an anti-ligand antibody or antigen-binding fragment thereof is capable of binding/targeting GDF8. In some embodiments, the anti-ligand antibody or antigen-binding fragment thereof is multi-specific and is capable of binding/targeting multiple TGF-β superfamily ligands (e.g., more than one of activin A, activin B, activin AB, nodal, GDF11, GDF8).

As used herein, the term "epitope" or "antigenic determinant" refers to a site on an antigen (e.g., GDF8) to which an immunoglobulin or antibody specifically binds. An epitope can be formed both from contiguous amino acids or noncontiguous amino acids juxtaposed by tertiary folding of a protein. An epitope formed from contiguous amino acids is typically retained on exposure to denaturing solvents, whereas an epitope formed by tertiary folding is typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from, e.g., GDF8, are tested for reactivity with the given antibody or antigen-binding fragment. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

In some embodiments, any of the anti-ligand antibodies or antigen-binding fragments disclosed herein are capable of binding to a TGF-β superfamily ligand (e.g., activin A, activin B, activin AB, nodal, GDF11, GDF8) in a manner such that the bound ligand is no longer capable of interacting with a receptor (e.g., ActRIIA, ActRIIB, ALK4, ALK7, BMPRII, ALK1, ALK2, ALK3, ALK6, and/or TGFβRII). In some embodiments, any of the anti-ligand antibodies or antigen-binding fragments disclosed herein are capable of binding to a TGF-β superfamily ligand (e.g., activin A, activin B, activin AB, nodal, GDF11, GDF8) in a manner such that the bound ligand is no longer capable of triggering any downstream signaling event. In some embodiments, any of the anti-ligand antibodies or antigen-binding fragments are capable of inhibiting SMAD2, SMAD3, SMAD1, SMADS and/or SMAD8 signaling in a cell. In some embodiments, any of the anti-ligand antibodies or antigen-binding fragments are capable of inhibiting SMAD2, SMAD3, SMAD1, SMADS and/or SMAD8 signaling in a cell by at least 5%, 10%, 15%, 20%, 25%, 30%, 35%, 40%, 45%, 50%, 55%, 60%, 70%, 75%, 80%, 85%, 90%, 95% or 100% as compared to the same cell type under essentially the same conditions in the absence of the antibody or antigen-binding fragment. In particular embodiments, any of the anti-ligand antibodies or antigen-binding fragments are capable of inhibiting SMAD2 and/or SMAD3 signaling in a cell. In particular embodiments, any of the anti-ligand antibodies or antigen-binding fragments are capable of inhibiting SMAD2 and/or SMAD3 signaling in a cell by at least 5%, 10%, 15%, 20%, 25%, 30%, 35%, 40%, 45%, 50%, 55%, 60%, 70%, 75%, 80%, 85%, 90%, 95% or 100% as compared to the same cell type under similar conditions in the absence of the antibody or antigen-binding fragment.

In some embodiments, the antibody or antigen-binding fragment is capable of binding to a GDF8 polypeptide. In some embodiments, the antibody or antigen-binding fragment is capable of binding to a GDF8 polypeptide having an amino acid sequence that is at least 80%, 85%, 90%, 91%, 92%, 93%, 94%, 95%, 96%, 97%, 98%, 99% or 100% identical to the amino acid sequence of SEQ ID NO: 149, or a functional fragment thereof. A functional fragment of GDF8 would be capable of binding one or more TGFβ-superfamily receptors (e.g., ActRIIA, ActRIIB, ALK4 and/or ALK7) and triggering downstream signaling of the receptor(s). In some embodiments, the antibody or antigen-binding fragment binds to the wrist region of GDF8 (see, e.g., Walker et al., 2017, BMC Biol., 15:19).

(GenBank Accesion No. NP_005250.1):

SEQ ID NO: 149

MQKLQLCVYIYLFMLIVAGPVDLNENSEQKENVEKEGLCNACTWRQNTKSS

RIEAIKIQILSKLRLETAPNISKDVIRQLLPKAPPLRELIDQYDVQRDDSS

DGSLEDDDYHATTETIITMPTESDFLMQVDGKPKCCFFKFSSKIQYNKVVK

AQLWIYLRPVETPTTVFVQILRLIKPMKDGTRYTGIRSLKLDMNPGTGIWQ

SIDVKTVLQNWLKQPESNLGIEIKALDENGHDLAVTFPGPGEDGLNPFLEV

KVTDTPKRSRRDFGLDCDEHSTESRCCRYPLTVDFEAFGWDWIIAPKRYKA

NYCSGECEFVFLQKYPHTHLVHQANPRGSAGPCCTPTKMSPINMLYFNGKE

QIIYGKIPAMVVDRCGCS

In some embodiments, the antibody or antigen-binding fragment is capable of binding to a GDF11 polypeptide. In some embodiments, the antibody or antigen-binding fragment is capable of binding to a GDF11 polypeptide having an amino acid sequence that is at least 80%, 85%, 90%, 91%, 92%, 93%, 94%, 95%, 96%, 97%, 98%, 99% or 100% identical to the amino acid sequence of SEQ ID NO: 150, or a functional fragment thereof. A functional fragment of GDF11 would be capable of binding one or more TGFβ-superfamily receptors (e.g., ActRIIA, ActRIIB, ALK4 and/or ALK7) and triggering downstream signaling of the receptor(s). In some embodiments, the antibody or antigen-binding fragment binds to the wrist region of GDF11 (see, e.g., Walker et al., 2017, BMC Biol., 15:19).

(GenBank Accesion No. NP_005802.1):

SEQ ID NO: 150
MVLAAPLLLGFLLLALELRPRGEAAEGPAAAAAAAAAAAAAGVGGERSSRP

APSVAPEPDGCPVCVWRQHSRELRLESIKSQILSKLRLKEAPNISREVVKQ

LLPKAPPLQQILDLHDFQGDALQPEDFLEEDEYHATTETVISMAQETDPAV

QTDGSPLCCHFHFSPKVMFTKVLKAQLWVYLRPVPRPATVYLQILRLKPLT

GEGTAGGGGGGRRHIRIRSLKIELHSRSGHWQSIDFKQVLHSWFRQPQSNW

GIEINAFDPSGTDLAVTSLGPGAEGLHPFMELRVLENTKRSRRNLGLDCDE

HSSESRCCRYPLTVDFEAFGWDWIIAPKRYKANYCSGQCEYMFMQKYPHTH

LVQQANPRGSAGPCCTPTRMSPINMLYFNDKQQIIYGKIPGMVVDRCGCS

In some embodiments, the antibody or antigen-binding fragment binds both GDF8 and GDF11. In some embodiments, the antibody or antigen-binding fragment binds an epitope common to both GDF8 and GDF11.

In some embodiments, the antibody or antigen-binding fragment comprises one or more of the CDRs selected from the group consisting of SEQ ID NOs: 151-162. In some embodiments, the antibody or antigen-binding fragment comprises one or more of the CDRs selected from the group consisting of SEQ ID NOs: 151-162, but with 1, 2, 3, 4, 5 or 6 conservative substitutions. In some embodiments, the antibody or antigen-binding fragment comprises a variable heavy chain (VH) and a variable light chain (VL), wherein the VH CDR1 comprises SEQ NO:151 or SEQ ID NO:157, wherein the VH CDR2 comprises SEQ ID NO:152 or SEQ ID NO:158, and wherein the VH CDR3 comprises SEQ ID NO:153 or SEQ ID NO:159; and wherein the VL CDR1 comprises SEQ ID NO:154 or SEQ ID NO:160, wherein the VL CDR2 comprises SEQ ID NO:155 or SEQ ID NO:161, and wherein the VL CDR3 comprises SEQ ID NO:156 or SEQ ID NO:162.

(VH CDR1)
SEQ ID NO: 151
SYWMQ (VH CDR2)
SEQ ID NO: 152
AIYPGDGDTRYTQKFKG (VH CDR3)
SEQ ID NO: 153
ARMGGYDRYYTDY (VL CDR1)
SEQ ID NO: 154
KSSQSLLNSANQKNYLA (VL CDR2)
SEQ ID NO: 155
FASTRES (VL CDR3)
SEQ ID NO: 156
QQHYNTPLT (VH CDR1)
SEQ ID NO: 157
GYIFTSYWMQ (VH CDR2)
SEQ ID NO: 158
AIYPGDGDT (VH CDR3)
SEQ ID NO: 159
ARMGGYDRYYFDY (VL CDR1)
SEQ ID NO: 160
KSSQSLINSANQKNYLA (VL CDR2)
SEQ ID NO: 161
FASTRES (VL CDR3)
SEQ ID NO: 162
QQTTYNTPLT

In some embodiments, the antibody or antigen-binding fragment is a full-length antibody. In some embodiments, the antibody is a monoclonal antibody. In some embodiments, the antibody is a human antibody. In some embodiments, the antibody is a humanized antibody.

In some embodiments, the antibody or antigen-binding fragment is a chimeric antibody. In some embodiments, the antibody or antigen-binding fragment is a humanized antibody or antigen-binding fragment. In some embodiments, the antibody or antigen-binding fragment is an antigen-binding fragment. In some embodiments, the antigen-binding fragment is selected from the group consisting of a Fab fragment, a F(ab')2 fragment, a Fab' fragment, a dAb, or an scFv.

Antibodies that recognize the same or overlapping epitope as a known antibody or compete for binding with a known antibody can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as GDF8. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using I-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least about 50-55%, 55-60%, 60-65%, 65-70%, 70-75% or more.

Other techniques include, for example, epitope mapping methods, such as, x-ray analyses of crystals of antigen:antibody complexes which provides atomic resolution of the epitope and mass spectrometry combined with hydrogen/deuterium (H/D) exchange which studies the conformation and dynamics of antigen: antibody interactions. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

The disclosure also features methods for producing any of the anti-ligand antibodies or antigen-binding fragments thereof described herein. In some embodiments, methods for preparing an antibody described herein can include immunizing a subject (e.g., a non-human mammal) with an appropriate immunogen (e.g., GDF8). Suitable immunogens for generating any of the antibodies described herein are set forth herein. For example, to generate an antibody that binds to GDF8, a skilled artisan can immunize a suitable subject (e.g., a non human mammal such as a rat, a mouse, a gerbil, a hamster, a dog, a cat, a pig, a goat, a horse, or a non-human primate) with human GDF8.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) Autoimmunity 31(1):15-24. See also, e.g., Lodmell et al. (2000) Vaccine 18:1059-1066; Johnson et al. (1999) J Med Chem 42:4640-4649; Baldridge et al. (1999) Methods 19:103-107; and Gupta et al. (1995) Vaccine 13(14): 1263-1276.

In some embodiments, the methods include preparing a hybridoma cell line that secretes a monoclonal antibody that binds to the immunogen. For example, a suitable mammal such as a laboratory mouse is immunized with a ligand, e.g., GDF8, as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybrid cells are then screened for secretion of the desired antibodies, e.g., an antibody that binds to a TGF-β superfamily ligand (e.g., GDF8) as described herein.

In some embodiments, a skilled artisan can identify an anti-ligand antibody from a non-immune biased library as described in, e.g., U.S. Pat. No. 6,300,064 (to Knappik et al.; Morphosys AG) and Schoonbroodt et al. (2005) Nucleic Acids Res 33(9):e81.

In some embodiments, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) J Bacteriol 183:6924-6935; Cornelis (2000) Curr Opin Biotechnol 11:450-454; Klemm et al. (2000) Microbiology 146:3025-3032; Kieke et al. (1997) Protein Eng 10:1303-1310; Yeung et al. (2002) BiotechnolProg 18:212-220; Boder et al. (2000) Methods Enzymology 328:430-444; Grabherr et al. (2001) Comb Chem High Throughput Screen 4:185-192; Michael et al. (1995) Gene Ther 2:660-668; Pereboev et al. (2001) J Virol 75:7107-7113; Schaffitzel et al. (1999) J Immunol Methods 231:119-135; and Hanes et al. (2000) Nat Biotechnol 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly fused protein to any of the phage coat proteins pIII, pVIII, or pIX. See, e.g., Shi et al. (2010) JMB 397:385-396. Examples of phage display methods that can be used to make the immunoglobulins, or fragments thereof, described herein include those disclosed in Brinkman et al. (1995) J Immunol Methods 182:41-50; Ames et al. (1995) J Immunol Methods 184:177-186; Kettleborough et al. (1994) Eur J Immunol 24:952-958; Persic et al. (1997) Gene 187:9-18; Burton et al. (1994) Advances in Immunology 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the phage display antibody libraries can be generated using mRNA collected from B cells from the immunized mammals. For example, a splenic cell sample comprising B cells can be isolated from mice immunized with a TGF-β superfamily ligand (e.g., GDF8) as described above. mRNA can be isolated from the cells and converted to cDNA using standard molecular biology techniques. See, e.g., Sambrook et al. (1989) "Molecular Cloning: A Laboratory Manual, 2nd Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) J Neurosci Methods 62(1-2):213-

9; Di Niro et al. (2005) Biochem J 388(Pt 3):889-894; and Engberg et al. (1995) Methods Mol Biol 51:355-376.

In some embodiments, a combination of selection and screening can be employed to identify an antibody of interest from, e.g., a population of hybridoma-derived antibodies or a phage display antibody library. Suitable methods are known in the art and are described in, e.g., Hoogenboom (1997) Trends in Biotechnology 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., E. coli). Expression of the bacteriophage in bacteria can, in some embodiments, require use of a helper phage. In some embodiments, no helper phage is required (see, e.g., Chasteen et al., (2006) Nucleic Acids Res 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., GDF8) using any immunological or biochemical based method known in the art. For example, specific binding of an antibody to a TGF-β superfamily ligand (e.g., GDF8), may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) Nucleic Acids Symposium Series 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody.

In some embodiments, the anti-ligand antibodies described herein comprise an altered heavy chain constant region that has reduced (or no) effector function relative to its corresponding unaltered constant region. Effector functions involving the constant region of the anti-ligand antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the anti-ligand antibody comprises an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-ligand antibody described herein comprising an altered constant region displaying reduced ADCC and/or CDC may exhibit reduced or no ADCC and/or CDC activity.

In some embodiments, an anti-ligand antibody or antigen-binding fragment described herein exhibits reduced or no effector function. In some embodiments, an anti-ligand antibody comprises a hybrid constant region, or a portion thereof, such as a G2/G4 hybrid constant region (see e.g., Burton et al. (1992) Adv Immun 51:1-18; Canfield et al. (1991) J Exp Med 173:1483-1491; and Mueller et al. (1997) Mol Immunol 34(6):441-452). See above.

In some embodiments, an anti-ligand antibody or antigen-binding fragment may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) J Exp Med 176:1191-1195 and Shopes (1992) Immunol 148:2918-2922; PCT publication nos. WO 99/51642 and WO 94/29351; Duncan and Winter (1988) Nature 322:738-40; and U.S. Pat. Nos. 5,648,260 and 5,624,821.

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as E. coli gpt (Mulligan and Berg (1981) Proc Natl Acad Sci USA 78:2072) or Tn5 neo (Southern and Berg (1982) Mol Appl Genet 1:327). The selectable marker gene can be either linked to the DNA gene sequences to be expressed, or introduced into the same cell by co-transfection (Wigler et al. (1979) Cell 16:77). A second class of vectors utilizes DNA elements which confer autonomously replicating capabilities to an extrachromosomal plasmid. These vectors can be derived from animal viruses, such as bovine papillomavirus (Sarver et al. (1982) Proc Natl Acad Sci USA, 79:7147), cytomegalovirus, polyoma virus (Deans et al. (1984) Proc Natl Acad Sci USA 81:1292), or SV40 virus (Lusky and Botchan (1981) Nature 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as E. coli, fungi such as Saccharomyces cerevisiae and Pichia pastoris, insect cells such as SF9, mammalian cell lines (e.g., human cell lines), as well as primary cell lines.

In some embodiments, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) Curr Opin Biotechnol 13(6):625-629; van Kuik-Romeijn et al. (2000) Transgenic Res 9(2):155-159; and Pollock et al. (1999) J Immunol Methods 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in E. coli can be refolded from inclusion bodies (see, e.g., Hou et al. (1998) Cytokine 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) Protein Expression and Purification 18:213-220).

Following expression, the antibodies and fragments thereof can be isolated. An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, 3rd edition," Springer-Verlag, New York City, New York. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

The antibodies or antigen-binding fragments thereof can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the antibodies or antigen-binding fragments thereof can be conjugated to a heterologous moiety. The heterologous moiety can be, e.g., a heterologous polypeptide, a therapeutic agent (e.g., a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO: 177)), polyhistidine (6-His; HHHHHH (SEQ ID NO: 178), hemagglutinin (HA; YPYDVPDYA (SEQ ID NO: 179)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., 32P, 33P, 14C, 125I, 131I, 35S, and 3H. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylenetriaminepentaaceticacid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyl oxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimido benzoyl-N-hydroxy succinimide ester), an amino group and a carboxyl group (e.g., 4-[p-azidosalicylamido] butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as partofalargermolecule (e.g., $^{125}$Iinmeta-[$^{125}$I] iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) J Nucl Med 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) Bioconjug Chem 10(6): 973-8; Kinstler et al. (2002) Advanced Drug Deliveries Reviews 54:477-485; and Roberts et al. (2002) Advanced Drug Delivery Reviews 54:459-476 or HESylated (Fresenius Kabi, Germany; see, e.g., Pavisić et al. (2010) Int J Pharm 387(1-2):110-119). The stabilization moiety can improve the stability, or retention of, the antibody (or fragment) by at least about 1.5 (e.g., at least about 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) EMBO J 10(10):2717-2723; and Co et al. (1993) Mol Immunol 30:1361.

In some embodiments, any of the multispecific binders disclosed herein comprises any of the TβRII portions disclosed herein and any of the antibodies or antigen-binding fragment portions disclosed herein. In some embodiments, the multispecific binder has a structural layout similar to that illustrated in FIG. 14B. In some embodiments, the multispecific binder comprises an amino acid sequence that is at least 80%, 85%, 90%, 91%, 92%, 93%, 94%, 95%, 96%, 97%, 98%, 99% or 100% identical to the amino acid sequence of any one of or combination of SEQ ID NOs: 167-175. In some embodiments, the multispecific binder comprises an amino acid sequence that is at least 80%, 85%, 90%, 91%, 92%, 93%, 94%, 95%, 96%, 97%, 98%, 99% or 100% identical to the amino acid sequence of SEQ ID NO: 167. In some embodiments, the multispecific binder comprises an amino acid sequence that is at least 80%, 85%, 90%, 91%, 92%, 93%, 94%, 95%, 96%, 97%, 98%, 99% or 100% identical to the amino acid sequence of SEQ ID NO: 170. In some embodiments, the multispecific binder comprises an amino acid sequence that is at least 80%, 85%, 90%, 91%, 92%, 93%, 94%, 95%, 96%, 97%, 98%, 99% or 100% identical to the amino acid sequence of SEQ ID NO: 174. In particular embodiments, the multispecific binder comprises amino acid sequences that are at least 80%, 85%, 90%, 91%, 92%, 93%, 94%, 95%, 96%, 97%, 98%, 99% or 100% identical to the amino acid sequences of SEQ ID NOs: 167, 170 and 174. In further embodiments, the multispecific binder comprises amino acid sequences that are at least 80%, 85%, 90%, 91%, 92%, 93%, 94%, 95%, 96%, 97%, 98%, 99% or 100% identical to the amino acid sequences of SEQ ID NOs: 172 and 182. In some embodiments, the polypeptides in the multispecific binder comprise a leader/signal sequence (e.g., a signal sequence having an amino acid sequence that is at least 80%, 85%, 90%, 91%, 92%, 93%, 94%, 95%, 96%, 97%, 98%, 99% or 100% identical to the amino acid sequence of SEQ ID NO: 176).

SEQ ID NO: 167-(Variable Heavy Chain)
QVQLQQSGAELARPGASVKLSCKASGYTFTSYWMQWVKQRPGQGLEWIGAI
YPGDGDTRYTQKFKGKATLTADKSSSTAYMQLSSLASEDSAVYYCARMGGY
DRYYFDYWGQGTTLTVSS SEQ ID NO: 168-(Constant region delta K)
ASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGF
YPSDIAVEWESNGQPENNYKFTPPVLDSDGSFFLYSKLTVDKSRWQQGNVF
SCSVMHEALHNHYTQKSLSLSPG SEQ ID NO: 169-(Linker)
GGGSGGGGSGGGGSGGGGSG SEQ ID NO: 170-(TβRII)
TIPPHVQKSDVEMEAQKDEIICPSCNRTAHPLRHINNDMIVTDNNGAVKFP
QLCKFCDVRFSTCDNQKSCMSNCSITSICEKPQEVCVAVWRKNDENITLET
VCHDPKLPYHDFILEDAASPKCIMKEKKKPGETFFMCSCSSDECNDNIIFS
EEYNTSNPD SEQ ID NO: 171-(Constant Region of Heavy chain + TβRII)
ASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVF
SCSVMHEALHNHYTQKSLSLSPGTGGGGSGGGGSGGGGSGGGGSTIPPHVQ
KSDVEMEAQKDEIICPSCNRTAHPLRHINNDMIVTDNNGAVKFPQLCKFCD
VRFSTCDNQKSCMSNCSITSICEKPQEVCVAVWRKNDENITLETVCHDPKL
PYHDFILEDAASPKCIMKEKKKPGETFFMCSCSSDECNDNIIFSEEYNTSN
PD SEQ ID NO: 172-(Heavy chain + TβRII)
QVQLQQSGAELARPGASVKLSCKASGYTFTSYWMQWVKQRPGQGLEWIGAI
YPGDGDTRYTQKFKGKATLTADKSSSTAYMQLSSLASEDSAVYYCARMGGY
DRYYFDYWGQGTTLTVSSASTKGPSVFPLAPSSKSTSGGTAALGCLVKDYF
PEPVTVSWNSGALTSGVHTFPAVLQSSGLYSLSSVVTVPSSSLGTQTYICN
VNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFL
YSKLTVDKSRWQQGNVFSCSVMHEALHNHYTQKSLSLSPGTGGGGSGGGGS
GGGGSGGGGSTIPPHVQKSDVEMEAQKDEIICPSCNRTAHPLRHINNDMIV
TDNNGAVKFPQLCKFCDVRFSTCDNQKSCMSNCSITSICEKPQEVCVAVWR
KNDENITLETVCHDPKLPYHDFILEDAASPKCIMKEKKKPGETFFMCSCSS
DECNDNIIFSEEYNTSNPD SEQ ID NO: 173-(Heavy chain + TβRII + leader)
MGWSCIMLFLAATATGAHSQVQLQQSGAELARPGASVKLSCKASGYTFTSY
WMQWVKQRPGQGLEWIGAIYPGDGDTRYTQKFKGKATLTADKSSSTAYMQL
SSLASEDSAVYYCARMGGYDRYYFDYWGQGTTLTVSSASTKGPSVFPLAPS
SKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYT
QKSLSLSPGTGGGGSGGGGSGGGGSGGGGSTIPPHVQKSDVEMEAQKDEII
CPSCNRTAHPLRHINNDMIVTDNNGAVKFPQLCKFCDVRFSTCDNQKSCMS
NCSITSICEKPQEVCVAVWRKNDENITLETVCHDPKLPYHDFILEDAASPK
CIMKEKKKPGETFFMCSCSSDECNDNIIFSEEYNTSNPD SEQ ID NO: 174-(Variable Light Chain)
DIVMTQSPSSLAMSVGQKVTMSCKSSQSLLNSANQKNYLAWYQQKPGQSPK
LLVYFASTRESGVPDRFIGSGSGTDFTLTISSVQAEDLADYFCQQHYNTPL
TFGAGTKLELK SEQ ID NO: 175-(Constant Kappa LC)
RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSF
NRGEC SEQ ID NO: 182: (Light Chain)
DIVMTQSPSSLAMSVGQKVTMSCKSSQSLLNSANQKNYLAWYQQKPGQSPK
LLVYFASTRESGVPDRFIGSGSGTDFTLTISSVQAEDLADYFCQQHYNTPL
TFGAGTKLELKRTVAAPSVFIFPPSDEQLKSGTASVVCLLNNFYPREAKVQ
WKVDNALQSGNSQESVTEQDSKDSTYSLSSTLTLSKADYEKHKVYACEVTH
QGLSSPVTKSFNRGEC SEQ ID NO: 176 (Leader Sequence)
MGWSCIMLFLAATATGAHS

3. Nucleic Acids and Methods of Manufacture

In certain embodiments, the present disclosure makes available isolated and/or purified forms of polypeptides of any of the multispecific binders of TGFβ-superfamily ligands disclosed herein (e.g., TβRII or ActRIIA polypeptides as well as ActRIIA:TβRII heteromultimers comprising the same), which are isolated from, or otherwise substantially free of (e.g., at least 80%, 90%, 95%, 96%, 97%, 98%, or 99% free of), other proteins and/or other polypeptide species. Polypeptides will generally be produced by expression from recombinant nucleic acids.

In certain embodiments, the disclosure includes nucleic acids encoding soluble polypeptides of any of the multispecific binders of TGFβ-superfamily ligands disclosed herein (e.g., TβRII or ActRIIA polypeptides as well as ActRIIA:TβRII heteromultimers comprising the same) comprising the coding sequence for an extracellular portion of a protein (e.g., a TβRII and/or ActRIIA protein). In further embodiments, this disclosure also pertains to a host cell comprising such nucleic acids. The host cell may be any prokaryotic or eukaryotic cell. For example, a polypeptide of the present disclosure may be expressed in bacterial cells such as *E. coli*, insect cells (e.g., using a baculovirus expression system), yeast, or mammalian cells. Other suitable host cells are known to those skilled in the art. Accordingly, some embodiments of the present disclosure further pertain to methods of producing the polypeptides.

In certain aspects, the disclosure provides isolated and/or recombinant nucleic acids encoding any of the polypeptides of any of the multispecific binders of TGFβ-superfamily ligands disclosed herein (e.g., TβRII or ActRIIA polypeptides as well as ActRIIA:TβRII heteromultimers comprising the same), including fragments, functional variants and fusion proteins disclosed herein. SEQ ID NOs: 8, 10, 12, 14, 16, 46, 47, 56, 57, 83, 86, 89, and 92 encode TβRII or ActRIIA polypeptides as well as variants thereof comprising an extracellular domain fused to an IgG Fc domain. Other nucleotide sequences of the disclosure include SEQ ID NOs: 136, 140, and 166. The subject nucleic acids may be single-stranded or double stranded. Such nucleic acids may be DNA or RNA molecules. These nucleic acids may be used, for example, in methods for making polypeptides or as direct therapeutic agents (e.g., in an antisense, RNAi or gene therapy approach).

In certain aspects, the subject nucleic acids encoding polypeptides are further understood to include nucleic acids that are variants of SEQ ID NOs: 8, 10, 12, 14, 16, 46, 47, 56, 57, 83, 86, 89, 92, 136, 140, and 166. Variant nucleotide sequences include sequences that differ by one or more nucleotide substitutions, additions or deletions, such as allelic variants.

In certain embodiments, the disclosure provides isolated or recombinant nucleic acid sequences that are at least 70%, 75%, 80%, 85%, 90%, 91%, 92%, 93%, 94%, 95%, 96%, 97%, 98%, 99% or 100% identical to SEQ ID NOs: 8, 10, 12, 14, 16, 46, 47, 56, 57, 83, 86, 89, 92, 136, 140, and 166. In particular embodiments, the disclosure provides isolated or recombinant nucleic acid sequences that are at least 70%, 75%, 80%, 85%, 90%, 91%, 92%, 93%, 94%, 95%, 96%, 97%, 98%, 99% or 100% identical to SEQ ID NOs: 83, 86, 89, 92, 136, 140, and 166 or fragments thereof. One of ordinary skill in the art will appreciate that nucleic acid sequences complementary to SEQ ID NOs: 8, 10, 12, 14, 16, 46, 47, 56, 57, 83, 86, 89, 92, 136, 140, and 166 and variants of SEQ ID NOs: 8, 10, 12, 14, 16, 46, 47, 56, 57, 83, 86, 89, 92, 136, 140, and 166 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the disclosure also include nucleotide sequences that hybridize under highly stringent conditions to the nucleotide sequences designated in SEQ ID NOs: 8, 10, 12, 14, 16, 46, 47, 56, 57, 83, 86, 89, 92, 136, 140, and 166 complement sequences of SEQ ID NOs: 8, 10, 12, 14, 16, 46, 47, 56, 57, 83, 86, 89, 92, 136, 140, and 166 or fragments thereof. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In some embodiments, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 8, 10, 12, 14, 16, 46, 47, 56, 57, 83, 86, 89, 92, 136, 140, and 166 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

It will be appreciated by one of skill in the art that corresponding variants based on the long isoform of TβRII will include nucleotide sequences encoding the 25-amino acid insertion along with a conservative Val-Ile substitution at the flanking position C-terminal to the insertion. It will also be appreciated that corresponding variants based on either the long (A) or short (B) isoforms of TβRII will include variant nucleotide sequences comprising an insertion of 108 nucleotides, encoding a 36-amino-acid insertion (SEQ ID NO: 41), at the same location described for naturally occurring TβRII isoform C.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects disclosed herein, the subject nucleic acid is provided in an expression vector comprising a nucleotide sequence encoding a polypeptide of any of the multispecific binders of TGFβ-superfamily ligands disclosed herein (e.g., TβRII or ActRIIA polypeptides as well as ActRIIA:TβRII heteromultimers comprising the same)

and operably linked to at least one regulatory sequence. Regulatory sequences are art-recognized and are selected to direct expression of the T polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, CA (1990). For instance, any of a wide variety of expression control sequences that control the expression of a DNA sequence when operatively linked to it may be used in these vectors to express DNA sequences encoding a polypeptide of any of the multispecific binders of TGFβ-superfamily ligands disclosed herein (e.g., TβRII or ActRIIA polypeptides as well as ActRIIA:TβRII heteromultimers comprising the same). Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid included in the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide of any of the multispecific binders of TGFβ-superfamily ligands disclosed herein (e.g., TβRII or ActRIIA polypeptides as well as ActRIIA:TβRII heteromultimers comprising the same) include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the B-gal containing pBlueBac III).

In certain embodiments, a vector will be designed for production of the subject polypeptides of any of the multispecific binders of TGFβ-superfamily ligands disclosed herein (e.g., TβRII or ActRIIA polypeptides as well as ActRIIA:TβRII heteromultimers comprising the same) in CHO cells, such as a Pcmv-Script vector (Stratagene, La Jolla, Calif.), pcDN4 vectors (Invitrogen, Carlsbad, Calif) and pCI-neo vectors (Promega, Madison, Wisc.). In a preferred embodiment, a vector will be designed for production of the subject polypeptides in HEK-293 cells. As will be apparent, the subject gene constructs can be used to cause expression of the subject polypeptides in cells propagated in culture, e.g., to produce proteins, including fusion proteins or variant proteins, for purification.

This disclosure also pertains to a host cell transfected with a recombinant gene including a coding sequence (e.g., SEQ ID NOs: 8, 10, 12, 14, 16, 46, 47, 56, 57, 83, 86, 89, 92, 136, 140, and 166) for one or more of the subject polypeptides of any of the multispecific binders of TGFβ-superfamily ligands disclosed herein (e.g., TβRII or ActRIIA polypeptides as well as ActRIIA:TβRII heteromultimers comprising the same). The host cell may be any prokaryotic or eukaryotic cell. For example, a ActRIIA:TβRII protein disclosed herein may be expressed in bacterial cells such as E. coli, insect cells (e.g., using a baculovirus expression system), yeast, or mammalian cells. Other suitable host cells are known to those skilled in the art.

Accordingly, the present disclosure further pertains to methods of producing the subject polypeptides of any of the multispecific binders of TGFβ-superfamily ligands disclosed herein (e.g., TβRII or ActRIIA polypeptides as well as ActRIIA:TβRII heteromultimers comprising the same). For example, a host cell transfected with an expression vector encoding a polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically or in a membrane fraction and the cells harvested, lysed and the protein isolated. A cell culture includes host cells, and media. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the polypeptides and affinity purification with an agent that binds to a domain fused to the polypeptide (e.g., a protein A column may be used to purify an Fc fusion). In a preferred embodiment, the polypeptide is a fusion protein containing a domain which facilitates its purification. As an example, purification may be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another embodiment, a fusion gene coding for a purification leader sequence, such as a poly-(His)/enterokinase cleavage site sequence at the N-terminus of the desired portion of the recombinant polypeptide of any of the multispecific binders of TGFβ-superfamily ligands disclosed herein (e.g., TβRII or ActRIIA polypeptides as well as ActRIIA:TβRII heteromultimers comprising the same), can allow purification of the expressed fusion protein by affinity chromatography using a Nit metal resin. The purification leader sequence can then be subsequently removed by treatment with enterokinase to provide the purified polypeptide (e.g., see Hochuli et al., (1987) J. Chromatography 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

4. Screening Assays

In certain aspects, the present invention relates to the use of a multispecific binder of a TGFβ-superfamily ligand, such as an ActRIIA:TβRII heteromultimer (e.g., soluble ActRIIA: TβRII heterodimers) to identify compounds (agents) which are agonist or antagonists of the ActRIIA and TβRII signaling pathways. Compounds identified through this screening can be tested to assess their ability to modulate, for example, TGFβ1, TGFβ3, activin, GDF8 and/or GDF11 signaling activity in vitro. Optionally, these compounds can further be tested in animal models to assess their ability to modulate tissue growth in vivo.

There are numerous approaches to screening for therapeutic agents for modulating tissue growth by targeting TGFβ1, TGFβ3, activin, GDF8 and/or GDF11 polypeptides. In certain embodiments, high-throughput screening of compounds can be carried out to identify agents that perturb ActRIIA- or TβRII-mediated cell signaling. In certain embodiments, the assay is carried out to screen and identify compounds that specifically inhibit or reduce binding of a TβRII or ActRIIA polypeptide to TGFβ1, TGFβ3, activin, GDF8 and/or GDF11. Alternatively, the assay can be used to identify compounds that enhance binding of a TβRII or ActRIIA polypeptide to TGFβ1, TGFβ3, activin, and/or GDF11. In a further embodiment, the compounds can be identified by their ability to interact with a TGFβ1, TGFβ3, activin, GDF8, GDF11, ActRIIA, or TβRII polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatable crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TβRII or ActRIIA polypeptide and TGFβ1, TGFβ3, activin, GDF8, and/or GDF11 polypeptides.

Merely to illustrate, in an exemplary screening assay of the present invention, the compound of interest is contacted with an isolated and purified ActRIIA:TβRII heteromultimer which is ordinarily capable of binding to TGFβ1 and activin A. To the mixture of the compound and ActRIIA:TβRII heteromultimer is then added a composition containing a ActRIIA:TβRII-binding ligand (e.g., TGFβ1 or activin A). Detection and quantification of ActRIIA:TβRII/TGFβ1 or ActRIIA:TβRII/activin A complexes provides a means for determining the compound's efficacy at inhibiting (or potentiating) complex formation between the ActRIIA:TβRII protein and TGFβ1 or activin A. The efficacy of the compound can be assessed by generating dose response curves from data obtained using various concentrations of the test compound. Moreover, a control assay can also be performed to provide a baseline for comparison. For example, in a control assay, isolated and a purified TGFβ1 or activin A is added to a composition containing the ActRIIA:TβRII heteromultimer, and the formation of ActRIIA:TβRII/TGFβ1 or ActRIIA:TβRII/activin A complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between any of the multispecific binders of TGFβ-superfamily ligands disclosed herein (e.g., an ActRIIA:TβRII heteromultimer) and TGFβ1, GDF8 and/or activin A may be detected by a variety of techniques. For instance, modulation of the formation of complexes can be quantitated using, for example, detectably labeled proteins such as radiolabeled (e.g., $^{32}P$ $^{35}S$, $^{14}C$ or $^{3}H$), fluorescently labeled (e.g., FITC), or enzymatically labeled ActRIIA:TβRII heteromultimer or TGFβ1 or activin A, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a ActRIIA:TβRII heteromultimer and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between any of the multispecific binders of TGFβ-superfamily ligands disclosed herein (e.g., an ActRIIA:TβRII heteromultimer) and its binding protein. See for example, U.S. Pat. No. 5,283,317; Zervos et al. (1993) Cell 72:223-232; Madura et al. (1993) J Biol Chem 268: 12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between a ActRIIA:TβRII heteromultimer and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with any of the multispecific binders of TGFβ-superfamily ligands disclosed herein (e.g. an ActRIIA:TβRII heteromultimer) and TGFβ1, TGFβ3, activin, GDF8, and/or GDF11 polypeptide. The interaction between the compound and the multispecific binder or TGFβ1, TGFβ3, activin, and/or GDF11 polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a TGFβ1, TGFβ3, activin, and/or GDF11 polypeptide or multispecific binder (e.g., ActRIIA:TβRII heteromultimer). This may include a solid-phase or fluid-phase binding event. Alternatively, the gene encoding a TGFβ1, TGFβ3, activin, and/or GDF11 polypeptide or multispecific binder (e.g., ActRIIA:TβRII heteromultimer) can be transfected with a reporter system (e.g., β-galactosidase, luciferase, or green fluorescent protein) into a cell and screened against the library preferably by a high-throughput screening or with individual members of the library. Other mechanism-based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for modulating (stimulating or inhibiting) TGFβ1-, TGFβ3-, activin-, GDF8-, GDF11-mediated cell signaling. Therefore, any compound identified can be tested in whole cells or tissues, in vitro or in vivo, to confirm their ability to modulate TGFβ1, TGFβ3, activin, GDF8, and/or GDF11 signaling. Various methods known in the art can be utilized for this purpose.

5. Exemplary Therapeutic Uses

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treatment", "treating", "alleviation" and the like are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease (disorder) or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms).

The terms "patient", "subject", or "individual" are used interchangeably herein and refer to either a human or a non-human animal. These terms include mammals, such as humans, non-human primates, laboratory animals, livestock animals (including bovines, porcines, camels, etc.), companion animals (e.g., canines, felines, other domesticated animals, etc.) and rodents (e.g., mice and rats). In particular embodiments, the patient, subject or individual is a human.

As used herein, "combination", "in combination with", "conjoint administration" and the like refers to any form of administration such that the second therapy is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more of any of the multispecific binders of TGFβ-superfamily ligands disclosed herein (e.g. an ActRIIA:TβRII heteromultimer) can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

Naturally occurring ActRIIA and TβRII receptor-ligand complexes play essential roles in tissue growth as well as early developmental processes such as the correct formation of various structures or in one or more post-developmental capacities. Thus, ActRIIA:TβRII-associated conditions or disorders include, but are not limited to, abnormal tissue growth and developmental defects. In addition, ActRIIA:TβRII-associated conditions or disorders include, but are not limited to, conditions or disorders of red blood cell formation (e.g., anemia), pulmonary conditions or diseases, kidney conditions or diseases, and tumors or cancers.

In part, the disclosure provides methods of treating ActRIIA:TβRII-associated conditions or diseases by administering to a patient in need thereof an effective amount of an ActRIIA:TβRII heteromultimer. For example, in some embodiments, the methods relate to preventing or reducing the severity and/or duration of an ActRIIA:TβRII-associated condition or diseases in a patient in need thereof by administering an effective amount of any of the multispecific binders of TGFβ-superfamily ligands disclosed herein (e.g. an ActRIIA:TβRII heteromultimer). Optionally, such methods further include administering any of the multispecific binders of TGFβ-superfamily ligands disclosed herein (e.g. an ActRIIA:TβRII heteromultimer) in combination with one or more additional active agents or supportive therapies for treating an ActRIIA:TβRII-associated condition or diseases.

In some embodiments, the present disclosure relates to methods of treating pulmonary hypertension (e.g., pulmonary arterial hypertension) comprising administering to a patient in need thereof an effective amount of any of the multispecific binders of TGFβ-superfamily ligands disclosed herein (e.g. an ActRIIA:TβRII heteromultimer). For example, in some embodiments, the disclosure related to methods of preventing or reducing the severity or progression rate of one or more complications of pulmonary hypertension (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount of any of the multispecific binders of TGFβ-superfamily ligands disclosed herein (e.g. an ActRIIA:TβRII heteromultimer). Optionally, methods disclosed herein for treating pulmonary hypertension may further comprise administering to the patient one or more supportive therapies or additional active agents for treating pulmonary hypertension. For example, the patient also may be administered one or more supportive therapies or active agents selected from the group consisting of: prostacyclin and derivatives thereof (e.g., epoprostenol, treprostinil, and iloprost); prostacyclin receptor agonists (e.g., selexipag); endothelin receptor antagonists (e.g., thelin, ambrisentan, macitentan, and bosentan); calcium channel blockers (e.g., amlodipine, diltiazem, and nifedipine; anticoagulants (e.g., warfarin); diuretics; oxygen therapy; atrial septostomy; pulmonary thromboendarterectomy; phosphodiesterase type 5 inhibitors (e.g., sildenafil and tadalafil); activators of soluble guanylate cyclase (e.g., cinaciguat and riociguat); ASK-1 inhibitors (e.g., CIIA; SCH79797; GS-4997; MSC2032964A; 3H-naphtho[1,2,3-de]quiniline-2,7-diones, NQDI-1; 2-thioxo-thiazolidines, 5-bromo-3-(4-oxo-2-thioxo-thiazolidine-5-ylidene)-1,3-dihydro-indol-2-one); NF-κB antagonists (e.g., dh404, CDDO-epoxide; 2.2-difluoropropionamide; C28 imidazole (CDDO-Im); 2-cyano-3,12-dioxoolean-1,9-dien-28-oic acid (CDDO); 3-Acetyloleanolic Acid; 3-Triflouroacetyloleanolic Acid; 28-Methyl-3-acetyloleanane; 28-Methyl-3-trifluoro-acetyloleanane; 28-Methyloxyoleanolic Acid; SZC014; SCZ015; SZC017; PEGylated derivatives of oleanolic acid; 3-O-(beta-D-glucopyranosyl) oleanolic acid; 3-O-[beta-D-glucopyranosyl-(1→3)-beta-D-glucopyranosyl] oleanolic acid; 3-O-[beta-D-glucopyranosyl-(1→2)-beta-D-glucopyranosyl] oleanolic acid; 3-O-[beta-D-glucopyranosyl-(1→3)-beta-D-glucopyranosyl] oleanolic acid 28-O-beta-D-glucopyranosyl ester; 3-O-[beta-D-glucopyranosyl-(1→2)-beta-D-glucopyranosyl] oleanolic acid 28-O-beta-D-glucopyranosyl ester; 3-O-[a-L-rhamnopyranosyl-(1→3)-beta-D-glucuronopyranosyl] oleanolic acid; 3-O-[alpha-L-rhamnopyranosyl-(1→3)-beta-D-glucuronopyranosyl] oleanolic acid 28-O-beta-D-glucopyranosyl ester; 28-O-β-D-glucopyranosyl-oleanolic acid; 3-O-β-D-glucopyranosyl (1→3)-β-D-glucopyranosiduronic acid (CS1); oleanolic acid 3-O-β-D-glucopyranosyl (1→3)-β-D-glucopyranosiduronic acid (CS2); methyl 3,11-dioxoolean-12-en-28-olate (DIOXOL); ZCVI$_4$-2; Benzyl3-dehydr-oxy-1,2,5-oxadiazolo[3',4':2,3]oleanolate) lung and/or heart transplantation.

Pulmonary hypertension (PH) has been previously classified as primary (idiopathic) or secondary. Recently, the World Health Organization (WHO) has classified pulmonary hypertension into five groups: Group 1: pulmonary arterial hypertension (PAH); Group 2: pulmonary hypertension with left heart disease; Group 3: pulmonary hypertension with lung disease and/or hypoxemia; Group 4: pulmonary hypertension due to chronic thrombotic and/or embolic disease; and Group 5: miscellaneous conditions (e.g., sarcoidosis, histiocytosis X, lymphangiomatosis and compression of pulmonary vessels). See, for example, Rubin (2004) Chest 126:7-10. In some embodiments, the methods disclosed herein relate treating PH designated as any one of Group 1-5 by the WHO. In some embodiments, the methods relate to treating PAH.

Pulmonary arterial hypertension is a serious, progressive and life-threatening disease of the pulmonary vasculature, characterized by profound vasoconstriction and an abnormal proliferation of smooth muscle cells in the walls of the pulmonary arteries. Severe constriction of the blood vessels in the lungs leads to very high pulmonary arterial pressures. These high pressures make it difficult for the heart to pump blood through the lungs to be oxygenated. Patients with PAH suffer from extreme shortness of breath as the heart struggles to pump against these high pressures. Patients with PAH typically develop significant increases in pulmonary vascular resistance (PVR) and sustained elevations in pulmonary artery pressure (PAP), which ultimately lead to right ventricular failure and death. Patients diagnosed with PAH have a poor prognosis and equally compromised quality of life, with a mean life expectancy of 2 to 5 years from the time of diagnosis if untreated.

A variety of factors contribute to the pathogenesis of pulmonary hypertension including proliferation of pulmonary cells which can contribute to vascular remodeling (i.e., hyperplasia). For example, pulmonary vascular remodeling occurs primarily by proliferation of arterial endothelial cells and smooth muscle cells of patients with pulmonary hypertension. Overexpression of various cytokines is believed to promote pulmonary hypertension. Further, it has been found that pulmonary hypertension may rise from the hyperproliferation of pulmonary arterial smooth cells and pulmonary endothelial cells. Still further, advanced PAH may be characterized by muscularization of distal pulmonary arterioles, concentric intimal thickening, and obstruction of the vascular lumen by proliferating endothelial cells. Pietra et al., J. Am. Coll. Cardiol., 43:255-325 (2004).

In some embodiments, the present disclosure relates to methods of treating an interstitial lung disease (e.g., idiopathic pulmonary fibrosis) comprising administering to a patient in need thereof an effective amount of any of the multispecific binders of TGFβ-superfamily ligands disclosed herein (e.g. an ActRIIA:TβRII heteromultimer). In some embodiments, the interstitial lung disease is pulmonary fibrosis. In some embodiments, the interstitial lung disease is caused by any one of the following: silicosis, asbestosis, berylliosis, hypersensitivity pneumonitis, drug use (e.g., antibiotics, chemotherapeutic drugs, antiarrhythmic agents, statins), systemic sclerosis, polymyositis, dermatomyositis, systemic lupus erythematosus, rheumatoid arthritis, an infection (e.g., atypical pneumonia, *pneumocystis* pneumonia, tuberculosis, *Chlamydia trachomatis*, and/or respiratory syncytial virus), lymphangitic carcinomatosis, cigarette smoking, or developmental disorders. In some embodiments, the interstitial lung disease is idiopathic (e.g., sarcoidosis, idiopathic pulmonary fibrosis, Hamman-Rich syndrome, and/or antisynthetase syndrome). In particular embodiments, the interstitial lung disease is idiopathic pulmonary fibrosis. In some embodiments, the treatment for idiopathic pulmonary fibrosis is administered in combination with an additional therapeutic agent. In some embodiments, the additional therapeutic agent is selected from the group consisting of: pirfenidone, N-acetylcysteine, prednisone, azathioprine, nintedanib, derivatives thereof and combinations thereof.

In some embodiments, the disclosure relates to methods of treating a fibrotic or sclerotic disease, disorder or condition. As used herein, the terms "fibrotic disorder", "fibrotic condition," and "fibrotic disease," are used interchangeably to refer to a disorder, condition or disease characterized by fibrosis. Examples of fibrotic disorders include, but are not limited to lupus, sclerotic disorders (e.g., scleroderma, atherosclerosis, and systemic sclerosis including, e.g., diffuse systemic sclerosis and progressive systemic sclerosis), vascular fibrosis, pancreatic fibrosis, liver fibrosis (e.g., cirrhosis), renal fibrosis, musculoskeletal fibrosis, cardiac fibrosis (e.g., endomyocardial fibrosis, idiopathic myocardiopathy), skin fibrosis (e.g., scleroderma, post-traumatic, operative cutaneous scarring, keloids and cutaneous keloid formation), eye fibrosis (e.g., glaucoma, sclerosis of the eyes, conjunctival and corneal scarring, and pterygium), myelofibrosis, chronic graft-versus-host disease, Peyronie's disease, post-cystoscopic urethral stenosis, idiopathic and pharmacologically induced retroperitoneal fibrosis, mediastinal fibrosis, proliferative fibrosis, neoplastic fibrosis, Dupuytren's disease, strictures, neural scarring, dermal scarring, idiopathic pulmonary fibrosis and radiation induced fibrosis.

In some embodiments, the present disclosure relates to methods of treating a tumor or cancer comprising administering to a patient in need thereof an effective amount of any of the multispecific binders of TGFβ-superfamily ligands disclosed herein (e.g. an ActRIIA:TβRII heteromultimer). For example, in some embodiments, the disclosure related to methods of preventing or reducing the severity or progression rate of one or more complications of a tumor or cancer. Optionally, methods disclosed herein for treating a tumor or cancer may further comprise administering to the patient one or more supportive therapies or additional active agents for treating the tumor or cancer. In addition, any of the multispecific binders of TGFβ-superfamily ligands disclosed herein (e.g. an ActRIIA:TβRII heteromultimer) may be used to treat malignant or premalignant conditions and to prevent progression to a neoplastic or malignant state, including but not limited to those disorders described herein. Such uses are indicated in conditions known or suspected of preceding progression to neoplasia or cancer, in particular, where non-neoplastic cell growth consisting of hyperplasia, metaplasia, or most particularly, dysplasia has occurred.

In general, "tumors" refers to benign and malignant cancers as well as dormant tumors. In general, "cancer" refers to primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Metastasis can be local or distant. Metastases are most often detected through the sole or combined use of magnetic resonance imaging (MRI) scans, computed tomography (CT) scans, blood and platelet counts, liver function studies, chest X-rays, bone scans in addition to the monitoring of specific symptoms, and combinations thereof.

In some embodiments, any of the multispecific binders of TGFβ-superfamily ligands disclosed herein (e.g. an ActRIIA:TβRII heteromultimer) may be used in the treatment of various forms of cancer, including, but not limited to, cancer of the bladder, breast, colon, kidney, liver, lung, ovary, cervix, pancreas, rectum, prostate, stomach, epidermis; a hematopoietic tumor of lymphoid or myeloid lineage; a tumor of mesenchymal origin such as a fibrosarcoma or rhabdomyosarcoma; other tumor types such as melanoma, teratocarci-noma, neuroblastoma, glioma, adenocarcinoma and non-small lung cell carcinoma. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer.

Other examples of cancers or malignancies include, but are not limited to: acute childhood Other examples of cancers or malignancies include, but are not limited to: acute childhood lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalamic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous t-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatic bile duct cancer, eye cancer, female breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lymphoproliferative disorders, macroglobulinemia, male breast cancer, malignant mesothelioma, malignant thymoma, medulloblastoma, melanoma, mesothelioma, metastatic occult primary squamous neck cancer, metastatic primary squamous neck cancer, metastatic squamous neck cancer, multiple myeloma, multiple myeloma/plasma cell neoplasm, myelodysplastic syndrome, myelogenous leukemia, myeloid leukemia, myeloproliferative disorders, nasal cavity and paranasal sinus cancer, nasopharyngeal cancer, neuroblastoma, non-Hodgkin's lymphoma, nonmelanoma skin cancer, non-small cell lung cancer, occult primary metastatic squamous neck cancer, oropharyngeal cancer, osteo-/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, parathyroid cancer, penile cancer, pheochromocytoma, pituitary tumor, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, Sezary syndrome, skin cancer, small cell lung cancer, small intestine cancer, soft tissue sarcoma, squamous neck cancer, stomach cancer, supratentorial primitive neuroectodermal and pineal tumors, t-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethral cancer, uterine cancer, uterine sarcoma, vaginal cancer, visual pathway and hypothalamic glioma, vulvar cancer, Waldenstrom's macroglobulinemia, Wilms' tumor, and any other hyperproliferative disease, besides neoplasia, located in an organ system listed above.

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. In some embodiments, any of the multispecific binders of TGFβ-superfamily ligands disclosed herein (e.g. an ActRIIA:TβRII heteromultimer) may be used to treat a dysplastic disorders. Dysplastic disorders include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis *punctata*, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which may be treated with any of the multispecific binders of TGFβ-superfamily ligands disclosed herein (e.g. an ActRIIA:TβRII heteromultimer) include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

Additional hyperproliferative diseases, disorders, and/or conditions which may be treated with an any of the multispecific binders of TGFβ-superfamily ligands disclosed herein (e.g. an ActRIIA:TβRII heteromultimer), include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

In certain aspects, therapeutic cancer agents such as cytotoxic agents, anti-angiogenic agents, pro-apoptotic agents, immunomodulator agents, antibiotics, hormones, hormone antagonists, chemokines, drugs, prodrugs, toxins, enzymes or other active agents may be used in combination with any of the multispecific binders of TGFβ-superfamily ligands disclosed herein (e.g. an ActRIIA:TβRII heteromultimer). Drugs of use may possess a pharmaceutical property selected from, for example: antimitotic, anti-kinase, alkylating, antimetabolite, antibiotic, alkaloid, anti-angiogenic, pro-apoptotic agents, and combinations thereof.

For example, anti-PD1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD1 antibodies include lambrolizumab (MK-3475, MERCK), nivolumab (BMS-936558, Bristol-Myers Squibb), AMP-224 (Merck), and pidilizumab (CT-011, Curetech Ltd.). Anti-PD1 antibodies are commercially available, for example from ABCAM (AB137132), Biolegend (EH12.2H7, RMP1-14) and Affymetrix Ebioscience (J105, J116, MIH4).

Anti-CTL4A antibodies have been used in clinical trials for treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). Exemplary anti-CTLA4 antibodies include ipilimumab (Bristol-Myers Squibb) and tremelimumab (Pfizer). Anti-PD1 antibodies are commercially available, for example from ABCAM (AB134090), Sino Biological Inc. (11159-H03H, 11159-H08H), and Thermo Scientific Pierce (PA5-29572, PA5-23967, PA5-26465, MA1-12205, MA1-35914). Ipilimumab has recently received FDA approval for treatment of metastatic melanoma (Wada et al., 2013, J Transl Med 11:89).

Although checkpoint inhibitor against CTLA4, PD1 and PD-L1 are the most clinically advanced, other potential checkpoint antigens are known and may be used as the target of therapeutic inhibitors in combination with the subject ActRIIA:TβRII heteromultimer, such as LAG3, B7-H3, B7-H4 and TIM3 (Pardoll, 2012, Nature Reviews Cancer 12:252-264). These and other known agents that stimulate immune response to tumors and/or pathogens may be used in combination with ActRIIA:TβRII heteromultimer alone or in further combination with an interferon, such as interferon-α, and/or an antibody-drug conjugate for improved cancer therapy. Other known co-stimulatory pathway modulators that may be used in combination include, but are not limited to, agatolimod, belatacept, blinatumomab, CD40 ligand, anti-B7-1 antibody, anti-B7-2 antibody, anti-B7-H4 antibody, AG4263, eritoran, anti-OX40 antibody, ISF-154, and SGN-70; B7-1, B7-2, ICAM-1, ICAM-2, ICAM-3, CD48, LFA-3, CD30 ligand, CD40 ligand, heat stable antigen, B7h, OX40 ligand, LIGHT, CD70 and CD24.

In some embodiments, the present disclosure relates to methods of treating a kidney (renal) disease or condition comprising administering to a patient in need thereof an effective amount of any of the multispecific binders of TGFβ-superfamily ligands disclosed herein (e.g. an ActRIIA:TβRII heteromultimer). For example, in some embodiments, the disclosure relates to methods of preventing or reducing the severity or progression rate of one or more complications of a kidney disease or condition. Optionally, methods disclosed herein for treating a kidney disease or condition may further comprise administering to the patient one or more supportive therapies or additional active agents for treating the kidney disease or condition. For example, the patient also may be administered one or more supportive therapies or active agents selected from the group consisting of: angiotensin-converting enzyme (ACE) inhibitors, angiotensin II receptor blockers, water pills, statins, erythropoietin, diuretics, calcium and/or vitamin D supplement, a phosphate binder, calcium, glucose or sodium polystyrene sulfonate (e.g., Kayexalate, Kionex), by hemodialysis and/or peritoneal dialysis, Lasix® (furosemide), Demadex® (torsemide), Edecrin® (ethacrynic acid), and sodium edecrin.

The kidneys maintain many features of the blood, including volume, pH balance, electrolyte concentrations, and blood pressure, as well as bearing responsibility for toxin and waste filtration. These functions depend upon the intricate structure of the kidney nephrons, constant flow of blood through the various capillaries of the kidney, and the regulation of the kidney by signals from the rest of the body, including endocrine hormones. Problems with kidney function manifest by direct mechanisms (e.g., genetic defects, infection, or toxin exposure) and by indirect mechanisms progressively proceeding from long term stressors like hypertrophy and hyperfiltration (themselves often a result of more direct insults to kidney function). Due to the central role of the kidney in blood maintenance and waste secretion, kidney-associated disease manifestations are many and varied; they can be reviewed in Harrison's Principles of Internal Medicine, 18$^{th}$ edition, McGraw Hill, N.Y., Part 13, Chp 277-289.

Therefore, methods of this disclosure can be applied to various kidney-associated diseases or conditions. As used herein, kidney-associated disease or condition can refer to any disease, disorder, or condition that affects the kidneys or the renal system. Examples of kidney-associated diseases or conditions include, but are not limited to, chronic kidney diseases (or failure), acute kidney diseases (or failure), primary kidney diseases, non-diabetic kidney diseases, glomerulonephritis, interstitial nephritis, diabetic kidney diseases, diabetic chronic kidney disease, diabetic nephropathy, glomerulosclerosis, rapid progressive glomerulonephritis, renal fibrosis, Alport syndrome, IDDM nephritis, mesangial proliferative glomerulonephritis, membranoproliferative glomerulonephritis, crescentic glomerulonephritis, renal interstitial fibrosis, focal segmental glomerulosclerosis, membranous nephropathy, minimal change disease, pauci-immune rapid progressive glomerulonephritis, IgA nephropathy, polycystic kidney disease, Dent's disease, nephrocytinosis, Heymann nephritis, polycystic kidney disease (e.g., autosomal dominant (adult) polycystic kidney disease and autosomal recessive (childhood) polycystic kidney disease), acute kidney injury, nephrotic syndrome, renal ischemia, podocyte diseases or disorders, proteinuria, glomerular diseases, membranous glomerulonephritis, focal segmental glomerulonephritis, pre-eclampsia, eclampsia, kidney lesions, collagen vascular diseases, benign orthostatic (postural) proteinuria, IgM nephropathy, membranous nephropathy, sarcoidosis, diabetes mellitus, kidney damage due to drugs, Fabry's disease, aminoaciduria, Fanconi syndrome, hypertensive nephrosclerosis, interstitial nephritis, acute interstitial nephritis, Sickle cell disease, hemoglobinuria, myoglobinuria, Wegener's Granulomatosis, Glycogen Storage Disease Type 1, chronic kidney disease, chronic renal failure, low Glomerular Filtration Rate (GFR), nephroangiosclerosis, lupus nephritis, ANCA-positive pauci-immune crescentic glomerulonephritis, chronic allograft nephropathy, nephrotoxicity, renal toxicity, kidney necrosis, kidney damage, glomerular and tubular injury, kidney dysfunction, nephritic syndrome, acute renal failure, chronic renal failure, proximal tubal dysfunction, acute kidney transplant rejection, chronic kidney transplant rejection, non-IgA mesangioproliferative glomerulonephritis, postinfectious glomerulonephritis, vasculitides with renal involvement of any kind, any hereditary renal disease, any interstitial nephritis, renal transplant failure, kidney cancer, kidney disease associated with other conditions (e.g., hypertension, diabetes, and autoimmune disease), Dent's disease, nephrocytinosis, Heymann nephritis, a primary kidney disease, a collapsing glomerulopathy, a dense deposit disease, a cryoglobulinemia-associated glomerulonephritis, an Henoch-Schonlein disease, a postinfectious glomerulonephritis, a bacterial endocarditis, a microscopic polyangitis, a Churg-Strauss syndrome, an anti-GBM-antibody mediated glomerulonephritis, amyloidosis, a monoclonal immunoglobulin deposition disease, a fibrillary glomerulonephritis, an immunotactoid glomerulopathy, ischemic tubular injury, a medication-induced tubulo-interstitial nephritis, a toxic tubulo-interstitial nephritis, an infectious tubulo-interstitial nephritis, a bacterial pyelonephritis, a viral infectious tubulo-interstitial nephritis which results from a polyomavirus infection or an HIV infection, a metabolic-induced tubulo-interstitial disease, a mixed connective disease, a cast nephropathy, a crystal nephropathy which may results from urate or oxalate or drug-induced crystal deposition, an acute cellular tubulo-interstitial allograft rejection, a tumoral infiltrative disease which results from a lymphoma or a post-transplant lymphoproliferative disease, an obstructive disease of the kidney, vascular disease, a thrombotic microangiopathy, a nephroangiosclerosis, an atheroembolic disease, a mixed connective tissue disease, a polyarteritis nodosa, a calcineurin-inhibitor induced-vascular disease, an acute cellular vascular allograft rejection, an acute humoral allograft rejection, early renal function decline (ERFD), end stage renal disease (ESRD), renal vein thrombosis, acute tubular necrosis, acute interstitial nephritis, established chronic kidney disease, renal artery stenosis, ischemic nephropathy, uremia, drug and toxin-induced chronic tubulointerstitial nephritis, reflux nephropathy, kidney stones, Goodpasture's syndrome, normocytic normochromic anemia, renal anemia, diabetic chronic kidney disease, IgG4-related disease, von Hippel-Lindau syndrome, tuberous sclerosis, nephronophthisis, medullary cystic kidney disease, renal cell carcinoma, adenocarcinoma, nephroblastoma, lymphoma, leukemia, hyposialylation disorder, chronic cyclosporine nephropathy, renal reperfusion injury, renal dysplasia, azotemia, bilateral arterial occlusion, acute uric acid nephropathy, hypovolemia, acute bilateral obstructive uropathy, hypercalcemic nephropathy, hemolytic uremic syndrome, acute urinary retention, malignant nephrosclerosis, postpartum glomerulosclerosis, scleroderma, non-Goodpasture's anti-GBM disease, microscopic polyarteritis nodosa, allergic granulomatosis, acute radiation nephritis, post-streptococcal glomerulonephritis, Waldenstrom's macroglobulinemia, analgesic nephropathy, arteriovenous fistula, arteriovenous graft, dialysis, ectopic kidney, medullary sponge kidney, renal osteodystrophy, solitary kidney, hydronephrosis, microalbuminuria, uremia, haematuria, hyperlipidemia, hypoalbuminaemia, lipiduria, acidosis, edma, tubulointerstitial renal fibrosis, hypertensive sclerosis, juxtaglomerular cell tumor, Fraser syndrome, Horseshoe kidney, renal tubular dysgenesis, hypokalemia, hypomagnesemia, hypercalcemia, hypophosphatemia, uromodulin-associated kidney disease, Nail-patella syndrome, lithium nephrotoxicity, TNF-alpha nephrotoxicity, honeybee resin related renal failure, sugarcane harvesting acute renal failure, complete LCAT deficiency, Fraley syndrome, Page kidney, reflux nephropathy, Bardet-Biedl syndrome, collagenofibrotic glomerulopathy, Dent disease, Denys-Drash syndrome, congenital nephrotic syndrome, immunotactoid glomerulopathy, fibronextin glomerulopathy, Galloway Mowat syndrome, lipoprotein glomerulopathy, MesoAmerican nephropathy, beta-thalassemia renal disease, haemolytic uraemic syndrome, Henoch-Schonlein-Purpura disease, retroperitoneal fibrosis, polyarteritis nodose, cardiorenal syndrome, medullary kidney disease, renal artery stenosis, uromodulin kidney disease, and hyperkalemia.

In some embodiments, any of the multispecific binders of TGFβ-superfamily ligands disclosed herein (e.g. an ActRIIA:TβRII heteromultimer) of the present disclosure may be used to treat chronic kidney disease, optionally in combination with one or more supportive therapies for treating chronic kidney disease. Chronic kidney disease (CKD), also known as chronic renal disease, is a progressive loss in renal function over a period of months or years. The symptoms of worsening kidney function may include feeling generally unwell and experiencing a reduced appetite. Often, chronic kidney disease is diagnosed as a result of screening of people known to be at risk of kidney problems, such as those with high blood pressure or diabetes and those with a blood relative with CKD. This disease may also be identified when it leads to one of its recognized complications, such as cardiovascular disease, anemia, or pericarditis. Recent professional guidelines classify the severity of CKD in five stages, with stage 1 being the mildest and usually causing few symptoms and stage 5 being a severe illness with poor life expectancy if untreated. Stage 5 CKD is often called end-stage kidney disease, end-stage renal disease, or end-stage kidney failure, and is largely synonymous with the now outdated terms chronic renal failure or chronic kidney failure; and usually means the patient requires renal replacement therapy, which may involve a form of dialysis, but ideally constitutes a kidney transplant. CKD is initially without specific symptoms and is generally only detected as an increase in serum creatinine or protein in the urine. As the kidney function decreases, various symptoms may manifest as described below. Blood pressure may be increased due to fluid overload and production of vasoactive hormones created by the kidney via the renin-angiotensin system, increasing one's risk of developing hypertension and/or suffering from congestive heart failure. Urea may accumulate, leading to azotemia and ultimately uremia (symptoms ranging from lethargy to pericarditis and encephalopathy). Due to its high systemic circulation, urea is excreted in eccrine sweat at high concentrations and crystallizes on skin as the sweat evaporates ("uremic frost"). Potassium may accumulate in the blood (hyperkalemia with a range of symptoms including malaise and potentially fatal cardiac arrhythmias). Hyperkalemia usually does not develop until the glomerular filtration rate falls to less than 20-25 ml/min/1.73 m$^2$, at which point the kidneys have decreased ability to excrete potassium. Hyperkalemia in CKD can be exacerbated by acidemia (which leads to extracellular shift of potassium) and from lack of insulin. Erythropoietin synthesis may be decreased causing anemia. Fluid volume overload symptoms may occur, ranging from mild edema to life-threatening pulmonary edema. Hyperphosphatemia, due to reduced phosphate excretion, may occur generally following the decrease in glomerular filtration. Hyperphosphatemia is associated with increased cardiovascular risk, being a direct stimulus to vascular calcification. Hypocalcemia may manifest, which is generally caused by stimulation of fibroblast growth factor-23. Osteocytes are responsible for the increased production of FGF23, which is a potent inhibitor of the enzyme 1-alpha-hydroxylase (responsible for the conversion of 25-hydroxycholecalciferol into 1,25-dihydroxyvitamin D3). Later, this progresses to secondary hyperparathyroidism, renal osteodystrophy, and vascular calcification that further impairs cardiac function. Metabolic acidosis (due to accumulation of sulfates, phosphates, uric acid etc.) may occur and cause altered enzyme activity by excess acid acting on enzymes; and also increased excitability of cardiac and neuronal membranes by the promotion of hyperkalemia due to excess acid (acidemia). Acidosis is also due to decreased capacity to generate enough ammonia from the cells of the proximal tubule. Iron deficiency anemia, which increases in prevalence as kidney function decreases, is especially prevalent in those requiring haemodialysis. It is multifactoral in cause, but includes increased inflammation, reduction in erythropoietin, and hyperuricemia leading to bone marrow suppression. People with CKD suffer from accelerated atherosclerosis and are more likely to develop cardiovascular disease than the general population. Patients afflicted with CKD and cardiovascular disease tend to have significantly worse prognoses than those suffering only from the latter.

In certain embodiments, any of the multispecific binders of TGFβ-superfamily ligands disclosed herein (e.g. a multispecific binder comprising: i) a TβRII portion and ii) either a follistatin or follistatin-like polypeptide portion or an anti-GDF8 antibody or antigen-binding portion) may be used as part of a treatment for a muscular disorder. In some embodiments, the muscular disorder is associated with muscle wasting or muscle loss. In some embodiments, the muscular disorder is associated with muscle fibrosis. In some embodiments, the muscular disorder is associated with both muscle wasting/loss and muscle fibrosis. In some embodiments, any of the multispecific binders disclosed herein treats both the muscle wasting/loss and the muscle fibrosis in the subject.

In certain embodiments, any of the multispecific binders of TGFβ-superfamily ligands disclosed herein (e.g. a multispecific binder comprising: i) a TβRII portion and ii) either a follistatin or follistatin-like polypeptide portion or an anti-GDF8 antibody or antigen-binding portion) may be used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject TGF-beta superfamily heteromultimer complexes include: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSH or FSHD) (also known as Landouzy-Dejerine), myotonic dystrophy (MMD; also known as Steinert's Disease), oculopharyngeal muscular dystrophy (OPMD), distal muscular dystrophy (DD), congenital muscular dystrophy (CMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is defective. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

In DMD patients, muscle becomes injured, therefore muscle attempts to regenerate and recover. Muscle has the ability to regenerate after injury. Two processes are involved in skeletal muscle regeneration: myolysis and muscle reconstruction. Myolysis involves the degradation of muscle fibers followed by infiltration of inflammatory cells to the injury site. The muscle reconstruction involves the activation of muscle stem cells and satellite cells, to proliferate and to differentiate into myoblasts to form myofibers. Differentiating myoblasts synthesize extracellular matrix (ECM) with the goal to reconstruct the proper muscle, however, muscle regeneration often results in accumulation of ECM that develops into fibrosis (Delaney, K., et al., 2017, Cell Biology International, 41(7), 706-715.). TGFβ signaling has been found to negatively regulate skeletal muscle and muscle mass development. During embryonic development, TGFβ1 is expressed during myogenesis, and is correlated with the fiber-type composition of the surrounding myotubes (McLennan, 1993, Developmental Dynamics, 197(4):281-290). In mature adult muscle, TGFβ has been shown to negatively regulate skeletal muscle regeneration by inhibiting or influencing a dormant population of satellite cells, as well as decreasing myofiber fusion and expression of muscle-specific genes, such as MyoD and myogenin via the SMAD 3 signaling pathway (Allen, 1987, Journal of Cellular Physiology, 133(3):567-72; and Liu, 2001, Genes & Development, 15(22):2950-66). This inhibition can also lead to muscle atrophy (Narola, 2013, PLoS One, 8(11): E79356). In mouse models studying muscle loss and age, TGFβ1 and TGFβ3 have been found to be correlated with age related muscle loss. When TGFβ is suppressed there is improvement in muscle growth, implying that high levels of TGFβ contribute to muscle loss (Beggs, 2004, Aging Cell, 3(6):353-361). Upregulation of TGFβ superfamily signaling has been shown to play a key role in DMD pathology. Higher levels of TGFβ1, TGFβ type I and TGFβ type II receptors is associated with the severity of DMD phenotype in mdx mice (Zhou, 2006). In DMD patients, mRNA profiling studies using DMD muscle tissue from patients at various disease stages have shown increased levels of TGFβ-1 signaling (Chen, 2005). Another study also show that upregulated TGFβ1 expression in skeletal muscle of DMD patients correlates between fibrotic pathology and clinical severity (Song, 2017, Experimental and Therapeutic Medicine, 13(4):1209-1214). One characteristic in DMD pathology is connective tissue proliferation in muscles, which leads to irreversible tissue damage of tissue muscle organization in dystrophic muscles. This characteristic also correlates with the observation that TGFβ-1 upregulation triggers extracellular matrix formation (Bernasconi, 1995, Journal of Clinical Investigation, 96(2):1137-44). For example, TGFβ1 regulates the extracellular matrix by increasing fibroblasts production and specific extracellular matrix proteins, type I and III collagen (Gumucio, 2015, Exercise and Sport Sciences Reviews, 43(2):93-99). Moreover, TGFβ1 stimulates muscle derived stem cells (MDSC) to differentiate into myofibroblasts, which then causes extracellular matrix overproduction and inhibits matrix degradation, ultimately resulting in muscle fibrosis (Li, 2004). The expression of TGFβ1 in muscle cells in vitro and in vivo show that TGFβ1 stimulates fibrotic cascades (Li, 2004, American Journal of Pathology, 164(3):1007-1019; Serrano, 2010, Experimental Cell Research, 316(18):3050-3058). These studies all demonstrate the role of TGFβ-1 in DMD, especially in connective tissue proliferation that results in muscle fibrosis. More evidence supports the role of TGFβ in DMD pathology. Macrophage is the source to produce TGFβ1, which contributes to fibrosis by activating fibroblasts that produce collagen and other factors that create the extracellular matrix (Wynn, 2007, Journal of Pathology, 214(2):199-210). In DMD, inflammatory response is also prevalent with the recruitment of macrophages, T-cells, neutrophils, mast cells, and eosinophils. Although there is recruitment of various inflammatory cell populations, DMD models show an exceptionally high number of macrophages (Villalta, 2010, Human Molecular Genetics, 20(4):790-805). When depleting macrophages in mdx models, myopathy decreased; therefore macrophages may play a role in muscle pathology (Tidball, 2010, American Journal of Physiology-Regulatory Integrative and Comparative Physi, 298(5): R1173-R1187).

In some embodiments, any of the multispecific binders disclosed herein (e.g. a multispecific binder comprising: i) a TβRII portion and ii) either a follistatin or follistatin-like polypeptide portion or an anti-GDF8 antibody or antigen-binding portion) may be used to treat a disorder associated with both muscle wasting/muscle loss and muscle fibrosis. In some embodiments, the multispecific binder is capable of both increasing muscle mass and decreasing muscle fibrosis in a subject having a muscle disorder (e.g., DMD).

BMD results from different mutations in the dystrophin gene. BMD patients have some dystrophin, but it is either of insufficient quantity or poor quality. The presence of some dystrophin protects the muscles of patients with BMD from degenerating as severely or as quickly as those of patients with DMD.

Similarly, any of the multispecific binders of TGFβ-superfamily ligands disclosed herein (e.g. a multispecific binder comprising: i) a TβRII portion and ii) either a follistatin or follistatin-like polypeptide portion or an anti-GDF8 antibody or antigen-binding portion) may provide an effective means to increase muscle mass in other disease conditions that are in need of muscle growth. For example, amyotrophic lateral sclerosis (ALS), also called Lou Gehrig's disease or motor neuron disease, is a chronic, progressive, and incurable CNS disorder that attacks motor neurons, which are components of the central nervous system required for initiation of skeletal muscle contraction. In ALS, motor neurons deteriorate and eventually die, and though a person's brain normally remains fully functioning and alert, initiation of muscle contraction is blocked at the spinal level. Individuals who develop ALS are typically between 40 and 70 years old, and the first motor neurons to degenerate are those innervating the arms or legs. Patients with ALS may have trouble walking, may drop things, fall, slur their speech, and laugh or cry uncontrollably. As the disease progresses, muscles in the limbs begin to atrophy from disuse. Muscle weakness becomes debilitating, and patients eventually require a wheel chair or become confined to bed. Most ALS patients die from respiratory failure or from complications of ventilator assistance like pneumonia 3-5 years from disease onset.

In another embodiment, any of the multispecific binders of TGFβ-superfamily ligands disclosed herein (e.g. an ActRIIA:TβRII heteromultimer) of the disclosure may be used in patients with chronic kidney disease mineral bone disorder (CKD-MBD), a broad syndrome of interrelated skeletal, cardiovascular, and mineral-metabolic disorders arising from kidney disease. CKD-MBD encompasses various skeletal pathologies often referred to as renal osteodystrophy (ROD), which is a preferred embodiment for treatment with, an activin and/or GDF antagonist, or combinations of such antagonists. Depending on the relative contribution of different pathogenic factors, ROD is manifested as diverse pathologic patterns of bone remodeling (Hruska et al., 2008, Chronic kidney disease mineral bone disorder (CKD-MBD); in Rosen et al. (ed) Primer on the Metabolic Bone Diseases and Disorders of Mineral Metabolism, 7th ed. American Society for Bone and Mineral Research, Washington D.C., pp 343-349). At one end of the spectrum is ROD with uremic osteodystrophy and low bone turnover, characterized by a low number of active remodeling sites, profoundly suppressed bone formation, and low bone resorption. At the other extreme is ROD with hyperparathyroidism, high bone turnover, and osteitis fibrosa. Given that any of the multispecific binders of TGFβ-superfamily ligands disclosed herein (e.g. an ActRIIA:TβRII heteromultimer) may exert both anabolic and antiresorptive effects, these agents may be useful in patients across the ROD pathology spectrum.

In some embodiments, the present disclosure relates to methods of increasing red blood cell levels in a patient comprising administering to a patient in need thereof (e.g., for treating anemia or disease or condition associated with anemia) an effective amount of any of the multispecific binders of TGFβ-superfamily ligands disclosed herein (e.g. an ActRIIA:TβRII heteromultimer). For example, in some embodiments, the disclosure relates to methods of preventing or reducing the severity or progression rate of one or more complications of anemia. Optionally, methods disclosed herein for treating anemia or disease or condition associated with anemia may further comprise administering to the patient one or more supportive therapies or additional active agents for treating anemia or disease or condition associated with anemia.

In some embodiments, any of the multispecific binders of TGFβ-superfamily ligands disclosed herein (e.g. an ActRIIA:TβRII heteromultimer) of the disclosure may be used to increase red blood cell, hemoglobin or reticulocyte levels in healthy individuals, and such multispecific binders may be used in selected patient populations. Examples of appropriate patient populations include those with undesirably low red blood cell or hemoglobin levels, such as patients having an anemia, and those that are at risk for developing undesirably low red blood cell or hemoglobin levels, such as those patients that are about to undergo major surgery or other procedures that may result in substantial blood loss. In one embodiment, a patient with adequate red blood cell levels is treated with any of the multispecific binders of TGFβ-superfamily ligands disclosed herein (e.g. an ActRIIA:TβRII heteromultimer) to increase red blood cell levels, and then blood is drawn and stored for later use in transfusions.

In some embodiments, any of the multispecific binders of TGFβ-superfamily ligands disclosed herein (e.g. an ActRIIA:TβRII heteromultimer) may be used to increase red blood cell levels in patients having an anemia. When observing hemoglobin levels in humans, a level of less than normal for the appropriate age and gender category may be indicative of anemia, although individual variations are taken into account. For example, a hemoglobin level of 12 g/dl is generally considered the lower limit of normal in the general adult population. Potential causes include blood-loss, nutritional deficits, medication reaction, various problems with the bone marrow and many diseases. More particularly, anemia has been associated with a variety of disorders that include, for example, chronic renal failure, myelodysplastic syndrome, rheumatoid arthritis, bone marrow transplantation. Anemia may also be associated with the following conditions: solid tumors (e.g. breast cancer, lung cancer, colon cancer); tumors of the lymphatic system (e.g. chronic lymphocyte leukemia, non-Hodgkins and Hodgkins lymphomas); tumors of the hematopoietic system (e.g. leukemia, myelodysplastic syndrome, multiple myeloma); radiation therapy; chemotherapy (e.g. platinum containing regimens); inflammatory and autoimmune diseases, including, but not limited to, rheumatoid arthritis, other inflammatory arthritides, systemic lupus erythematosis (SLE), acute or chronic skin diseases (e.g. psoriasis), inflammatory bowel disease (e.g. Crohn's disease and ulcerative colitis); acute or chronic renal disease or failure including idiopathic or congenital conditions; acute or chronic liver disease; acute or chronic bleeding; situations where transfusion of red blood cells is not possible due to patient allo- or auto-antibodies and/or for religious reasons (e.g. some Jehovah's Witnesses); infections (e.g. malaria, osteomyelitis); hemoglobinopathies, including, for example, sickle cell disease, thalassemias; drug use or abuse, e.g. alcohol misuse; pediatric patients with anemia from any cause to avoid transfusion; and elderly patients or patients with underlying cardiopulmonary disease with anemia who cannot receive transfusions due to concerns about circulatory overload.

In some embodiments, any of the multispecific binders of TGFβ-superfamily ligands disclosed herein (e.g. an ActRIIA:TβRII heteromultimer) of the disclosure may be used for treating ineffective erythropoiesis. Originally distinguished from aplastic anemia, hemorrhage, or peripheral hemolysis on the basis of ferrokinetic studies (Ricketts et al., 1978, Clin Nucl Med 3:159-164), ineffective erythropoiesis describes a diverse group of anemias in which production of mature RBCs is less than would be expected given the number of erythroid precursors (erythroblasts) present in the bone marrow (Tanno et al., 2010, Adv Hematol 2010: 358283). In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis (Aizawa et al, 2003, Am J Hematol 74:68-72), erythroblast-induced bone pathology (Di Matteo et al, 2008, J Biol Regul Homeost Agents 22:211-216), and tissue iron overload, even in the absence of therapeutic RBC transfusions (Pippard et al, 1979, Lancet 2:819-821). Thus, by boosting erythropoietic effectiveness, an ActRIIA:TβRII heteromultimer may break the aforementioned cycle and may alleviate not only the underlying anemia but also the associated complications of elevated erythropoietin levels, splenomegaly, bone pathology, and tissue iron overload. In some embodiments, an ActRIIA:TβRII heteromultimers of the disclosure may be used to treat ineffective erythropoiesis, including anemia and elevated EPO levels, as well as complications such as splenomegaly, erythroblast-induced bone pathology, and iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors (Musallam et al., 2012, Cold Spring Harb Perspect Med 2:a013482). With erythroblast-induced bone pathology, attendant pathologies include low bone mineral density, osteoporosis, and bone pain (Haidar et al., 2011, Bone 48:425-432). With iron overload, attendant pathologies include hepcidin suppression and hyperabsorption of dietary iron (Musallam et al., 2012, Blood Rev 26(Suppl 1):516-519), multiple endocrinopathies and liver fibrosis/cirrhosis (Galanello et al., 2010, Orphanet J Rare Dis 5:11), and iron-overload cardiomyopathy (Lekawanvijit et al., 2009, Can J Cardiol 25:213-218).

In some embodiments, any of the multispecific binders of TGFβ-superfamily ligands disclosed herein (e.g. an ActRIIA:TβRII heteromultimer) of the disclosure may be used for treating thalassemia. The most common causes of ineffective erythropoiesis are the thalassemia syndromes, hereditary hemoglobinopathies in which imbalances in the production of intact alpha- and beta-hemoglobin chains lead to increased apoptosis during erythroblast maturation (Schrier, 2002, Curr Opin Hematol 9:123-126). Thalassemias are collectively among the most frequent genetic disorders worldwide, with changing epidemiologic patterns predicted to contribute to a growing public health problem in both the U.S. and globally (Vichinsky, 2005, Ann NY Acad Sci 1054:18-24). Thalassemia syndromes are named according to their severity. Thus, a-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia (Rund et al, 2005, N Engl J Med 353:1135-1146).

In some embodiments, any of the multispecific binders of TGFβ-superfamily ligands disclosed herein (e.g. an ActRIIA:TβRII heteromultimer) can be used for treating diseases of ineffective erythropoiesis other than thalassemia syndromes. Such disorders include siderblastic anemia (inherited or acquired); dyserythropoietic anemia (Types I and II); sickle cell anemia (sickle cell disease); hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anema, refractory megaloblastic anemia, or erythroleukemia); myelophthisic anemias, including myelofibrosis (myeloid metaplasia) and myelophthisis; congenital erythropoietic porphyria; and lead poisoning.

In some embodiments, any of the multispecific binders of TGFβ-superfamily ligands disclosed herein (e.g. an ActRIIA:TβRII heteromultimer) may be used for treating myelodysplastic syndrome (MDS). MDS is a diverse collection of hematological conditions characterized by ineffective production of myeloid blood cells and risk of transformation to acute mylogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effect due to frequency of such therapies. For example, patients who receive frequent red blood cell transfusion can have tissue and organ damage from the buildup of extra iron. In some embodiments, patient suffering from MDS may be treated using a combination of an ActRIIA:TβRII heteromultimer and one or more additional therapeutic agents for treating MDS including, for example, thalidomide, lenalidomide, azacitadine, decitabine, erythropoietins, deferoxamine, antihymocyte globulin, filgrastrim (G-CSF) and an erythropoietin signaling pathway agonist.

In some embodiments, any of the multispecific binders of TGFβ-superfamily ligands disclosed herein (e.g. an ActRIIA:TβRII heteromultimer) may be used for treating anemias of hypoproliferative bone marrow, which are typically associated with little change in red blood cell (RBC) morphology. Hypoproliferative anemias include: 1) anemia of chronic disease, 2) anemia of kidney disease, and 3) anemia associated with hypometabolic states. In each of these types, endogenous erythropoietin levels are inappropriately low for the degree of anemia observed. Other hypoproliferative anemias include: 4) early-stage iron-deficient anemia, and 5) anemia caused by damage to the bone marrow. In these types, endogenous erythropoietin levels are appropriately elevated for the degree of anemia observed.

In some embodiments, any of the multispecific binders of TGFβ-superfamily ligands disclosed herein (e.g. an ActRIIA:TβRII heteromultimer) may be used to treat anemia associated with chronic disease. The most common type is anemia of chronic disease, which encompasses inflammation, infection, tissue injury, and conditions such as cancer, and is distinguished by both low erythropoietin levels and an inadequate response to erythropoietin in the bone marrow (Adamson, 2008, Harrison's Principles of Internal Medicine, 17th ed.; McGraw Hill, New York, pp 628-634). Many factors can contribute to cancer-related anemia. Some are associated with the disease process itself and the generation of inflamatory cytokines such as interleukin-1, interferon-gamma, and tumor necrosis factor (Bron et al., 2001, Semin Oncol 28(Suppl 8):1-6). Among its effects, inflammation induces the key iron-regulatory peptide hepcidin, thereby inhibiting iron export from macrophages and generally limiting iron availability for erythropoiesis (Ganz, 2007, J Am Soc Nephrol 18:394-400). Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality.

Chronic kidney disease is associated with hypoproliferative anemia that varies in severity Many conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. Mild-to-moderate anemia can also occur with reduced dietary intake of protein, a condition particularly prevalent in the elderly. Finally, anemia can develop in patients with chronic liver disease arising from nearly any cause (Adamson, 2008, Harrison's Principles of Internal Medicine, 17th ed.; McGraw Hill, New York, pp 628-634).

In some embodiments, any of the multispecific binders of TGFβ-superfamily ligands disclosed herein (e.g. an ActRIIA:TβRII heteromultimer) may be used to treat anemia resulting from acute blood loss. Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency.

In some embodiments, any of the multispecific binders of TGFβ-superfamily ligands disclosed herein (e.g. an ActRIIA:TβRII heteromultimer) may be used to treat iron-deficiency anemias. Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs (Adamson, 2008, Harrison's Principles of Internal Medicine, 17th ed.; McGraw Hill, New York, pp 628-634). Appropriate therapy for iron-deficiency anemia depends on its cause and severity, with oral iron preparations, parenteral iron formulations, and RBC transfusion as major conventional options.

In some embodiments, any of the multispecific binders of TGFβ-superfamily ligands disclosed herein (e.g. an ActRIIA:TβRII heteromultimer) may be used to treat hypoproliferative anemia. Hypoproliferative anemias can result from primary dysfunction or failure of the bone marrow, instead of dysfunction secondary to inflammation, infection, or cancer progression. Prominent examples would be myelosuppression caused by cancer chemotherapeutic drugs or cancer radiation therapy. A broad review of clinical trials found that mild anemia can occur in 100% of patients after chemotherapy, while more severe anemia can occur in up to 80% of such patients (Groopman et al., 1999, J Natl Cancer Inst 91:1616-1634). Myelosuppressive drugs include: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide).

In some embodiments, any of the multispecific binders of TGFβ-superfamily ligands disclosed herein (e.g. an ActRIIA:TβRII heteromultimer) may be used for treating anemias of disordered RBC maturation, which are characterized in part by undersized (microcytic), oversized (macrocytic), misshapen, or abnormally colored (hypochromic) RBCs.

In some embodiments, any of the multispecific binders of TGFβ-superfamily ligands disclosed herein (e.g. an ActRIIA:TβRII heteromultimer) may be used in combination with supportive therapies for treating anemia or diseases associated with anemia. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with anemia, particularly ineffective erythropoiesis, also include treatment with one or more iron-chelating molecules to promote iron excretion in the urine and/or stool and thereby prevent, or reverse, tissue iron overload (Hershko, 2006, Haematologica 91:1307-1312; Cao et al, 2011, Pediatr Rep 3(2):e17). Effective iron-chelating agents must be able to selectively bind and neutralize ferric iron, the oxidized form of non-transferrin bound iron which likely accounts for most iron toxicity through catalytic production of hydroxyl radicals and oxidation products (Esposito et al, 2003, Blood 102:2670-2677). These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) (Kalinowski et al, 2005, Pharmacol Rev 57:547-583). Effective iron-chelating agents also are relatively low molecular weight (less than 700 daltons), with solubility in both water and lipid to enable access to affected tissues. Specific examples of iron-chelating molecules are deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone (Cao et al, 2011, Pediatr Rep 3(2):e17; Galanello et al, 2010, Ann NY Acad Sci 1202:79-86).

In certain embodiments, any of the multispecific binders of TGFβ-superfamily ligands disclosed herein (e.g. an ActRIIA:TβRII heteromultimer) may be used in combination with hepcidin agonists for treating anemia, particularly anemias associated with ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis (Nemeth, 2010, Adv Hematol 2010:750643). This view is supported by beneficial effects of increased hepcidin expression in a mouse model of β-thalassemia (Gardenghi et al, 2010, J Clin Invest 120:4466-4477).

In some embodiments, any of the multispecific binders of TGFβ-superfamily ligands disclosed herein (e.g. an ActRIIA:TβRII heteromultimer) of the disclosure may be used in combination with EPO receptor activators to achieve an increase in red blood cells at lower dose ranges. This may be beneficial in reducing the known off-target effects and risks associated with high doses of EPO receptor activators. In certain embodiments, the present invention provides methods of treating or preventing anemia in an individual in need thereof by administering to the individual a therapeutically effective amount of any of the multispecific binders of TGFβ-superfamily ligands disclosed herein (e.g. an ActRIIA:TβRII heteromultimer) or a combination (or concomitant therapy) of the multispecific binder and a EPO receptor activator.

Any of the multispecific binders of TGFβ-superfamily ligands disclosed herein (e.g. an ActRIIA:TβRII heteromultimer) may be used in combination with EPO receptor activators to reduce the required dose of these activators in patients that are susceptible to adverse effects of EPO. The primary adverse effects of EPO are an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which related to hypertension, are headaches, influenza-like syndrome, obstruction of shunts, myocardial infarctions and cerebral convulsions due to thrombosis, hypertensive encephalopathy, and red cell blood cell applasia (Singibarti, (1994) J. Clin Investig 72(suppl 6), S36-S43; Horl et al. (2000) Nephrol Dial Transplant 15(suppl 4), 51-56; Delanty et al. (1997) Neurology 49, 686-689; Bunn (2002) N Engl J Med 346(7), 522-523).

In some embodiments, patients may be treated with a multispecific binder dosing regimen intended to restore the patient to a target hemoglobin level, usually between about 10 g/dl and about 12.5 g/dl, and typically about 11.0 g/dl (see also Jacobs et al. (2000) Nephrol Dial Transplant 15, 15-19), although lower target levels may cause fewer cardiovascular side effects. Alternatively, hematocrit levels (percentage of the volume of a blood sample occupied by the cells) can be used as a measure for the condition of red blood cells. Hematocrit levels for healthy individuals range from 41 to 51% for adult males and from 35 to 45% for adult females. Target hematocrit levels are usually around 30-33%. Moreover, hemoglobin/hematocrit levels vary from person to person. Thus, optimally, the target hemoglobin/hematocrit level can be individualized for each patient.

In certain embodiments, the present invention provides methods for managing a patient that has been treated with, or is a candidate to be treated with, any of the multispecific binders of TGFβ-superfamily ligands disclosed herein (e.g. an ActRIIA:TβRII heteromultimer) by measuring one or more hematologic parameters in the patient. The hematologic parameters may be used to evaluate appropriate dosing for a patient who is a candidate to be treated with any of the multispecific binders of TGFβ-superfamily ligands disclosed herein (e.g. an ActRIIA:TβRII heteromultimer), to monitor the hematologic parameters during treatment with any of the multispecific binders of TGFβ-superfamily ligands disclosed herein (e.g. an ActRIIA:TβRII heteromultimer), to evaluate whether to adjust the dosage during treatment with any of the multispecific binders of TGFβ-superfamily ligands disclosed herein (e.g. an ActRIIA:TβRII heteromultimer), and/or to evaluate an appropriate maintenance dose of an ActRIIA:TβRII heteromultimer. If one or more of the hematologic parameters are outside the normal level, dosing with any of the multispecific binders of TGFβ-superfamily ligands disclosed herein (e.g. an ActRIIA:TβRII heteromultimer) may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range, or on the high side of normal, in a patient who is a candidate to be treated with any of the multispecific binders of TGFβ-superfamily ligands disclosed herein (e.g. an ActRIIA:TβRII heteromultimer) then onset of administration of the multispecific binder may be delayed until the hematologic parameters have returned to a normal or acceptable level either naturally or via therapeutic intervention. For example, if a candidate patient is hypertensive or prehypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of any of the multispecific binders of TGFβ-superfamily ligands disclosed herein (e.g. an ActRIIA:TβRII heteromultimer) may be delayed until the levels have returned to a normal or acceptable level.

In certain embodiments, if one or more hematologic parameters are outside the normal range, or on the high side of normal, in a patient who is a candidate to be treated with any of the multispecific binders of TGFβ-superfamily ligands disclosed herein (e.g. an ActRIIA:TβRII heteromultimer) then the onset of administration may be not be delayed. However, the dosage amount or frequency of dosing of the multispecific binder may be set at an amount that would reduce the risk of an unacceptable increase in the hematologic parameters arising upon administration of the ActRIIA:TβRII heteromultimer. Alternatively, a therapeutic regimen may be developed for the patient that combines any of the multispecific binders of TGFβ-superfamily ligands disclosed herein (e.g. an ActRIIA:TβRII heteromultimer) with a therapeutic agent that addresses the undesirable level of the hematologic parameter. For example, if the patient has elevated blood pressure, then a therapeutic regimen involving administration of any of the multispecific binders of TGFβ-superfamily ligands disclosed herein (e.g. an ActRIIA:TβRII heteromultimer) and a blood pressure lowering agent may be designed. For a patient having lower than desired iron stores, a therapeutic regimen of any of the multispecific binders of TGFβ-superfamily ligands disclosed herein (e.g. an ActRIIA:TβRII heteromultimer) and iron supplementation may be developed.

In one embodiment, baseline parameter(s) for one or more hematologic parameters may be established for a patient who is a candidate to be treated with any of the multispecific binders of TGFβ-superfamily ligands disclosed herein (e.g. an ActRIIA:TβRII heteromultimer) and an appropriate dosing regimen establish for that patient based on the baseline value(s). Alternatively, established baseline parameters based on a patient's medical history could be used to inform an appropriate multispecific binder dosing regimen for a patient. For example, if a healthy patient has an established baseline blood pressure reading that is above the defined normal range it may not be necessary to bring the patient's blood pressure into the range that is considered normal for the general population prior to treatment with the multispecific binder. A patient's baseline values for one or more hematologic parameters prior to treatment with any of the multispecific binders of TGFβ-superfamily ligands disclosed herein (e.g. an ActRIIA:TβRII heteromultimer) may also be used as the relevant comparative values for monitoring any changes to the hematologic parameters during treatment with the multispecific binder.

In certain embodiments, one or more hematologic parameters are measured in patients who are being treated with any of the multispecific binders of TGFβ-superfamily ligands disclosed herein (e.g. an ActRIIA:TβRII heteromultimer). The hematologic parameters may be used to monitor the patient during treatment and permit adjustment or termination of the dosing with the multispecific binder or additional dosing with another therapeutic agent. For example, if administration of the multispecific binder results in an increase in blood pressure, red blood cell level, or hemoglobin level, or a reduction in iron stores, then the dose of the multispecific binder may be reduced in amount or frequency in order to decrease the effects of the multispecific binder on the one or more hematologic parameters. If administration or a multispecific binder results in a change in one or more hematologic parameters that is adverse to the patient, then the dosing of the multispecific binder may be terminated either temporarily, until the hematologic parameter(s) return to an acceptable level, or permanently. Similarly, if one or more hematologic parameters are not brought within an acceptable range after reducing the dose or frequency of administration of the multispecific binder heteromultimer then the dosing may be terminated. As an alternative, or in addition to, reducing or terminating the dosing with the multispecific binder, the patient may be dosed with an additional therapeutic agent that addresses the undesirable level in the hematologic parameter(s), such as, for example, a blood pressure lowering agent or an iron supplement. For example, if a patient being treated with a multispecific binder has elevated blood pressure, then dosing with the multispecific binder may continue at the same level and a blood pressure lowering agent is added to the treatment regimen, dosing with the multispecific binder may be reduce (e.g., in amount and/or frequency) and a blood pressure lowering agent is added to the treatment regimen, or dosing with the multispecific binder may be terminated.

6. Pharmaceutical Compositions

The therapeutic agents described herein (e.g., ActRIIA: TβRII heteromultimer) may be formulated into pharmaceutical compositions. Pharmaceutical compositions for use in accordance with the present disclosure may be formulated in conventional manner using one or more physiologically acceptable carriers or excipients. Such formulations will generally be substantially pyrogen-free, in compliance with most regulatory requirements.

In certain embodiments, the therapeutic method of the disclosure includes administering the composition systemically, or locally as an implant or device. When administered, the therapeutic composition for use in this disclosure is in a pyrogen-free, physiologically acceptable form. Therapeutically useful agents other than the multispecific binder which may also optionally be included in the composition as described above, may be administered simultaneously or sequentially with the subject compounds in the methods disclosed herein.

Typically, protein therapeutic agents disclosed herein will be administered parentally, and particularly intravenously or subcutaneously. Pharmaceutical compositions suitable for parenteral administration may comprise one or more of any of the multispecific binders of TGFβ-superfamily ligands disclosed herein (e.g. an ActRIIA:TβRII heteromultimer) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration Further, the composition may be encapsulated or injected in a form for delivery to a target tissue site. In certain embodiments, compositions of the present invention may include a matrix capable of delivering one or more therapeutic compounds (e.g., ActRIIA:TβRII heteromultimer) to a target tissue site, providing a structure for the developing tissue and optimally capable of being resorbed into the body. For example, the matrix may provide slow release of any of the multispecific binders of TGFβ-superfamily ligands disclosed herein (e.g. an ActRIIA:TβRII heteromultimer). Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above-mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRIIA:TβRII heteromultimer). The various factors include, but are not limited to, the patient's age, sex, and diet, the severity disease, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, the present invention also provides gene therapy for the in vivo production of any of the multispecific binders of TGFβ-superfamily ligands disclosed herein (e.g. an ActRIIA:TβRII heteromultimer). Such therapy would achieve its therapeutic effect by introduction of the multispecific binder polynucleotide sequences into cells or tissues having the disorders as listed above. Delivery of multispecific binder polynucleotide sequences can be achieved using a recombinant expression vector such as a chimeric virus or a colloidal dispersion system. Preferred for therapeutic delivery of multispecific binder polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the multispecific binder polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for multispecific binder polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

Exemplification

The invention now being generally described, it will be more readily understood by reference to the following examples, which are included merely for purposes of illustration of certain embodiments of the present invention, and are not intended to limit the invention.

Example 1. Generation of TβRII Receptor Fusion Protein Variants

TβRII ECD Variants

TβRII fusion proteins comprising a soluble extracellular portion of human TβRII and a human Fc portion were generated. For each fusion protein, a TβRII amino acid sequence having the amino acid sequence of SEQ ID NO: 18 was fused to an IgG Fc portion having the amino acid sequence of SEQ ID NO: 49 by means of one of several different linkers. Each of the fusion proteins also included a TPA leader sequence having the amino acid sequence of SEQ ID NU: L3 (below).

```
Tissue plasminogen activator (TPA):
                                          (SEQ ID NO: 23)
MDAMKRGLCCVLLLCGAVFVSP
```

Figure 3:
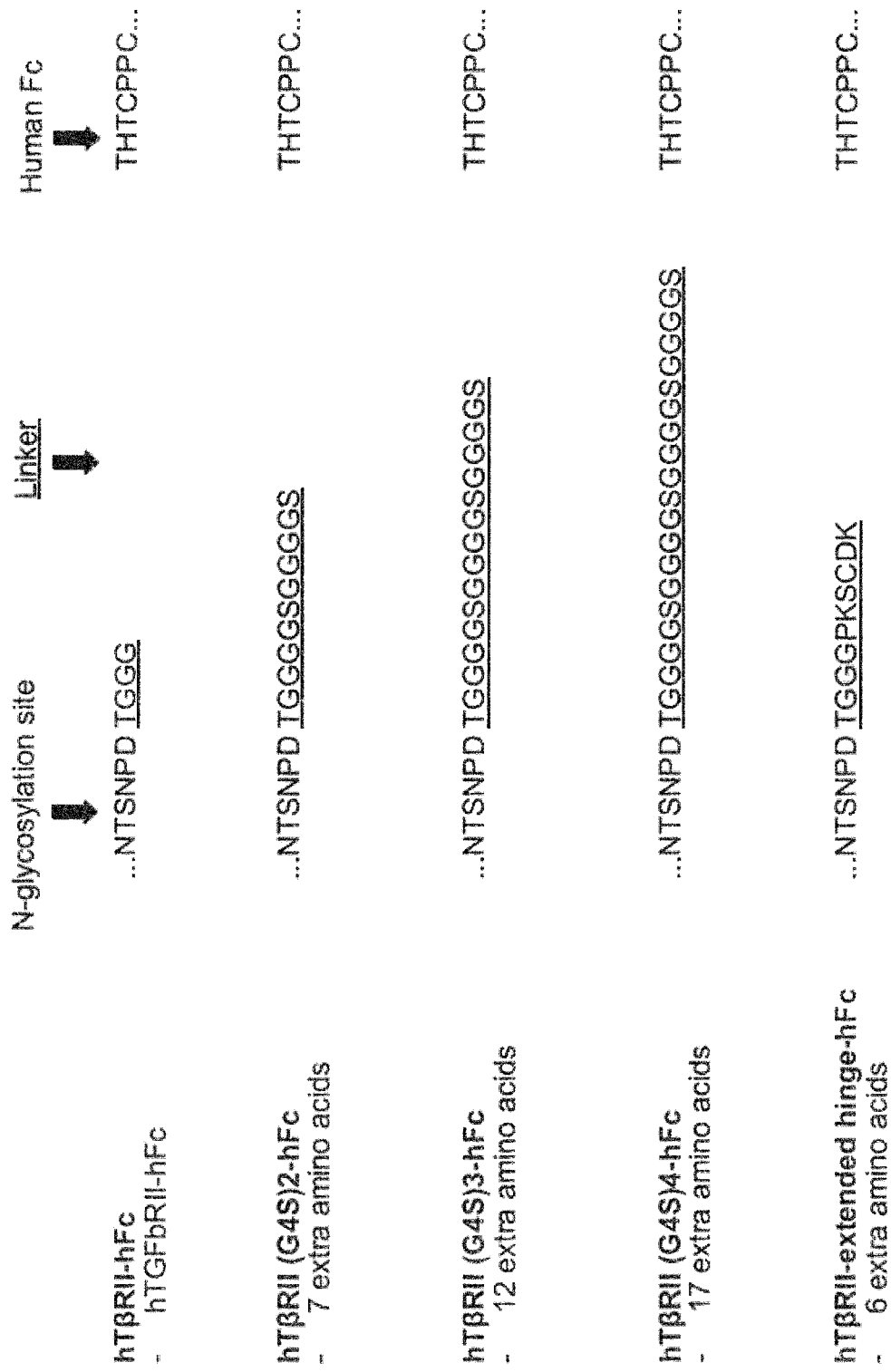
FIG. 3 shows a comparison of the linker sequences of five different TβRII constructs.

An illustration summary of several of the constructs designed is provided as FIG. 3. A table detailing the sequences for the different constructs tested in the Exemplification section is provided below:

| Construct Name | Construct Amino Acid Sequence | Linker Sequence |
|---|---|---|
| hTβRII-hFc | SEQ ID NO: 9 | TGGG (SEQ ID NO: 3) |
| hTβRII(G4S)2-hFc | SEQ ID NO: 15 | TGGGGSGGGGS (SEQ ID NO: 4) |
| hTβRII(G4S)3-hFc | SEQ ID NO: 11 | TGGGGSGGGGSGGGGS (SEQ ID NO: 5) |
| hTβRII(G4S)4-hFc | SEQ ID NO: 13 | TGGGGSGGGGSGGGGSGGGGS (SEQ ID NO: 6) |
| hTβRII extended hinge-hFc | SEQ ID NO: 17 | TGGGPKSCDK (SEQ ID NO: 7) |
| hTβRII(G4S)5-hFc | SEQ ID NO: 44 | TGGGGSGGGGSGGGGSGGGGSGGGGS (SEQ ID NO: 25) |
| hTβRII(G4S)6-hFc | SEQ ID NO: 45 | TGGGGSGGGGSGGGGSGGGGSGGGGSGGGGS (SEQ ID NO: 26) |

The amino acid sequences for the construct components and each of the constructs, along with the nucleic acid sequence used to express these constructs, are provided below.

TβRII Portion: Amino Acid Sequence (SEQ ID NO: 18)

```
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PD
```

FC Portion: Amino Acid Sequence (SEQ ID NO: 49)

```
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
``` hTβRII-hFc: Nucleic Acid Sequence (SEQ ID NO: 8)

```
  1 ATGGATGCAA TGAAGAGAGG GCTCTGCTGT GTGCTGCTGC TGTGTGGAGC

51 AGTCTTCGTT TCGCCCGGCG CCAGGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TCCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC
```

-continued

```
 501 TGATGAGTGC AATGACAACA TCATCTTCTC AGAAGAATAT AACACCAGCA
 551 ATCCTGACAC CGGTGGTGGA ACTCACACAT GCCCACCGTG CCCAGCACCT
 601 GAACTCCTGG GGGGACCGTC AGTCTTCCTC TTCCCCCCAA AACCCAAGGA
 651 CACCCTCATG ATCTCCCGGA CCCCTGAGGT CACATGCGTG GTGGTGGACG
 701 TGAGCCACGA AGACCCTGAG GTCAAGTTCA ACTGGTACGT GGACGGCGTG
 751 GAGGTGCATA ATGCCAAGAC AAAGCCGCGG GAGGAGCAGT ACAACAGCAC
 801 GTACCGTGTG GTCAGCGTCC TCACCGTCCT GCACCAGGAC TGGCTGAATG
 851 GCAAGGAGTA CAAGTGCAAG GTCTCCAACA AAGCCCTCCC AGCCCCCATC
 901 GAGAAAACCA TCTCCAAAGC CAAAGGGCAG CCCCGAGAAC CACAGGTGTA
 951 CACCCTGCCC CCATCCCGGG AGGAGATGAC CAAGAACCAG GTCAGCCTGA
1001 CCTGCCTGGT CAAAGGCTTC TATCCCAGCG ACATCGCCGT GGAGTGGGAG
1051 AGCAATGGGC AGCCGGAGAA CAACTACAAG ACCACGCCTC CCGTGCTGGA
1101 CTCCGACGGC TCCTTCTTCC TCTATAGCAA GCTCACCGTG GACAAGAGCA
1151 GGTGGCAGCA GGGGAACGTC TTCTCATGCT CCGTGATGCA TGAGGCTCTG
1201 CACAACCACT ACACGCAGAA GAGCCTCTCC CTGTCTCCGG GTAAATGA
``` hTβRII-hFc: Amino Acid Sequence
(SEQ ID NO: 9)

```
  1 MDAMKRGLCC VLLLCGAVFV SPGATIPPHV QKSDVEMEAQ KDEIICPSCN
 51 RTAHPLRHIN NDMIVTDNNG AVKFPQLCKF CDVRFSTCDN QKSCMSNCSI
101 TSICEKPQEV CVAVWRKNDE NITLETVCHD PKLPYHDFIL EDAASPKCIM
151 KEKKKPGETF FMCSCSSDEC NDNIIFSEEY NTSNPDTGGG THTCPPCPAP
201 ELLGGPSVFL FPPKPKDILM ISRTPEVTCV VVDVSHEDPE VKFNWYNDGV
251 EVHNAKTKPR EEQYNSTYRV VSVLTVLHQD WLNGKEYKCK VSNKALPAPI
301 EKTISKAKGQ PREPQVYTLP PSREEMTKNQ VSLTCLVKGF YPSDIAVEWE
351 SNGQPENNYK TTPPVLDSDG SFFLYSKLTV DKSRWQQGNV FSCSVMHEAL
401 HNHYTQKSLS LSPGK
``` hTβRII(G4S)3-hFC: Nucleic Acid Sequence
(SEQ ID NO: 10)

```
  1 ATGGATGCAA TGAAGAGAGG GCTCTGCTGT GTGCTGCTGC TGTGTGGAGC
 51 AGTCTTCGTT TCGCCCGGCG CCACGATCCC ACCGCACGTT CAGAAGTCGG
101 ATGTGGAAAT GGAGGCCCAG AAAGATGAAA TCATCTGCCC CAGCTGTAAT
151 AGGACTGCCC ATCCACTGAG ACATATTAAT AACGACATGA TAGTCACTGA
201 CAACAACGGT GCAGTCAAGT TTCCACAACT GTGTAAATTT TGTGATGTGA
251 GATTTTCCAC CTGTGACAAC CAGAAATCCT GCATGAGCAA CTGCAGCATC
301 ACCTCCATCT GTGAGAAGCC ACAGGAAGTC TGTGTGGCTG TATGGAGAAA
351 GAATGACGAG AACATAACAC TAGAGACAGT TTGCCATGAC CCCAAGCTCC
401 CCTACCATGA CTTTATTCTG GAAGATGCTG CTTCTCCAAA GTGCATTATG
451 AAGGAAAAAA AAAAGCCTGG TGAGACTTTC TTCATGTGTT CCTGTAGCTC
501 TGATGAGTGC AATGACAACA TCATCTTCTC AGAAGAATAT AACACCAGCA
551 ATCCTGACAC CGGTGGTGGA GGAAGTGGTG GAGGTGGTTC TGGAGGTGGT
601 GGAAGTACTC ACACATGCCC ACCGTGCCCA GCACCTGAAC TCCTGGGGGG
651 ACCGTCAGTC TTCCTCTTCC CCCCAAAACC CAAGGACACC CTCATGATCT
701 CCCGGACCCC TGAGGTCACA TGCGTGGTGG TGGACGTGAG CCACGAAGAC
```

-continued

```
 751 CCTGAGGTCA AGTTCAACTG GTACGTGGAC GGCGTGGAGG TGCATAATGC
 801 CAAGACAAAG CCGCGGGAGG AGCAGTACAA CAGCACGTAC CGTGTGGTCA
 851 GCGTCCTCAC CGTCCTGCAC CAGGACTGGC TGAATGGCAA GGAGTACAAG
 901 TGCAAGGTCT CCAACAAAGC CCTCCCAGCC CCCATCGAGA AAACCATCTC
 951 CAAAGCCAAA GGGCAGCCCC GAGAACCACA GGTGTACACC CTGCCCCCAT
1001 CCCGGGAGGA GATGACCAAG AACCAGGTCA GCCTGACCTG CCTGGTCAAA
1051 GGCTTCTATC CCAGCGACAT CGCCGTGGAG TGGGAGAGCA ATGGGCAGCC
1101 GGAGAACAAC TACAAGACCA CGCCTCCCGT GCTGGACTCC GACGGCTCCT
1151 TCTTCCTCTA TAGCAAGCTC ACCGTGGACA AGAGCAGGTG GCAGCAGGGG
1201 AACGTCTTCT CATGCTCCGT GATGCATGAG GCTCTGCACA ACCACTACAC
1251 GCAGAAGAGC CTCTCCCTGT CTCCGGGTAA ATGA
``` hTβRII(G4S)3-hFc: Amino Acid Sequence
(SEQ ID NO: 11)

```
  1 MDAMKRGLCC VLLLCGAVFV SPGATIPPHV QKSDVEMEAQ KDEIICPSCN
 51 RTAHPLRHIN NDMIVTDNNG AVKFPQICKF CDVRFSTCDN QKSCMSNCSI
101 TSICEKPQEV CVAVWRKNDE NITLETVCHD PKLPYHDFIL EDAASPKCIM
151 KEKKKPGETF FMCSCSSDEC NDNIIFSEEY NTSNPDTGGG GSGGGGSGGG
201 GSTHTCPPCP APELLGGPSV FLFPPKPKDT LMISRTPEVT CVVVDVSHED
251 PEVKFNWYVD GVEVHNAKTK PREEQYNSTY RVVSVLTVLH QDWLNGKEYK
301 CKVSNKALPA PIEKTISKAK GQPREPQVYT LPPSREEMTK NQVSLTCLVK
351 GFYPSDIAVE WESNGQPENN YKTTPPVLDS DGSFFLYSKL TVDKSRWQQG
401 NVFSCSVMHE ALHNHYTQKS LSLSPGK
``` hTβRII(G4S)4-hFC: Nucleic Acid Sequence
(SEQ ID NO: 12)

```
  1 ATGGATGCAA TGAAGAGAGG GCTCTGCTGT GTGCTGCTGC TGTGTGGAGC
 51 AGTCTTCGTT TCGCCCGGCG CCACGATCCC ACCGCACGTT CAGAAGTCGG
101 ATGTGGAAAT GGAGGCCCAG AAAGATGAAA TCATCTGCCC CAGCTGTAAT
151 AGGACTGCCC ATCCACTGAG AGATATTAAT AACGACATGA TAGTCACTGA
201 CAACAAEGGT GCAGTCAAGT TTCCACAACT GTGTAAATTT TGTGATGTGA
251 GATTTTCCAC CTGTGACAAC CAGAAATCCT GCATGAGCAA CTGCAGCATC
301 ACCTCCATCT GTGAGAAGCG ACAGGAAGTC TGTGTGGCTG TATGGAGAAA
351 GAATGACGAG AACATAACAC TAGAGACAGT TTGCCATGAC CCAAGCTCC
401 CCTACCATGA CTTTATTCTG GAAGATGCTG CTTCTCCAAA GTGGATTATG
451 AAGGAAAAAA AAAAGCCTGG TGAGACTTTC TTCATGTGTT CCTGTAGCTC
501 TGATGAGTGC AATGACAACA TCATCTTCTC AGAAGAATAT AACACCAGCA
551 ATCCTGACAC CGGTGGTGGA GGTTCTGGAG GTGGAGGAAG TGGTGGAGGT
601 GGTTCTGGAG GTGGTGGAAG TACTCACACA TGCCCACCGT GCCCAGCACC
651 TGAACTCCTG GGGGGACCGT CAGTCTTCCT CTTCCCCCCA AAACCCAAGG
701 ACACCCTCAT GATCTCCCGG ACCCCTGAGG TCACATGCGT GGTGGTGGAC
751 GTGAGCCACG AAGACCCTGA GGTCAAGTTC AACTGGTACG TGGACGGCGT
801 GGAGGTGCAT AATGCCAAGA GALAGCCGCG GGAGGAGGAG TACAACAGCA
851 CGTAGCGTGT GGTCAGCGTC CTCACCGTCC TGCACCAGGA CTGGCTGAAT
```

-continued
```
 901 GGCAAGGAGT ACAAGTGCAA GGTCTCCAAC AAAGCCCTCC CAGGCCCCAT

951 CGAGAAAACC ATCTCCAAAG CCAAGGGGA GCCCCGAGAA CCACAGGTGT

1001 ACACCCTGCG CCCATCCCGG GAGGAGATGA CCAAGAACCA GGTCAGCCTG

1051 ACCTGCCTGG TCAAAGGCTT CTATCCCAGC GACATCGCCG TGGAGTGGGA

1101 GAGCAATGGG CAGCCGGAGA AGAACTACAA GACCACGCCT CCCGTGCTGG

1151 ACTCCGACGG CTCCTTCTTC CTCTATAGCA AGCTCACCGT GGACAAGAGC

1201 AGGTGGCAGC AGGGGAACGT CTTCTCATGC TCCGTGATGC ATGAGGCTCT

1251 GCACAACCAC TACACGCAGA AGAGCCTCTC CCTGTCTCGG GGTAAATGA
``` hTβRII(G4S)4-hFc: Amino Acid Sequence
(SEQ ID NO: 13)
```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPCEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSGGGGSTHT CPPCPAPELL GGPSVFLFPP KPKDTLMISR TPEVTCVVVD

251 VSHEDPEVKF NWYVDGVEVH NAKTKPREEQ YNSTYRVVSV LTVLHQDWLN

301 GKEYKCKVSN KALPAPIEKT ISKAKGQPRE PQVYTLPPSR EEMTKNQVSL

351 TCLVKGFYPS DIAVEWESNG QPENNYKTTP PVLDSDGSFF LYSKLTVDKS

401 RWQQGNVESC SVMHEALHNH YTQKSLSLSP GK
``` hTβRII(G4S)4-hFc: Amino Acid Sequence lacking leader sequence
(SEQ ID NO: 94)
```
  1 GATIPPHVQK SDVEMEAQKD EIICPSCNRT AHPLRHINND MIVTDNNGAV

51 KFPQLCKFCD VRESTCDNQK SCMSNCSITS ICEKPQEVCV AVWRKNDENI

101 TLETVCHDPK LPYHDFILED AASPKCIMKE KKKPGETFFM CSCSSDECND

151 NIIFSEEYNT SNPDTGGGGS GGGGSGGGGS GGGSTHTCP PCPAPELLGG

201 PSVFLFPPKP KDTLMISRTP EVTCVVVDVS HEDPEVKFNW YVDGVEVHNA

251 KTKPREEQYN STYRVVSVLT VLHQDWINGK EYKCKVSNKA LPAPIEKTIS

301 KAKGQPREPQ VYTLPPSREE MTKNQVSLTC LVKGFYPSDI AVEWESNGQP

351 ENNYKTTPPV LDSDGSFFLY SKLTVDKSRW QQGNVFSCSV MHEALHNHYT

401 QKSLSLSPGK
``` hTβRII(G4S)4-hFc: Amino Acid Sequence lacking leader sequence and lacking glycine prior to hTβRII portion
(SEQ ID NO: 95)
```
  1 ATIPPHVQKS DVEMEAQKDE IICPSCNRTA HPLRHINNDM IVTDNNGAVK

51 FPQLCKFCDV RESTCDNQKS CMSNCSITSI CEKPQEVCVA VWRENDENIT

101 LETVCHDPKL PYHDFILEDA ASPKCIMKEK KKPGETFFMC SCSSDECNDN

151 IIFSEEYNTS NPDTGGGSG GGGSGGGGSG GGGSTHTCPP CPAPELLGGP

201 SVFLFPPKPK DTLMISRTPE VTCVVVDVSH EDPEVKFNWY VDGVEVHNAK

251 TKPREEQYNS TYRVVSVLTV IHQDWLNGKE YKCKVSNKAL PAPIEKTISK

301 AKGQPREPQV YTLPPSREEM TKNQVSLTCL VKGFYPSDIA VEWESNGQPE

351 NNYKTTPPVL DSDGSFFLYS KLTVDKSRWQ QGNVESCSVM HEALHNHYTQ

401 KSLSLSPGK
``` hTβRII(G4S)4-hFc: Amino Acid Sequence lacking leader sequence and lacking glycine and alanine prior to hTβRII portion (SEQ ID NO: 96)

```
  1 TIPPHVQKSD VEMEAQKDEI ICPSCNRTAH PLRHINNDMI VTDNNGAVKF
 51 PQLCKFCDVR FSTCDNQKSC MSNCSITSIC EKPQEVCVAV WRKNDENITL
101 ETVCHDPKLP YHDFILEDAA SPKCIMKEKK KPGETFFMCS CSSDECNDNI
151 IFSEEYNTSN PDTGGGGSGG GGSGGGGSGG GGSTHTCPPC PAPELLGGPS
201 VFLFPPKPKD TLMISRTPEV TCVVVDVSHE DPEVKFNWYV DGVEVHNAKT
251 KPREEQYNST YRVVSVLTVL HQDWLNGKEY KCKVSNKALP APIEKTISKA
301 KGQPREPQVY TLPPSREEMT KNQVSLTCLV KGFYPSDIAV EWESNGQPEN
351 NYKTTPPVLD SDGSFFLYSK LTVDKSRWQQ GNVFSCSVMH EALHNHYTQK
401 SLSLSPGK
``` hTβRII(G4S)4-hFc: Amino Acid Sequence lacking leader sequence and lacking glycine, alanine, and threonine prior to hTβRII portion (SEQ ID NO: 97)

```
  1 IPPRVQKSDV EMEAQKDEII CPSCNRTAHP LRHINNDMIV TDNNGAVKFP
 51 QLCKFCDVRF STCDNQKSCM SNCSITSICE KPQEVCVAVW RKNDENITLE
101 TVCHDPKLPY HDFILEDAAS PKCIMKEKKK PGETFFMCSC SSDECNDNII
151 FSEEYNTSNP DTGGGGSGGG GSGGGGSGGG GSTHTCPPCP APELLGGPSV
201 FLFPPKPKDT LMISRTPEVT CVVVDVSHED PEVKFNWYVD GVEVHNAKTK
251 PREEQYNSTY RVVSVLTVLH QDWLNGKEYK CKVSNKALPA PIEKTISKAK
301 GQPREPQVYT LPPSREEMTK NQVSLTCLVK GFYPSDIAVE WESNGQPENN
351 YKTTPPVLDS DGSFFLYSKL TVDKSRWQQG NVFSCSVMHE ALHNHYTQKS
401 LSLSPGK
``` hTβRII(G4S)4-hFc: Amino Acid Sequence lacking leader sequence and lacking glycine, alanine, threonine, and isoleucine prior to hTβRII portion (SEQ ID NO: 98)

```
  1 PPHVQKSDVE MEAQKDEIIC PSCNRTAHPL RHINNDMIVT DNNGAVKFPQ
 51 LCKFCDVRFS TCDNQKSCMS NCSITSICEK PQEVCVAVWR KNDENITLET
101 VCHDPKLPYH DFILEDAASP KCIMKEKKKP GETFFMCSCS SDECNDNIIF
151 SEEYNTSNPD TGGGGSGGGG SGGGGSGGGG STHTCPPCPA PELLGGPSVF
201 LFPPKPKDIL MISRTPEVTC VVVDVSHEDP EVKFNWYVDG VEVENAKTKP
251 REEQYNSTYR VVSVLTVLHQ DWLNGKEYKC KVSNKALPAP IEKTISKAKG
301 QPREPQVYTL PPSREEMTKN QVSLTCLVKG FYPSDIAVEW ESNGQPENNY
351 KTTPPVLDSD GSFFLYSKLT VDKSRWQQGN VFSCSVMHEA LHNHYTQKSL
401 SLSPGK
``` hTβRII(G4S)4-hFc: Amino Acid Sequence lacking sequence and lacking glycine, alanine, threonine, isoleucine, and proline prior to hTβRII portion (SEQ ID NO: 99)

```
  1 PHVQKSDVEM EAQKDEIICP SCNRTAHPLR HINNDMIVTD NNGAVKFPQL
 51 CKFCDVRFST CDNQKSCMSN CSITSICEKP QEVCVAVWRK NDENITLETV
101 CHDPKLPYHD FILEDAASPK CIMKEKKKPG ETFFMCSCSS DECNDNIIFS
151 EEYNTSNPDT GGGGSGGGGS GGGGSGGGGS THTCPPCPAP ELLGGPSVFL
```

-continued

```
201 FPPKPKDTLM ISRTPEVTCV VVDVSHEDPE VKFNWYVDGV EVHNAKTKPR

251 EEQYNSTYRV VSVLTVLHQD WLNGKEYKCK VSNKALPAPI EKTISKAKGQ

301 PREPQVYTLP PSREEMTKNQ VSLTCLVKGF YPSDIAVEWE SNGQPENNYK

351 TTPPVLDSDG SFFLYSKLTV DKSRWQQGNV FSCSVMHEAL HNHYTQKSLS

401 LSPGK
``` hTβRII(G4S)4-hFc: Amino Acid Sequence lacking sequence
and lacking glycine, alanine, threonine, isoleucine, and
proline prior to hTβRII portion
(SEQ ID NO: 100)

```
  1 HVQKSDVEME AQKDEIICPS CNRTAHPLRH INNDMIVTDN NGAVKFPQLC

51 KFCDVRFSTC DNQKSCMSNC SITSICEKPQ EVCVAVWRKN DENITLETVC

101 HDPKLPYHDF ILEDAASPKC IMKEKKKPGE TFFMCSCSSD ECNDNIIFSE

151 EYNTSNPDTG GGGSGGGGSG GGGSGGGGST HTCPPCPAPE LLGGPSVFLF

201 PPKPKDTLMI SRIPEVTCVV VDVSHEDPEV KFNWYVDGVE VHNAKTKPRE

251 EQYNSTYRVV SVLTVLHQDW LNGKEYKCKV SNKALPAPIE KTISKAKGQP

301 REPQVYTLPP SREEMTKNQV SLTCLVKGFY PSDIAVEWES NGQPENNYKT

351 TPPVLDSDGS FFLYSKLTVD KSRWQQGNVF SCSVMEEALH NHYTQKSLSL

401 SPGK
``` hTβRII(G4S)2-hFc: Nucleic Acid Sequence
(SEQ ID NO: 14)

```
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TCCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGAGGT GGTTCTGGAG GTGGTGGAAG TACTCACACA

601 TGCCCACCGT GCCCAGCACC TGAACTCCTG GGGGGACCGT CAGTCTTCCT

651 CTTCCCCCCA AAACCCAAGG ACACCCTCAT GATCTCCCGG ACCCCTGAGG

701 TCACATGCGT GGTGGTGGAC GTGAGCCACG AAGACCCTGA GGTCAAGTTC

751 AACTGGTACG TGGACGGCGT GGAGGTGCAT AATGCCAAGA CAAAGCCGCG

801 GGAGGAGCAG TACAACAGCA CGTACCGTGT GGTCAGCGTC CTCACCGTCC

851 TGCACCAGGA CTGGCTGAAT GGCAAGGAGT ACAAGTGCAA GGTCTCCAAC

901 AAAGCCCTCC CAGCCCCCAT CGAGAAAACC ATCTCCAAAG CCAAAGGGCA

951 GCCCCGAGAA CCACAGGTGT ACACCCTGCC CCCATCCCGG GAGGAGATGA

1001 CCAAGAACCA GGTCAGCCTG ACCTGCCTGG TCAAAGGCTT CTATCCCAGC

1051 GACATCGCCG TGGAGTGGGA GAGCAATGGG CAGCCGGAGA ACAACTACAA

1101 GACCACGCCT CCCGTGCTGG ACTCCGACGG CTCCTTCTTC CTCTATAGCA
```

-continued

```
1151 AGCTCACCGT GGACAAGAGC AGGTGGCAGC AGGGGAACGT CTTCTCATGC

1201 TCCGTGATGC ATGAGGCTCT GCACAACCAC TACACGCAGA AGAGCCTCTC

1251 CCTGTCTCCG GGTAAATGA
``` hTβRII(G4S)2-hFC: Amino Acid Sequence (SEQ ID NO: 15)

```
  1 MDAMKRGLCC VLLLCGAVFV SPGATIPPHV QKSDVEMEAQ KDEIICPSCN

51 RTAHPLRHIN NDMIVTDNNG AVKFPQLCKT CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NISNPDTGGG GSGGGGSTHT

201 CPPCPAPELL GGPSVFLFPP KFKDILMISR TPEVTCVVVD VSHEDPEVKF

251 NWYVDGVEVH NAKTKPREEQ YNSTYRVVSV LTVLHQDWLN GKEYKEKVSN

301 KALPAPIEKT ISKAKGQPRE PQVYTLPPSR EEMTKNQVSL TCLVKGFYPS

351 DIAVEWESNG QPENNYKTTP PVLDSDGSFF LYSKLTVDKS RWQQGNVFSC

401 SVMHEALHNH YTQKSLSLSP GK
``` hTβRII extended hinge-hFc: Nucleic Acid Sequence (SEQ ID NO: 16)

```
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA CCCAAATCTT GTGACAAAAC TCACACATGC

601 CCACCGTGCC CAGCACCTGA ACTCCTGGGG GGACCGTCAG TCTTCCTCTT

651 CCCCCCAAAA CCCAAGGACA CCCTCATGAT CTCCCGGACC CCTGAGGTCA

701 CATGCGTGGT GGTGGACGTG AGCCACGAAG ACCCTGAGGT CAAGTTCAAC

751 TGGTACGTGG ACGGCGTGGA GGTGCATAAT GCCAAGACAA AGCCGCGGGA

801 GGAGCAGTAC AACAGCACGT ACCGTGTGGT CAGCGTCCTC ACCGTCCTGC

851 ACCAGGACTG GCTGAATGGC AAGGAGTACA AGTGCAAGGT CTCCAACAAA

901 GCCCTCCCAG CCCCCATCGA GAAAACCATC TCCAAAGCCA AAGGGCAGCC

951 CCGAGAACCA CAGGTGTACA CCCTGCCCCC ATCCCGGGAG GAGATGACCA

1001 AGAACCAGGT CAGCCTGACC TGCCTGGTCA AAGGCTTCTA TCCCAGCGAC

1051 ATCGCCGTGG AGTGGGAGAG CAATGGGCAG CCGGAGAACA ACTACAAGAC

1101 CACGCCTCCC GTGCTGGACT CCGACGGCTC CTTCTTCCTC TATAGCAAGC

1151 TCACCGTGGA CAAGAGCAGG TGGCAGGAGG GGAACGTCTT CTCATGCTCC

1201 GTGATGCATG AGGCTCTGCA CAACCACTAC ACGCAGAAGA GCCTCTCCCT

1251 GTCCCCGGGT AAATGA
``` hTβRII extended hinge-hFc: Amino Acid Sequence
(SEQ ID NO: 17)
```
  1 MDAMKRGLCC VLLLCGAVFV SPGATIPPHV QKSDVEMEAQ KDEIICPSCN
 51 RTAHPLRHIN NDMIVTDNNG AVKFPQLCKF CDVRFSTCDN QKSCMSNCSI
101 TSICEKPQEV CVAVWRKNDE NITLETVCHD PKLPYHDFIL EDAASPKCIM
151 KEKKKPGETF FMCSCSSDEC NDNIIFSEEY NTSNPDTGGG PKSCDKIHTC
201 PPCPAPELLG GPSVFLFPPK PKDTLMISRT PEVTCVVVDV SHEDPEVKFN
251 WYVDGVEVHN AKTKPREEQY NSTYRVVSVL TVLHQDWLNG KEYKCKVSNK
301 ALPAPIEKTI SKAKGQPREP QVYTLPPSRE EMTKNQVSLT CLVKGFYPSD
351 IAVEWESNGQ PENNYKTTPP VLDSDGSFFL YSKLTVDKSR WQQGNVFSCS
401 VMHEALHNHY TQKSLSLSPG K
``` hTβRII(G4S)5-hFc: Amino Acid Sequence
(SEQ ID NO: 44)
```
  1 MDAMKRGLCC VLLLCGAVFV SPGATIPPHV QKSDVEMEAQ KDEIICPSCN
 51 RTAHPLRHIN NDMIVTDNNG AVKFPQLCKF CDVRESTCDN QKSCMSNCSI
101 TSICEKPQEV CVAVWRKNDE NITLETVCHD PKLPYHDFIL EDAASPKCIM
151 KEKKKPGETF FMCSCSSDEC NDNIIFSEEY NTSNPDTGGG GSGGGGSGGG
201 GSGGGGSGGG GSTHTCFPCP APELLGGPSV FLFPPKPKDT LMISRTPEVT
251 CVVVDVSHED PEVKFNWYVD GVEVHNAKTK PREEQYNSTY RVVSVLTVLH
301 QDWLNGKEYK CKVSNKALPA PIEKTISKAK GQPREPQVYT LPPSREEMTK
351 NQVSLTCLVK GFYPSDIAVE WESNGQPENN YKTTPPVLDS DGSFFLYSKL
401 TVDKSRWQQG NVFSCSVMHE ALHNHYTQKS LSLSPGK
``` hTβRII(G4S)5-hFc: Amino Acid Sequence
(SEQ ID NO: 45)
```
  1 MDAMKRGLCC VLLLCGAVFV SPGATIPPHV QKSDVEMEAQ KDEIICPSCN
 51 RTAHPLRHIN NDMIVTDNNG AVKFPQLCKF CDVRFSTCDN QKSCMSNCSI
101 TSICEKPQEV CVAVWRKNDE NITLETVCHD PKLPYHDFIL EDAASPKCIM
151 KEKKKPGETF FMGSCSSDEC NDNIIFSEEY NTSNPDTGGG GSGGGGSGGG
201 GSGGGGSGGG GSGGGGSTHT CPPCPAPELL GGPSVFLEPP KPKDTLMISR
251 TPEVTCVVVD VSHEDPEVKF NWYVDGVEVH NAKTKPREEQ YNSTYRVVSV
301 LTVLHQDWLN GKEYKCKVSN KALPAPIEKT ISKAKGQPRE PQVYTLPPSR
351 EEMTKNQVSL TCLVKGFYPS DIAVEWESNG QPENNYKTTP PVLDSDGSFF
401 LYSKLTVDKS RWQQGNVFSC SVMHEALHNH YTQKSLSLSP GK
``` hTβRII(G4S)5-hFc: Nucleotide Sequence
(SEQ ID NO: 46)
```
  1 ATGGATGCAA TGAAGAGAGG GCTCTGCTGT GTGCTGCTGC TGTGTGGAGC
 51 AGTCTTCGTT TCGCCCGGCG CCACGATCCC ACCGCACGTT CAGAAGTCGG
101 ATGTGGAAAT GGAGGCCCAG AAAGATGAAA TCATCTGCCC CAGCTGTAAT
151 AGGACTGGCC ATCCACTGAG AGATATTAAT AACGACATGA TAGTCACTGA
201 GAACAACGGT GCAGTCAAGT TCCCACAACT GTGTAAATTT TGTGATGTGA
251 GATTTTCCAC CTGTGACAAC CAGAAATCCT GCATGAGCAA CTGCAGCATC
301 ACCTCCATCT GTGAGAAGCC ACAGGAAGTC TGTGTGGCTG TATGGAGAAA
351 GAATGACGAG AAGATAACAC TAGAGACAGT TTGCCATGAC CCCAAGCTCC
401 CCTACCATGA CTTTATTCTG GAAGATGCTG CTTCTCCAAA GTGGATTATG
```

```
451 AAGGAAAAAA AAAAGCCTGG TGAGACTTTC TTCATGTGTT CCTGTAGGTC

501 TGATGAGTGC AATGACAACA TCATCTTCTC AGAAGAATAT AACACCAGCA

551 ATCCTGACAC CGGTGGAGGA GGTTCTGGTG GTGGAGGTTC TGGAGGTGGA

601 GGAAGTGGTG GAGGTGGTTC TGGAGGTGGT GGAAGTACTC AGACATGCCC

651 ACCGTGCCCA GCACCTGAAC TCCTGGGGGA CCGTCAGTC TTCCTCTTCC

701 CCCCAAAACC CAAGGACACG CTCATGATCT CCCGGACCGC TGAGGTCACA

751 TGCGTGGTGG TGGACGTGAG CCAGGAAGAC CCTGAGGTCA AGTTCAAGTG

801 GTACGTGGAC GGCGTGGAGG TGCATAATGC CAAGAGAAAG CCGCGGGAGG

851 AGCAGTACAA CAGCACGTAC CGTGTGGTCA GCGTCCTCAC CGTCCTGCAC

901 CAGGACTGGG TGAATGGCAA GGAGTACAAG TGCAAGGTGT CCAACAAAGC

951 CCTCCCAGCG CCCATCGAGA AAACCATCTC CAAAGCCAAA GGGCAGCCCC

1001 GAGAACCACA GGTGTACAGC CTGCCCCCAT CCCGGGAGGA GATGACCAAG

1051 AACCAGGTCA GCCTGACCTG CCTGGTCAAA GGCTTCTATC CAGCGACAT

1101 CGGCGTGGAG TGGGAGAGCA ATGGGCAGCC GGAGAACAAC TACAAGACCA

1151 CGGCTCCCGT GCTGGACTCC GACGGCTCCT TCTTCCTCTA TAGCAAGCTC

1201 ACCGTGGACA AGAGCAGGTG GCAGCAGGGG AACGTCTTGT CATGCTCCGT

1251 GATGCATGAG GCTCTGCACA ACCACTACAC GCAGAAGAGC CTCTCCCTGT

1301 CTCCGGGTAA ATGA
``` hTβRII(G4S)6-hFc: Nucleotide Sequence (SEQ ID NO: 47)

```
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGGAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGAGGT GGAAGTGGTG GAGGAGGTTC TGGTGGTGGA

601 GGTTCTGGAG GTGGAGGAAG TGGTGGAGGT GGTTCTGGAG GTGGTGGAAG

651 TACTCACACA TGCCCACCGT GCCCAGCACC TGAACTCCTG GGGGACCGT

701 CAGTCTTCCT CTTCCCCCCA AAACCCAAGG ACACCCTCAT GATCTCCCGG

751 ACCCCTGAGG TCACATGCGT GGTGGTGGAC GTGAGCCACG AAGACCCTGA

801 GGTCAAGTTC AACTGGTACG TGGACGGCGT GGAGGTGCAT AATGCCAAGA

851 CAAAGCCGCG GGAGGAGCAG TACAACAGCA CGTACCGTGT GGTCAGCGTC

901 CTCACCGTCC TGCACCAGGA CTGGCTGAAT GGCAAGGAGT ACAAGTGCAA
```

```
 951 GGTCTCCAAC AAAGCCCTCC CAGCCCCCAT CGAGAAAACC ATCTCCAAAG

1001 CCAAGGGGA  GCCCCGAGAA CCACAGGTGT ACACCCTGCC CCCATCCCGG

1051 GAGGAGATGA CCAAGAACCA GGTCAGCCTG ACCTGCCTGG TCAAAGGCTT

1101 CTATCCCAGC GACATCGCCG TGGAGTGGGA GAGCAATGGG CAGCCGGAGA

1151 ACAACTACAA GACCACGCCT CCCGTGCTGG ACTCCGACGG CTCCTTCTTC

1201 CTCTATAGCA AGCTCACCGT GGACAAGAGC AGGTGGCAGC AGGGGAACGT

1251 CTTCTCATGC TCCGTGATGC ATGAGGCTCT GCACAACCAC TACACGCAGA

1301 AGAGCCTCTC CCTGTCTCCG GGTAAATGA
```

The various constructs were successfully expressed in CHO cells and were purified to a high degree of purity as determined by analytical size-exclusion chromatography and SDS-PAGE. The hTβRII (G4S)2-hFc, hTβRII (G4S)3-hFc, hTβRII (G4S)4-hFc, hTβRII (G4S)5-hFc and hTβRII (G4S)6-hFc proteins displayed similarly strong stability as determined by SDS-PAGE analysis when maintained in PBS for 13 days at 37° C. The hTβRII (G4S)2-hFc, hTβRII (G4S)3-hFc, hTβRII (G4S)4-hFc proteins were also maintained in rat, mouse or human serum and displayed similarly strong stability.

TβRII ECD Variants

In addition to the TβRII domains included in the fusion proteins described above (e.g., SEQ ID NO: 18), the disclosure also contemplates fusion proteins comprising alternative TβRII domains. For example, the fusion protein may comprise the wild-type hTβRII$_{short}$(23-159) sequence shown below (SEQ ID NO: 27) or any of the other TβRII polypeptides disclosed below:

```
                                               (SEQ ID NO: 27)
  1 TIPPHVQKSV NNDMIVTDNN GAVKFPQLCK FCDVRFSTCD
    NQKSCMSNCS

51 ITSICEKPQE VCVAVWRKND ENITLETVCH DPKLPYHDFI
    LEDAASPKCI

101 MKEKKKPGET FFMCSCSSDE CNDNIIFSEE YNTSNPD
```

(1) The hTβRII$_{short}$(23-159/D110K) amino acid sequence shown below (SEQ ID NO: 36), in which the substituted residue is underlined.

```
                                               (SEQ ID NO: 36)
  1 TIPPHVQKSV NNDMIVTDNN GAVKFPQLCK FCDVRFSTCD
    NQKSCMSNCS

51 ITSICEKPQE VCVAVWRKND ENITLETVCH DPKLPYHKFI
    LEDAASPKCI

101 MKEKKKPGET FFMCSCSSDE CNDNIIFSEE YNTSNPD
```

(2) The N-terminally truncated hTβRII$_{short}$(29-159) amino acid sequence shown below (SEQ ID NO: 28).

```
                                               (SEQ ID NO: 28)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEYNTSNP D
```

(3) The N-terminally truncated hTβRII$_{short}$(35-159) amino acid sequence shown below (SEQ ID NO: 29).

```
                                               (SEQ ID NO: 29)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEYN TSNPD
```

(4) The C-terminally truncated hTβRII$_{short}$(23-153) amino acid sequence shown below (SEQ ID NO: 30).

```
                                               (SEQ ID NO: 30)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE Y
```

(5) The C-terminally truncated hTβRII$_{short}$(23-153/N70D) amino acid sequence shown below (SEQ ID NO: 38), in which the substituted residue is underlined.

```
                                                     (SEQ ID NO: 38)
  1   TIPPHVQKSV NNDMIVTDNN GAVKFPQLCK FCDVRESTCD NQKSCMSDCS
                                                       -
 51   ITSICEKPQE VCVAVWRKND ENITLETVCH DPKLPYHDFI LEDAASPKCI

101   MKEKKKPGET FFMCSCSSDE CNDNIIFSEE Y
```

Applicants also envision five corresponding variants (SEQ ID NOs: 37, 33, 34, 39) based on the wild-type hTβRII$_{long}$(23-184) sequence shown above and below (SEQ ID NO: 20), in which the 25 amino-acid insertion is underlined. Note that splicing results in a conservative amino acid substitution (Val-Ile) at the flanking position C-terminal to the insertion.

```
                                                     (SEQ ID NO: 20)
  1   TIPPHVQKSD VEMEAQKDEI ICPSCNRTAH PLRHINNDMI VTDNNGAVKF

51   PQLCKFCDVR FSTCDNQKSC MSNCSITSIC EKPQEVCVAV WRKNDENITL

101   ETVCHDPKLP YHDFILEDAA SPKCIMKEKK KPGETFFMCS CSSDECNDNI

151   IFSEEYNTSN PD
```

(1) The hTβRII$_{long}$(23-184/D135K) amino acid sequence shown below (SEQ ID NO: 37), in which the substituted residue is double underlined.

```
                                                     (SEQ ID NO: 37)
  1   TIPPHVQKSD VEMEAQKDEI ICPSCNRTAH PLRHINNDMI VTDNNGAVKF

51   PQLCKFCDVR FSTCDNQKSC MSNCSITSIC EKPQEVCVAV WRKNDENITL

101   ETVCHDPKLP YHKFILEDAA SPKCIMKEKK KPGETFFMCS CSSDECNDNI
                    =
151   IFSEEYNTSN PD
```

(2) The N-terminally truncated hTβRII$_{long}$(29-184) amino acid sequence shown below (SEQ ID NO: 33).

```
                                                     (SEQ ID NO: 33)
  1   QKSDVEMEAQ KDEIICPSCN RTAHPLRHIN NDMIVTDNNG AVXFPQLCKF

51   CDVRFSTCDN QKSCMSNCSI TSICEKPQEV CVAVWRKNDE NITLETVCHD

101   PKLPYHDFIL EDAASPKCIM KEKKKPGETF FMCSCSSDEC NDNIIFSEEY

151   NTSNPD (SEQ ID NO: 33)
 51   CDVRFSTCDN QKSCMSNCSI TSICEKPQEV CVAVWRKNDE NITLETVCHD

101   PKLPYHDFIL EDAASPKCIM KEKKKPGETF FMCSCSSDEC NDNIIFSEEY

151   NTSNPD
```

(3) The N-terminally truncated hTβRII$_{long}$(60-184) amino acid sequence shown below (same as SEQ ID NO: 29).

```
                                                  (same as SEQ ID NO: 29)
  1   DMIVTDNNGA VKFPQLCKFC DVRFSTCDNQ KSCMSNCSIT SICEKPQEVC

51   VAVWRKNDEN ITLETVCHDP KLPYHDFILE DAASPKCIMK EKKKPGETFF

101   MCSCSSDECN DNIIFSEEYN TSNPD
```

(4) The C-terminally truncated hTβRII$_{long}$(23-178) amino acid sequence shown below (SEQ ID NO: 34).

```
                                              (SEQ ID NO: 34)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEY
```

(5) The C-terminally truncated hTβRII$_{long}$(23-178/N95D) amino acid sequence shown below (SEQ ID NO: 39), in which the substituted residue is double underlined.

```
                                              (SEQ ID NO: 39)
  1 TIPPHVQKSD VEMEAQKDEI ICPSCNRTAH PLRHINNDMI VTDNNGAVKF

51 PQLCKFCDVR FSTCDNQKSC MSDCSITSIC EKPQEVCVAV WRKNDENITL

101 ETVCHDPKLP YHDFILEDAA SPKCIMKEKK KPGETFFMCS CSSDECNDNI

151 IFSEEY
```

Additional TβRII ECD variants include:
(A) The N- and C-terminally truncated hTβRII$_{short}$(35-153) or hTβRII$_{long}$(60-178) amino acid sequence shown below (SEQ ID NO: 32).

```
                                              (SEQ ID NO: 32)
  1    DMIVTDNNGA VKFPQLCKFC DVRESTCDNQ KSCMSNCSIT SICEKPQEVC

51    VAVWRKNDEN ITLETVCHDP KLPYHDFILE DAASPKCIMK EKKKPGETFF

101    MCSCSSDECN DNIIFSEEY
```

(B) The N- and C-terminally truncated hTβRII$_{short}$(29-153) amino acid sequence shown below (SEQ ID NO: 31).

```
                                              (SEQ ID NO: 31)
  1    QKSVNNDMIV TDNNGAVKFP QLCKFCDVRF STCDNQKSCM SNCSITSICE

51    KPQEVCVAVW RKNDENITLE TVCHDPKLPY HDFILEDAAS PKCIMKEKKK

101    PGETFFMCSC SSDECNDNII FSEEY
```

(C) The N- and C-terminally truncated hTβRII$_{long}$(29-178) amino acid sequence shown below (SEQ ID NO: 35).

```
                                              (SEQ ID NO: 35)
  1 QKSDVEMEAQ KDEIICPSCN RTAHPLRHIN NDMIVTDNNG AVXFPQLCKF

51 CDVRFSTCDN QKSCMSNCSI TSICEKPQEV CVAVWRKNDE NITLETVCHD

101 PKLPYHDFIL EDAASPKCIM KEKKKPGETF FMCSCSSDEC NDNIIFSEEY
```

Any of the above variants (SEQ ID NOs: 36, 28, 29, 30, 38, 37, 33, 34, 39, 32, 31, and 35) could incorporate an insertion of 36 amino acids (SEQ ID NO: 41) between the pair of glutamate residues (positions 151 and 152 of SEQ ID NO: 1, or positions 176 and 177 of SEQ ID NO: 2) located near the C-terminus of the hTβRII ECD, as occurs naturally in the hTβRII isoform C (Konrad et al., BMC Genomics 8:318, 2007).

```
                                              (SEQ ID NO: 41)
   GRCKIRHIGS NNRLQRSTCQ NTGWESAHVM KTPGFR
```

As an example, the paired glutamate residues flanking the optional insertion site are denoted below (underlined) for the hTβRII$_{short}$(29-159) variant (SEQ ID NO: 28).

```
                                                          (SEQ ID NO: 28)
  1  QKSVNNDMIV  TDNNGAVKFP  QLCKFCDVRF  STCDNQKSCM  SNCSITSICE

51  KPQEVCVAVW  RKNDENITLE  TVCHDPKLPY  HDFILEDAAS  PKCIMKEKKK

101  PGETFFMCSC  SSDECNDNII  FSEEYNTSNP  D
```

Fc Domain Variants

While the constructs described above were generated with an Fc domain having the amino acid sequence of SEQ ID NO: 49, the disclosure contemplates hTβRII-hFc fusion proteins comprising alternative Fc domains, including a human IgG2 Fc domain (SEQ ID NO: 42, below) or full-length human IgG1 Fc (hG1Fc) (SEQ ID NO: 43, below). Optionally, a polypeptide unrelated to an Fc domain could be attached in place of the Fc domain.

```
                                                          (SEQ ID NO: 42)
  1     VECPPCPAPP  VAGPSVFLFP  PKPKDTLMIS  RTPEVTCVVV  DVSHEDPEVQ

51     FNWYVDGVEV  HNAKTKPREE  QFNSTFRVVS  VLTVVHQDWL  NGKEYKCKVS

101     NKGLPAPIEK  TISKTKGQPR  EPQVYTLPPS  REEMTKNQVS  LTCLVKGFYP

151     SDIAVEWESN  GQPENNYKTT  PPMLDSDGSF  FLYSKLTVDK  SRWQQGNVFS

201     CSVMHEALHN  HYTQKSLSLS  PGK
```

```
                                                          (SEQ ID NO: 43)
  1     GGPKSCDKTH  TCPPCPAPEL  LGGPSVFLFP  PKPKDTLMIS  RTPEVTCVVV

51     DVSHEDPEVK  FNWYVDGVEV  HNAKTKPREE  QYNSTYRVVS  VLTVLHQDWL

101     NGKEYKCKVS  NKALPAPIEK  TISKAKGQPR  EPQVYTLPPS  REEMTKNQVS

151     LTCLVKGFYP  SDIAVEWESN  GQPENNYKTT  PPVLDSDGSF  FLYSKLTVDK

201     SRWQQGNVFS  CSVMHEALHN  HYTQKSLSLS  PGK
```

Leader Sequence Variants

While the generated constructs described above included the TPA leader sequence, alternative leader sequences may be used, such as the native leader sequence (SEQ ID NO: 22—below) or the honey bee melittin (SEQ ID NO: 24—below) leader sequences.

```
        Native:
                                    (SEQ ID NO: 22)
        MGRGLLRGLWPLHIVLWTRIAS Honey bee melittin (HBML):
                                    (SEQ ID NO: 24)
        MKFLVNVALVFMVVYISYIYA
```

Example 2. Differential Ligand Inhibition by Receptor Fusion Protein Variants in Cell-Based Assay Affinities of TGFβ1, TGFβ2 and TGFβ3 for hTβRII (G4S)2-hFc; hTβRII (G4S)3-hFc; hTβRII (G4S)4-hFc; hTβRII-hFc; and hTβRII extended hinge-hFc proteins were evaluated in vitro with a Biacore™ instrument, and the results are summarized in FIGS. 4A and 4B. Each of the fusion proteins was capable of binding TGFβ1 and TGFβ3 with high affinity, but the constructs having linker lengths longer than or equal to (G4S)4 (SEQ ID NO: 203) were surprisingly capable of binding to both TGFβ1 and TGFβ3 with higher affinity than constructs having linker lengths shorter than (G4S)4 (SEQ ID NO: 203). Binding between TGFβ2 and any of the constructs was low or transient. Deglycosylation of the constructs did not change binding.

A reporter gene assay in A549 cells was used to determine the ability of hTβRII-hFc variants to inhibit activity of TGFβ1, TGFβ2 and TGFβ3. This assay is based on a human lung carcinoma cell line transfected with a pGL3(CAGA)12 reporter plasmid (Dennler et al, 1998, EMBO 17: 3091-3100) as well as a Renilla reporter plasmid (pRLCMV) to control for transfection efficiency. The CAGA motif is present in the promoters of TGFβ-responsive genes (for example, PAT-1), so this vector is of general use for factors signaling through SMAD2 and SMAD3.

On the first day of the assay, A549 cells (ATCC®: CCL-185™) were distributed in 48-well plates. On the second day, a solution containing pGL3(CAGA)$_{12}$, pRLCMV, X-tremeGENE 9 (Roche Applied Science), and OptiMEM (Invitrogen) was preincubated, then added to Eagle's minimum essential medium (EMEM, ATCC®) supplemented with 0.1% BSA, which was applied to the plated cells for incubation overnight at 37° C., 5% CO$_2$. On the third day, medium was removed, and cells were incubated overnight at 37° C., 5% CO$_2$ with a mixture of ligands and inhibitors prepared as described below.

Serial dilutions of test articles were made in a 48-well plate in assay buffer (EMEM+0.1% BSA). An equal volume of assay buffer containing the test ligand was added to obtain a final ligand concentration equal to the EC50 determined previously. Human TGFβ1, human TGFβ2, and human TGFβ3 were obtained from PeproTech. Test solutions were incubated at 37° C. for 30 minutes, then a portion of the mixture was added to all wells. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred in duplicate to a chemiluminescence plate (96-well) and analyzed in a luminometer with reagents from a Dual-Luciferase Reporter Assay system (Promega E1980) to determine normalized luciferase activity.

Figure 5A:
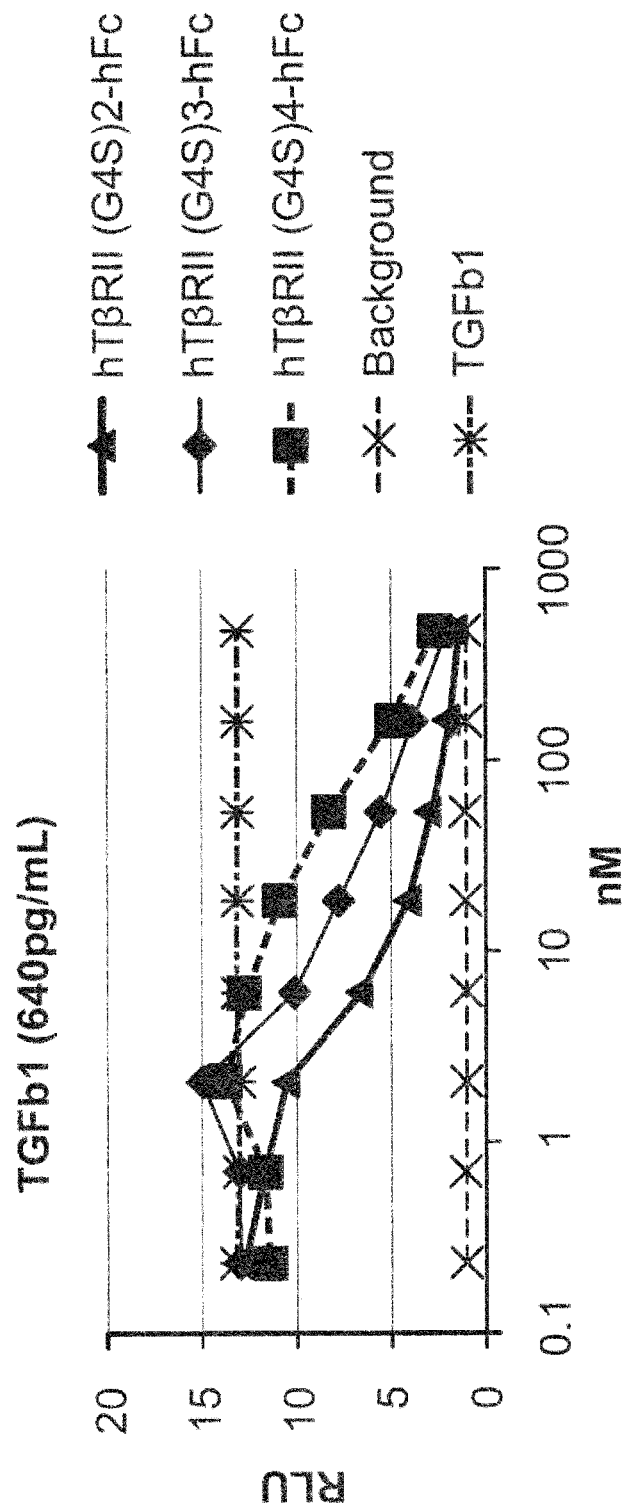
FIGS. 5A and 5C graph the results from reporter gene assays testing the affinity of TGFβ1 for one of several different TβRII-Fc fusion protein constructs.
Figure 5B:
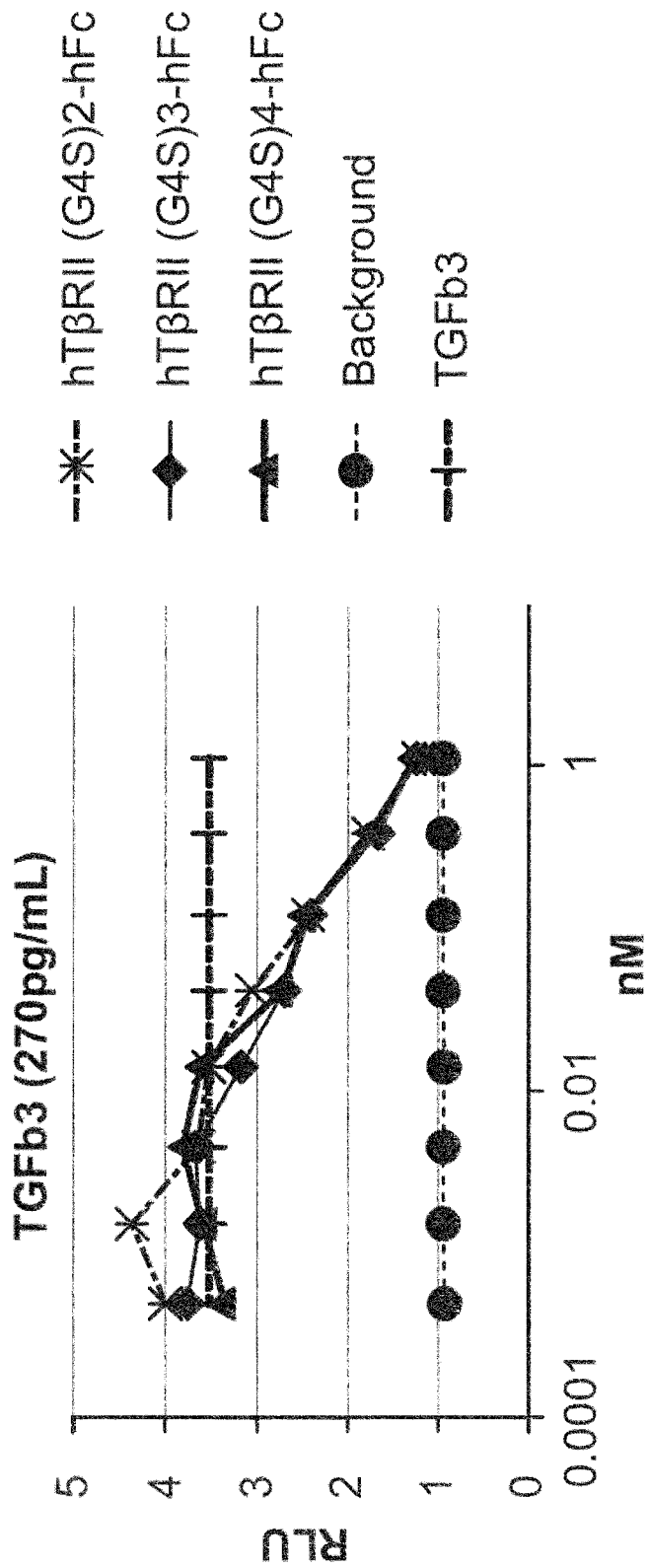
FIGS. 5B and 5D graph the results from reporter gene assays testing the affinity of the TGFβ3 for one of several different TβRII-Fc fusion protein constructs.
Figure 5C:
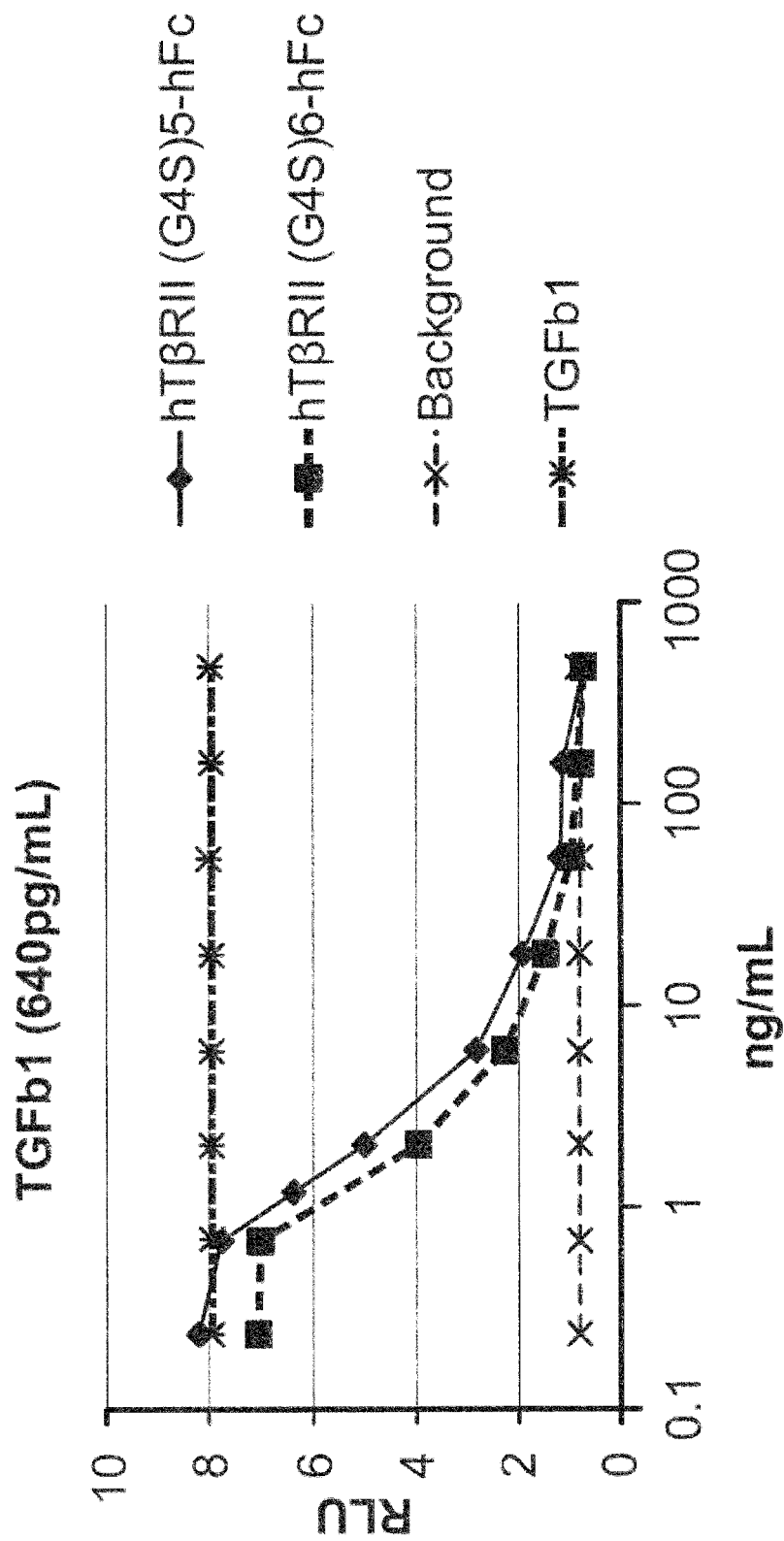
Figure 5D:
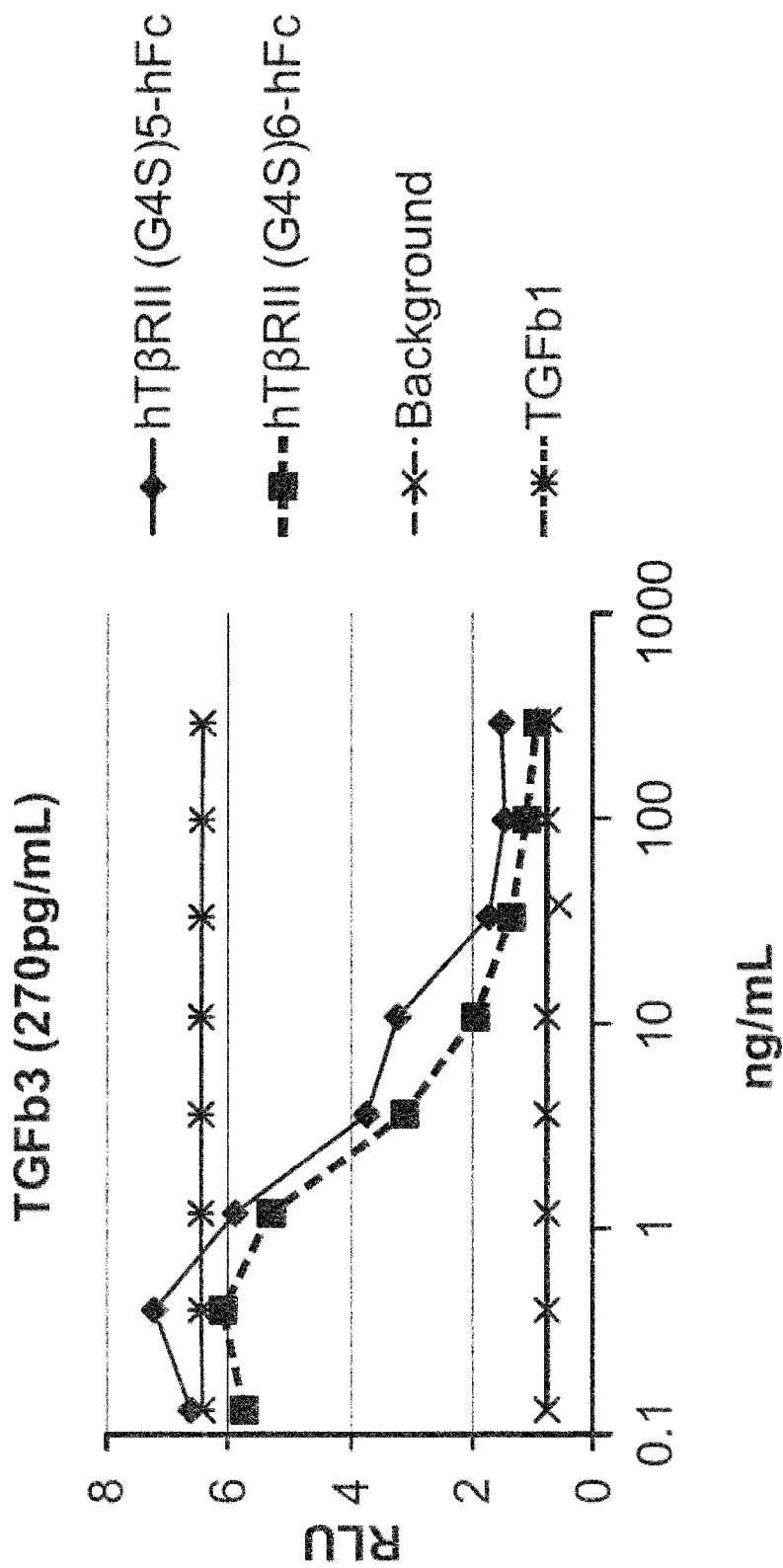

As illustrated in FIGS. 5A-5F, the hTβRII (G4S)2-hFc; hTβRII (G4S)3-hFc; hTβRII (G4S)4-hFc; hTβRII (G4S)5-hFc; hTβRII (G4S)6-hFc; hTβRII-hFc; and hTβRII extended hinge-hFc proteins all were capable of inhibiting both TGFβ 1 and TGFβ3. Interestingly, while there was a correlation between improved TGFβ1 and TGFβ3 inhibition and linker length for the hTβRII (G4S)2-hFc; hTβRII (G4S)3-hFc and hTβRII (G4S)4-hFc constructs (FIG. 5E), this improvement trend appeared to have plateaued for hTβRII (G4S)5-hFc and hTβRII (G4S)6-hFc constructs (FIG. 5F).

Example 3. Generation of an ActRIIA:TβRII Heterodimer

Soluble ActRIIA-Fc:TβRII-Fc heteromeric complexes comprising the extracellular domains of human ActRIIA and human TβRII, which are each separately fused to an Fc domain with a linker positioned between the extracellular domain and the Fc domain, were constructed. The individual constructs are referred to as ActRIIA-Fc fusion polypeptide and TβRII-Fc fusion polypeptide, respectively, and the sequences for each are provided below.

A methodology for promoting formation of ActRIIA-Fc:TβRII-Fc heteromeric complexes, as opposed to ActRIIA-Fc or TβRII-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIA-Fc and TβRII-Fc polypeptide sequences of SEQ ID NOs: 82, 84, 85 and 87, respectively, one Fc domain is altered to introduce cationic amino acids at the interaction face, while the other Fc domain is altered to introduce anionic amino acids at the interaction face. ActRIIA-Fc fusion polypeptide and TβRII-Fc fusion polypeptide each employ the tissue plasminogen activator (TPA) leader: MDAMKRGLCCVLLLCGAVFVSP (SEQ ID NO: 23) and a (G4S)4 linker (SEQ ID NO: 203) positioned between the ActRIIA or TβRII extracellular portion and the modified Fc portion.

The ActRIIA-Fc polypeptide sequence (SEQ ID NO: 82) is shown below:

```
                                           (SEQ ID NO: 82)
  1 MDAMKRGLCC VLLLCGAVFV SPGAAILGRS ETQECLFFNA
    NWEKDRTNQT

51 GVEPCYGDKD KRRHCFATWK NISGSIEIVK QGCWLDDINC
    YDRTDCVEKK

101 DSPEVYFCCC EGNMCNEKFS YFPEMEVTQP TSNPVTPKPP
    TGGGGSGGGG

151 SGGGGSGGGG STHTCPPCPA PELLGGPSVF LFPPKPKDTL
    MISRTPEVTC

201 VVVDVSHEDP EVKFNWYVDG VEVHNARTKP REEQYNSTYR
    VVSVLTVLHQ

251 DWLNGKEYKC KVSNKALPAP IEKTISKAKG QPREPQVYTL
    PPSRKEMTKN

301 QVSLTCLVKG FYPSDIAVEW ESNGQPENNY KTTPPVLKSD
    GSFFLYSKLT

351 VDKSRWQQGN VFSCSVMHEA LHNHYTQKSL SLSPGK
```

The leader (signal) sequence and linker are underlined. To promote formation of ActRIIA-Fc:TβRII-Fc heterodimer rather than either of the possible homodimeric complexes, two amino acid substitutions (replacing acidic amino acids with lysine) can be introduced into the Fc domain of the ActRIIA fusion protein as indicated by double underline above. The amino acid sequence of SEQ ID NO: 82 may optionally be provided with lysine (K) removed from the C-terminus.

This ActRIIA-Fc fusion protein is encoded by the following nucleic acid sequence (SEQ ID NO: 83):

```
                                           (SEQ ID NO: 83)
   1 ATGGATGCAA TGAAGAGAGG GCTCTGCTGT GTGCTGCTGC
     TGTGTGGAGC

51 AGTCTTCGTT TCGCCCGGCG CCGCTATACT TGGTAGATCA
     GAAACTCAGG

101 AGTGTCTTTT CTTTAATGCT AATTGGGAAA AAGACAGAAC
     CAATCAAACT

151 GGTGTTGAAC CGTGTTATGG TGACAAAGAT AAACGGCGGC
     ATTGTTTTGC

201 TACCTGGAAG AATATTTCTG GTTCCATTGA AATAGTGAAA
     CAAGGTTGTT

251 GGCTGGATGA TATCAACTGC TATGACAGGA CTGATTGTGT
     AGAAAAAAAA

301 GACAGCCCTG AAGTATATTT CTGTTGCTGT GAGGGCAATA
     TGTGTAATGA

351 AAAGTTTTCT TATTTTCCGG AGATGGAAGT CACACAGCCC
     ACTTCAAATC

401 CAGTTACACC TAAGCCACCC ACCGGTGGTG GAGGTTCTGG
     AGGTGGAGGA

451 AGTGGTGGAG GTGGTTCTGG AGGTGGTGGA AGTACTCACA
     CATGCCCACC

501 GTGCCCAGCA CCTGAACTCC TGGGGGGACC GTCAGTCTTC
     CTCTTCCCCC

551 CAAAACCCAA GGACACCCTC ATGATCTCCC GGACCCCTGA
     GGTCACATGC

601 GTGGTGGTGG ACGTGAGCCA CGAAGACCCT GAGGTCAAGT
     TCAACTGGTA

651 CGTGGACGGC GTGGAGGTGC ATAATGCCAA GACAAAGCCG
     CGGGAGGAGC

701 AGTACAACAG CACGTACCGT GTGGTCAGCG TCCTCACCGT
     CCTGCACCAG

751 GACTGGCTGA ATGGCAAGGA GTACAAGTGC AAGGTCTCCA
     ACAAAGCCCT

801 CCCAGCCCCC ATCGAGAAAA CCATCTCCAA AGCCAAAGGG
     CAGCCCCGAG

851 AACCACAGGT GTACACCCTG CCCCCATCCC GGAAGGAGAT
     GACCAAGAAC

901 CAGGTCAGCC TGACCTGCCT GGTCAAAGGC TTCTATCCCA
     GCGACATCGC

951 CGTGGAGTGG GAGAGCAATG GGCAGCCGGA GAACAACTAC
     AAGACCACGC

1001 CTCCCGTGCT GAAGTCCGAC GGCTCCTTCT TCCTCTATAG
     CAAGCTCACC
```

```
1051  GTGGACAAGA GCAGGTGGCA GCAGGGGAAC GTCTTCTCAT
      GCTCCGTGAT

1101  GCATGAGGCT CTGCACAACC ACTACACGCA GAAGAGCCTC
      TCCCTGTCTC

1151  CGGGTAAATG A
```

The processed ActRIIA-Fc fusion polypeptide (SEQ ID NO: 84) is as follows, and may optionally be provided with lysine (K) removed from the C-terminus.

```
                                              (SEQ ID NO: 84)
  1   ILGRSETQEC LFFNANWEKD RTNQTGVEPC YGDKDKRRHC FATWKNISGS IEIVKQGCWL

61   DDINCYDRTD CVEKKDSPEV YFCCCEGNMC NEKFSYFPEM EVTQPTSNPV TPKPPTGGGG

121   SGGGGSGGGG SGGGGSTHTC PPCPAPELLG GPSVFLFPPK PKDTLMISRT PEVTCVVVDV

181   SHEDPEVKFN WYVDGVEVHN AKTKPREEQY NSTYRVVSVL TVLHQDWLNG KEYKCKVSNK

241   ALPAPIEKTI SKAKGQPREP QVYTLPPSRK EMTKNQVSLT CLVKGFYPSD IAVEWESNGQ

301   PENNYKTTPP VLKSDGSFFL YSKLTVDKSR WQQGNVFSCS VMHEALHNHY TQKSLSLSPG

361   K
```

The complementary form of TβRII-Fc fusion polypeptide (SEQ ID NO: 85) is as follows:

```
                                              (SEQ ID NO: 85)
  1   MDAMKRGLCC VLLLCGAVFV SPGATIPPHV QKSDVEMEAQ
      KDEIICPSCN

51   RTAHPLRHIN NDMIVTDNNG AVKFPQLCKF CDVRFSTCDN
      QKSCMSNCSI

101   TSICEKPQEV CVAVWRKNDE NITLETVCHD PKLPYHDFIL
      EDAASPKCIM

151   KEKKKPGETF FMCSCSSDEC NDNIIFSEEY NTSNPDTGGG
      GSGGGGSGGG

201   GSGGGGSTHT CPPCPAPELL GGPSVFLFPP KPKDTLMISR
      TPEVTCVVVD

251   VSHEDPEVKF NWYVDGVEVH NAKTKPREEQ YNSTYRVVSV
      LTVLHQDWLN

301   GKEYKCKVSN KALPAPIEKT ISKAKGQPRE PQVYTLPPSR
      EEMTKNQVSL

351   TCLVKGFYPS DIAVEWESNG QPENNYDTTP PVLDSDGSFF
      LYSDLTVDKS

401   RWQQGNVFSC SVMHEALHNH YTQKSLSLSP GK
```

The leader sequence and linker are underlined. To guide heterodimer formation with the ActRIIA-Fc fusion polypeptide of SEQ ID NOs: 82 and 84 above, two amino acid substitutions (replacing lysines with aspartic acids) can be introduced into the Fc domain of the TβRII-Fc fusion polypeptide as indicated by double underline above. The amino acid sequence of SEQ ID NO: 85 may optionally be provided with lysine (K) added at the C-terminus.

This TβRII-Fc fusion protein is encoded by the following nucleic acid (SEQ ID NO: 86):

```
                                              (SEQ ID NO: 86)
  1   ATGGATGCGA TGAAACGCGG CCTGTGCTGC GTGCTGCTGC
      TGTGCGGCGC

51   GGTGTTTGTG AGCCCGGGCG CCACCATTCC GCCGCATGTG
      CAGAAAAGCG

101   ATGTGGAAAT GGAAGCGCAG AAAGATGAAA TTATTTGCCC
      GAGCTGGAAC

151   CGCACCGCGC ATCCGCTGCG CCATATTAAC AACGATATGA
      TTGTGACCGA

201   TAACAACGGC GCGGTGAAAT TTCCGCAGCT GTGCAAATTT
      TGCGATGTGC

251   GCTTTAGCAC CTGCGATAAC CAGAAAAGCT GCATGAGCAA
      CTGCAGCATT

301   ACCAGCATTT GCGAAAAACC GCAGGAAGTG TGCGTGGCGG
      TGTGGCGCAA

351   ALACGATGAA AACATTACCC TGGAAACCGT GTGCCATGAT
      CCGAAACTGC

401   CGTATCATGA TTTTATTCTG GAAGATGCGG CGAGCCCGAA
      ATGCATTATG

451   AAAGAAAAAA AAAAACCGGG CGAAACCTTT TTTATGTGCA
      GCTGCAGCAG

501   CGATGAATGC AACGATAACA TTATTTTTAG CGAAGAATAT
      AACACCAGCA

551   ACCCGGATAC CGGTGGCGGC GGCAGCGGCG GCGGCGGCAG
      CGGCGGCGGC

601   GGCAGCGGCG GCGGCGGCAG CACCCATACC TGCCCGCCGT
      GCCCGGCGCC

651   GGAACTGCTG GGCGGCCCGA GCGTGTTTCT GTTTCCGCCG
      AAACCGAAAG

701   ATACGCTGAT GATTAGCCGC AGCGCGGAAG TGAGCTGGGT
      GGTGGTGGAT

751   GTGAGCCATG AAGATCCGGA AGTGAAATTT AACTGGTATG
      TGGATGGCGT

801   GGAAGTGCAT AACGCGAAAA CCAAACCGCG CGAAGAAaAG
      TATAACAGCA
```

```
 851 CCTATCGCGT GGTGAGCGTG CTGACCGTGC TGCATCAGGA
     TTGGCTGAAC

901 GGCAAAGAAT ATAAATGCAA AGTGAGCAAC AAAGCGCTGC
     CGGCGCCGAT

951 TGAAAAAACC ATTAGCAAAG CGAAAGGCCA GCCGCGCGAA
     CCGCAGGTGT

1001 ATACCCTGCC GCCGAGCCGC GAAGAAATGA CCAAALACCA
     GGTGAGCCTG

1051 ACCTGCCTGG TGALAGGCTT TTATCCGAGC GATATTGCGG
     TGGAATGGGA

1101 AAGCAACGGC CAGCCGGALA ACAACTATGA TACCACCCCG
     CCGGTGCTGG

1151 ATAGCGATGG CAGCTTTTTT CTGTATAGCG ATCTGACCGT
     GGATAAAAGC

1201 CGCTGGCAGC AGGGCAACGT GTTTAGCTGC AGCGTGATGC
     ATGAAGCGCT

1251 GCATAACCAT TATACCCAGA AAAGCCTGAG CCTGAGCCCG
     GGCGATGATG

1301 ATGATAAAGC GCATCATCAT CATCATCATT AA
```

The processed TβRII-Fc fusion protein sequence (SEQ ID NO: 87) is as follows and may optionally be provided with lysine (K) added at the C-terminus.

```
                                                  (SEQ ID NO: 87)
  1 TIPPHVQKSD VEMEAQKDEI ICPSCNRTAH PLRHINNDMI VTDNNGAVKF PQLCKFCDVR

61 FSTCDNQKSC MSNCSITSIC EKPQEVCVAV WRKNDENITL ETVCHDPKLP YHDFILEDAA

121 SPKCIMKEKK KPGETFFMCS CSSDECNDNI IFSEEYNTSN PDTGGGGSGG GGSGGGGSGG

181 GGSTHTCPPC PAPELLGGPS VFLFPPKPKD TLMISRTPEV TCVVVDVSHE DPEVKFNWYV

241 DGVEVHNAKT KPREEQYNST YRVVSVLTVL HQDWLNGKEY KCKVSNKALP APIEKTISKA

301 KGQPREPQVY TLPPSREEMT KNQVSLTCLV KGFYPSDIAV EWESNGQPEN NYDTTPPVLD

361 SDGSFFLYSD LTVDKSRWQQ GNVFSCSVMH EALHNHYTQK SLSLSPGK
```

The ActRIIA-Fc and TβRII-Fc proteins of SEQ ID NO: 84 and SEQ ID NO: 87, respectively, may be co-expressed and purified from a CHO cell line, to give rise to a heteromeric complex comprising ActRIIA-Fc:TβRII-Fc.

In another approach to promote the formation of heteromultimer complexes using asymmetric Fc fusion proteins the Fc domains are altered to introduce complementary hydrophobic interactions and an additional intermolecular disulfide bond as illustrated in the ActRIIA-Fc and TβRII-Fc polypeptide sequences of SEQ ID NOs: 88-90 and 91-93, respectively. The ActRIIA-Fc fusion polypeptide and TβRII-Fc fusion polypeptide each employ the tissue plasminogen activator (TPA) leader.

The ActRIIA-Fc polypeptide sequence (SEQ ID NO: 88) is shown below:

```
                                                  (SEQ ID NO: 88)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK

101 DSPEVYFCCC EGNMCNEKFS YFPEMEVTQP TSNPVTPKPP TGGGGSGGGG

151 SGGGGSGGGG STHTCPPCPA PELLGGPSVF LFPPKPKDTL MISRTPEVTC

201 VVVDVSHEDP EVKFNWYVDG VEVHNAKTKP REEQYNSTYR VVSVLIVLHQ

251 DWLNGKEXKC KVSNKALPAP IEKTISKAKG QPREPQVYTL PPCREEMTKN

301 QVSLWCLVKG FYPSDIAVEW ESNGQPENNY KTTPPVLDSD GSFFLYSKLT

351 VDKSRWQQGN VFSCSVMHEA LHNHYTQKSL SLSPGK
```

The leader (signal) sequence and linker are underlined. To promote formation of the ActRIIA-Fc:TβRII-Fc heterodimer rather than either of the possible homodimeric complexes, two amino acid substitutions (replacing a serine with a cysteine and a threonine with a tryptophan) can be introduced into the Fc domain of the fusion protein as indicated by double underline above. The amino acid sequence of SEQ ID NO: 88 may optionally be provided with lysine (K) removed from the C-terminus.

This ActRIIA-Fc fusion protein is encoded by the following nucleic acid sequence (SEQ ID NO: 89):

```
                                                           (SEQ ID NO: 89)
    1   ATGGATGCAA TGAAGAGAGG GCTCTGCTGT GTGCTGCTGC TGTGTGGAGC
   51   AGTCTTCGTT TCGCCCGGCG CCGCTATACT TGGTAGATCA GAAACTCAGG
  101   AGTGTCTTTT CTTTAATGCT AATTGGGAAA AGACAGAAC CAATCAAACT
  151   GGTGTTGAAC CGTGTTATGG TGACAAAGAT AAACGGCGGC ATTGTTTTGC
  201   TACCTGGAAG AATATTTCTG GTTCCATTGA AATAGTGAAA CAAGGTTGTT
  251   GGCTGGATGA TATCAACTGC TATGACAGGA CTGATTGTGT AGAAAAAAAA
  301   GACAGCCCTG AAGTATATTT CTGTTGCTGT GAGGGCAATA TGTGTAATGA
  351   AAAGTTTTCT TATTTTCCGG AGATGGAAGT CACACAGCCC ACTTCAAATC
  401   CAGTTACAGG TAAGCCACCC ACCGGTGGTG GAGGTTCTGG AGGTGGAGGA
  451   AGTGGTGGAG GTGGTTCTGG AGGTGGTGGA AGTACTCACA CATGCCCACC
  501   GTGCCCAGCA CCTGAAGTCC TGGGGGGACC GTCAGTCTTC CTCTTCCCCC
  551   CAAAACCCAA GGACACCCTC ATGATCTCCC GGACCCCTGA GGTCACATGC
  601   GTGGTGGTGG ACGTGAGCCA CGAAGACCCT GAGGTCAAGT TCAACTGGTA
  651   CGTGGACGGC GTGGAGGTGC ATAATGCCAA GACAAAGCCG CGGGAGGAGC
  701   AGTACAACAG CACGTACCGT GTGGTCAGCG TCCTCACCGT CCTGCACCAG
  751   GACTGGCTGA ATGGCAAGGA GTACAAGTGC AAGGTCTCCA ACAAAGCCCT
  801   CCCAGCCCCC ATCGAGAAAA CCATCTCCAA AGCCAAAGGG CAGCCCCGAG
  851   AACCACAGGT GTACACCCTG CCCCCATGCC GGGAGGAGAT GACCAAGAAC
  901   CAGGTCAGCC TGTGGTGCCT GGTCAAAGGC TTCTATCCCA GCGACATCGC
  951   CGTGGAGTGG GAGAGCAATG GGCAGCCGGA GAACAACTAC AAGACCACGC
 1001   CTCCCGTGCT GGACTCCGAC GGCTCCTTCT TCCTCTATAC CAAGCTCACC
 1051   GTGGACAAGA GCAGGTGGCA GCAGGGGAAC GTCTTCTCAT GCTCCGTGAT
 1101   GCATGAGGCT CTGCACAACC ACTACACGCA GAAGAGCCTC TCCCTGTCTC
 1151   CGGGTAAATG A
```

The processed ActRIIA-Fc fusion polypeptide is as follows:

```
                                                           (SEQ ID NO: 90)
    1   ILGRSETQEC LFFNANWEKD RTNQTGVEPC YGDKDKRRHC FATWKNISGS IEIVKQGCWL
   61   DDINCYDRTD CVEKKDSPEV YFCCCEGNMC NEKFSYFPEM EVTQPTSNPV TPKPPTGGGG
  121   SGGGGSGGGG SGGGGSTHTC PPCPAPELLG GPSVFLFPPK PKDTLMISRT PEVTCVVVDV
  181   SHEDPEVKFN WYVDGVEVHN AKTKPREEQY NSTYRVVSVL TVLHQDWLNG KEYKCKVSNK
  241   ALPAPIEKTI SKAKGQPREP QVYTLPPCRE EMTKNQVSLW CLVKGFYPSD IAVEWESNGQ
  301   PENNYKTTPP VLDSDGSFFL YSKLTVDKSR WQQGNVFSCS VMHEALHNHY TQKSLSLSPG
  361   K
```

The complementary form of TβRII-Fc fusion polypeptide (SEQ ID NO: 91) is as follows and may optionally be provided with lysine (K) removed from the C-terminus.

(SEQ ID NO: 91)
```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSGGGGSTHT CPPCPAPELL GGPSVFLFPP KPKDTLMISR TPEVTCVVVD

251 VSHEDPEVKF NWYVDGVEVH NAKTKPREEQ YNSTYRVVSV LTVLHQDWLN

301 GKEYKCKVSN KALPAPIEKT ISKAKGQPRE PQVCTLPPSR EEMTKNQVSL

351 SCAVKGFYPS DIAVEWESNG QPENNYKTTP PVLDSDGSFF LVSKLTVDKS

401 RWQQGNVFSC SVMHEALHNH YTQKSLSLSP GK
```

The leader sequence and the linker are underlined. To guide heterodimer formation with the ActRIIA-Fc fusion polypeptide of SEQ ID NOs: 88 and 91 above, four amino acid substitutions can be introduced into the Fc domain of the TβRII fusion polypeptide as indicated by double underline above. The amino acid sequence of SEQ ID NO: 91 may optionally be provided with lysine (K) removed from the C-terminus.

This A TβRII-Fc fusion protein is encoded by the following nucleic acid sequence (SEQ ID NO: 92):

(SEQ ID NO: 92)
```
   1 ATGGATGCAA TGAAGAGAGG GCTCTGCTGT GTGCTGCTGC
     TGTGTGGAGC

51 AGTCTTCGTT TCGCCCGGCG CCACGATCCC ACCGCACGTT
     CAGAAGTCGG

101 ATGTGGAAAT GGAGGCCCAG AAAGATGAAA TCATCTGCCC
     CAGCTGTAAT

151 AGGACTGCCC ATCCACTGAG ACATATTAAT AACGACATGA
     TAGTCACTGA

201 CAACAACGGT GCAGTCAAGT TCCACAACT GTGTAAATTT
     TGTGATGTGA

251 GATTTTCCAC CTGTGACAAC CAGAAATCCT GCATGAGCAA
     CTGCAGCATC

301 ACCTCCATCT GTGAGAAGCC ACAGGAAGTC TGTGTGGCTG
     TATGGAGAAA

351 GAATGACGAG AACATAACAC TAGAGACAGT TTGCCATGAC
     CCCAAGCTCC

401 CCTACCATGA CTTTATTCTG GAAGATGCTG CTTCTCCAAA
     GTGCATTATG

451 AAGGAAAAAA AAAAGCCTGG TGAGACTTTC TTCATGTGTT
     CCTGTAGCTC

501 TGATGAGTGC AATGACAACA TCATCTTCTC AGAAGAATAT
     AACACCAGCA

551 ATCCTGACAC CGGTGGTGGA GGTTCTGGAG GTGGAGGAAG
     TGGTGGAGGT

601 GGTTCTGGAG GTGGTGGAAG TACTCACACA TGCCCACCGT
     GCCCAGCACC
```

```
 651 TGAACTCCTG GGGGGACCGT CAGTCTTCCT CTTCCCCCCA
     AAACCCAAGG

701 ACACCCTCAT GATCTCCCGG ACCCCTGAGG TCACATGCGT
     GGTGGTGGAC

751 GTGAGCCACG AAGACCCTGA GGTCAAGTTC AACTGGTACG
     TGGACGGCGT

801 GGAGGTGCAT AATGCCAAGA CAAAGCCGCG GGAGGAGCAG
     TACAACAGCA

851 CGTACCGTGT GGTCAGCGTC CTCACCGTCC TGCACCAGGA
     CTGGCTGAAT

901 GGCAAGGAGT ACAAGTGCAA GGTCTCCAAC AAAGCCCTCC
     CAGCCCCCAT

951 CGAGAAAACC ATCTCCAAAG CCAAAGGGCA GCCCCGAGAA
     CCACAGGTGT

1001 GCACCCTGCC CCCATCCCGG GAGGAGATGA CCAAGAACCA
     GGTCAGCCTG

1051 TCCTGCGCCG TCAAAGGCTT CTATCCCAGC GACATCGCCG
     TGGAGTGGGA

1101 GAGCAATGGG CAGCCGGAGA ACAACTACAA GACCACGCCT
     CCCGTGCTGG

1151 ACTCCGACGG CTCCTTCTTC CTCGTGAGCA AGCTCACCGT
     GGACAAGAGC

1201 AGGTGGCAGC AGGGGAACGT CTTCTCATGC TCCGTGATGC
     ATGAGGCTCT

1251 GCACAACCAC TACACGCAGA AGAGCCTCTC CCTGTCTCCG
     GGTAAATGA
```

A processed TβRII-Fc fusion protein sequence is as follows and may optionally be provided with lysine (K) removed from the C-terminus.

```
                                                          (SEQ ID NO: 93)
  1   TIPPHVQKSD VEMEAQKDEI ICPSCNRTAH PLRHINNDMI VTDNNGAVKF PQLCKFCDVR

61   FSTCDNQKSC MSNCSITSIC EKPQEVCVAV WRKNDENITL ETVCHDPKLP YHDFILEDAA

121   SPKCIMKEKK KPGETFFMCS CSSDECNDNI IFSEEYNTSN PDTGGGGSGG GGSGGGGSGG

181   GGSTHTCPPC PAPELLGGPS VFLFPPKPKD TLMISRTPEV TCVVVDVSHE DPEVKFNWYV

241   DGVEVHNAKT KPREEQYNST YRVVSVLTVL HQDWLNGKEY KCKVSNKALP APIEKTISKA

301   KGQPREPQVC TLPPSREEMT KNQVSLSCAV KGFYPSDIAV EWESNGQPEN NYKTTPPVLD

361   SDGSFFLVSK LTVDKSRWQQ GNVFSCSVMH EALHNHYTQK SLSLSPGK
```

ActRIIA-Fc and TβRII-Fc proteins of SEQ ID NO: 90 and SEQ ID NO: 93, respectively, may be co-expressed and purified from a CHO cell line, to give rise to a heteromeric complex comprising ActRIIA-Fc:TβRII-Fc.

In order to compare the activity of the ActRIIA-Fc:TβRII-Fc heterodimers, ActRIIA-Fc and TβRII-Fc homodimers were generated, which each comprise either the ActRIIA or TβRII extracellular domains as present in any one of SEQ ID NO: 82, 84, 85, 87, 88, 90, 91, or 93; an unmodified hG1Fc domain (promotes homodimer formation); and a (G4S)4 linker (SEQ ID NO: 203) positioned between the ActRIIA or TβRII extracellular portion and the unmodified Fc portion. Both of these homodimers were expressed using the TPA leader sequence of SEQ ID NO: 23.

Purification of various heterodimer and homodimers described above could be achieved by a series of column chromatography steps, including, for example, three or more of the following, in any order: protein A chromatography, Q sepharose chromatography, phenylsepharose chromatography, size exclusion chromatography and epitope-based affinity chromatography (e.g., with an antibody or functionally equivalent ligand directed against an epitope on TβRII or ActRIIA), and multimodal chromatography (e.g., with resin containing both electrostatic and hydrophobic ligands). The purification could be completed with viral filtration and buffer exchange.

Example 4. Differential Ligand Inhibition by Receptor Fusion Protein Variants in Cell-Based Assay A reporter gene assay in A549 cells was used to determine the ability of an ActRIIA-Fc:TβRII-Fc heterodimer to inhibit activity of TGFβ1, TGFβ2, TGFβ3, activin A, activin B, GDF11, and BMP10 and compared to the inhibiting activity of an ActRIIA-Fc homodimer and TβRII-Fc homodimer, which are all described above in Example 3. This assay is based on a human lung carcinoma cell line transfected with a pGL3(CAGA)12 reporter plasmid (Dennler et al, 1998, EMBO 17: 3091-3100) as well as a Renilla reporter plasmid (pRLCMV) to control for transfection efficiency. The CAGA motif is present in the promoters of TGFβ-responsive genes (for example, PAI-1), so this vector is of general use for factors signaling through SMAD2 and SMAD3.

On the first day of the assay, A549 cells (ATCC® CCL-185™) were distributed in 48-well plates. On the second day, a solution containing pGL3(CAGA)12, pRLCMV, X-tremeGENE 9 (Roche Applied Science), and OptiMEM (Invitrogen) was preincubated, then added to Eagle's minimum essential medium (EMEM, ATCC®) supplemented with 0.1% BSA, which was applied to the plated cells for incubation overnight at 37° C., 5% $CO_2$. On the third day, medium was removed, and cells were incubated overnight at 37° C., 5% $CO_2$ with a mixture of ligands and inhibitors prepared as described below.

Serial dilutions of test articles were made in a 48-well plate in assay buffer (EMEM+0.1% BSA). An equal volume of assay buffer containing the test ligand was added to obtain a final ligand concentration equal to the EC50 determined previously. Test solutions were incubated at 37° C. for 30 minutes, then a portion of the mixture was added to all wells. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred in duplicate to a chemiluminescence plate (96-well) and analyzed in a luminometer with reagents from a Dual-Luciferase Reporter Assay system (Promega E1980) to determine normalized luciferase activity.

As illustrated in FIG. 12, the TβRII-Fc homodimer was capable of inhibiting TGFβ1 and TGFβ3 in this cell-based assay but did not inhibit TGFβ2, activin A, activin B, GDF11, or BMP10. In contrast, the ActRIIA-Fc homodimer was capable of inhibiting activin A, activin B, GDF11, and BMP10 but did not inhibit TGFβ1, TGFβ2, or TGFβ3. The ActRIIA-Fc:TβRII-Fc heterodimer was capable of inhibiting TGFβ1, TGFβ3, activin A, activin B, and GDF11 and but did not inhibit BMP10 or TGFβ2. These data demonstrate that ActRIIA-Fc:TβRII-Fc heterodimers retain many of potent inhibitor characteristics of ActRIIA-Fc and TβRII-Fc homodimers and thus represent an interesting class of ligand traps that are uniquely capable of affecting two distinct groups of Smad 2/3-related TGFβ superfamily ligands (i.e., the TGFβs and activin/GDFs). Moreover, the ActRIIA-Fc:TβRII-Fc heterodimer did not inhibit BMP910, and thus with respect to ActRIIA-associated ligands, ActRIIA-Fc:TβRII-Fc is a more selective antagonist than an ActRIIA homodimer. Accordingly, ActRIIA-Fc:TβRII-Fc heterodimers will be more useful than ActRIIA homodimer in certain applications where such selective antagonism is desired in combination with inhibition of TGFβ 1 and TGFβ3.

Example 5. Synthesis of Alternative Multispecific Binders

Multispecific binders capable of binding to both GDF8 and TGFβ via follistatin-TGFβRII or αGDF8-TGFβRII will be generated.

A fusion protein follistatin-TGFβRII consisting of the binding domains of follistatin and TGFβRII (referred to in this example as FS288.Fc (G4S)4-TGFβBRII) will be designed to be in a single bifunctional construct. The design of FS288.Fc (G4S)4-TGFβRII consists of the follistatin native signal peptide, followed by the follistatin-288 isoform (SEQ ID NO: 111), a TGGG linker (SEQ ID NO: 3) to the Fc IgG2 domain (SEQ ID NO: 163) which includes the hinge region that contains two disulfide bonds, a (G4S)4 linker (SEQ ID NO:203) and then TGFβRII ECD (SEQ ID NO: 170) (FIG. 14A). In some embodiments, the FS288.Fc (G4S)4-TGFβRII will comprise the amino acid sequence of SEQ ID NO: 180 or 181.

A second protein will be developed that will include the TGFβRII portion and an antigen-binding fragment portion capable of binding GDF8 (referred to in this example as αGDF8-hIgG1-(G4S)4-TGFβRII). αGDF8-hIgG1-(G4S)4-TGFβRII will be made by the assembly of two protein sub-molecules. One contains the sequence of the αGDF8 antibody variable heavy chain region (SEQ ID NO: 167), followed by the sequences of human IgG1 constant region (SEQ ID NO: 168) which includes the hinge region with two disulfide bonds, a (G4S)4 linker (SEQ ID NO:203) and then TGFβRII ECD (SEQ ID NO: 170) (FIG. 14B). The second protein sub-molecule contains the sequence of the αGDF8 antibody variable light chain region (SEQ ID NO: 174), followed by sequence of the human kappa constant light chain region (SEQ ID NO: 175). The signal peptide (SEQ ID NO: 176) is used so that all the proteins expressed will be secreted outside of the cells and into the condition media. The DNA constructs of those two new molecules will either be synthesized or cloned by using existing constructs. In some embodiments, the αGDF8-hIgG1-(G4S)4-TGFβRII will comprise the amino acid sequences of SEQ ID NOs: 172 and 182.

A small scale expression of the newly constructed plasmids will be performed in HEK293FT cells to verify if the constructs are made and if cells can express the molecule properly before investing materials and time into larger scale transfections. HEK293FT cells exhibit high transfection efficiency and protein production and will be used for small scale expression experiments. The protein production and quality will be checked via Western Blot assay and detecting with an anti-IgG Fc antibody.

After verifying the expression of these two new molecules in HEK293FT cells, all the studied molecules will be expressed in EXPI-CHO cells. Chinese hamster ovary (CHO) cells, an epithelial cell line derived from the ovary of the Chinese hamster, are the most commonly used mammalian hosts for industrial production of recombinant proteins. EXPI-CHO is a subtype of CHO cells. Conditioned media will be harvested and purified via mAb Protein A drip column. mAb columns made of Protein A bind to the heavy chain constant region (Fc) of IgG proteins, therefore this type of purification can yield high purified Fc-fusion protein in single step. After collecting the purified protein, the studied proteins will be used for ELISA analysis and Reporter Gene Assay (RGA) to characterize their binding to ligands and their activity to alter ligand-mediated signaling pathways in cell based assays.

ELISA is used to detect and quantify proteins via high specific protein to protein interactions. The plate will be coated with various ligands: GDF8, GDF11, Activin A, and Activin B to bind FS288; GDF11 and GDF8 to bind αGDF8 antibody; TGFβ1, TGFβ2, TGFβ3 to bind TGFβRII. FS288.Fc (G4S)4-TGFβBRII, αGDF8-hIgG1-(G4S)4-TGFβRII and their control molecule, αGDF8 antibody, FS288.Fc, and TGFβRII.Fc will be applied to the plate coated with ligands to determine binding. Finally anti-IgG Fc antibody will be used to detect and amplify the binding signals. As a negative control, wells coated with proteins of interest without ligands will be used to determine if there is any background signal because of non-specific binding.

RGA is a cell based assay used to characterize the activation of certain signaling pathways. The RGA assay may be used to investigate the activation of TGFβ SMAD 2/3 signaling activity using a reporter gene plasmid that contains CAGA12 as the response element and firefly luciferase as the reporter gene. Another plasmid containing CMV-renilla luciferase will be used as a transfection control. Upon SMAD 2/3-related ligands binding to cell surface receptors, intracellular SMAD signaling complexes will translocate to the nucleus and bind to CAGA12 and stimulate promoter activation and transcription of luciferase. When the studied molecules are hypothesized to trap specific ligands, the activation of CAGA12 mediated luciferase activity decreases accordingly.

It is expected that FS288.Fc (G4S)4-TGFβBRII to bind all tested ligands via ELISA and to trap and neutralize all tested ligands signaling activity via RGA. However, for αGDF8-hIgG1-(G4S)4-TGFβRII, because αGDF8 antibody only binds GDFs but not Activins, the binding and thus the neutralizing of this molecule to Activins is not expected. With the proposed finding, these two proteins can potentially be used as therapies for patients with DMD and increase their quality of life by improving muscle function.

The FS288.Fc (G4S)4-TGFβBRII and/or αGDF8-hIgG1-(G4S)4-TGFβRII molecules may also be used to treat a DMD animal model (e.g., the mdx mouse model) or human model.

Example 6. Synthesis of Four-Armed and Three-Armed ActRIIA-TGFβRII Multimers

A "four-armed" homodimer comprising two ActRIIA-TGFβRII fusions proteins will be generated. Each of the ActRIIA-TGFβRII fusions proteins (referred to as ActRIIA-Fc-(G4S)4-TGFβRII) in the homodimer will comprise the binding domains of ActRIIA and TGFβRII and be designed in a single bifunctional construct. The design of ActRIIA-Fc-(G4S)4-TGFβRII will comprise an ActRIIA polypeptide portion (SEQ ID NO: 51), followed by a GGG linker (SEQ ID NO: 63), followed by an Fc portion (SEQ ID NO: 163), followed by a linker (SEQ ID NO: 165), and then TGFβRII ECD (SEQ ID NO: 170) (FIG. 15A). In some embodiments, the ActRIIA-Fc-(G4S)4-TGFβRII will comprise the amino acid sequence of SEQ ID NO: 183.

In addition, a "three-armed" heterodimer comprising: a) one fusion protein comprising a TGFβRII polypeptide portion and an ActRIIA polypeptide portion (referred to as ActRIIA-Fc-knob-(G4S)4G-TGFβRII) and b) a fusion protein comprising a TGFβRII polypeptide portion but lacking an ActRIIA polypeptide portion (referred to as Fc1-hole-(G4S)4G-TGFβRII) will be generated (FIG. 15B). The ActRIIA-Fc-knob-(G4S)4G-TGFβRII protein will comprise an ActRIIA polypeptide portion (SEQ ID NO: 51), followed by a GGG linker (SEQ ID NO: 63), followed by an Fc portion (SEQ ID NO: 72, but lacking the C-terminal lysine), followed by a linker (SEQ ID NO: 165), followed by a TGFβRII polypeptide portion (SEQ ID NO: 170). The Fc1-hole-(G4S)4G-TGFβRII protein will comprise nine amino acids from CH1 (SNTKVD KRV—SEQ ID NO: 189), followed by a linker (TGGG (SEQ ID NO: 3)), followed by an Fc portion (SEQ ID NO: 73), followed by a linker (SEQ ID NO: 165), followed by a TGFβRII polypeptide portion (SEQ ID NO: 170) (FIG. 15B). In some embodiments, the ActRIIA-Fc-knob-(G4S)4G-TGFβRII protein will comprise the amino acid sequence of SEQ ID NO: 184, and the Fc1-hole-(G4S)4G-TGFβRII protein will comprise the amino acid sequence of SEQ ID NO: 185.

A small scale expression of the plasmids encoding a) ActRIIA-Fc (G4S)4-TGFβRII, or b) ActRIIA-Fc-knob-(G4S)4G-TGFβRII and Fc1-hole-(G4S)4G-TGFβRII, will be performed in HEK293FT cells to verify if the constructs are made and if cells can express the multimers properly before investing materials and time into larger scale transfections. HEK293FT cells exhibit high transfection efficiency and protein production will be used for small scale expression experiments. The multimer production and quality will be checked via Western Blot assay and detection with an anti-IgG Fc antibody.

After verifying the expression of the four-armed and/or the three-armed multimers in HEK293FT cells, all the studied multimers will be expressed in EXPI-CHO cells. Conditioned media will be harvested and purified via mAb Protein A drip column. mAb columns made of Protein A bind to the heavy chain constant region (Fc) of IgG proteins, therefore this type of purification can yield high purified Fc-fusion protein in single step.

A reporter gene assay in A549 cells similar to that described in Example 4 will be used to determine the ability of the three- and/or four-armed multimers to inhibit activity of TGFβ1, TGFβ2, TGFβ3, activin A, activin B, GDF11, and/or BMP10 as compared to the inhibiting activity of an ActRIIA-Fc homodimer and TβRII-Fc homodimer, which are all described above in Example 3.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A heteromultimer comprising an ActRIIA fusion protein and a TβRII fusion protein, wherein the ActRIIA fusion protein comprises an ActRIIA polypeptide comprising:
   a. a sequence beginning at any one of positions 21 to 30 of SEQ ID NO: 50, and ending at any one of positions 110 to 135 of SEQ ID NO: 50;
   b. a sequence beginning at position 21 of SEQ ID NO: 50, and ending at position 135 of SEQ ID NO: 50;
   c. a sequence beginning at position 30 of SEQ ID NO: 50 and ending at position 110 of SEQ ID NO: 50;
   d. the sequence of SEQ ID NO: 51; or
   e. the sequence of SEQ ID NO: 52;
   wherein the TβRII fusion protein comprises a TβRII polypeptide comprising:
   a. a sequence beginning at any one of positions 23 to 35 of SEQ ID NO: 1, and ending at any one of positions 153 to 159 of SEQ ID NO: 1;
   b. a sequence beginning at any one of positions 23 to 60 of SEQ ID NO: 2, and ending at any one of positions 178 to 184 of SEQ ID NO: 2;
   c. the sequence of SEQ ID NO: 18;
   d. the sequence of SEQ ID NO: 27; or
   e. the sequence of any one of SEQ ID NOs: 20, 28, 29, 30, 31, 32, 33, 34, 35, 36, 37, 38; and 39;
   wherein the heteromultimer binds to and/or inhibits one or more of GDF11, activin A, activin B, TGFβ1, and TGFβ3; and
   wherein the ActRIIA fusion protein and the TβRII fusion protein comprise a heterologous portion.

2. The heteromultimer of claim 1, wherein the ActRIIA fusion protein further comprises a linker domain positioned between the ActRIIA polypeptide and the heterologous portion, wherein the linker domain:
   1) is between 10 and 25 amino acids in length, and comprises an amino acid sequence selected from:
      a. (GGGGS)n, wherein n=>2;
      b. (GGGGS)n, wherein n=>3;
      c. (GGGGS)n, wherein n=>4;
      d. (GGGGS)n, wherein n≠>5; or
   2) consists of the amino acid sequence of any one of SEQ ID Nos: 4-7, 19, 21, 25, 26, 40, and 63-67.

3. The heteromultimer of claim 1, wherein the ActRIIA fusion protein comprises the amino acid sequence of SEQ ID NO: 84 or 90.

4. The heteromultimer of claim 1, wherein the TβRII fusion protein further comprises a linker domain positioned between the TβRII polypeptide and the heterologous portion, wherein the linker domain:
   1) is between 10 and 25 amino acids in length, and comprises an amino acid sequence selected from:
      a. (GGGGS)n, wherein n=>2;
      b. (GGGGS)n, wherein n=>3;
      c. (GGGGS)n, wherein n=>4;
      d. GGGGS)n, wherein n≠>5; or
   2) consists of the amino acid sequence of any one of SEQ ID Nos: 4-7, 19, 21, 25, 26, 40, and 63-67.

5. The heteromultimer of claim 1, wherein the TβRII fusion protein comprises the amino acid sequence of SEQ ID NO: 87 or 93.

6. The heteromultimer of claim 1, wherein the heterologous portion comprises: 1) a first or second member of an interaction pair; and/or 2) one or more amino acid modifications that promotes heterodimer formation.

7. The heteromultimer of claim 6, wherein the heterologous portion is an immunoglobulin Fc domain.

8. The heteromultimer of claim 7, wherein the immunoglobulin Fc domain comprises an amino acid sequence that is at least 75% identical to:
   a. the amino acid sequence of SEQ ID NO: 68, wherein the sequence comprises a lysine (K) at position 356 and a K at position 399 based on the amino acid positioning of the EU numbering scheme of Kabat;
   b. the amino acid sequence of SEQ ID NO: 69, wherein the sequence comprises a aspartic acid (D) at position 392 and a D at position 409 based on the amino acid positioning of the EU numbering scheme of Kabat;
   c. the amino acid sequence of SEQ ID NO: 72, wherein the sequence comprises a cysteine (C) at position 354 and a tryptophan (W) at position 366 based on the amino acid positioning of the EU numbering scheme of Kabat; or
   d. the amino acid sequence of SEQ ID NO: 73, wherein the sequence comprises a C at position 349, a serine (S) at position 366, an alanine (A) at position 368, and a valine at position 407 based on the amino acid positioning of the EU numbering scheme of Kabat.

\* \* \* \* \*